US007235374B2

(12) United States Patent
Palmer et al.

(10) Patent No.: US 7,235,374 B2
(45) Date of Patent: Jun. 26, 2007

(54) SYSTEMS FOR SENSITIVE DETECTION OF G-PROTEIN COUPLED RECEPTOR AND ORPHAN RECEPTOR FUNCTION USING REPORTER ENZYME MUTANT COMPLEMENTATION

(75) Inventors: Michelle A. J. Palmer, Arlington, MA (US); Melissa Gee, Bedford, MA (US); Bonnie Tillotson, Belmont, MA (US); Xiao-jia Chang, Lincoln, MA (US)

(73) Assignee: Applera Corporation, Foster City, CA (US)

( * ) Notice: Subject to any disclaimer, the term of this patent is extended or adjusted under 35 U.S.C. 154(b) by 60 days.

(21) Appl. No.: 10/959,611

(22) Filed: Oct. 5, 2004

(65) Prior Publication Data

US 2006/0040250 A1    Feb. 23, 2006

Related U.S. Application Data

(63) Continuation of application No. 09/759,152, filed on Jan. 16, 2001, now Pat. No. 6,800,445, which is a continuation-in-part of application No. 09/654,499, filed on Sep. 1, 2000, now Pat. No. 6,893,827.

(60) Provisional application No. 60/180,669, filed on Feb. 7, 2000.

(51) Int. Cl.
*C07K 14/705* (2006.01)
*C07K 19/00* (2006.01)
*C12N 15/62* (2006.01)
*G01N 33/566* (2006.01)

(52) U.S. Cl. .................. 435/7.2; 435/7.21; 435/69.7; 536/23.4

(58) Field of Classification Search .............. None
See application file for complete search history.

(56) References Cited

U.S. PATENT DOCUMENTS

| | | | |
|---|---|---|---|
| 4,931,569 A | 6/1990 | Edwards et al. |
| 4,978,614 A | 12/1990 | Bronstein |
| 5,145,772 A | 9/1992 | Voyta et al. |
| 5,326,882 A | 7/1994 | Bronstein et al. |
| 5,538,847 A | 7/1996 | Bronstein et al. |
| 5,851,771 A | 12/1998 | Bronstein et al. |
| 5,891,646 A | 4/1999 | Barak et al. |
| 6,110,693 A | 8/2000 | Barak et al. |
| 6,342,345 B1 | 1/2002 | Blau et al. |
| 6,800,445 B2 | 10/2004 | Palmer et al. |
| 6,893,827 B1 | 5/2005 | Palmer et al. |

FOREIGN PATENT DOCUMENTS

| | | |
|---|---|---|
| WO | WO 98/44350 | 10/1998 |
| WO | WO 01/37896 | 5/2001 |
| WO | WO 01/59451 | 8/2001 |

OTHER PUBLICATIONS

V. Gurevich et al., "Arrestin Interactions With G Protein-Coupled Receptors", The Journal of Biological Chemistry, vol. 270, No. 2, Jan. 13, 1995, pp. 720-731.
S. Vishnivetskiy et al., "How Does Arrestin Respond to The Phosphorylated State of Rhodopsin"?, The Journal of Biological Chemistry, vol. 274, No. 17, Apr. 23, 1999, pp. 11451-11454.
R. Oakley et al., Association of β-Arrestin With G Protein-Coupled Receptors During Clathrin-Mediated Endocytosis Dictates The Profile Of Receptor Resensitization, The Journal of Biological Chemistry, vol. 274, No. 45, Nov. 5, 1999, pp. 32248-32257.
B Blakely et al., "Epidermal Growth Factor Receptor Dimerization Monitored In Live Cells", Nature Biotechnology, vol. 18, Feb. 2000, pp. 218-222.
Supplementary European Search Report issued in European Patent Application No. 01906531 on Aug. 17, 2005, 4 pages Dated Aug. 3, 2005.
Angers et al., "Detection of β2-adrenergic receptor dimerization in living cells using bioluminescence resonance energy transfer (BRET)", Proc. Nat. Acad. Sci. USA, 97(7) :3684-3689 (2000).
Gurevich et al., "Mechanism of Phosphorylation-Recognition by Visual Arrestin and the Transition of Arrestin into a High Affinity Binding State", Mol. Pharmacol., 51:161-169 (1997).
Rossi et al., "Monitoring Protein-Protein Interactions in Intact Eukaryotic Cells by β-galactosidase complementation", Proc. Natl. Acad. Sci., 94:8405-8410 (1997).

(Continued)

*Primary Examiner*—John Ulm
(74) *Attorney, Agent, or Firm*—Andrew Finn

(57) ABSTRACT

Methods for detecting G-protein coupled receptor (GPCR) activity; methods for assaying GPCR activity; and methods for screening for GPCR ligands, G-protein-coupled receptor kinase (GRK) activity, and compounds that interact with components of the GPCR regulatory process are described. Included are methods for expanding ICAST technologies for assaying GPCR activity with applications for ligand fishing, and agonist or antagonist screening. These methods include: engineering seronine/threonine phosphorylation sites into known or orphan GPCR open reading frames in order to increase the affinity of arrestin for the activated form of the GPCR or to increase the reside time of arrestin on the activated GPCR; engineering mutant arrestin proteins that bind to activated GPCRs in the absence of G-protein coupled receptor kinases which may be limiting; and engineering mutant super arrestin proteins that have an increased affinity for activated GPCRs with or without phosphorylation. These methods are intended to increase the robustness of the GPCR/ICAST technology in situations in which G-protein coupled receptor kinases are absent or limiting, or in which the GPCR is not efficiently down-regulated or is rapidly resensitized (thus having a labile interaction with arrestin). Included are also more specific methods for using ICAST complementary enzyme fragments to monitor GPCR homo- and hetero-dimerization with applications for drug lead discovery and ligand and function discovery for orphan GPCRs.

5 Claims, 71 Drawing Sheets

OTHER PUBLICATIONS

Barak et al., "A β-Arrestin/Green Fluorescent Protein Biosensor for Detecting G Protein-coupled Receptor Activation", the Journal of Biological Chemistry, 272 (44) :27497-27500 (1997).

Ferguson et al., "G-protein-coupled receptor regulation: role of G-protein-coupled receptor Kinases and arrestins", Can. J. Physiol Pharmacol., 74:1095-110 (1996).

Pitcher et al., "G-protein-coupled receptor kinases", Annu. Rev. Biochem., 67:653-692 (1998).

Lefkowitz et al., "Adenylate cyclase-coupled beta-adrenergic receptors: structure and mechanisms of activation and desensitization", Annul. Rev. Biochem., 52:159-186 (1983).

Germino et al., "Screening for in vivo protein-protein interactions", Proc. Natl. Acad. Sci., 90:933-937 (1993).

Phizicky et al., "Protein-protein interactions: methods for detection and analysis", Microbiol. Rev., 59(1) :94-123 (1995).

Offermanns et al., "Gα15 and gα16 couple a wide variety of receptors to phospholipase C", J. Biol. Chem., 270(25) :15175-15180 (1995).

AbdAlla et al., "AT1-Receptor heterodimers show enhanced G-protein activation and altered receptor sequestration", Nature, 407:94-98 (2000).

Bockaert et al., "Molecular tinkering of G protein-coupled receptors: an evolutionary success", The EMBO Journal, 18(7)1723-1729 (1999).

Jordan et al., "G-protein-coupled receptor heterodimerization modulates receptor function", Nature, 399:697-700 (1999).

Ng et al., "Dopamine D2 receptor dimers and receptor-blocking peptides" Bioch. Biophys. Res. Commun., 227:200-204 (1996).

Hebert et al., "A peptide derived from a β2-adrenergic receptor transmembrane domain inhibits both receptor dimerization and activation", J. Biol. Chem. 271(27) :16384-16392 (1996).

Krupnick et al., "The role of receptor kinases and arrestins in G protein-coupled receptor regulation" Ann. Rev. Pharmacol. Toxicol., 38:289-319 (1998).

Hamm "The many faces of G-protein Signaling", J. Biol. Chem., 273(2) :669-672 (1998).

Zhang et al., "Cellular trafficking of G protein-coupled receptor/β-arrestin endocytic complexes", J. Biol. Chem., 274(16) :10999-11006 (1999).

Kovoor et al., "Targeted construction of phosphorylation-independent β-arrestin mutants with constitutive activity in cells", J. Biol. Chem., 274(11) :6831-6834 (1999).

```
  1 CTGCAGCCTG AATATGGGCC AAACAGGATA TCTGTGGTAA GCAGTTCCTG
    GACGTCGGAC TTATACCCGG TTTGTCCTAT AGACACCATT CGTCAAGGAC

51 CCCCGGCTCA GGGCCAAGAA CAGATGGAAC AGCTGAATAT GGGCCAAACA
    GGGGCCGAGT CCCGGTTCTT GTCTACC11G TCGACTTATA CCCGGTTTGT

101 GGATATCTGT GGTAAGCAGT TCCTGCCCCG GCTCAGGGCC AAGAACAGAT
    CCTATAGACA CCATTCGTCA AGGACGGGGC CGAGTCCCGG TTCTTGTCTA

151 GGTCCCCAGA TGCGGTCCAG CCCTCAGCAG TTTCTAGAGA ACCATCAGAT
    CCAGGGGTCT ACGCCAGGTC GGGAGTCGTC AAAGATCTCT TGGTAGTCTA

201 GTTTCCAGGG TGCCCCAAGG ACCTGAAATG ACCCTGTGCC TTATTTGAAC
    CAAAGGTCCC ACGGGGTTCC TGGACTTTAC TGGGACACGG AATAAACTTG

251 TAACCAATCA GTTCGCTTCT CGCTTCTGTT CGCGCGCTTC TGCTCCCCGA
    ATTGGTTAGT CAAGCGAAGA GCGAAGACAA GCGCGCGAAG ACGAGGGGCT

301 GCTCAATAAA AGAGCCCACA ACCCCTCACT CGGGGCGCCA GTCCTCCGAT
    CGAGTTATTT TCTCGGGTGT TGGGGAGTGA GCCCCGCGGT CAGGAGGCTA

351 TGACTGAGTC GCCCGGGTAC CCGTGTATCC AATAAACCCT CTTGCAGTTG
    ACTGACTCAG CGGGCCCATG GGCACATAGG TTATTTGGGA GAACGTCAAC

401 CATCCGACTT GTGGTCTCGC TGTTCCTTGG GAGGGTCTCC TCTGAGTGAT
    GTAGGCTGAA CACCAGAGCG ACAAGGAACC CTCCCAGAGG AGACTCACTA

451 TGACTACCCG TCAGCGGGGG TCTTTCATTT GGGGGCTCGT CCGGGATCGG
    ACTGATGGGC AGTCGCCCCC AGAAAGTAAA CCCCCGAGCA GGCCCTAGCC

501 GAGACCCCTG CCCAGGGACC ACCGACCCAC CACCGGGAGG CAAGCTGGCC
    CTCTGGGGAC GGGTCCCTGG TGGCTGGGTG GTGGCCCTCC GTTCGACCGG

551 AGCAACTTAT CTGTGTCTGT CCGATTGTCT AGTGTCTATG ACTGATTTTA
    TCGTTGAATA GACACAGACA GGCTAACAGA TCACAGATAC TGACTAAAAT

601 TGCGCCTGCG TCGGTACTAG TTAGCTAACT AGCTCTGTAT CTGGCGGACC
    ACGCGGACGC AGCCATGATC AATCGATTGA TCGAGACATA GACCGCCTGG

651 CGTGGTGGAA CTGACGAGTT CTGAACACCC GGCCGCAACC CTGGGAGACG
    GCACCACCTT GACTGCTCAA GACTTGTGGG CCGGCGTTGG GACCCTCTGC

701 TCCCAGGGAC ITTGGGGGCC GTTTTTGTGG CCCGACCTGA GGAAGGGAGT
    AGGGTCCCTG AAACCCCCGG CAAAACACC GGGCTGGACT CCTTCCCTCA

751 CGATGTGGAA TCCGACCCCG TCAGGATATG TGGTTCTGGT AGGAGACGAG
    GCTACACCTT AGGCTGGGGC AGTCCTATAC ACCAAGACCA TCCTCTGCTC

801 AACCTAAAAC AGTTCCCGCC TCCGTCTGAA TTTTTGCTTT CGGTTTGGAA
    TTGGATTTTG TCAAGGGCGG AGGCAGACTT AAAAACGAAA GCCAAACCTT

851 CCGAAGCCGC GCGTCTTGTC TGCTGCAGCA TCGTTCTGTG TTGTCTCTGT
    GGCTTCGGCG CGCAGAACAG ACGACGTCGT AGCAAGACAC AACAGAGACA

901 CTGACTGTGT TTCTGTATTT GTCTGAAAAT TAGGGCCAGA CTGTTACCAC
    GACTGACACA AAGACATAAA CAGACTTTTA ATCCCGGTCT GACAATGGTG
```

FIGURE 10B

```
 951  TCCCTTAAGT TTGACCTTAG GTAACTGGAA AGATGTCGAG CGGCTCGCTC
      AGGGAATTCA AACTGGAATC CATTGACCTT TCTACAGCTC GCCGAGCGAG

1001  ACAACCAGTC GGTAGATGTC AAGAAGAGAC GTTGGGTTAC CTTCTGCTCT
      TGTTGGTCAG CCATCTACAG TTCTTCTCTG CAACCCAATG GAAGACGAGA

1051  GCAGAATGGC CAACCTTTAA CGTCGGATGG CCGCGAGACG GCACCTTTAA
      CGTCTTACCG GTTGGAAATT GCAGCCTACC GGCGCTCTGC CGTGGAAATT

1101  CCGAGACCTC ATCACCCAGG TTAAGATCAA GGTCTTTTCA CCTGGCCCGC
      GGCTCTGGAG TAGTGGGTCC AATTCTAGTT CCAGAAAAGT GGACCGGGCG

1151  ATGGACACCC AGACCAGGTC CCCTACATCG TGACCTGGGA AGCCTTGGCT
      TACCTGTGGG TCTGGTCCAG GGGATGTAGC ACTGGACCCT TCGGAACCGA

1201  TTTGACCCCC CTCCCTGGGT CAAGCCCTTT GTACACCCTA AGCCTCCGCC
      AAACTGGGGG GAGGGACCCA GTTCGGGAAA CATGTGGGAT TCGGAGGCGG

1251  TCCTCTTCCT CCATCCGCCC CGTCTCTCCC CCTTGAACCT CCTCGTTCGA
      AGGAGAAGGA GGTAGGCGGG GCAGAGAGGG GGAACTTGGA GGAGCAAGCT

1301  CCCCGCCTCG ATCCTCCCTT TATCCAGCCC TCACTCCTTC TCTAGGCGCC
      GGGGCGGAGC TAGGAGGGAA ATAFFTCGGG AGTGAGGAAG AGATCCGCGG

1351  GGCCGCTCTA GCCCATTAAT ACGACTCACT ATAGGGCGAT TCGAATCAGG
      CCGGCGAGAT CGGGTAATTA TGCTGAGTGA TATCCCGCTA AGCTTAGTCC

1401  CCTTGGCGCG CCGGATCCTT AATTAAGCGC AATTGGGAGG TGGCGGTAGC
      GGAACCGCGC GGCCTAGGAA TTAATTCGCG TTAACCCTCC ACCGCCATCG

+2         M  G  V  I  T  D  S  L  A  V  V  A  R  T  D
           ]
1451  CTCGAGATGG GCGTGATTAC GGATTCACTG GCCGTCGTGG CCCGCACCGA
      GAGCTCTACC CGCACTAATG CCTAAGTGAC CGGCAGCACC GGGCGTGGCT

+2    R  P  S  Q  Q  L  R  S  L  N  G  E  W  R  F  A
1501  TCGCCCTTCC CAACAGTTAC GCAGCCTGAA TGGCGAATGG CGCTTTGCCT
      AGCGGGAAGG GTTGTCAATG CGTCGGACTT ACCGCTTACC GCGAAACGGA

+2    W  F  P  A  P  E  A  V  P  E  S  W  L  E  C  D  L
1551  GGTTTCCGGC ACCAGAAGCG GTGCCGGAAA GCTGGCTGGA GTGCGATCTT
      CCAAAGGCCG TGGTCTTCGC CACGGCCTTT CGACCGACCT CACGCTAGAA

+2    P  E  A  D  T  V  V  V  P  S  N  W  Q  M  H  G  Y
1601  CCTGAGGCCG ATACTGTCGT CGTCCCCTCA AACTGGCAGA TGCACGGTTA
      GGACTCCGGC TATGACAGCA GCAGGGGAGT TTGACCGTCT ACGTGCCAAT

+2    D  A  P  I  Y  T  N  V  T  Y  P  I  T  V  N  P
1651  CGATGCGCCC ATCTACACCA ACGTGACCTA TCCCATTACG GTCAATCCGC
      GCTACGCGGG TAGATGTGGT TGCACTGGAT AGGGTAATGC CAGTTAGGCG
```

FIGURE 10C

```
     +2  P   F   V   P   T   E   N   P   T   G   C   Y   S   L   T   F   N
   1701  CGTTTGTTCC CACGGAGAAT CCGACGGGTT GTTACTCGCT CACATTTAAT
         GCAAACAAGG GTGCCTCTTA GGCTGCCCAA CAATGAGCGA GTGTAAATTA

+2  V   D   E   S   W   L   Q   E   G   Q   T   R   I   I   F   D   G
   1751  GTTGATGAAA GCTGGCTACA GGAAGGCCAG ACGCGAATTA TTTTTGATGG
         CAACTACTTT CGACCGATGT CCTTCCGGTC TGCGCTTAAT AAAAACTACC

+2  V   N   S   A   F   H   L   W   C   N   G   R   W   V   G   Y
   1801  CGTTAACTCG GCGTTTCATC TCTGGTGCAA CGGGCGCTGG GTCGGTTACG
         GCAATTGAGC CGCAAAGTAG ACACCACGTT GCCCGCGACC CAGCCAATGC

+2  G   Q   D   S   R   L   P   S   E   F   D   L   S   A   F   L   R
   1851  GCCAGGACAG TCGTTTGCCG TCTGAATTTG ACCTGAGCGC ATTTTTACGC
         CGGTCCTGTC AGCAAACGGC AGACTTAAAC TGGACTCGCG TAAAAATGCG

+2  A   G   E   N   R   L   A   V   M   V   L   R   W   S   D   G   S
   1901  GCCGGAGAAA ACCGCCTCGC GGTGATGGTG CTGCGCTGGA GTGACGGCAG
         CGGCCTCTTT TGGCGGAGCG CCACTACCAC GACGCGACCT CACTGCCGTC

+2  Y   L   E   D   Q   D   M   W   R   M   S   G   I   F   R   D
   1951  TTATCTGGAA GATCAGGATA TGTGGCGGAT GAGCGGCATT TTCCGTGACG
         AATAGACCTT CTAGTCCTAT ACACCGCCTA CTCGCCGTAA AAGGCACTGC

+2  V   S   L   L   H   K   P   T   T   Q   I   S   D   F   H   V   A
   2001  TCTCGTTGCT GCATAAACCG ACTACACAAA TCAGCGATTT CCATGTTGCC
         AGAGCAACGA CGTATTTGGC TGATGTGTTT AGTCGCTAAA GGTACAACGG

+2  T   R   F   N   D   D   F   S   R   A   V   L   E   A   E   V   Q
   2051  ACTCGCTTTA ATGATGATTT CAGCCGCGCT GTACTGGAGG CTGAAGTTCA
         TGAGCGAAAT TACTACTAAA GTCGGCGCGA CATGACCTCC GACTTCAAGT

+2  M   C   G   E   L   R   D   Y   L   R   V   T   V   S   L   W
   2101  GATGTGCGGC GAGTTGCGTG ACTACCTACG GGTAACAGTT TCTTTATGGC
         CTACACGCCG CTCAACGCAC TGATGGATGC CCATTGTCAA AGAAATACCG

+2  Q   G   E   T   Q   V   A   S   G   T   A   P   F   G   G   E   I
   2151  AGGGTGAAAC GCAGGTCGCC AGCGGCACCG CGCCTTTCGG CGGTGAAATT
         TCCCACTTTG CGTCCAGCGG TCGCCGTGGC GCGGAAAGCC GCCACTTTAA

+2  I   D   E   R   G   G   Y   A   D   R   V   T   L   R   L   N   V
   2201  ATCGATGAGC GTGGTGGTTA TGCCGATCGC GTCACACTAC GTCTGAACGT
         TAGCTACTCG CACCACCAAT ACGGCTAGCG CAGTGTGATG CAGACTTGCA

+2  E   N   P   K   L   W   S   A   E   I   P   N   L   Y   R   A
   2251  CGAAAACCCG AAACTGTGGA GCGCCGAAAT CCCGAATCTC TATCGTGCGG
         GCTTTTGGGC TTTGACACCT CGCGGCTTTA GGGCTTAGAG ATAGCACGCC
```

FIGURE 10D

```
       +2  V  V  E  L    H  T  A    D  G  T    L    I  E  A    E  A  C
           ------------------------------------------------------------
      2301 TGGTTGAACT GCACACCGCC GACGGCACGC TGATTGAAGC AGAAGCCTGC
           ACCAACTTGA CGTGTGGCGG CTGCCGTGCG ACTAACTTCG TCTTCGGACG

+2   D  V  G  F    R  E  V    R  I  E    N  G  L    L  L  N
           ------------------------------------------------------------
      2351 GATGTCGGTT CCGCGAGGT GCGGATTGAA AATGGTCTGC TGCTGCTGAA
           CTACAGCCAA AGGCGCTCCA CGCCTAACTT TTACCAGACG ACGACGACTT

+2   G  K  P    L  L  I  R    G  V  N    R  H    E  H  H  P
           ------------------------------------------------------------
      2401 CGGCAAGCCG TTGCTGATTC GAGGCGTTAA CCGTCACGAG CATCATCCTC
           GCCGTTCGGC AACGACTAAG CTCCGCAATT GGCAGTGCTC GTAGTAGGAG

+2  L  H  G  Q    V  M  D    E  Q  T    M    V  Q  D    I  L  L
           ------------------------------------------------------------
      2451 TGCATGGTCA GGTCATGGAT GAGCAGACGA TGGTGCAGGA TATCCTGCTG
           ACGTACCAGT CCAGTACCTA CTCGTCTGCT ACCACGTCCT ATAGGACGAC

+2   M  K  Q  N    N  F  N    A  V  R    C  S  H  Y    P  N  H
           ------------------------------------------------------------
      2501 ATGAAGCAGA ACAACTTTAA CGCCGTGCGC TGTTCGCATT ATCCGAACCA
           TACTTCGTCT TGTTGAAATT GCGGCACGCG ACAAGCGTAA TAGGCTTGGT

+2   P  L  W    Y  T  L  C    D  R  Y    G  L  Y    V  V  D
           ------------------------------------------------------------
      2551 TCCGCTGTGG TACACGCTGT GCGACCGCTA CGGCCTGTAT GTGGTGGATG
           AGGCGACACC ATGTGCGACA CGCTGGCGAT GCCGGACATA CACCACCTAC

+2  E  A  N  I    E  T  H    G  M  V  P    M  N  R    L  T  D
           ------------------------------------------------------------
      2601 AAGCCAATAT TGAAACCCAC GGCATGGTGC CAATGAATCG TCTGACCGAT
           TTCGGTTATA ACTTTGGGTG CCGTACCACG GTTACTTAGC AGACTGGCTA

+2   D  P  R  W    L  P  A    M  S  E    R  V  T  R    M  V  Q
           ------------------------------------------------------------
      2651 GATCCGCGCT GGCTACCGGC GATGAGCGAA CGCGTAACGC GAATGGTGCA
           CTAGGCGCGA CCGATGGCCG CTACTCGCTT GCGCATTGCG CTTACCACGT

+2   R  D  R    N  H  P  S    V  I  I    W  S  L    G  N  E
           ------------------------------------------------------------
      2701 GCGCGATCGT AATCACCCGA GTGTGATCAT CTGGTCGCTG GGGAGTGAAT
           CGCGCTAGCA TTAGTGGGCT CACACTAGTA GACCAGCGAC CCCTCACTTA

+2  S  G  H  G    A  N  H    D  A  L  Y    R  W  I    K  S  V
           ------------------------------------------------------------
      2751 CAGGCCACGG CGCTAATCAC GACGCGCTGT ATCGCTGGAT CAAATCTGTC
           GTCCGGTGCC GCGATTAGTG CTGCGCGACA TAGCGACCTA GTTTAGACAG

+2   D  P  S  R    P  V  Q    Y  E  G    G  A  D    T  T  A
           ------------------------------------------------------------
      2801 GATCCTTCCC GCCCGGTGCA GTATGAAGGC GGCGGAGCCG ACACCACGGC
           CTAGGAAGGG CGGGCCACGT CATACTTCCG CCGCCTCGGC TGTGGTGCCG

+2   T  D  I    I  C  P  M    Y  A  R    V  D  E    D  Q  R
           ------------------------------------------------------------
      2851 CACCGATATT ATTTGCCCGA TGTACGCGCG CGTGGATGAA GACCAGCCCT
           GTGGCTATAA TAAACGGGCT ACATGCGCGC GCACCTACTT CTGGTCGGGA
```

FIGURE 10E

```
    +2   F   P   A   V   P   K   W   S   I   K   K   W   L   S   L   P   G
         -------------------------------------------------------------------
  2901   TCCCGGCTGT GCCGAAATGG TCCATCAAAA AATGGCTTTC GCTACCTGGA
         AGGGCCGACA CGGCTTTACC AGGTAGTTTT TTACCGAAAG CGATGGACCT

+2     E   T   R   P   L   I   L   C   E   Y   A   H   A   M   G   N   S
         -------------------------------------------------------------------
  2951   GAGACGCGCC CGCTGATCCT TTGCGAATAC GCCCACGCGA TGGGTAACAG
         CTCTGCGCGG GCGACTAGGA AACGCTTATG CGGGTGCGCT ACCCATTGTC

+2     L   G   G   F   A   K   Y   W   Q   A   F   R   Q   Y   P   R
         -------------------------------------------------------------------
  3001   TCTTGGCGGT TTCGCTAAAT ACTGGCAGGC GTTTCGTCAG TATCCCCGTT
         AGAACCGCCA AAGCGATTTA TGACCGTCCG CAAAGCAGTC ATAGGGGCAA

+2   L   Q   G   G   F   V   W   D   W   V   D   Q   S   L   I   K   Y
         -------------------------------------------------------------------
  3051   TACAGGGCGG CTTCGTCTGG GACTGGGTGG ATCAGTCGCT GATTAAATAT
         ATGTCCCGCC GAAGCAGACC CTGACCCACC TAGTCAGCGA CTAATTTATA

+2     D   E   N   G   N   P   W   S   A   Y   G   G   D   F   G   D   T
         -------------------------------------------------------------------
  3101   GATGAAAACG GCAACCCGTG GTCGGCTTAC GGCGGTGATT TTGGCGATAC
         CTACTTTTGC CGTTGGGCAC CAGCCGAATG CCGCCACTAA AACCGCTATG

+2     P   N   D   R   Q   F   C   M   N   G   L   V   F   A   D   R
         -------------------------------------------------------------------
  3151   GCCGAACGAT CGCCAGTTCT GTATGAACGG TCTGGTCTTT GCCGACCGCA
         CGGCTTGCTA GCGGTCAAGA CATACTTGCC AGACCAGAAA CGGCTGGCGT

+2   T   P   H   P   A   L   T   E   A   K   H   Q   Q   Q   F   F   Q
         -------------------------------------------------------------------
  3201   CGCCGCATCC AGCGCTGACG GAAGCAAAAC ACCAGCAGCA GTTTTTCCAG
         GCGGCGTAGG TCGCGACTGC CTTCGTTTTG TGGTCGTCGT CAAAAAGGTC

+2     F   R   L   S   G   Q   T   I   E   V   T   S   E   Y   L   F   R
         -------------------------------------------------------------------
  3251   TTCCGTTTAT CCGGGCAAAC CATCGAAGTG ACCAGCGAAT ACCTGTTCCG
         AAGGCAAATA GGCCCGTTTG GTAGCTTCAC TGGTCGCTTA TGGACAAGGC

+2       H   S   D   N   E   L   L   H   W   M   V   A   L   D   G   K
         -------------------------------------------------------------------
  3301   TCATAGCGAT AACGAGCTCC TGCACTGGAT GGTGGCGCTG GATGGTAAGC
         AGTATCGCTA TTGCTCGAGG ACGTGACCTA CCACCGCGAC CTACCATTCG

+2     P   L   A   S   G   E   V   P   L   D   V   A   P   Q   G   K   Q
         -------------------------------------------------------------------
  3351   CGCTGGCAAG CGGTGAAGTG CCTCTGGATG TCGCTCCACA AGGTAAACAG
         GCGACCGTTC GCCACTTCAC GGAGACCTAC AGCGAGGTGT TCCATTTGTC

+2   L   I   E   L   P   E   L   P   Q   P   E   S   A   G   Q   L   W
         -------------------------------------------------------------------
  3401   TTGATTGAAC TGCCTGAACT ACCGCAGCCG GAGAGCGCCG GGCAACTCTG
         AACTAACTTG ACGGACTTGA TGGCGTCGGC CTCTCGCGGC CCGTTGAGAC

+2     L   T   V   R   V   V   Q   P   N   A   T   A   W   S   E   A
         -------------------------------------------------------------------
  3451   GCTCACAGTA CGCGTAGTGC AACCGAACGC GACCGCATGG TCAGAAGCCG
         CGAGTGTCAT GCGCATCACG TTGGCTTGCG CTGGCGTACC AGTCTTCGGC
```

FIGURE 10F

```
     +2  G   H   I   S   A   W   Q   Q   W   R   L   A   E   N   L   S   V
  3501  GGCACATCAG CGCCTGGCAG CAGTGGCGTC TGGCGGAAAA CCTCAGTGTC
        CCGTGTAGTC GCGGACCGTC GTCACCGCAG ACCGCCTTTT GGAGTCACAC

+2  T   L   P   A   A   S   H   A   I   P   H   L   T   T   S   E   M
  3551  ACGCTCCCCG CCGCGTCCCA CGCCATCCCG CATCTGACCA CCAGCGAAAT
        TGCGAGGGGC GGCGCAGGGT GCGGTAGGGC GTAGACTGGT GGTCGCTTTA

+2  D   F   C   I   E   L   G   N   K   R   W   Q   F   N   R   Q
  3601  GGATTTTTGC ATCGAGCTGG GTAATAAGCG TTGGCAATTT AACCGCCAGT
        CCTAAAAACG TAGCTCGACC CATTATTCGC AACCGTTAAA TTGGCGGTCA

+2  S   G   F   L   S   Q   M   W   I   G   D   K   K   Q   L   L   T
  3651  CAGGCTTTCT TTCACAGATG TGGATTGGCG ATAAAAAACA ACTGCTGACG
        GTCCGAAAGA AAGTGTCTAC ACCTAACCGC TATTTTTTGT TGACGACTGC

+2  P   L   R   F   Q   F   T   R   A   P   L   D   N   D   I   G   V
  3701  CCGCTGCGCG ATCAGTTCAC CCGTGCACCG CTGGATAACG ACATTGGCGT
        GGCGACGCGC TAGTCAAGTG GGCACGTGGC GACCTATTGC TGTAACCGCA

+2  S   E   A   T   R   I   D   P   N   A   W   V   E   R   W   K
  3751  AAGTGAAGCG ACCCGCATTG ACCCTAACGC CTGGGTCGAA CGCTGGAAGG
        TTCACTTCGC TGGGCGTAAC TGGGATTGCG GACCCAGCTT GCGACCTTCC

+2  A   A   G   H   Y   Q   A   E   A   A   L   L   Q   C   T   A   D
  3801  CGGCGGGCCA TTACCAGGCC GAAGCAGCGT TGTTGCAGTG CACGGCAGAT
        GCCGCCCGGT AATGGTCCGG CTTCGTCGCA ACAACGTCAC GTGCCGTCTA

+2  T   L   A   D   A   V   L   I   T   T   A   H   A   W   Q   H   Q
  3851  ACACTTGCTG ATGCGGTGCT GATTACGACC GCTCACGCGT GGCAGCATCA
        TGTGAACGAC TACGCCACGA CTAATGCTGG CGAGTGCGCA CCGTCGTAGT

+2  G   K   T   L   F   I   S   R   K   T   Y   R   I   D   G   S
  3901  GGGGAAAACC TTATTTATCA GCCGGAAAAC CTACCGGATT GATGGTAGTG
        CCCCTTTTGG AATAAATAGT CGGCCTTTTG GATGGCCTAA CTACCATCAC

+2  G   Q   M   A   I   T   V   D   V   E   V   A   S   D   T   P   H
  3951  GTCAAATGGC GATTACCGTT GATGTTGAAG TGGCGAGCGA TACACCGCAT
        CAGTTTACCG CTAATGGCAA CTACAACTTC ACCGCTCGCT ATGTGGCGTA

+2  P   A   R   I   G   L   N   C   Q   L   A   Q   V   A   E   R   V
  4001  CCGGCGCGGA TTGGCCTGAA CTGCCAGCTG GCGCAGGTAG CAGAGCGGGT
        GGCCGCGCCT AACCGGACTT GACGGTCGAC CGCGTCCATC GTCTCGCCCA

+2  N   W   L   G   L   G   P   Q   E   N   Y   P   D   R   L   T
  4051  AAACTGGCTC GGATTAGGGC CGCAAGAAAA CTATCCCGAC CGCCTTACTG
        TTTGACCGAG CCTAATCCCG GCGTTCTTTT GATAGGGCTG GCGGAATGAC
```

FIGURE 10G

```
       +2  A    A    C    F    D    R    W    D    L    P    L    S    D    M    Y    T    P
           - - - - - - - - - - - - - - - - - - - - - - - - - - - - - - - - - - - - - - - -
     4101  CCGCCTGTTT TGACCGCTGG GATCTGCCAT TGTCAGACAT GTATACCCCG
           GGCGGACAAA ACTGGCGACC CTAGACGGTA ACAGTCTGTA CATATGGGGC
     - - - - - - - - - - - - - - - - - - - - - - - - - - - - - - - - - - - - - - - - - - -
       +2  Y    V    F    P    S    E    N    G    L    R    C    G    T    R    E    L    N
           - - - - - - - - - - - - - - - - - - - - - - - - - - - - - - - - - - - -
     4151  TACGTCTTCC CGAGCGAAAA CGGTCTGCGC TGCGGGACGC GCGAATTGAA
           ATGCAGAAGG GCTCGCTTTT GCCAGACGCG ACGCCCTGCG CGCTTAACTT
     - - - - - - - - - - - - - - - - - - - - - - - - - - - - - - - - - - - - - - - - - - -
       +2    Y    G    P    H    Q    W    R    G    D    F    Q    F    N    I    S    R
           - - - - - - - - - - - - - - - - - - - - - - - - - - - - - - - - - - - -
     4201  TTATGGCCCA CACCAGTGGC GCGGCGACTT CCAGTTCAAC ATCAGCCGCT
           AATACCGGGT GTGGTCACCG CGCCGCTGAA GGTCAAGTTG TAGTCGGCGA
     - - - - - - - - - - - - - - - - - - - - - - - - - - - - - - - - - - - - - - - - - - -
       +2  Y    S    Q    Q    Q    L    M    E    T    S    H    R    H    L    L    H    A
           - - - - - - - - - - - - - - - - - - - - - - - - - - - - - - - - - - - -
     4251  ACAGTCAACA GCAACTGATG GAAACCAGCC ATCGCCATCT GCTGCACGCG
           TGTCAGTTGT CGTTGACTAC CTTTGGTCGG TAGCGGTAGA CGACGTGCGC
     - - - - - - - - - - - - - - - - - - - - - - - - - - - - - - - - - - - - - - - - - - -
       +2   E    E    G    T    W    L    N    I    D    G    F    H    M    G    I    G    G
           - - - - - - - - - - - - - - - - - - - - - - - - - - - - - - - - - - - -
     4301  GAAGAAGGCA CATGGCTGAA TATCGACGGT TTCCATATGG GGATTGGTGG
           CTTCTTCCGT GTACCGACTT ATAGCTGCCA AAGGTATACC CCTAACCACC
     - - - - - - - - - - - - - - - - - - - - - - - - - - - - - - - - - - - - - - - - - - -
       +2    D    D    S    W    S    P    S    V    S    A    E    F    Q    L    S    A
           - - - - - - - - - - - - - - - - - - - - - - - - - - - - - - - - - - - -
     4351  CGACGACTCC TGGAGCCCGT CAGTATCGGC GGAATTCCAG CTGAGCGCCG
           GCTGCTGAGG ACCTCGGGCA GTCATAGCCG CCTTAAGGTC GACTCGCGGC
     - - - - - - - - - - - - - - - - - - - - - - - - - - - - - - - - - - - - - - - - - - -
       +2  G    R    Y    H    Y    Q    L    V    W    C    Q    K    R    S    D    Y    K
           - - - - - - - - - - - - - - - - - - - - - - - - - - - - - - - - - - - -
     4401  GTCGCTACCA TTACCAGTTG GTCTGGTGTC AAAAAAGATC TGACTATAAA
           CAGCGATGGT AATGGTCAAC CAGACCACAG TTTTTTCTAG ACTGATATTT
     - - - - - - - - - - - - - - - - - - - - - - - - - - - - - - - - - - - - - - - - - - -
       +2   D    E    D    L    D    H    H    H    H    H    R
           - - - - - - - - - - - - - - - - - - - - - - - - - - - >
     4451  GATGAGGACC TCGACCATCA TCATCATCAT CACCGGTAAT AATAGGTAGA
           CTACTCCTGG AGCTGGTAGT AGTAGTAGTA GTGGCCATTA TTATCCATCT
     - - - - - - - - - - - - - - - - - - - - - - - - - - - - - - - - - - - - - - - - - - -
     4501  TAAGTGACTG ATTAGATGCA TTGATCCCTC GACCAATTCC GGTTATTTTC
           ATTCACTGAC TAATCTACGT AACTAGGGAG CTGGTTAAGG CCAATAAAAG
     - - - - - - - - - - - - - - - - - - - - - - - - - - - - - - - - - - - - - - - - - - -
     4551  CACCATATTG CCGTCTTTTG GCAATGTGAG GGCCCGGAAA CCTGGCCCTG
           GTGGTATAAC GGCAGAAAAC CGTTACACTC CCGGGCCTTT GGACCGGGAC
     - - - - - - - - - - - - - - - - - - - - - - - - - - - - - - - - - - - - - - - - - - -
     4601  TCTTCTTGAC GAGCATTCCT AGGGGTCTTT CCCCTCTCGC CAAAGGAATG
           AGAAGAACTG CTCGTAAGGA TCCCCAGAAA GGGGAGAGCG GTTTCCTTAC
     - - - - - - - - - - - - - - - - - - - - - - - - - - - - - - - - - - - - - - - - - - -
     4651  CAAGGTCTGT TGAATGTCGT GAAGGAAGCA GTTCCTCTGG AAGCTTCTTG
           GTTCCAGACA ACTTACAGCA CTTCCTTCGT CAAGGAGACC TTCGAAGAAC
     - - - - - - - - - - - - - - - - - - - - - - - - - - - - - - - - - - - - - - - - - - -
     4701  AAGACAAACA ACGTCTGTAG CGACCCTTTG CAGGCAGCGG AACCCCCCAC
           TTCTGTTTGT TGCAGACATC GCTGGGAAAC GTCCGTCGCC TTGGGGGGTG
     - - - - - - - - - - - - - - - - - - - - - - - - - - - - - - - - - - - - - - - - - - -
     4751  CTGGCGACAG GTGCCTCTGC GGCCAAAAGC CACGTGTATA AGATACACCT
           GACCGCTGTG CACGGAGACG CCGGTTTTCG GTGCACATAT TCTATGTGGA
```

FIGURE 10H

```
4801  GCAAAGGCGG CACAACCCCA GTGCCACGTT GTGAGTTGGA TAGTTGTGGA
      CGTTTCCGCC GTGTTGGGGT CACGGTGCAA CACTCAACCT ATCAACACCT

4851  AAGAGTCAAA TGGCTCTCCT CAAGCGTATT CAACAAGGGG CTGAAGGATG
      TTCTCAGTTT ACCGAGAGGA GTTCGCATAA GTTGTTCCCC GACTTCCTAC

4901  CCCAGAAGGT ACCCCATTGT ATGGGATCTG ATCTGGGCC TCGGTGCACA
      GGGTCTTCCA TGGGGTAACA TACCCTAGAC TAGACCCCGG AGCCACGTGT

4951  TGCTTTACAT GTGTTTAGTC GAGGTTAAAA AACGTCTAGG CCCCCCGAAC
      ACGAAATGTA CACAAATCAG CTCCAATTTT TTGCAGATCC GGGGGGCTTG

5001  CACGGGGACG TGGTTTTCCT TTGAAAAACA CGATGATAAT ACCATGATTG
      GTGCCCCTGC ACCAAAAGGA AACTTTTTGT GCTACTATTA TGGTACTAAC

5051  AACAAGATGG ATTGCACGCA GGTTCTCCGG CCGCTTGGGT GGAGAGGCTA
      TTGTTCTACC TAACGTGCGT CCAAGAGGCC GGCGAACCCA CCTCTCCGAT

5101  TTCGGCTATG ACTGGGCACA ACAGACAATC GGCTGCTCTG ATGCCGCCGT
      AAGCCGATAC TGACCCGTGT TGTCTGTTAG CCGACGAGAC TACGGCGGCA

5151  GTTCCGGCTG TCAGCGCAGG GGCGCCCGGT TCTTTTTGTC AAGACCGACC
      CAAGGCCGAC AGTCGCGTCC CCGCGGGCCA AGAAAAACAG TTCTGGCTGG

5201  TGTCCGGTGC CCTGAATGAA CTGCAGGACG AGGCAGCGCG GCTATCGTGG
      ACAGGCCACG GGACTTACTT GACGTCCTGC TCCGTCGCGC CGATAGCACC

5251  CTGGCCACGA CGGGCGTTCC TTGCGCAGCT GTGCTCGACG TTGTCACTGA
      GACCGGTGCT GCCCGCAAGG AACGCGTCGA CACGAGCTGC AACAGTGACT

5301  AGCGGGAAGG GACTGGCTGC TATTGGGCGA AGTGCCGGGG CAGGATCTCC
      TCGCCCTTCC CTGACCGACG ATAACCCGCT TCACGGCCCC GTCCTAGAGG

5351  TGTCATCTCA CCTTGCTCCT GCCGAGAAAG TATCCATCAT GGCTGATGCA
      ACAGTAGAGT GGAACGAGGA CGGCTCTTTC ATAGGTAGTA CCGACTACGT

5401  ATGCGGCGGC TGCATACGCT TGATCCGGCT ACCTGCCCAT TCGACCACCA
      TACGCCGCCG ACGTATGCGA ACTAGGCCGA TGGACGGGTA AGCTGGTGGT

5451  AGCGAAACAT CGCATCGAGC GAGCACGTAC TCGGATGGAA GCCGGTC1TG
      TCGCTTTGTA GCGTAGCTCG CTCGTGCATG AGCCTACCTT CGGCCAGAAC

5501  TCGATCAGGA TGATCTGGAC GAAGAGCATC AGGGGCTCGC GCCAGCCGAA
      AGCTAGTCCT ACTAGACCTG CTTCTCGTAG TCCCCGAGCG CGGTCGGCTT

5551  CTGTTCGCCA GGCTCAAGGC GCGCATGCCC GACGGCGAGG ATCTCGTCGT
      GACAAGCGGT CCGAGTTCCG CGCGTACGGG CTGCCGCTCC TAGAGCAGCA

5601  GACCCATGGC GATGCCTGCT TGCCGAATAT CATGGTGGAA AATGGCCGCT
      CTGGGTACCG CTACGGACGA ACGGCTTATA GTACCACCTT TTACCGGCGA

5651  TTTCTGGATT CATCGACTGT GGCCGGCTGG GTGTGGCGGA CCGCTATCAG
      AAAGACCTAA GTAGCTGACA CCGGCCGACC CACACCGCCT GGCGATAGTC

5701  GACATAGCGT TGGCTACCCG TGATATTGCT GAAGAGCTTG GCGGCGAATG
      CTGTATCGCA ACCGATGGGC ACTATAACGA CTTCTCGAAC CGCCGCTTAC
```

FIGURE 10I

```
5751  GGCTGACCGC TTCCTCGTGC TTTACGGTAT CGCCGCTCCC GATTCGCAGC
      CCGACTGGCG AAGGAGCACG AAATGCCATA GCGGCGAGGG CTAAGCGTCG

5801  GCATCGCCTT CTATCGCCTT CTTGACGAGT TCTTCTGAGC GGGACTCTGG
      CGTAGCGGAA GATAGCGGAA GAACTGCTCA AGAAGACTCG CCCTGAGACC

5851  GGTTCGCATC GATAAAATAA AAGATTTTAT TTAGTCTCCA GAAAAGGGG
      CCAAGCGTAG CTATTTTATT TTCTAAAATA AATCAGAGGT CTTTTTCCCC

5901  GGAATGAAAG ACCCCACCTG TAGGTTTGGC AAGCTAGCTT AAGTAACGCC
      CCTTACTTTC TGGGGTGGAC ATCCAAACCG TTCGATCGAA TTCATTGCGG

5951  ATTTTGCAAG GCATGGAAAA ATACATAACT GAGAATAGAG AAGTTCAGAT
      TAAAACGTTC CGTACCTTTT TATGTATTGA CTCTTATCTC TTCAAGTCTA

6001  CAAGGTCAGG AACAGATGGA ACAGCTGAAT ATGGGCCAAA CAGGATATCT
      GTTCCAGTCC TTGTCTACCT TGTCGACTTA TACCCGGTTT GTCCTATAGA

6051  GTGGTAAGCA GTTCCTGCCC CGGCTCAGGG CCAAGAACAG ATGGAACAGC
      CACCATTCGT CAAGGACGGG GCCGAGTCCC GGTTCTTGTC TACCTTGTCG

6101  TGAATATGGG CCAAACAGGA TATCTGTGGT AAFCAGTTCC TGCCCCGGCT
      ACTTATACCC GGTTTGTCCT ATAGACACCA TTCGTCAAGG ACGGGGCCGA

6151  CAGGGCCAAG AACAGATGGT CCCCAGATGC GGTCCAGCCC TCAGCAGTTT
      GTCCCGGTTC TTGTCTACCA GGGGTCTACG CCAGGTCGGG AGTCGTCAAA

6201  CTAGAGAACC ATCAGATGTT TCCAGGGTGC CCCAAGGACC TGAAATGACC
      GATCTCTTGG TAGTCTACAA AGGTCCCACG GGGTTCCTGG ACTTTACTGG

6251  CTGTGCCTTA TTTGAACTAA CCAATCAGTT CGCTTCTCGC TTCTGTTCGC
      GACACGGAAT AAACTTGATT GGTTAGTCAA GCGAAGAGCG AAGACAAGCG

6301  GCGCTTCTGC TCCCCGAGCT CAATAAAAGA GCCCACAACC CCTCACTCGG
      CGCGAAGACG AGGGGCTCGA GTTATTTTCT CGGGTGTTGG GGAGTGAGCC

6351  GGCGCCAGTC CTCCGATTGA CTGAGTCGCC CGGGTACCCG TGTATCCAAT
      CCGCGGTCAG GAGGCTAACT GACTCAGCGG GCCCATGGGC ACATAGGTTA

6401  AAACCCTCTT GCAGTTGCAT CCGACTTGTG GTCTCGCTGT TCCTTGGGAG
      TTTGGGAGAA CGTCAACGTA GGCTGAACAC CAGAGCGACA AGGAACCCTC

6451  GGTCTCCTCT GAGTGATTGA CTACCCGTCA GCGGGGGTCT TTCATTCATG
      CCAGAGGAGA CTCACTAACT GATGGGCAGT CGCCCCAGA AAGTAAGTAC

6501  CAGCATGTAT CAAAATTAAT TTGGTTTTTT TTCTTAAGTA TTTACATTAA
      GTCGTACATA GTTTTAATTA AACCAAAAAA AAGAATTCAT AAATGTAATT

6551  ATGGCCATAG TTGCATTAAT GAATCGGCCA ACGCGCGGGG AGAGGCGGTT
      TACCGGTATC AACGTAATTA CTTAGCCGGT TGCGCGCCCC TATCCGCCAA

6601  TGCGTATTGG CGCTCTTCCG CTTCCTCGCT CACTGACTCG CTGCGCTCGG
      ACGCATAACC GCGAGAAGGC GAAGGAGCGA GTGACTGAGC GACGCGAGCC

6651  TCGTTCGGCT GCGGCGAGCG GTATCAGCTC ACTCAAAGGC GGTAATACGG
      AGCAAGCCGA CGCCGCTCCC CATAGTCGAG TGAGTTTCCG CCATTATGCC
```

FIGURE 10J

```
  1  GTGCAGCCTG AATATGGGCC AAACAGGATA TCTGTGGTAA GCAGTTCCTG
     GACGTCGGAC TTATACCCGG TTTGTCCTAT AGACACCATT CGTCAAGGAC

51  CCCCGGCTCA GGGCCAAGAA CAGATGGAAC AGCTGAATAT GGGCCAAACA
     GGGGCCGAGT CCCGGTTCTT GTCTACCTTG TCGACTTATA CCCGGTTTGT

101  GGATATCTGT GGTAAGCAGT TCCTGCCCCG GCTCAGGGCC AAGAACAGAT
     CCTATAGACA CCATTCGTCA AGGACGGGGC CGAGTCCCGG TTCTTGTCTA

151  GGTCCCCAGA TGCGGTCCAG CCCTCAGCAG TTTCTAGAGA ACCATCAGAT
     CCAGGGGTCT ACGCCAGGTC GGGAGTCGTC AAAGATCTCT TGGTAGTCTA

201  GTTTCCAGGG TGCCCCAAGG ACCTGAAATG ACCCTGTGCC TTATTTGAAC
     CAAAGGTCCC ACGGGGTTCC TGGACTTTAC TGGGACACGG AATAAACTTG

251  TAACCAATCA GTTCGCTTCT CGCTTCTGTT CGCGCGCTTC TGCTCCCCGA
     ATTGGTTAGT CAAGCGAAGA GCGAAGACAA GCGCGCGAAG ACGAGGGGCT

301  GCTCAATAAA AGAGCCCACA ACCCCTCACT CGGGGCGCCA GTCCTCCGAT
     CGAGTTATTT TCTCGGGTGT TGGGGAGTGA GCCCCGCGGT CAGGAGGCTA

351  TGACTGAGTC GCCCGGGTAC CCGTGTATCC AATAAACCCT CTTGCAGTTG
     ACTGACTCAG CGGGCCCATG GGCACATAGG TTATTTGGGA GAACGTCAAC

401  CATCCGACTT GTGGTCTCGC TGTTCCTTGG GAGGGTCTCC TCTGAGTGAT
     GTAGGCTGAA CACCAGAGCG ACAAGGAACC CTCCCAGAGG AGACTCACTA

451  TGACTACCCG TCAGCGGGGG TCTTTCATTT GGGGGCTCGT CCGGGATCGG
     ACTGATGGGC AGTCGCCCCC AGAAAGTAAA CCCCGAGCA GGCCCTAGCC

501  GAFACCCCTG CCCAGGGACC ACCGACCCAC CACCGGGAGG CAAGCTGGCC
     CTCTGGGGAC GGGTCCCTGG TGGCTGGGTG GTGGCCCTCC GTTCGACCGG

551  AGCAACTTAT CTGTGTCTGT CCGATTGTCT AGTGTCTATG ACTGATTTTA
     TCGTTGAATA GACACAGACA GGCTAACAGA TCACAGATAC TGACTAAAAT

601  TGCGCCTGCG TCGGTACTAG TTAGCTAACT AGCTCTGTAT CTGGCGGACC
     ACGCGGACGC AGCCATGATC AATCGATTGA TCGAGACATA GACCGCCTGG

651  CGTGGTGGAS CTGACGAGTT CTGAACACCC GGCCGCAACC CTGGGAGACG
     GCACCACCTT GACTGCTCAA GACTTGTGGG CCGGCGTTGG GACCCTCTGC

701  TCCCAGGGAC TTTGGGGGCC GTTTTTGTGG CCCGACCTGA GGAAGGGAGT
     AGGGTCCCTG AAACCCCCGG CAAAAACACC GGGCTGGACT CCTTCCCTCA

751  CGATGTGGAA TCCGACCCCG TCAGGATATG TGGTTCTGGT AGGAGACGAG
     GCTACACCTT AGGCTGGGGC AGTCCTATAC ACCAAGACCA TCCTCTGCTC

801  AACCTAAAAC AGTTCCCGCC TCCGTCTGAA TTTTTGCTTT CGGTTTGGAA
     TTGGATTTTG TCAAGGGCGG AGGCAGACTT AAAAACGAAA GCCAAACCTT

851  CCGAAGCCGC GCGTCTTGTG TGCTGCAGCA TCGTTCTGTG TTGTGTCTGT
     GGCTTCGGCG CGCAGAACAG ACGACGTCGT AGCAAGACAC AACAGAGACA

901  CTGACTGTGT TTCTGTATTT GTCTGAAAAT TAGGGCCAGA CTGTTACCAC
     GACTGACACA AAGACATAAA CAGACTTTTA ATCCGGTCT GACAATGGTG
```

FIGURE 11B

```
 951  TCCCTTAAGT TTGACCTTAG GTAACTGGAA AGATGTCGAG CGGCTCGCTC
      AGGGAATTCA AACTGGAATC CATTGACCTT TCTACAGCTC GCCGAGCGAG

1001  ACAACCAGTC GGTAGATGTC AAGAAGAGAC GTTGGGTTAC CTTCTGCTCT
      TGTTGGTCAG CCATCTACAG TTCTTCTCTG CAACCCAATG GAAGACGAGA

1051  GCAGAATGGC CAACCTTTAA CGTCGGATGG CCGCGAGACG GCACCTTTAA
      CGTCTTACCG GTTGGAAATT GCAGCCTACC GGCGCTCTGC CGTGGAAATT

1101  CCGAGACCTC ATCACCCAGG TTAAGATCAA GGTCTTTTCA CCTGGCCCGC
      GGCTCTGGAG TAGTGGGTCC AATTCTAGTT CCAGAAAAGT GGACCGGGCG

1151  ATGGACACCC AGACCAGGTC CCCTACATCG TGACCTGGGA AGCCTTGGCT
      TACCTGTGGG TCTGGTCCAG GGGATGTAGC ACTGGACCCT TCGGAACCGA

1201  TTTGACCCCC CTCCCTGGGT CAAGCCCTTT GTACACCCTA AGCCTCCGCC
      AAACTGGGGG GAGGGACCCA GTTCGGGAAA CATGTGGGAT TCGGAGGCGG

1251  TCCTCTTCCT CCATCCGCCC CGTCTCTCCC CCTTGAACCT CCTCGTTCGA
      AGGAGAAGGA GGTAGGCGGG GCAGAGAGGG GGAACTTGGA GGAGCAAGCT

1301  CCCCGCCTCG ATCCTCCCTT TATCCAGCCC TCACTCCTTC TCTAGGCGCC
      GGGGCGGAGC TAGGAGGGAA ATAGGTCGGG AGTGAGGAAG AGATCCGCGG

1351  GGCCGCTCTA GCCCATTAAT ACGACTCACT ATAGGGCGAT TCGAACACCA
      CCGGCGAGAT CGGGTAATTA TGCTGAGTGA TATCCCGCTA AGCTTGTGGT

1401  TCGACCATCA TCATCATCAC GTCGACTATA AAGATGAGGA CCTCGAGATG
      ACGTGGTAGT AGTAGTAGTG CAGCTGATAT TTCTACTCCT GGAGCTCTAC

1451  GGCGTGATTA CGGATTCACT GGCCGTCGTG GCCCGCACCG ATCGCCCTTC
      CCGCACTAAT GCCTAAGTGA CCGGCAGCAC CGGGCGTGGC TAGCGGGAAG

1501  CCAACAGTTA CGCAGCCTGA ATGGCGAATG GCGCTTTGCC TGGTTTCCGG
      GGTTGTCAAT GCGTCGGACT TACCGCTTAC CGCGAAACGG ACCAAAGGCC

1551  CACCAGAAGC GGTGCCGGAA AGCTGGCTGG AGTGCGATCT TCCTGAGGCC
      GTGGTCTTCG CCACGGCCTT TCGACCGACC TCACGCTAGA AGGACTCCGG

1601  GATACTGTCG TCGTCCCCTC AAACTGGCAG ATGCACGGTT ACGATGCGCC
      CTATGACAGC AGCAGGGGAG TTTGACCGTC TACGTGCCAA TGCTACGCGG

1651  CATCTACACC AACGTGACCT ATCCCATTAC GGTCAATCCG CCGTTTGTTC
      GTAGATGTGG TTGCACTGGA TAGGGTAATG CCAGTTAGGC GGCAAACAAG

1701  CCACGGAGAA TCCGACGGGT TGTTACTCGC TCACATTTAA TGTTGATGAA
      GGTGCCTCTT AGGCTGCCCA ACAATGAGCG AGTGTAAATT ACAACTACTT

1751  AGCTGGCTAC AGGAAGGCCA GACGCGAATT ATTTTTGATG GCGTTAACTG
      TCGACCGATG TCCTCCCGGT CTGCGCTTAA TAAAAACTAC CGCAATTGAG

1801  GGCGTTTCAT CTGTGGTGCA ACGGGCGCTG GGTCGGTTAC GGCCAGGACA
      CCGCAAAGTA GACACCACGT TGCCCGCGAC CCAGCCAATG CCGGTCCTGT

1851  GTCGTTTGCC GTCTGAATTT GACCTGAGCG CATTTTTACG CGCCGGAGAA
      CAGCAAACGG CAGACTTAAA CTGGACTCGC GTAAAAATGC GCGGCCTCTT
```

FIGURE 11C

```
1901 AACCGCCTCG CGGTGATGGT GCTGCGCTGG AGTGACGGCA GTTATCTGGA
     TTGGCGGAGC GCCACTACCA CGACGCGACC TCACTGCCGT CAATAGACCT

1951 AGATCAGGAT ATGTGGCGGA TGAGCGGCAT TTTCCGTGAC GTCTCGTTGC
     TCTAGTCCTA TACACCGCCT ACTCGCCGTA AAAGGCACTG CAGAGCAACG

2001 TGCATAAACC GACTACACAA ATCAGCGATT CCATGTTGC CACTCGCTTT
     ACGTATTTGG CTGATGTGTT TAGTCGCTAA AGGTACAACG GTGAGCGAAA

2051 AATGATGATT TCAGCCGCGC TGTACTGGAG GCTGAAGTTC AGATGTCCCG
     TTACTACTAA AGTCGGCGCG ACATGACCTC CGACTTCAAG TCTACACGCC

2101 CGAGTTGCGT GACTACCTAC GGGTAACAGT TTCTTTATGG CAGGGTGAAA
     GCTCAACGCA CTGATGGATG CCCATTGTCA AAGAAATACC GTCCCACTTT

2151 CGCAGGTCGC CAGCGGCACC GCGCCTTTCG GCGGTGAAAT TATCGATGAG
     GCGTCCAGCG CTCGCCGTGG CGCGGAAAGC CGCCACTTTA ATAGCTACTC

2201 CGTGGTGGTT ATGCCGATCG CGTCACACTA CGTCTGAACG TCGAAAACCC
     GCACCACCAA TACGGCTAGC GCAGTGTGAT GCAGACTTGC AGCTTTTGGG

2251 GAAACTGTGG AGCGCCGAAA TCCCGAATCT CTATCGTGCG GTGGTTGAAC
     CTTTGACACC TCGCGGCTTT AGGGCTTAGA GATAGCACGC CACCAACTTG

2301 TGCACACCGC CGACGGCACG CTGATTGAAG CAGAAGCCTG CGATGTCGGT
     ACGTGTGGCG GCTGCCGTGC GACTAACTTA GTCTTCGGAC GCTACAGCCA

2351 TTCCGCGAGG TGCGGATTGA AAATGGTCTG CTGCTGCTGA ACGGCAAGCC
     AAGGCGCTCC ACGCCTAACT TTTACCAGAC GACGACGACT TGCCGTTCGG

2401 GTTGCTGATT CGAGGCGTTA ACCGTACGA GCATCATCCT CTGCATGGTC
     CAACGACTAA GCTCCGCAAT TGGCAGTGCT CGTAGTAGGA GACGTACCAG

2451 AGGTCATGGA TGAGCAGACG ATGGTGCAGG ATATCCTGCT GATGAAGCAG
     TCCAGTACCT ACTCGTCTGC TACCACGTCC TATAGGACGA CTACTTCGTC

2501 AACAACTTTA ACGCCGTGCG CTGTTCGCAT TATCCGAACC ATCCGCTGTG
     TTGTTGAAAT TGCGGCACGC GACAAGCGTA ATAGGCTTGG TAGGCGACAC

2551 GTACACGCTG TGCGACCGCT ACGGCCTGTA TGTGGTGGAT GAAGCCAATA
     CATGTGCGAC ACGCTGGCGA TGCCGGACAT ACACCACCTA CTTCGGTTAT

2601 TTGAAACCCA CGGCATGGTG CCAATGAATC GTCTGACCGA TGATCCGCGC
     AACTTGGGT GCCGTACCAC GGTTACTTAG CAGACTGGCT ACTAGGCGCG

2651 TGGCTACCGG CGATGAGCGA ACGCGTAACG CGAATGGTGC AGCGCGATCG
     ACCGATGGCC GCTACTCGCT TGCGCATTGC GCTTACCACG TCGCGCTAGC

2701 TAATCACCCG AGTGTGATCA TCTGGTCGCT GGGGAATGAA TCAGGCCACG
     ATTAGTGGGC TCACACTAGT AGACCAGCGA CCCCTTACTT AGTCCGGTGC

2751 GCGCTAATCA CGACGCGCTG TATCGCTGGA TCAAATCTGT CGATCCTTCC
     CGCGATTAGT GCTGCGCGAC ATAGCGACCT AGTTTAGACA GCTAGGAAGG

2801 CGCCCGGTGC AGTATGAAGG CGGCGGAGCC GACACCACGG CCACCGATAT
     GCGGGCCACG TCATACTTCC GCCGCCTCGG CTGTGGTGCC GGTGGCTATA
```

FIGURE 11D

```
2851 TATTTGCCCG ATGTACGCGC GCGTGGATGA AGACCAGCCC TTCCCGGCTG
     ATAAACGGGC TACATGCGCG CGCACCTACT TCTGGTCGGG AAGGGCCGAC

2901 TGCCGAAATG GTCCATCAAA AAATGGCTTT CGCTACCTGG AGAGACGCGC
     ACGGCTTTAC CAGGTAGTTT TTTACCGAAA GCGATGGACC TCTCTGCGCG

2951 CCGCTGATCC TTTGCGAATA CGCCCACGCG ATGGGTAACA GTCTTGGCGG
     GGCGACTAGG AAACGCTTAT GCGGGTGCGC TACCCATTGT CAGAACCGCC

3001 TTTCGCTAAA TACTGGCAGG CGTTTCGTCA GTATCCCCGT TTACAGGGCG
     AAAGCGATTT ATGACCGTCC GCAAAGCAGT CATAGGGGCA AATGTCCCGC

3051 GCTTCGTCTG GGACTGGGTG GATCAGTCGC TGATTAAATA TGATGAAAAC
     CGAAGCAGAC CCTGACCCAC CTAGTCAGCG ACTAATTTAT ACTACTTTTG

3101 GGCAACCCGT GGTCGGCTTA CGGCGGTGAT TTTGGCGATA CGCCGAACGA
     CCGTTGGGCA CCAGCCGAAT GCCGCCACTA AAACCGCTAT GCGGCTTGCT

3151 TCGCCAGTTC TGTATGAACG GTCTGGTCTT TGCCGACCGC ACGCCGCATC
     AGCGGTCAAG ACATACTTGC CAGACCAGAA ACGGCTGGCG TGCGGCGTAG

3201 CAGCGCTGAC GGAAGCAAAA CACCAGCAGC AGTTTTTCCA GTTCCGTTTA
     GTCGCGACTG CCTTCGTTTT GTGGTCGTCG TCAAAAAGGT CAAGGCAAAT

3251 TCCGGGCAAA CCATCGAAGT GACCAGCGAA TACCTGTTCC GTCATAGCGA
     AGGCCCGTTT GGTAGCTTCA CTGGTCGCTT ATGGACAAGG CAGTATCGCT

3301 TAACGAGCTC CTGCACTGGA TGGTGGCGCT GGATGGTAAG CCGCTGGCAA
     ATTGCTCGAG GACGTGACCT ACCACCGCGA CCTACCATTC GGCGACCGTT

3351 GCGGTGAAGT GCCTCTGGAT GTCGCTCCAC AAGGTAAACA GTTGATTGAA
     CGCCACTTCA CGGAGACCTA CAGCGAGGTG TTCCATTTGT CAACTAACTT

3401 CTGCCTGAAC TACCGCAGCC GGAGAGCGCC GGGCAACTCT GGCTCACAGT
     GACGGACTTG ATGGCGTCGG CCTCTCGCGG CCCGTTGAGA CCGAGTGTCA

3451 ACGCGTAGTG CAACCGAACG CGACCGCATG GTCAGAAGCC GGGCACATCA
     TGCGCATCAC GTTGGCTTGC GCTGGCGTAC CAGTCTTCGG CCCGTGTAGT

3501 GCGCCTGGCA GCAGTGGCGT CTGGCGGAAA ACCTCAGTGT GACGCTCCCC
     CGCGGACCGT CGTCACCGCA GACCGCCTTT TGGAGTCACA CTGCGAGGGG

3551 GCCGCGTCCC ACGCCATCCC GCATCTGACC ACCAGCGAAA TGGATTTTTG
     CGGCGCAGGG TGCGGTAGGG CGTAGACTGG TGGTCGCTTT ACCTAAAAAC

3601 CATCGAGCTG GGTAATAAGC GTTGGCAATT TAACCGCCAG TCAGGCTTTC
     GTAGCTCGAC CCATTATTCG CAACCGTTAA ATTGGCGGTC AGTCCGAAAG

3651 TTTCACAGAT GTGGATTGGC GATAAAAAAC AACTGCTGAC GCCGCTGCGC
     AAAGTGTCTA CACCTAACCG CTATTTTTTG TTGACGACTG CGGCGACGCG

3701 GATCAGTTCA CCCGTGCACC GCTGGATAAC GACATTGGCG TAAGTGAAGC
     CTAGTCAAGT GGGCACGTGG CGACCTATTG CTGTAACCGC ATTCACTTCG

3751 GACCCGCATT GACCCTAACG CCTGGGTCGA ACGCTGGAAG GCGGCGGGCC
     CTGGGCGTAA CTGGGATTGC GGACCCAGCT TGCGACCTTC CGCCGCCCGG
```

FIGURE 11E

```
3801 ATTACCAGGC CGAAGCAGCG TTGTTGCAGT GCACGGCAGA TACACTTGCT
     TAATGGTCCG GCTTCGTCGC AACAACGTCA CGTGCCGTCT ATGTGAACGA

3851 GATGCGGTGC TGATTACGAC CGCTCACGCG TGGCAGCATC AGGGGAAAAC
     CTACGCCACG ACTAATGCTG GCGAGTGCGC ACCGTCGTAG TCCCCTTTTG

3901 CTTATTTATC AGCCGGAAAA CCTACCGGAT TGATGGTAGT GGTCAAATGG
     GAATAAATAG TCGGCCTTTT GGATGGCCTA ACTACCATCA CCAGTTTACC

3951 CGATTACCGT TGATGTTGAA GTGGCGAGCG ATACACCGCA TCCGGCGCGG
     GCTAATGGCA ACTACAACTT CACCGCTCGC TATGTGGCGT AGGCCGCGCC

4001 ATTGGCCTGA ACTGCCAGCT GGCGCAGGTA GCAGAGCGGG TAAACTGGCT
     TAACCGGACT TGACGGTCGA CCGCGTCCAT CGTCTCGCCC ATTTGACCGA

4051 CGGATTAGGG CCGCAAGAAA ACTATCCCGA CCGCCTTACT GCCGCCTGTT
     GCCTAATCCC GGCGTTCTTT TGATAGGGCT GGCGGAATGA CGGCGGACAA

4101 TTGACCGCTG GGATCTGCCA TTGTCAGACA TGTATACCCC GTACGTCTTC
     AACTGGCGAC CCTAGACGGT AACAGTCTGT ACATATGGGG CATGCAGAAG

4151 CCGAGCGAAA ACGGTCTGCG CTGCGGGACG CGCGAATTGA ATTATGGCCC
     GGCTCGCTTT TGCCAGACGC GACGCCCTGC GCGCTTAACT TAATACCGGG

4201 ACACCAGTGG CGCGGCGACT TCCAGTTCAA CATCAGCCGC TACAGTCAAC
     TGTGGTCACC GCGCCGCTGA AGGTCAAGTT GTAGTCGGCG ATGTCAGTTG

4251 AGCAACTGAT GGAAACCAGC CATCGCCATC TGCTGCACGC GGAAGAAGGC
     TCGTTGACTA CCTTTGGTCG GTAGCGGTAG ACGACGTGCG CCTTCTTCCG

4301 ACATGGCTGA ATATCGACGG TTTCCATATG GGGATTGGTG GCGACGACTC
     TGTACCGACT TATAGCTGCC AAAGGTATAC CCCTAACCAC CGCTGCTGAG

4351 CTGGAGCCCG TCAGTATCGG CGGAATTCCA GCTGAGCGCC GGTCGCTACC
     GACCTCGGGC AGTCATAGCC GCCTTAAGGT CGACTCGCGG CCAGCGATGG

4401 ATTACCAGTT GGTCTGGTGT CAAAAAAGAT CTGGAGGTGG TGGCAGCAGG
     TAATGGTCAA CCAGACCACA GTTTTTTCTA GACCTCCACC ACCGTCGTCC

4451 CCTTGGCGCG CCGGATCCTT AATTAACAAT TGACCGGTAA TAATAGGTAG
     GGAACCGCGC GGCCTAGGAA TTAATTGTTA ACTGGCCATT ATTATCCATC

4501 ATAAGTGACT GATTAGATGC ATTGATCCCT CGACCAATTC CGGTTATTTT
     TATTCACTGA CTAATCTACG TAACTAGGGA GCTGGTTAAG GCCAATAAAA

4551 CCACCATATT GCCGTCTTTT GGCAATGTGA GGGCCCGGAA ACCTGGCCCT
     GGTGGTATAA CGGCAGAAAA CCGTTACACT CCCGGGCCTT TGGACCGGGA

4601 GTCTTCTTGA CGAGCATTCC TAGGGGTCTT TCCCCTCTCG CCAAAGGAAT
     CAGAAGAACT GCTCGTAAGG ATCCCCAGAA AGGGGAGAGC GGTTTCCTTA

4651 GCAAGGTCTG TTGAATGTCG TGAAGGAAGC AGTTCCTCTG GAAGCTTCTT
     CGTTCCAGAC AACTTACAGC ACTTCCTTCG TCAAGGAGAC CTTCGAAGAA

4701 GAAGACAAAC AACGTCTGTA GCGACCCTTT GCAGGCAGCG GAACCCCCCA
     CTTCTGTTTG TTGCAGACAT CGCTGGGAAA CGTCCGTCGC CTTGGGGGGT
```

FIGURE 11F

```
4751 CCTGGCGACA GGTGCCTCTG CGGCCAAAAG CCACGTGTAT AAGATACACC
     GGACCGCTGT CCACGGAGAC GCCGGTTTTC GGTGCACATA TTCTATGTGG

4801 TGCAAAGGCG GCACAACCCC AGTGCCACGT TGTGAGTTGG ATAGTTGTGG
     ACGTTTCCGC CGTGTTGGGG TCACGGTGCA ACACTCAACC TATCAACACC

4851 AAAGAGTCAA ATGGCTCTCC TCAAGCGTAT TCAACAAGGG GCTGAAGGAT
     TTTCTCAGTT TACCGAGAGG AGTTCGCATA AGTTGTTCCC CGACTTCCTA

4901 GCCCAGAAGG TACCCCATTG TATGGGATCT GATCTGGGGC CTCGGTGCAC
     CGGGTCTTCC ATGGGGTAAC ATACCCTAGA CTAGACCCCG GAGCCACGTG

4951 ATGCTTTACA TGTGTTTAGT CGAGGTTAAA AAACGTCTAG GCCCCCCGAA
     TACGAAATGT ACACAAATCA GCTCCAATTT TTTGCAGATC CGGGGGGCTT

5001 CCACGGGGAC GTGGTTTTCC TTTGAAAAAC ACGATGATAA TACCATGATT
     GGTGCCCCTG CACCAAAAGG AAACTTTTTG TGCTACTATT ATGGTACTAA

5051 GAACAAGATG GATTGCACGC AGGTTCTCCG GCCGCTTGGG TGGAGAGGCT
     CTTGTTCTAC CTAACGTGCG TCCAAGAGGC CGGCGAACCC ACCTCTCCGA

5101 ATTCGGCTAT GACTGGGCAC AACAGACAAT CGGCTGCTCT GATGCCGCCG
     TAAGCCGATA CTGACCCGTG TTGTCTGTTA GCCGACGAGA CTACGGCGGC

5151 TGTTCCGGCT GTCAGCGCAG GGGCGCCCGG TTCTTTTTGT CAAGACCGAC
     ACAAGGCCGA CAGTCGCGTC CCCGCGGGCC AAGAAAAACA GTTCTGGCTG

5201 CTGTCCGGTG CCCTGAATGA ACTGCAGGAC GAGGCAGCGC GGCTATCGTG
     GACAGGCCAC GGGACTTACT TGACGTCCTG CTCCGTCGCG CCGATAGCAC

5251 GCTGGCCACG ACGGGCGTTC CTTGCGCAGC TGTGCTCGAC GTTGTCACTG
     CGACCGGTGC TGCCCGCAAG GAACGCGTCG ACACGAGCTG CAACAGTGAC

5301 AAGCGGGAAG GGACTGGCTG CTATTGGGCG AAGTGCCGGG GCAGGATCTC
     TTCGCCCTTC CCTGACCGAC GATAACCCGC TTCACGGCCC CGTCCTAGAG

5351 CTGTCATCTC ACCTTGCTCC TGCCGAGAAA GTATCCATCA TGGCTGATGC
     GACAGTAGAG TGGAACGAGG ACGGCTCTTT CATAGGTAGT ACCGACTACG

5401 AATGCGGCGG CTGCATACGC TTGATCCGGC TACCTGCCCA TTCGACCACC
     TTACGCCGCC GACGTATGCG AACTAGGCCG ATGGACGGGT AAGCTGGTGG

5451 AAGCGAAACA TCGCATCGAG CGAGCACGTA CTCGGATGGA AGCCGGTCTT
     TTCGCTTTGT AGCGTAGCTC GCTCGTGCAT GAGCCTACCT TCGGCCAGAA

5501 GTCGATCAGG ATGATCTGGA CGAAGAGCAT CAGGGGCTCG CGCCAGCCGA
     CAGCTAGTCC TACTAGACCT GCTTCTCGTA GTCCCCGAGC GCGGTCGGCT

5551 ACTGTTCGCC AGGCTCAAGG CGCGCATGCC CGACGGCGAG GATCTCGTCG
     TGACAAGCGG TCCGAGTTCC GCGCGTACGG GCTGCCGCTC CTAGAGCAGC

5601 TGACCCATGG CGATGCCTGC TTGCCGAATA TCATGGTGGA AAATGGCCGC
     ACTGGGTACC GCTACGGACG AACGGCTTAT AGTACCACCT TTTACCGGCG

5651 TTTTCTGGAT TCATCGACTG TGGCCGGCTG GGTGTGGCGG ACCGCTATCA
     AAAAGACCTA AGTAGCTGAC ACCGGCCGAC CCACACCGCC TGGCGATAGT
```

FIGURE 11G

```
5701 GGACATAGCG TTGGCTACCC GTGATATTGC TGAAGAGCTT GGCGGCGAAT
     CCTGTATCGC AACCGATGGG CACTATAACG ACTTCTCGAA CCGCCGCTTA

5751 GGGCTGACCG CTTCCTCGTG CTTTACGGTA TCGCCGCTCC CGATTCGCAG
     CCCGACTGGC GAAGGAGCAC GAAATGCCAT AGCGGCGAGG GCTAAGCGTC

5801 CGCATCGCCT TCTATCGCCT TCTTGACGAG TTCTTCTGAG CGGGACTCTG
     GCGTAGCGGA AGATAGCGGA AGAACTGCTC AAGAAGACTC GCCCTGAGAC

5851 GGGTTCGCAT CGATAAAATA AAAGATTTTA TTTAGTCTCC AGAAAAAGGG
     CCCAAGCGTA GCTATTTTAT TTTCTAAAAT AAATCAGAGG TCTTTTTCCC

5901 GGGAATGAAA GACCCCACCT GTAGGTTTGG CAAGCTAGCT TAAGTAACGC
     CCCTTACTTT CTGGGGTGGA CATCCAAACC GTTCGATCGA ATTCATTGCG

5951 CATTTTGCAA GGCATGGAAA AATACATAAC TGAGAATAGA GAAGTTCAGA
     GTAAAACGTT CCGTACCTTT TTATGTATTG ACTCTTATCT CTTCAAGTCT

6001 TCAAGGTCAG GAACAGATGG AACAGCTGAA TATGGGCCAA ACAGGATATC
     AGTTCCAGTC CTTGTCTACC TTGTCGACTT ATACCCGGTT TGTCCTATAG

6051 TGTGGTAAGC AGTTCCTGCC CCGGCTCAGG GCCAAGAACA GATGGAACAG
     ACACCATTCG TCAAGGACGG GGCCGAGTCC CGGTTCTTGT CTACCTTGTC

6101 CTGAATATGG GCCAAACAGG ATATCTGTGG TAAGCAGTTC CTGCCCCGGC
     GACTTATACC CGGTTTGTCC TATAGACACC ATTCGTCAAG GACGGGGCCG

6151 TCAGGGCCAA GAACAGATGG TCCCCAGATG CGGTCCAGCC CTCAGCAGTT
     AGTCCCGGTT CTTGTCTACC AGGGGTCTAC GCCAGGTCGG GAGTCGTCAA

6201 TCTAGAGAAC CATCAGATGT TTCCAGGGTG CCCCAAGGAC CTGAAATGAC
     AGATCTCTTG GTAGTCTACA AAGGTCCCAC GGGGTTCCTG GACTTTACTG

6251 CCTGTGCCTT ATTTGAACTA ACCAATCAGT TCGCTTCTCG CTTCTGTTCG
     GGACACGGAA TAAACTTGAT TGGTTAGTCA AGCGAAGAGC GAAGACAAGC

6301 CGCGCTTCTG CTCCCCGAGC TCAATAAAAG AGCCCACAAC CCCTCACTCG
     GCGCGAAGAC GAGGGGCTCG AGTTATTTTC TCGGGTGTTG GGGAGTGAGC

6351 GGGCGCCAGT CCTCCGATTG ACTGAGTCGC CCGGGTACCC GTGTATCCAA
     CCCGCGGTCA GGAGGCTAAC TGACTCAGCG GGCCCATGGG CACATAGGTT

6401 TAAACCCTCT TGCAGTTGCA TCCGACTTGT GGTCTCGCTG TTCCTTGGGA
     ATTTGGGAGA ACGTCAACGT AGGCTGAACA CCAGAGCGAC AAGGAACCCT

6451 GGGTCTCCTC TGAGTGATTG ACTACCCGTC AGCGGGGGTC TTTCATTCAT
     CCCAGAGGAG ACTCACTAAC TGATGGGCAG TCGCCCCCAG AAAGTAAGTA

6501 GCAGCATGTA TCAAAATTAA TTTGGTTTTT TTTCTTAAGT ATTTACATTA
     CGTCGTACAT AGTTTTAATT AAACCAAAAA AAAGAATTCA TAAATGTAAT

6551 AATGGCCATA GTTGCATTAA TGAATCGGCC AACGCGCGGG GAGAGGCGGT
     TTACCGGTAT CAACGTAATT ACTTAGCCGG TTGCGCGCCC CTCTCCGCCA

6601 TTGCGTATTG GCGCTCTTCC GCTTCCTCGC TCACTGACTC GCTGCGCTCG
     AACGCATAAC CGCGAGAAGG CGAAGGAGCG AGTGACTGAG CGACGCGAGC
```

FIGURE 11H

```
6651  GTCGTTCGGC TGCGGCGAGC GGTATCAGCT CACTCAAAGG CGGTAATACG
      CAGCAAGCCG ACGCCGCTCG CCATAGTCGA GTGAGTTTCC GCCATTATGC

6701  GTTATCCACA GAATCAGGGG ATAACGCAGG AAAGAACATG TGAGCAAAAG
      CAATAGGTGT CTTAGTCCCC TATTGCGTCC TTTCTTGTAC ACTCGTTTTC

6751  GCCAGCAAAA GGCCAGGAAC CGTAAAAAGG CCGCGTTGCT GGCGTTTTTC
      CGGTCGTTTT CCGGTCCTTG GCATTTTTCC GGCGCAACGA CCGCAAAAAG

6801  CATAGGCTCC GCCCCCCTGA CGAGCATCAC AAAAATCGAC GCTCAAGTCA
      GTATCCGAGG CGGGGGGACT GCTCGTAGTG TTTTTAGCTG CGAGTTCAGT

6851  GAGGTGGCGA AACCCGACAG GACTATAAAG ATACCAGGCG TTTCCCCCTG
      CTCCACCGCT TTGGGCTGTC CTGATATTTC TATGGTCCGC AAAGGGGGAC

6901  GAAGCTCCCT CGTGCGCTCT CCTGTTCCGA CCCTGCCGCT TACCGGATAC
      CTTCGAGGGA GCACGCGAGA GGACAAGGCT GGGACGGCGA ATGGCCTATG

6951  CTGTCCGCCT TTCTCCCTTC GGGAAGCGTG GCGCTTTCTC ATAGCTCACG
      GACAGGCGGA AAGAGGGAAG CCCTTCGCAC CGCGAAAGAG TATCGAGTGC

7001  CTGTAGGTAT CTCAGTTCGG TGTAGGTCGT TCGCTCCAAG CTGGGCTGTG
      GACATCCATA GAGTCAAGCC ACATCCAGCA AGCGAGGTTC GACCCGACAC

7051  TGCACGAACC CCCCGTTCAG CCCGACCGCT GCGCCTTATC CGGTAACTAT
      ACGTGCTTGG GGGGCAAGTC GGGCTGGCGA CGCGGAATAG GCCATTGATA

7101  CGTCTTGAGT CCAACCCGGT AAGACACGAC TTATCGCCAC TGGCAGCAGC
      GCAGAACTCA GGTTGGGCCA TTCTGTGCTG AATAGCGGTG ACCGTCGTCG

7151  CACTGGTAAC AGGATTAGCA GAGCGAGGTA TGTAGGCGGT GCTACAGAGT
      GTGACCATTG TCCTAATCGT CTCGCTCCAT ACATCCGCCA CGATGTCTCA

7201  TCTTGAAGTG GTGGCCTAAC TACGGCTACA CTAGAAGAAC AGTATTTGGT
      AGAACTTCAC CACCGGATTG ATGCCGATGT GATCTTCTTG TCATAAACCA

7251  ATCTGCGCTC TGCTGAAGCC AGTTACCTTC GGAAAAAGAG TTGGTAGCTC
      TAGACGCGAG ACGACTTCGG TCAATGGAAG CCTTTTTCTC AACCATCGAG

7301  TTGATCCGGC AAACAAACCA CCGCTGGTAG CGGTGGTTTT TTTGTTTGCA
      AACTAGGCCG TTTGTTTGGT GGCGACCATC GCCACCAAAA AAACAAACGT

7351  AGCAGCAGAT TACGCGCAGA AAAAAAGGAT CTCAAGAAGA TCCTTTGATC
      TCGTCGTCTA ATGCGCGTCT TTTTTTCCTA GAGTTCTTCT AGGAAACTAG

7401  TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA

7451  TTTGGTCATG AGATTATCAA AAAGGATCTT CACCTAGATC CTTTTGCGGC
      AAACCAGTAC TCTAATAGTT TTTCCTAGAA GTGGATCTAG GAAAACGCCG

7501  CGCAAATCAA TCTAAAGTAT ATATGAGTAA ACTTGGTCTG ACAGTTACCA
      GCGTTTAGTT AGATTTCATA TATACTCATT TGAACCAGAC TGTCAATGGT

7551  ATGCTTAATC AGTGAGGCAC CTATCTCAGC GATCTGTCTA TTTCGTTCAT
      TACGAATTAG TCACTCCGTG GATAGAGTCG CTAGACAGAT AAAGCAAGTA
```

FIGURE 11I

```
7601 CCATAGTTGC CTGACTCCCC GTCGTGTAGA TAACTACGAT ACGGGAGGGC
     GGTATCAACG GACTGAGGGG CAGCACATCT ATTGATGCTA TGCCCTCCCG

7651 TTACCATCTG GCCCCAGTGC TGCAATGATA CCGCGAGACC CACGCTCACC
     AATGGTAGAC CGGGGTCACG ACGTTACTAT GGCGCTCTGG GTGCGAGTGG

7701 GGCTCCAGAT TTATCAGCAA TAAACCAGCC AGCCGGAAGG GCCGAGCGCA
     CCGAGGTCTA AATAGTCGTT ATTTGGTCGG TCGGCCTTCC CGGCTCGCGT

7751 GAAGTGGTCC TGCAACTTTA TCCGCCTCCA TCCAGTCTAT TAATTGTTGC
     CTTCACCAGG ACGTTGAAAT AGGCGGAGGT AGGTCAGATA ATTAACAACG

7801 CGGGAAGCTA GAGTAAGTAG TTCGCCAGTT AATAGTTTGC GCAACGTTGT
     GCCCTTCGAT CTCATTCATC AAGCGGTCAA TTATCAAACG CGTTGCAACA

7851 TGCCATTGCT ACAGGCATCG TGGTGTCACG CTCGTCGTTT GGTATGGCTT
     ACGGTAACGA TGTCCGTAGC ACCACAGTGC GAGCAGCAAA CCATACCGAA

7901 CATTCAGCTC CGGTTCCCAA CGATCAAGGC GAGTTACATG ATCCCCCATG
     GTAAGTCGAG GCCAAGGGTT GCTAGTTCCG CTCAATGTAC TAGGGGGTAC

7951 TTGTGCAAAA AAGCGGTTAG CTCCTTCGGT CCTCCGATCG TTGTCAGAAG
     AACACGTTTT TTCGCCAATC GAGGAAGCCA GGAGGCTAGC AACAGTCTTC

8001 TAAGTTGGCC GCAGTGTTAT CACTCATGGT TATGGCAGCA CTGCATAATT
     ATTCAACCGG CGTCACAATA GTGAGTACCA ATACCGTCGT GACGTATTAA

8051 CTCTTACTGT CATGCCATCC GTAAGATGCT TTTCTGTGAC TGGTGAGTAC
     GAGAATGACA GTACGGTAGG CATTCTACGA AAAGACACTG ACCACTCATG

8101 TCAACCAAGT CATTCTGAGA ATAGTGTATG CGGCGACCGA GTTGCTCTTG
     AGTTGGTTCA GTAAGACTCT TATCACATAC GCCGCTGGCT CAACGAGAAC

8151 CCCGGCGTCA ATACGGGATA ATACCGCGCC ACATAGCAGA ACTTTAAAAG
     GGGCCGCAGT TATGCCCTAT TATGGCGCGG TGTATCGTCT TGAAATTTTC

8201 TGCTCATCAT TGGAAAACGT TCTTCGGGGC GAAAACTCTC AAGGATCTTA
     ACGAGTAGTA ACCTTTTGCA AGAAGCCCCG CTTTTGAGAG TTCCTAGAAT

8251 CCGCTGTTGA GATCCAGTTC GATGTAACCC ACTCGTGCAC CCAACTGATC
     GGCGACAACT CTAGGTCAAG CTACATTGGG TGAGCACGTG GGTTGACTAG

8301 TTCAGCATCT TTTACTTTCA CCAGCGTTTC TGGGTGAGCA AAAACAGGAA
     AAGTCGTAGA AAATGAAAGT GGTCGCAAAG ACCCACTCGT TTTTGTCCTT

8351 GGCAAAATGC CGCAAAAAAG GGAATAAGGG CGACACGGAA ATGTTGAATA
     CCGTTTTACG GCGTTTTTTC CCTTATTCCC GCTGTGCCTT TACAACTTAT

8401 CTCATACTCT TCCTTTTTCA ATATTATTGA AGCATTTATC AGGGTTATTG
     GAGTATGAGA AGGAAAAAGT TATAATAACT TCGTAAATAG TCCCAATAAC

8451 TCTCATGAGC GGATACATAT TTGAATGTAT TTAGAAAAAT AAACAAATAG
     AGAGTACTCG CCTATGTATA AACTTACATA AATCTTTTTA TTTGTTTATC

8501 GGGTTCCGCG CACATTTC
     CCCAAGGCGC GTGTAAAG
```

FIGURE 11J

```
  1 CTGCAGCCTG AATATGGGCC AAACAGGATA TCTGTGGTAA GCAGTTCCTG
    GACGTCGGAC TTATACCCGG TTTGTCCTAT AGACACCATT CGTCAAGGAC

51 CCCCGGCTCA GGGCCAAGAA CAGATGGAAC AGCTGAATAT GGGCCAAACA
    GGGGCCGAGT CCCGGTTCTT GTCTACCTTG TCGACTTATA CCCGGTTTGT

101 GGATATCTGT GGTAAGCAGT TCCTGCCCCG GCTCAGGGCC AAGAACAGAT
    CCTATAGACA CCATTCGTCA AGGACGGGGC CGAGTCCCGG TTCTTGTCTA

151 GGTCCCCAGA TGCGGTCCAG CCCTCAGCAG TTTCTAGAGA ACCATCAGAT
    CCAGGGGTCT ACGCCAGGTC GGGAGTCGTC AAAGATCTCT TGGTAGTCTA

201 GTTTCCAGGG TGCCCCAAGG ACCTGAAATG ACCCTGTGCC TTATTTGAAC
    CAAAGGTCCC ACGGGGTTCC TGGACTTTAC TGGGACACGG AATAAACTTG

251 TAACCAATCA GTTCGCTTCT CGCTTCTGTT CGCGCGCTTC TGCTCCCCGA
    ATTGGTTAGT CAAGCGAAGA GCGAAGACAA GCGCGCGAAG ACGAGGGGCT

301 GCTCAATAAA AGAGCCCACA ACCCCTCACT CGGGGCGCCA GTCCTCCGAT
    CGAGTTATTT TCTCGGGTGT TGGGGAGTGA GCCCCGCGGT CAGGAGGCTA

351 TGACTGAGTC GCCCGGGTAC CCGTGTATCC AATAAACCCT CTTGCAGTTG
    ACTGACTCAG CGGGCCCATG GGCACATAGG TTATTTGGGA GAACGTCAAC

401 CATCCGACTT GTGGTCTCGC TGTTCCTTGG GAGGGTCTCC TCTGAGTGAT
    GTAGGCTGAA CACCAGAGCG ACAAGGAACC CTCCCAGAGG AGACTCACTA

451 TGACTACCCG TCAGCGGGGG TCTTTCATTT GGGGGCTCGT CCGGGATCGG
    ACTGATGGGC AGTCGCCCCC AGAAAGTAAA CCCCGAGCA GGCCCTAGCC

501 GAGACCCCTG CCCAGGGACC ACCGACCCAC CACCGGGAGG CAAGCTGGCC
    CTCTGGGGAC GGGTCCCTGG TGGCTGGGTG GTGGCCCTCC GTTCGACCGG

551 AGCAACTTAT CTGTGTCTGT CCGATTGTCT AGTGTCTATG ACTGATTTTA
    TCGTTGAATA GACACAGACA GGCTAACAGA TCACAGATAC TGACTAAAAT

601 TGCGCCTGCG TCGGTACTAG TTAGCTAACT AGCTCTGTAT CTGGCGGACC
    ACGCGGACGC AGCCATGATC AATCGATTGA TCGAGACATA GACCGCCTGG

651 CGTGGTGGAA CTGACGAGTT CTGAACACCC GGCCGCAACC CTGGGAGACG
    GCACCACCTT GACTGCTCAA GACTTGTGGG CCGGCGTTGG GACCCTCTGC

701 TCCCAGGGAC TTTGGGGGCC GTTTTGTGG CCCGACCTGA GGAAGGGAGT
    AGGGTCCCTG AAACCCCCGG CAAAAACACC GGGCTGGACT CCTTCCCTCA

751 CGATGTGGAA TCCGACCCCG TCAGGATATG TGGTTCTGGT AGGAGACGAG
    GCTACACCTT AGGCTGGGGC AGTCCTATAC ACCAAGACCA TCCTCTGCTC

801 AACCTAAAAC AGTTCCCGCC TCCGTCTGAA TTTTTGCTTT CGGTTTGGAA
    TTGGATTTTG TCAAGGGCGG AGGCAGACTT AAAAACGAAA GCCAAACCTT

851 CCGAAGCCGC GCGTCTTGTG TGCTGCAGCA TCGTTCTGTG TTGTGTCTGT
    GGCTTCGGCG CGCAGAACAG ACGACGTCGT AGCAAGACAC AACAGAGACA

901 CTGACTGTGT TTCTGTATTT GTCTGAAAAT TAGGGCCAGA CTGTTACCAC
    GACTGACACA AAGACATAAA CAGACTTTTA ATCCCGGTCT GACAATGGTG
```

FIGURE 12B

```
 951 TCCCTTAAGT TTGACCTTAG GTAACTGGAA AGATGTCGAG CGGCTCGCTC
     AGGGAATTCA AACTGGAATC CATTGACCTT TCTACAGCTC GCCGAGCGAG

1001 ACAACCAGTC GGTAGATGTC AAGAAGAGAC GTTGGGTTAC CTTCTGCTCT
     TGTTGGTCAG CCATCTACAG TTCTTCTCTG CAACCCAATG GAAGACGAGA

1051 GCAGAATGGC CAACCTTTAA CGTCGGATGG CCGCGAGACG GCACCTTTAA
     CGTCTTACCG GTTGGAAATT GCAGCCTACC GGCGCTCTGC CGTGGAAATT

1101 CCGAGACCTC ATCACCCAGG TTAAGATCAA GGTCTTTTCA CCTGGCCCGC
     GGCTCTGGAG TAGTGGGTCC AATTCTAGTT CCAGAAAAGT GGACCGGGCG

1151 ATGGACACCC AGACCAGGTC CCCTACATCG TGACCTGGGA AGCCTTGGCT
     TACCTGTGGG TCTGGTCCAG GGGATGTAGC ACTGGACCCT TCGGAACCGA

1201 TTTGACCCCC CTCCCTGGGT CAAGCCCTTT GTACACCCTA AGCCTCCGCC
     AAACTGGGGG GAGGGACCCA GTTCGGGAAA CATGTGGGAT TCGGAGGCGG

1251 TCCTCTTCCT CCATCCGCCC CGTCTCTCCC CCTTGAACCT CCTCGTTCGA
     AGGAGAAGGA GGTAGGCGGG GCAGAGAGGG GGAACTTGGA GGAGCAAGCT

1301 CCCCGCCTCG ATCCTCCCTT TATCCAGCCC TCACTCCTTC TCTAGGCGCC
     GGGGCGGAGC TAGGAGGGAA ATAGGTCGGG AGTGAGGAAG AGATCCGCGG

1351 GGCCGCTCTA GCCCATTAAT ACGACTCACT ATAGGGCGAT TCGAATCAGG
     CCGGCGAGAT CGGGTAATTA TGCTGAGTGA TATCCCGCTA AGCTTAGTCC

1401 CCTTGGCGCG CCGGATCCTT AATTAAGCGC AATTGGGAGG TGGCGGTAGC
     GGAACCGCGC GGCCTAGGAA TTAATTCGCG TTAACCCTCC ACCGCCATCG

1451 CTCGAGATGG GCGTGATTAC GGATTCACTG GCCGTCGTTT TACAACGTCG
     GAGCTCTACC CGCACTAATG CCTAAGTGAC CGGCAGCAAA ATGTTGCAGC

1501 TGACTGGGAA AACCCTGGCG TTACCCAACT TAATCGCCTT GCAGCACATC
     ACTGACCCTT TTGGGACCGC AATGGGTTGA ATTAGCGGAA CGTCGTGTAG

1551 CCCCTTTCGC CAGCTGGCGT AATAGCGAAG AGGCCCGCAC CGATCGCCCT
     GGGGAAAGCG GTCGACCGCA TTATCGCTTC TCCGGGCGTG GCTAGCGGGA

1601 TCCAACAGT TACGCAGCCT GAATGGCGAA TGGCGCTTTG CCTGGTTTCC
     AGGGTTGTCA ATGCGTCGGA CTTACCGCTT ACCGCGAAAC GGACCAAAGG

1651 GGCACCAGAA GCGGTGCCGG AAAGCTGGCT GGAGTGCGAT CTTCCTGAGG
     CCGTGGTCTT CGCCACGGCC TTTCGACCGA CCTCACGCTA GAAGGACTCC

1701 CCGATACTGT CGTCGTCCCC TCAAACTGGC AGATGCACGG TTACGATGCG
     GGCTATGACA GCAGCAGGGG AGTTTGACCG TCTACGTGCC AATGCTACGC

1751 CCCATCTACA CCAACGTGAC CTATCCCATT ACGGTCAATC CGCCGTTTGT
     GGGTAGATGT GGTTGCACTG GATAGGGTAA TGCCAGTTAG GCGGCAAACA

1801 TCCCACGGAG AATCCGACGG GTTGTTACTC GCTCACATTT AATGTTGATG
     AGGGTGCCTC TTAGGCTGCC CAACAATGAG CGAGTGTAAA TTACAACTAC

1851 AAAGCTGGCT ACAGGAAGGC CAGACGCGAA TTATTTTTGA TGGCGTTAAC
     TTTCGACCGA TGTCCTTCCG GTCTGCGCTT AATAAAAACT ACCGCAATTG
```

FIGURE 12C

```
1901 TCGGCGTTTC ATCTGTGGTG CAACGGGCGC TGGGTCGGTT ACGGCCAGGA
     AGCCGCAAAG TAGACACCAC GTTGCCCGCG ACCCAGCCAA TGCCGGTCCT

1951 CAGTCGTTTG CCGTCTGAAT TTGACCTGAG CGCATTTTTA CGCGCCGGAG
     GTCAGCAAAC GGCAGACTTA AACTGGACTC GCGTAAAAAT GCGCGGCCTC

2001 AAAACCGCCT CGCGGTGATG GTGCTGCGCT GGAGTGACGG CAGTTATCTG
     TTTTGGCGGA GCGCCACTAC CACGACGCGA CCTCACTGCC GTCAATAGAC

2051 GAAGATCAGG ATATGTGGCG GATGAGCGGC ATTTTCCGTG ACGTCTCGTT
     CTTCTAGTCC TATACACCGC CTACTCGCCG TAAAAGGCAC TGCAGAGCAA

2101 GCTGCATAAA CCGACTACAC AAATCAGCGA TTTCCATGTT GCCACTCGCT
     CGACGTATTT GGCTGATGTG TTTAGTCGCT AAAGGTACAA CGGTGAGCGA

2151 TTAATGATGA TTTCAGCCGC GCTGTACTGG AGGCTGAAGT TCAGATGTGC
     AATTACTACT AAAGTCGGCG CGACATGACC TCCGACTTCA AGTCTACACG

2201 GGCGAGTTGC GTGACTACCT ACGGGTAACA GTTTCTTTAT GGCAGGGTGA
     CCGCTCAACG CACTGATGGA TGCCCATTGT CAAAGAAATA CCGTCCCACT

2251 AACGCAGGTC GCCAGCGGCA CCGCGCCTTT CGGCGGTGAA ATTATCGATG
     TTGCGTCCAG CGGTCGCCGT GGCGCGGAAA GCCGCCACTT TAATAGCTAC

2301 AGCGTGGTGG TTATGCCGAT CGCGTCACAC TACGTCTGAA CGTCGAAAAC
     TCGCACCACC AATACGGCTA GCGCAGTGTG ATGCAGACTT GCAGCTTTTG

2351 CCGAAACTGT GGAGCGCCGA AATCCCGAAT CTCTATCGTG CGGTGGTTGA
     GGCTTTGACA CCTCGCGGCT TTAGGGCTTA GAGATAGCAC GCCACCAACT

2401 ACTGCACACC GCCGACGGCA CGCTGATTGA AGCAGAAGCC TGCGATGTCG
     TGACGTGTGG CGGCTGCCGT GCGACTAACT TCGTCTTCGG ACGCTACAGC

2451 GTTTCCGCGA GGTGCGGATT GAAAATGGTC TGCTGCTGCT GAACGGCAAG
     CAAAGGCGCT CCACGCCTAA CTTTTACCAG ACGACGACGA CTTGCCGTTC

2501 CCGTTGCTGA TTCGAGGCGT TAACCGTCAC GAGCATCATC CTCTGCATGG
     GGCAACGACT AAGCTCCGCA ATTGGCAGTG CTCGTAGTAG GAGACGTACC

2551 TCAGGTCATG GATGAGCAGA CGATGGTGCA GGATATCCTG CTGATGAAGC
     AGTCCAGTAC CTACTCGTCT GCTACCACGT CCTATAGGAC GACTACTTCG

2601 AGAACAACTT TAACGCCGTG CGCTGTTCGC ATTATCCGAA CCATCCGCTG
     TCTTGTTGAA ATTGCGGCAC GCGACAAGCG TAATAGGCTT GGTAGGCGAC

2651 TGGTACACGC TGTGCGACCG CTACGGCCTG TATGTGGTGG ATGAAGCCAA
     ACCATGTGCG ACACGCTGGC GATGCCGGAC ATACACCACC TACTTCGGTT

2701 TATTGAAACC CACGGCATGG TGCCAATGAA TCGTCTGACC GATGATCCGC
     ATAACTTTGG GTGCCGTACC ACGGTTACTT AGCAGACTGG CTACTAGGCG

2751 GCTGGCTACC GGCGATGAGC GAACGCGTAA CGCGAATGGT GCAGCGCGAT
     CGACCGATGG CCGCTACTCG CTTGCGCATT GCGCTTACCA CGTCGCGCTA

2801 CGTAATCACC CGAGTGTGAT CATCTGGTCG CTGGGGAATG AATCAGGCCA
     GCATTAGTGG GCTCACACTA GTAGACCAGC GACCCCTTAC TTAGTCCGGT
```

FIGURE 12D

```
2851  CGGCGCTAAT CACGACGCGC TGTATCGCTG GATCAAATCT GTCGATCCTT
      GCCGCGATTA GTGCTGCGCG ACATAGCGAC CTAGTTTAGA CAGCTAGGAA

2901  CCCGCCCGGT GCAGTATGAA GGCGGCGGAG CCGACACCAC GGCCACCGAT
      GGGCGGGCCA CGTCATACTT CCGCCGCCTC GGCTGTGGTG CCGGTGGCTA

2951  ATTATTTGCC CGATGTACGC GCGCGTGGAT GAAGACCAGC CCTTCCCGGC
      TAATAAACGG GCTACATGCG CGCGCACCTA CTTCTGGTCG GGAAGGGCCG

3001  TGTGCCGAAA TGGTCCATCA AAAAATGGCT TTCGCTACCT GGAGAGACGC
      ACACGGCTTT ACCAGGTAGT TTTTTACCGA AAGCGATGGA CCTCTCTGCG

3051  GCCCGCTGAT CCTTTGCGAA TACGCCCACG CGATGGGTAA CAGTCTTGGC
      CGGGCGACTA GGAAACGCTT ATGCGGGTGC GCTACCCATT GTCAGAACCG

3101  GGTTTCGCTA ATACTGGCA GGCGTTTCGT CAGTATCCCC GTTTACAGGG
      CCAAAGCGAT TTATGACCGT CCGCAAAGCA GTCATAGGGG CAAATGTCCC

3151  CGGCTTCGTC TGGGACTGGG TGGATCAGTC GCTGATTAAA TATGATGAAA
      GCCGAAGCAG ACCCTGACCC ACCTAGTCAG CGACTAATTT ATACTACTTT

3201  ACGGCAACCC GTGGTCGGCT TACGGCGGTG ATTTTGGCGA TACGCCGAAC
      TGCCGTTGGG CACCAGCCGA ATGCCGCCAC TAAAACCGCT ATGCGGCTTG

3251  GATCGCCAGT TCTGTATGAA CGGTCTGGTC TTTGCCGACC GCACGCCGCA
      CTAGCGGTCA AGACATACTT GCCAGACCAG AAACGGCTGG CGTGCGGCGT

3301  TCCAGCGCTG ACGGAAGCAA AACACCAGCA GCAGTTTTTC CAGTTCCGTT
      AGGTCGCGAC TGCCTTCGTT TTGTGGTCGT CGTCAAAAAG GTCAAGGCAA

3351  TATCCGGGCA AACCATCGAA GTGACCAGCG AATACCTGTT CCGTCATAGC
      ATAGGCCCGT TTGGTAGCTT CACTGGTCGC TTATGGACAA GGCAGTATCG

3401  GATAACGAGC TCCTGCACTG GATGGTGGCG CTGGATGGTA AGCCGCTGGC
      CTATTGCTCG AGGACGTGAC CTACCACCGC GACCTACCAT TCGGCGACCG

3451  AAGCGGTGAA GTGCCTCTGG ATGTCGCTCC ACAAGGTAAA CAGTTGATTG
      TTCGCCACTT CACGGAGACC TACAGCGAGG TGTTCCATTT GTCAACTAAC

3501  AACTGCCTGA ACTACCGCAG CCGGAGAGCG CCGGGCAACT CTGGCTCACA
      TTGACGGACT TGATGGCGTC GGCCTCTCGC GGCCCGTTGA GACCGAGTGT

3551  GTACGCGTAG TGCAACCGAA CGCGACCGCA TGGTCAGAAG CCGGGCACAT
      CATGCGCATC ACGTTGGCTT GCGCTGGCGT ACCAGTCTTC GGCCCGTGTA

3601  CAGCGCCTGG CAGCAGTGGC GTCTGGCGGA AAACCTCAGT GTGACGCTCC
      GTCGCGGACC GTCGTCACCG CAGACCGCCT TTTGGAGTCA CACTGCGAGG

3651  CCGCCGCGTC CCACGCCATC CCGCATCTGA CCACCAGCGA AATGGATTTT
      GGCGGCGCAG GGTGCGGTAG GGCGTAGACT GGTGGTCGCT TTACCTAAAA

3701  TGCATCGAGC TGGGTAATAA GCGTTGGCAA TTTAACCGCC AGTCAGGCTT
      ACGTAGCTCG ACCCATTATT CGCAACCGTT AAATTGGCGG TCAGTCCGAA

3751  TCTTTCACAG ATGTGGATTG GCGATAAAAA ACAACTGCTG ACGCCGCTGC
      AGAAAGTGTC TACACCTAAC CGCTATTTTT TGTTGACGAC TGCGGCGACG
```

FIGURE 12E

```
3801 GCGATCAGTT CACCCGTGTC GATAGATCTG AACAGAAACT CATTTCCGAA
     CGCTAGTCAA GTGGGCACAG CTATCTAGAC TTGTCTTTGA GTAAAGGCTT

3851 GAAGACCTAG TCGACCATCA TCATCATCAT CACCGGTAAT AATAGGTAGA
     CTTCTGGATC AGCTGGTAGT AGTAGTAGTA GTGGCCATTA TTATCCATCT

3901 TAAGTGACTG ATTAGATGCA TTTCGACTAG ATCCCTCGAC CAATTCCGGT
     ATTCACTGAC TAATCTACGT AAAGCTGATC TAGGGAGCTG GTTAAGGCCA

3951 TATTTTCCAC CATATTGCCG TCTTTTGGCA ATGTGAGGGC CCGGAAACCT
     ATAAAAGGTG GTATAACGGC AGAAAACCGT TACACTCCCG GGCCTTTGGA

4001 GGCCCTGTCT TCTTGACGAG CATTCCTAGG GGTCTTTCCC CTCTCGCCAA
     CCGGGACAGA AGAACTGCTC GTAAGGATCC CCAGAAAGGG GAGAGCGGTT

4051 AGGAATGCAA GGTCTGTTGA ATGTCGTGAA GGAAGCAGTT CCTCTGGAAG
     TCCTTACGTT CCAGACAACT TACAGCACTT CCTTCGTCAA GGAGACCTTC

4101 CTTCTTGAAG ACAAACAACG TCTGTAGCGA CCCTTTGCAG GCAGCGGAAC
     GAAGAACTTC TGTTTGTTGC AGACATCGCT GGGAAACGTC CGTCGCCTTG

4151 CCCCCACCTG GCGACAGGTG CCTCTGCGGC CAAAAGCCAC GTGTATAAGA
     GGGGGTGGAC CGCTGTCCAC GGAGACGCCG GTTTTCGGTG CACATATTCT

4201 TACACCTGCA AAGGCGGCAC AACCCCAGTG CCACGTTGTG AGTTGGATAG
     ATGTGGACGT TTCCGCCGTG TTGGGGTCAC GGTGCAACAC TCAACCTATC

4251 TTGTGGAAAG AGTCAAATGG CTCTCCTCAA GCGTATTCAA CAAGGGGCTG
     AACACCTTTC TCAGTTTACC GAGAGGAGTT CGCATAAGTT GTTCCCCGAC

4301 AAGGATGCCC AGAAGGTACC CCATTGTATG GGATCTGATC TGGGGCCTCG
     TTCCTACGGG TCTTCCATGG GGTAACATAC CCTAGACTAG ACCCCGGAGC

4351 GTGCACATGC TTTACATGTG TTTAGTCGAG GTTAAAAAAC GTCTAGGCCC
     CACGTGTACG AAATGTACAC AAATCAGCTC CAATTTTTTG CAGATCCGGG

4401 CCCGAACCAC GGGGACGTGG TTTTCCTTTG AAAAACACGA TGATAATACC
     GGGCTTGGTG CCCCTGCACC AAAAGGAAAC TTTTTGTGCT ACTATTATGG

4451 ATGAAAAAGC CTGAACTCAC CGCGACGTCT GTCGAGAAGT TTCTGATCGA
     TACTTTTTCG GACTTGAGTG GCGCTGCAGA CAGCTCTTCA AAGACTAGCT

4501 AAAGTTCGAC AGCGTCTCCG ACCTGATGCA GCTCTCGGAG GGCGAAGAAT
     TTTCAAGCTG TCGCAGAGGC TGGACTACGT CGAGAGCCTC CCGCTTCTTA

4551 CTCGTGCTTT CAGCTTCGAT GTAGGAGGGC GTGGATATGT CCTGCGGGTA
     GAGCACGAAA GTCGAAGCTA CATCCTCCCG CACCTATACA GGACGCCCAT

4601 AATAGCTGCG CCGATGGTTT CTACAAAGAT CGTTATGTTT ATCGGCACTT
     TTATCGACGC GGCTACCAAA GATGTTTCTA GCAATACAAA TAGCCGTGAA

4651 TGCATCGGCC GCGCTCCCGA TTCCGGAAGT GCTTGACATT GGGGAATTTA
     ACGTAGCCGG CGCGAGGGCT AAGGCCTTCA CGAACTGTAA CCCCTTAAAT

4701 GCGAGAGCCT GACCTATTGC ATCTCCCGCC GTGCACAGGG TGTCACGTTG
     CGCTCTCGGA CTGGATAACG TAGAGGGCGG CACGTGTCCC ACAGTGCAAC
```

FIGURE 12F

```
4751  CAAGACCTGC CTGAAACCGA ACTGCCCGCT GTTCTGCAGC CGGTCGCGGA
      GTTCTGGACG GACTTTGGCT TGACGGGCGA CAAGACGTCG GCCAGCGCCT

4801  GGCCATGGAT GCGATCGCTG CGGCCGATCT TAGCCAGACG AGCGGGTTCG
      CCGGTACCTA CGCTAGCGAC GCCGGCTAGA ATCGGTCTGC TCGCCCAAGC

4851  GCCCATTCGG ACCGCAAGGA ATCGGTCAAT ACACTACATG GCGTGATTTC
      CGGGTAAGCC TGGCGTTCCT TAGCCAGTTA TGTGATGTAC CGCACTAAAG

4901  ATATGCGCGA TTGCTGATCC CCATGTGTAT CACTGGCAAA CTGTGATGGA
      TATACGCGCT AACGACTAGG GGTACACATA GTGACCGTTT GACACTACCT

4951  CGACACCGTC AGTGCGTCCG TCGCGCAGGC TCTCGATGAG CTGATGCTTT
      GCTGTGGCAG TCACGCAGGC AGCGCGTCCG AGAGCTACTC GACTACGAAA

5001  GGGCCGAGGA CTGCCCCGAA GTCCGGCACC TCGTGCACGC GGATTTCGGC
      CCCGGCTCCT GACGGGGCTT CAGGCCGTGG AGCACGTGCG CCTAAAGCCG

5051  TCCAACAATG TCCTGACGGA CAATGGCCGC ATAACAGCGG TCATTGACTG
      AGGTTGTTAC AGGACTGCCT GTTACCGGCG TATTGTCGCC AGTAACTGAC

5101  GAGCGAGGCG ATGTTCGGGG ATTCCCAATA CGAGGTCGCC AACATCTTCT
      CTCGCTCCGC TACAAGCCCC TAAGGGTTAT GCTCCAGCGG TTGTAGAAGA

5151  TCTGGAGGCC GTGGTTGGCT TGTATGGAGC AGCAGACGCG CTACTTCGAG
      AGACCTCCGG CACCAACCGA ACATACCTCG TCGTCTGCGC GATGAAGCTC

5201  CGGAGGCATC CGGAGCTTGC AGGATCGCCG CGGCTCCGGG CGTATATGCT
      GCCTCCGTAG GCCTCGAACG TCCTAGCGGC GCCGAGGCCC GCATATACGA

5251  CCGCATTGGT CTTGACCAAC TCTATCAGAG CTTGGTTGAC GGCAATTTCG
      GGCGTAACCA GAACTGGTTG AGATAGTCrC GAACCAACTG CCGTTAAAGC

5301  ATGATGCAGC TTGGGCGCAG GGTCGATGCG ACGCAATCGT CCGATCCGGA
      TACTACGTCG AACCCGCGTC CCAGCTACGC TGCGTTAGCA GGCTAGGCCT

5351  GCCGGGACTG TCGGGCGTAC ACAAATCGCC CGCAGAAGCG CGGCCGTCTG
      CGGCCCTGAC AGCCCGCATG TGTTTAGCGG GCGTCTTCGC GCCGGCAGAC

5401  GACCGATGGC TGTGTAGAAG TACTCGCCGA TAGTGGAAAC CGACGCCCCA
      CTGGCTACCG ACACATCTTC ATGAGCGGCT ATCACCTTTG GCTGCGGGGT

5451  GCACTCGTCC GAGGGCAAAG GAATAGAGTA GATGCCGACC GGGATCTATC
      CGTGAGCAGG CTCCCGTTTC CTTATCTCAT CTACGGCTGG CCCTAGATAG

5501  GATAAAATAA AAGATTTTAT TTAGTCTCCA GAAAAGGGG GGAATGAAAG
      CTATTTTATT TTCTAAAATA AATCAGAGGT CTTTTCCCC CCTTACTTTC

5551  ACCCCACCTG TAGGTTTGGC AAGCTAGCTT AAGTAACGCC ATTTTGCAAG
      TGGGGTGGAC ATCCAAACCG TTCGATCGAA TTCATTGCGG TAAAACGTTC

5601  GCATGGAAAA ATACATAACT GAGAATAGAG AAGTTCAGAT CAAGGTCAGG
      CGTACCTTTT TATGTATTGA CTCTTATCTC TTCAAGTCTA GTTCCAGTCC

5651  AACAGATGGA ACAGCTGAAT ATGGGCCAAA CAGGATATCT GTGGTAAGCA
      TTGTCTACCT TGTCGACTTA TACCCGGTTT GTCCTATAGA CACCATTCGT
```

FIGURE 12G

```
5701 GTTCCTGCCC CGGCTCAGGG CCAAGAACAG ATGGAACAGC TGAATATGGG
     CAAGGACGGG GCCGAGTCCC GGTTCTTGTC TACCTTGTCG ACTTATACCC

5751 CCAAACAGGA TATCTGTGGT AAGCAGTTCC TGCCCCGGCT CAGGGCCAAG
     GGTTTGTCCT ATAGACACCA TTCGTCAAGG ACGGGGCCGA GTCCCGGTTC

5801 AACAGATGGT CCCCAGATGC GGTCCAGCCC TCAGCAGTTT CTAGAGAACC
     TTGTCTACCA GGGGTCTACG CCAGGTCGGG AGTCGTCAAA GATCTCTTGG

5851 ATCAGATGTT TCCAGGGTGC CCCAAGGACC TGAAATGACC CTGTGCCTTA
     TAGTCTACAA AGGTCCCACG GGGTTCCTGG ACTTTACTGG GACACGGAAT

5901 TTTGAACTAA CCAATCAGTT CGCTTCTCGC TTCTGTTCGC GCGCTTCTGC
     AAACTTGATT GGTTAGTCAA GCGAAGAGCG AAGACAAGCG CGCGAAGACG

5951 TCCCCGAGCT CAATAAAAGA GCCCACAACC CCTCACTCGG GGCGCCAGTC
     AGGGGCTCGA GTTATTTTCT CGGGTGTTGG GGAGTGAGCC CCGCGGTCAG

6001 CTCCGATTGA CTGAGTCGCC CGGGTACCCG TGTATCCAAT AAACCCTCTT
     GAGGCTAACT GACTCAGCGG GCCCATGGGC ACATAGGTTA TTTGGGAGAA

6051 GCAGTTGCAT CCGACTTGTG GTCTCGCTGT TCCTTGGGAG GGTCTCCTCT
     CGTCAACGTA GGCTGAACAC CAGAGCGACA AGGAACCCTC CCAGAGGAGA

6101 GAGTGATTGA CTACCCGTCA GCGGGGGTCT TTCATTCATG CAGCATGTAT
     CTCACTAACT GATGGGCAGT CGCCCCAGA AAGTAAGTAC GTCGTACATA

6151 CAAAATTAAT TTGGTTTTTT TTCTTAAGTA TTTACATTAA ATGGCCATAG
     GTTTTAATTA AACCAAAAAA AAGAATTCAT AAATGTAATT TACCGGTATC

6201 TTGCATTAAT GAATCGGCCA ACGCGCGGGG AGAGGCGGTT TGCGTATTGG
     AACGTAATTA CTTAGCCGGT TGCGCGCCCC TCTCCGCCAA ACGCATAACC

6251 CGCTCTTCCG CTTCCTCGCT CACTGACTCG CTGCGCTCGG TCGTTCGGCT
     GCGAGAAGGC GAAGGAGCGA GTGACTGAGC GACGCGAGCC AGCAAGCCGA

6301 GCGGCGAGCG GTATCAGCTC ACTCAAAGGC GGTAATACGG TTATCCACAG
     CGCCGCTCGC CATAGTCGAG TGAGTTTCCG CCATTATGCC AATAGGTGTC

6351 AATCAGGGGA TAACGCAGGA AAGAACATGT GAGCAAAAGG CCAGCAAAAG
     TTAGTCCCCT ATTGCGTCCT TTCTTGTACA CTCGTTTTCC GGTCGTTTTC

6401 GCCAGGAACC GTAAAAAGGC CGCGTTGCTG GCGTTTTTCC ATAGGCTCCG
     CGGTCCTTGG CATTTTTCCG GCGCAACGAC CGCAAAAAGG TATCCGAGGC

6451 CCCCCCTGAC GAGCATCACA AAAATCGACG CTCAAGTCAG AGGTGGCGAA
     GGGGGGACTG CTCGTAGTGT TTTTAGCTGC GAGTTCAGTC TCCACCGCTT

6501 ACCCGACAGG ACTATAAAGA TACCAGGCGT TTCCCCCTGG AAGCTCCCTC
     TGGGCTGTCC TGATATTTCT ATGGTCCGCA AAGGGGGACC TTCGAGGGAG

6551 GTGCGCTCTC CTGTTCCGAC CCTGCCGCTT ACCGGATACC TGTCCGCCTT
     CACGCGAGAG GACAAGGCTG GGACGGCGAA TGGCCTATGG ACAGGCGGAA

6601 TCTCCCTTCG GGAAGCGTGG CGCTTTCTCA TAGCTCACGC TGTAGGTATC
     AGAGGGAAGC CCTTCGCACC GCGAAAGAGT ATCGAGTGCG ACATCCATAG
```

FIGURE 12H

```
6651 TCAGTTCGGT GTAGGTCGTT CGCTCCAAGC TGGGCTGTGT GCACGAACCC
     AGTCAAGCCA CATCCAGCAA GCGAGGTTCG ACCCGACACA CGTGCTTGGG

6701 CCCGTTCAGC CCGACCGCTG CGCCTTATCC GGTAACTATC GTCTTGAGTC
     GGGCAAGTCG GGCTGGCGAC GCGGAATAGG CCATTGATAG CAGAACTCAG

6751 CAACCCGGTA AGACACGACT TATCGCCACT GGCAGCAGCC ACTGGTAACA
     GTTGGGCCAT TCTGTGCTGA ATAGCGGTGA CCGTCGTCGG TGACCATTGT

6801 GGATTAGCAG AGCGAGGTAT GTAGGCGGTG CTACAGAGTT CTTGAAGTGG
     CCTAATCGTC TCGCTCCATA CATCCGCCAC GATGTCTCAA GAACTTCACC

6851 TGGCCTAACT ACGGCTACAC TAGAAGAACA GTATTTGGTA TCTGCGCTCT
     ACCGGATTGA TGCCGATGTG ATCTTCTTGT CATAAACCAT AGACGCGAGA

6901 GCTGAAGCCA GTTACCTTCG GAAAAAGAGT TGGTAGCTCT TGATCCGGCA
     CGACTTCGGT CAATGGAAGC CTTTTTCTCA ACCATCGAGA ACTAGGCCGT

6951 AACAAACCAC CGCTGGTAGC GGTGGTTTTT TTGTTTGCAA GCAGCAGATT
     TTGTTTGGTG GCGACCATCG CCACCAAAAA AACAAACGTT CGTCGTCTAA

7001 ACGCGCAGAA AAAAAGGATC TCAAGAAGAT CCTTTGATCT TTTCTACGGG
     TGCGCGTCTT TTTTTCCTAG AGTTCTTCTA GGAAACTAGA AAAGATGCCC

7051 GTCTGACGCT CAGTGGAACG AAAACTCACG TTAAGGGATT TTGGTCATGA
     CAGACTGCGA GTCACCTTGC TTTTGAGTGC AATTCCCTAA AACCAGTACT

7101 GATTATCAAA AAGGATCTTC ACCTAGATCC TTTTAAATTA AAAATGAAGT
     CTAATAGTTT TTCCTAGAAG TGGATCTAGG AAAATTTAAT TTTTACTTCA

7151 TTGCGGCCGC AAATCAATCT AAAGTATATA TGAGTAAACT TGGTCTGACA
     AACGCCGGCG TTTAGTTAGA TTTCATATAT ACTCATTTGA ACCAGACTGT

7201 GTTACCAATG CTTAATCAGT GAGGCACCTA TCTCAGCGAT CTGTCTATTT
     CAATGGTTAC GAATTAGTCA CTCCGTGGAT AGAGTCGCTA GACAGATAAA

7251 CGTTCATCCA TAGTTGCCTG ACTCCCCGTC GTGTAGATAA CTACGATACG
     GCAAGTAGGT ATCAACGGAC TGAGGGGCAG CACATCTATT GATGCTATGC

7301 GGAGGGCTTA CCATCTGGCt CCAGTGCTGC AATGATACCG CGAGACCCAC
     CCTCCCGAAT GGTAGACCGG GGTCACGACG TTACTATGGC GCTCTGGGTG

7351 GCTCACCGGC TCCAGATTTA TCAGCAATAA ACCAGCCAGC CGGAAGGGCC
     CGAGTGGCCG AGGTCTAAAT AGTCGTTATT TGGTCGGTCG GCCTTCCCGG

7401 GAGCGCAGAA GTGGTCCTGC AACTTTATCC GCCTCCATCC AGTCTATTAA
     CTCGCGTCTT CACCAGGACG TTGAAATAGG CGGAGGTAGG TCAGATAATT

7451 TTGTTGCCGG GAAGCTAGAG TAAGTAGTTC GCCAGTTAAT AGTTTGCGCA
     AACAACGGCC CTTCGATCTC ATTCATCAAG CGGTCAATTA TCAAACGCGT

7501 ACGTTGTTGC CATTGCTACA GGCATCGTGG TGTCACGCTC GTCGTTTGGT
     TGCAACAACG GTAACGATGT CCGTAGCACC ACAGTGCGAG CAGCAAACCA

7551 ATGGCTTCAT TCAGCTCCGG TTCCCAACGA TCAAGGCGAG TTACATGATC
     TACCGAAGTA AGTCGAGGCC AAGGGTTGCT AGTTCCGCTC AATGTACTAG
```

FIGURE 12I

```
7601  CCCCATGTTG TGCAAAAAAG CGGTT1GCTC CTTCGGTCCT CCGATCGTTG
      GGGGTACAAC ACGTTTTTTC GCCAATCGAG GAAGCCAGGA GGCTAGCAAC

7651  TCAGAAGTAA GTTGGCCGCA GTGTTATCAC TCATGGTTAT GGCAGCACTG
      AGTCTTCATT CAACCGGCGT CACAATAGTG AGTACCAATA CCGTCGTGAC

7701  CATAATTCTC TTACTGTCAT GCCATCCGTA AGATGCTTTT CTGTGACTGG
      GTATTAAGAG AATGACAGTA CGGTAGGCAT TCTACGAAAA GACACTGACC

7751  TGAGTACTCA ACCAAGTCAT TCTGAGAATA GTGTATGCGG CGACCGAGTT
      ACTCATGAGT TGGTTCAGTA AGACTCTTAT CACATACGCC GCTGGCTCAA

7801  GCTCTTGCCC GGCGTCAATA CGGGATAATA CCGCGCCACA TAGCAGAACT
      CGAGAACGGG CCGCAGTTAT GCCCTATTAT GGCGCGGTGT ATCGTCTTGA

7851  TTAAAAGTGC TCATCATTGG AAAACGTTCT TCGGGGCGAA AACTCTCAAG
      AATTTTCACG AGTAGTAACC TTTTGCAAGA AGCCCCGCTT TTGAGAGTTC

7901  GATCTTACCG CTGTTGAGAT CCAGTTCGAT GTAACCCACT CGTGCACCCA
      CTAGAATGGC GACAACTCTA GGTCAAGCTA CATTGGGTGA GCACGTGGGT

7951  ACTGATCTTC AGCATCTTTT ACTTTCACCA GCGTTTCTGG GTGAGCAAAA
      TGACTAGAAG TCGTAGAAAA TGAAAGTGGT CGCAAAGACC CACTCGTTTT

8001  ACAGGAAGGC AAAATGCCGC AAAAAAGGGA ATAAGGGCGA CACGGAAATG
      TGTCCTTCCG TTTTACGGCG TTTTTTCCCT TATTCCCGCT GTGCCTTTAC

8051  TTGAATACTC ATACTCTTCC TTTTTCAATA TTATTGAAGC ATTTATCAGG
      AACTTATGAG TATGAGAAGG AAAAAGTTAT AATAACTTCG TAAATAGTCC

8101  GTTATTGTCT CATGAGCGGA TACATATTTG AATGTATTTA GAAAAATAAA
      CAATAACAGA GTACTCGCCT ATGTATAAAC TTACATAAAT CTTTTTATTT

8151  CAAATAGGGG TTCCGCGCAC ATTTC
      GTTTATCCCC AAGGCGCGTG TAAAG
```

FIGURE 12J

```
  1 CTGCAGCCTG AATATGGGCC AAACAGGATA TCTGTGGTAA GCAGTTCCTG
    GACGTCGGAC TTATACCCGG TTTGTCCTAT AGACACCATT CGTCAAGGAC

51 CCCCGGCTCA GGGCCAAGAA CAGATGGAAC AGCTGAATAT GGGCCAAACA
    GGGGCCGAGT CCCGGTTCTT GTCTACCTTG TCGACTTATA CCCGGTTTGT

101 GGATATCTGT GGTAAGCAGT TCCTGCCCCG GCTCAGGGCC AAGAACAGAT
    CCTATAGACA CCATTCGTCA AGGACGGGGC CGAGTCCCGG TTCTTGTCTA

151 GGTCCCCAGA TGCGGTCCAG CCCTCAGCAG TTTCTAGAGA ACCATCAGAT
    CCAGGGGTCT ACGCCAGGTC GGGAGTCGTC AAAGATCTCT TGGTAGTCTA

201 GTTTCCAGGG TGCCCCAAGG ACCTGAAATG ACCCTGTGCC TTATTTGAAC
    CAAAGGTCCC ACGGGGTTCC TGGACTTTAC TGGGACACGG AATAAACTTG

251 TAACCAATCA GTTCGCTTCT CGCTTCTGTT CGCGCGCTTC TGCTCCCCGA
    ATTGGTTAGT CAAGCGAAGA GCGAAGACAA GCGCGCGAAG ACGAGGGGCT

301 GCTCAATAAA AGAGCCCACA ACCCCTCACT CGGGGCGCCA GTCCTCCGAT
    CGAGTTATTT TCTCGGGTGT TGGGGAGTGA GCCCCGCGGT CAGGAGGCTA

351 TGACTGAGTC GCCCGGGTAC CCGTGTATCC AATAAACCCT CTTGCAGTTG
    ACTGACTCAG CGGGCCCATG GGCACATAGG TTATTTGGGA GAACGTCAAC

401 CATCCGACTT GTGGTCTCGC TGTTCCTTGG GAGGGTCTCC TCTGAGTGAT
    GTAGGCTGAA CACCAGAGCG ACAAGGAACC CTCCCAGAGG AGACTCACTA

451 TGACTACCCG TCAGCGGGGG TCTTTCATTT GGGGGCTCGT CCGGGATCGG
    ACTGATGGGC AGTCGCCCCC AGAAAGTAAA CCCCCGAGCA GGCCCTAGCC

501 GAGACCCCTG CCCAGGGACC ACCGACCCAC CACCGGGAGG CAAGCTGGCC
    CTCTGGGGAC GGGTCCCTGG TGGCTGGGTG GTGGCCCTCC GTTCGACCGG

551 AGCAACTTAT CTGTGTCTGT CCGATTGTCT AGTGTCTATG ACTGATTTTA
    TCGTTGAATA GACACAGACA GGCTAACAGA TCACAGATAC TGACTAAAAT

601 TGCGCCTGCG TCGGTACTAG TTAGCTAACT AGCTCTGTAT CTGGCGGACC
    ACGCGGACGC AGCCATGATC AATCGATTGA TCGAGACATA GACCGCCTGG

651 CGTGGTGGAA CTGACGAGTT CTGAACACCC GGCCGCAACC CTGGGAGACG
    GCACCACCTT GACTGCTCAA GACTTGTGGG CCGGCGTTGG GACCCTCTGC

701 TCCCAGGGAC TTTGGGGGCC GTTTTGTGG CCCGACCTGA GGAAGGGAGT
    AGGGTCCCTG AAACCCCCGG CAAAAACACC GGGCTGGACT CCTTCCCTCA

751 CGATGTGGAA TCCGACCCCG TCAGGATATG TGGTTCTGGT AGGAGACGAG
    GCTACACCTT AGGCTGGGGC AGTCCTATAC ACCAAGACCA TCCTCTGCTC

801 AACCTAAAAC AGTTCCCGCC TCCGTCTGAA TTTTTGCTTT CGGTTTGGAA
    TTGGATTTTG TCAAGGGCGG AGGCAGACTT AAAAACGAAA GCCAAACCTT

851 CCGAAGCCGC GCGTCTTGTC TGCTGCAGCA TCGTTCTGTG TTGTCTCTGT
    GGCTTCGGCG CGCAGAACAG ACGACGTCGT AGCAAGACAC AACAGAGACA

901 CTGACTGTGT TTCTGTATTT GTCTGAAAAT TAGGGCCAGA CTGTTACCAC
    GACTGACACA AAGACATAAA CAGACTTTTA ATCCCGGTCT GACAATGGTG
```

FIGURE 13B

```
 951 TCCCTTAAGT TTGACCTTAG GTAACTGGAA AGATGTCGAG CGGCTCGCTC
     AGGGAATTCA AACTGGAATC CATTGACCTT TCTACAGCTC GCCGAGCGAG

1001 ACAACCAGTC GGTAGATGTC AAGAAGAGAC GTTGGGTTAC CTTCTGCTCT
     TGTTGGTCAG CCATCTACAG TTCTTCTCTG CAACCCAATG GAAGACGAGA

1051 GCAGAATGGC CAACCTTTAA CGTCGGATGG CCGCGAGACG GCACCTTTAA
     CGTCTTACCG GTTGGAAATT GCAGCCTACC GGCGCTCTGC CGTGGAAATT

1101 CCGAGACCTC ATCACCCAGG TTAAGATCAA GGTCTTTTCA CCTGGCCCGC
     GGCTCTGGAG TAGTGGGTCC AATTCTAGTT CCAGAAAAGT GGACCGGGCG

1151 ATGGACACCC AGACCAGGTC CCCTACATCG TGACCTGGGA AGCCTTGGCT
     TACCTGTGGG TCTGGTCCAG GGGATGTAGC ACTGGACCCT TCGGAACCGA

1201 TTTGACCCCC CTCCCTGGGT CAAGCCCTTT GTACACCCTA AGCCTCCGCC
     AAACTGGGGG GAGGGACCCA GTTCGGGAAA CATGTGGGAT TCGGAGGCGG

1251 TCCTCTTCCT CCATCCGCCC CGTCTCTCCC CCTTGAACCT CCTCGTTCGA
     AGGAGAAGGA GGTAGGCGGG GCAGAGAGGG GGAACTTGGA GGAGCAAGCT

1301 CCCCGCCTCG ATCCTCCCTT TATCCAGCCC TCACTCCTTC TCTAGGCGCC
     GGGGCGGAGC TAGGAGGGAA ATAGGTCGGG AGTGAGGAAG AGATCCGCGG

1351 GGCCGCTCTA GCCCATTAAT ACGACTCACT ATAGGGCGAT TCGAACACCA
     CCGGCGAGAT CGGGTAATTA TGCTGAGTGA TATCCCGCTA AGCTTGTGGT

1401 TGCACCATCA TCATCATCAC GTCGACGAAC AGAAACTCAT TTCCGAAGAA
     ACGTGGTAGT AGTAGTAGTG CAGCTGCTTG TCTTTGAGTA AAGGCTTCTT

1451 GACCTACTCG AGATGGGCGT GATTACGGAT TCACTGGCCG TCGTTTTACA
     CTGGATGAGC TCTACCCGCA CTAATGCCTA AGTGACCGGC AGCAAAATGT

1501 ACGTCGTGAC TGGGAAAACC CTGGCGTTAC CCAACTTAAT CGCCTTGCAG
     TGCAGCACTG ACCCTTTTGG GACCGCAATG GGTTGAATTA GCGGAACGTC

1551 CACATCCCCC TTTCGCCAGC TGGCGTAATA GCGAAGAGGC CCGCACCGAT
     GTGTAGGGGG AAAGCGGTCG ACCGCATTAT CGCTTCTCCG GGCGTGGCTA

1601 CGCCCTTCCC AACAGTTACG CAGCCTGAAT GGCGAATGGC GCTTTGCCTG
     GCGGGAAGGG TTGTCAATGC GTCGGACTTA CCGCTTACCG CGAAACGGAC

1651 GTTTCCGGCA CCAGAAGCGG TGCCGGAAAG CTGGCTGGAG TGCGATCTTC
     CAAAGGCCGT GGTCTTCGCC ACGGCCTTTC GACCGACCTC ACGCTAGAAG

1701 CTGAGGCCGA TACTGTCGTC GTCCCTCAA ACTGGCAGAT GCACGGTTAC
     GACTCCGGCT ATGACAGCAG CAGGGGAGTT TGACCGTCTA CGTGCCAATG

1751 GATGCGCCCA TCTACACCAA CGTGACCTAT CCCATTACGG TCAATCCGCC
     CTACGCGGGT AGATGTGGTT GCACTGGATA GGGTAATGCC AGTTAGGCGG

1801 GTTTGTTCCC ACGGAGAATC CGACGGGTTG TTACTCGCTC ACATTTAATG
     CAAACAAGGG TGCCTCTTAG GCTGCCCAAC AATGAGCGAG TGTAAATTAC

1851 TTGATGAAAG CTGGCTACAG GAAGGCCAGA CGCGAATTAT TTTTGATGGC
     AACTACTTTC GACCGATGTC CTTCCGGTCT GCGCTTAATA AAAACTACCG
```

FIGURE 13C

```
1901 GTTAACTCGG CGTTTCATCT GTGGTGCAAC GGGCGCTGGG TCGGTTACGG
     CAATTGAGCC GCAAAGTAGA CACCACGTTG CCCGCGACCC AGCCAATGCC
1951 CCAGGACAGT CGTTTGCCGT CTGAATTTGA CCTGAGCGCA TTTTTACGCG
     GGTCCTGTCA GCAAACGGCA GACTTAAACT GGACTCGCGT AAAAATGCGC
2001 CCGGAGAAAA CCGCCTCGCG GTGATGGTGC TGCGCTGGAG TGACGGCAGT
     GGCCTCTTTT GGCGGAGCGC CACTACCACG ACGCGACCTC ACTGCCGTCA
2051 TATCTGGAAG ATCAGGATAT GTGGCGGATG AGCGGCATTT TCCGTGACGT
     ATAGACCTTC TAGTCCTATA CACCGCCTAC TCGCCGTAAA AGGCACTGCA
2101 CTCGTTGCTG CATAAACCGA CTACACAAAT CAGCGATTTC CATGTTGCCA
     GAGCAACGAC GTATTTGGCT GATGTGTTTA GTCGCTAAAG GTACAACGGT
2151 CTCGCTTTAA TGATGATTTC AGCCGCGCTG TACTGGAGGC TGAAGTTCAG
     GAGCGAAATT ACTACTAAAG TCGGCGCGAC ATGACCTCCG ACTTCAAGTC
2201 ATGTGCGGCG AGTTGCGTGA CTACCTACGG GTAACAGTTT CTTTATGGCA
     TACACGCCGC TCAACGCACT GATGGATGCC CATTGTCAAA GAAATACCGT
2251 GGGTGAAACG CAGGTCGCCA GCGGCACCGC GCCTTTCGGC GGTGAAATTA
     CCCACTTTGC GTCCAGCGGT CGCCGTGGCG CGGAAAGCCG CCACTTTAAT
2301 TCGATGAGCG TGGTGGTTAT GCCGATCGCG TCACACTACG TCTGAACGTC
     AGCTACTCGC ACCACCAATA CGGCTAGCGC AGTGTGATGC AGACTTGCAG
2351 GAAAACCCGA AACTGTGGAG CGCCGAAATC CCGAATCTCT ATCGTGCGGT
     CTTTTGGGCT TTGACACCTC GCGGCTTTAG GGCTTAGAGA TAGCACGCCA
2401 GGTTGAACTG CACACCGCCG ACGGCACGCT GATTGAAGCA GAAGCCTGCG
     CCAACTTGAC GTGTGGCGGC TGCCGTGCGA CTAACTTCGT CTTCGGACGC
2451 ATGTCGGTTT CCGCGAGGTG CGGATTGAAA ATGGTCTGCT GCTGCTGAAC
     TACAGCCAAA GGCGCTCCAC GCCTAACTTT TACCAGACGA CGACGACTTG
2501 GGCAAGCCGT TGCTGATTCG AGGCGTTAAC CGTCACGAGC ATCATCCTCT
     CCGTTCGGCA ACGACTAAGC TCCGCAATTG GCAGTGCTCG TAGTAGGAGA
2551 GCATGGTCAG GTCATGGATG AGCAGACGAT GGTGCAGGAT ATCCTGCTGA
     CGTACCAGTC CAGTACCTAC TCGTCTGCTA CCACGTCCTA TAGGACGACT
2601 TGAAGCAGAA CAACTTTAAC GCCGTGCGCT GTTCGCATTA TCCGAACCAT
     ACTTCGTCTT GTTGAAATTG CGGCACGCGA CAAGCGTAAT AGGCTTGGTA
2651 CCGCTGTGGT ACACGCTGTG CGACCGCTAC GGCCTGTATG TGGTGGATGA
     GGCGACACCA TGTGCGACAC GCTGGCGATG CCGGACATAC ACCACCTACT
2701 AGCCAATATT GAAACCCACG GCATGGTGCC AATGAATCGT CTGACCGATG
     TCGGTTATAA CTTTGGGTGC CGTACCACGG TTACTTAGCA GACTGGCTAC
2751 ATCCGCGCTG GCTACCGGCG ATGAGCGAAC GCGTAACGCG AATGGTGCAG
     TAGGCGCGAC CGATGGCCGC TACTCGCTTG CGCATTGCGC TTACCACGTC
2801 CGCGATCGTA ATCACCCGAG TGTGATCATC TGGTCGCTGG GGAATGAATC
     GCGCTAGCAT TAGTGGGCTC ACACTAGTAG ACCAGCGACC CCTTACTTAG
```

FIGURE 13D

```
2851 AGGCCACGGC GCTAATCACG ACGCGCTGTA TCGCTGGATC AAATCTGTCG
     TCCGGTGCCG CGATTAGTGC TGCGCGACAT AGCGACCTAG TTTAGACAGC

2901 ATCCTTCCCG CCCGGTGCAG TATGAAGGCG GCGGAGCCGA CACCACGGCC
     TAGGAAGGGC GGGCCACGTC ATACTTCCGC CGCCTCGGCT GTGGTGCCGG

2951 ACCGATATTA TTTGCCCGAT GTACGCGCGC GTGGATGAAG ACCAGCCCTT
     TGGCTATAAT AAACGGGCTA CATGCGCGCG CACCTACTTC TGGTCGGGAA

3001 CCCGGCTGTG CCGAAATGGT CCATCAAAAA ATGGCTTTCG CTACCTGGAG
     GGGCCGACAC GGCTTTACCA GGTAGTTTTT TACCGAAAGC GATGGACCTC

3051 AGACGCGCCC GCTGATCCTT TGCGAATACG CCCACGCGAT GGGTAACAGT
     TCTGCGCGGG CGACTAGGAA ACGCTTATGC GGGTGCGCTA CCCATTGTCA

3101 CTTGGCGGTT TCGCTAAATA CTGGCAGGCG TTTCGTCAGT ATCCCCGTTT
     GAACCGCCAA AGCGATTTAT GACCGTCCGC AAAGCAGTCA TAGGGGCAAA

3151 ACAGGGCGGC TTCGTCTGGG ACTGGGTGGA TCAGTCGCTG ATTAAATATG
     TGTCCCGCCG AAGCAGACCC TGACCCACCT AGTCAGCGAC TAATTTATAC

3201 ATGAAAACGG CAACCCGTGG TCGGCTTACG GCGGTGATTT TGGCGATACG
     TACTTTTGCC GTTGGGCACC AGCCGAATGC CGCCACTAAA ACCGCTATGC

3251 CCGAACGATC GCCAGTTCTG TATGAACGGT CTGGTCTTTG CCGACCGCAC
     GGCTTGCTAG CGGTCAAGAC ATACTTGCCA GACCAGAAAC GGCTGGCGTG

3301 GCCGCATCCA GCGCTGACGG AAGCAAAACA CCAGCAGCAG TTTTTCCAGT
     CGGCGTAGGT CGCGACTGCC TTCGTTTTGT GGTCGTCGTC AAAAAGGTCA

3351 TCCGTTTATC CGGGCAAACC ATCGAAGTGA CCAGCGAATA CCTGTTCCGT
     AGGCAAATAG GCCCGTTTGG TAGCTTCACT GGTCGCTTAT GGACAAGGCA

3401 CATAGCGATA ACGAGCTCCT GCACTGGATG GTGGCGCTGG ATGGTAAGCC
     GTATCGCTAT TGCTCGAGGA CGTGACCTAC CACCGCGACC TACCATTCGG

3451 GCTGGCAAGC GGTGAAGTGC CTCTGGATGT CGCTCCACAA GGTAAACAGT
     CGACCGTTCG CCACTTCACG GAGACCTACA GCGAGGTGTT CCATTTGTCA

3501 TGATTGAACT GCCTGAACTA CCGCAGCCGG AGAGCGCCGG GCAACTCTGG
     ACTAACTTGA CGGACTTGAT GGCGTCGGCC TCTCGCGGCC CGTTGAGACC

3551 CTCACAGTAC GCGTAGTGCA ACCGAACGCG ACCGCATGGT CAGAAGCCGG
     GAGTGTCATG CGCATCACGT TGGCTTGCGC TGGCGTACCA GTCTTCGGCC

3601 GCACATCAGC GCCTGGCAGC AGTGGCGTCT GGCGGAAAAC CTCAGTGTGA
     CGTGTAGTCG CGGACCGTCG TCACCGCAGA CCGCCTTTTG GAGTCACACT

3651 CGCTCCCCGC CGCGTCCCAC GCCATCCCGC ATCTGACCAC CAGCGAAATG
     GCGAGGGGCG GCGCAGGGTG CGGTAGGGCG TAGACTGGTG GTCGCTTTAC

3701 GATTTTTGCA TCGAGCTGGG TAATAAGCGT TGGCAATTTA ACCGCCAGTC
     CTAAAAACGT AGCTCGACCC ATTATTCGCA ACCGTTAAAT TGGCGGTCAG

3751 AGGCTTTCTT TCACAGATGT GGATTGGCGA TAAAAAACAA CTGCTGACGC
     TCCGAAAGAA AGTGTCTACA CCTAACCGCT ATTTTTGTT GACGACTGCG
```

FIGURE 13E

```
3801 CGCTGCGCGA TCAGTTCACC CGTGTCGATA GATCTGGAGG TGGTGGCAGC
     GCGACGCGCT AGTCAAGTGG GCACAGCTAT CTAGACCTCC ACCACCGTCG

3851 AGGCCTTGGC GCGCCGGATC CTTAATTAAC AATTGACCGG TAATAATAGG
     TCCGGAACCG CGCGGCCTAG GAATTAATTG TTAACTGGCC ATTATTATCC

3901 TAGATAAGTG ACTGATTAGA TGCATTTCGA CTAGATCCCT CGACCAATTC
     ATCTATTCAC TGACTAATCT ACGTAAAGCT GATCTAGGGA GCTGGTTAAG

3951 CGGTTATTTT CCACCATATT GCCGTCTTTT GGCAATGTGA GGGCCCGGAA
     GCCAATAAAA GGTGGTATAA CGGCAGAAAA CCGTTACACT CCCGGGCCTT

4001 ACCTGGCCCT GTCTTCTTGA CGAGCATTCC TAGGGGTCTT TCCCCTCTCG
     TGGACCGGGA CAGAAGAACT GCTCGTAAGG ATCCCCAGAA AGGGGAGAGC

4051 CCAAAGGAAT GCAAGGTCTG TTGAATGTCG TGAAGGAAGC AGTTCCTCTG
     GGTTTCCTTA CGTTCCAGAC AACTTACAGC ACTTCCTTCG TCAAGGAGAC

4101 GAAGCTTCTT GAAGACAAAC AACGTCTGTA GCGACCCTTT GCAGGCAGCG
     CTTCGAAGAA CTTCTGTTTG TTGCAGACAT CGCTGGGAAA CGTCCGTCGC

4151 GAACCCCCCA CCTGGCGACA GGTGCCTCTG CGGCCAAAAG CCACGTGTAT
     CTTGGGGGGT GGACCGCTGT CCACGGAGAC GCCGGTTTTC GGTGCACATA

4201 AAGATACACC TGCAAAGGCG GCACAACCCC AGTGCCACGT TGTGAGTTGG
     TTCTATGTGG ACGTTTCCGC CGTGTTGGGG TCACGGTGCA ACACTCAACC

4251 ATAGTTGTGG AAAGAGTCAA ATGGCTCTCC TCAAGCGTAT TCAACAAGGG
     TATCAACACC TTTCTCAGTT TACCGAGAGG AGTTCGCATA AGTTGTTCCC

4301 GCTGAAGGAT GCCCAGAAGG TACCCCATTG TATGGGATCT GATCTGGGGC
     CGACTTCCTA CGGGTCTTCC ATGGGGTAAC ATACCCTAGA CTAGACCCCG

4351 CTCGGTGCAC ATGCTTTACA TGTGTTTAGT CGAGGTTAAA AAACGTCTAG
     GAGCCACGTG TACGAAATGT ACACAAATCA GCTCCAATTT TTTGCAGATC

4401 GCCCCCCGAA CCACGGGGAC GTGGTTTTCC TTTGAAAAAC ACGATGATAA
     CGGGGGGCTT GGTGCCCCTG CACCAAAAGG AAACTTTTTG TGCTACTATT

4451 TACCATGAAA AAGCCTGAAC TCACCGCGAC GTCTGTCGAG AAGTTTCTGA
     ATGGTACTTT TTCGGACTTG AGTGGCGCTG CAGACAGCTC TTCAAAGACT

4501 TCGAAAAGTT CGACAGCGTC TCCGACCTGA TGCAGCTCTC GGAGGGCGAA
     AGCTTTTCAA GCTGTCGCAG AGGCTGGACT ACGTCGAGAG CCTCCCGCTT

4551 GAATCTCGTG CTTTCAGCTT CGATGTAGGA GGGCGTGGAT ATGTCCTGCG
     CTTAGAGCAC GAAAGTCGAA GCTACATCCT CCCGCACCTA TACAGGACGC

4601 GGTAAATAGC TGCGCCGATG GTTTCTACAA AGATCGTTAT GTTTATCGGC
     CCATTTATCG ACGCGGCTAC CAAAGATGTT TCTAGCAATA CAAATAGCCG

4651 ACTTTGCATC GGCCGCGCTC CCGATTCCGG AAGTGCTTGA CATTGGGGAA
     TGAAACGTAG CCGGCGCGAG GGCTAAGGCC TTCACGAACT GTAACCCCTT

4701 TTTAGCGAGA GCCTGACCTA TTGCATCTCC CGCCGTGCAC AGGGTGTCAC
     AAATCGCTCT CGGACTGGAT AACGTAGAGG GCGGCACGTG TCCCACAGTG
```

FIGURE 13F

```
4751 GTTGCAAGAC CTGCCTGAAA CCGAACTGCC CGCTGTTCTG CAGCCGGTCG
     CAACGTTCTG GACGGACTTT GGCTTGACGG GCGACAAGAC GTCGGCCAGC

4801 CGGAGGCCAT GGATGCGATC GCTGCGGCCG ATCTTAGCCA GACGAGCGGG
     GCCTCCGGTA CCTACGCTAG CGACGCCGGC TAGAATCGGT CTGCTCGCCC

4851 TTCGGCCCAT TCGGACCGCA AGGAATCGGT CAATACACTA CATGGCGTGA
     AAGCCGGGTA AGCCTGGCGT TCCTTAGCCA GTTATGTGAT GTACCGCACT

4901 TTTCATATGC GCGATTGCTG ATCCCCATGT GTATCACTGG CAAACTGTGA
     AAAGTATACG CGCTAACGAC TAGGGTACA CATAGTGACC GTTTGACACT

4951 TGGACGACAC CGTCAGTGCG TCCGTCGCGC AGGCTCTCGA TGAGCTGATG
     ACCTGCTGTG GCAGTCACGC AGGCAGCGCG TCCGAGAGCT ACTCGACTAC

5001 CTTTGGGCCG AGGACTGCCC CGAAGTCCGG CACCTCGTGC ACGCGGATTT
     GAAACCCGGC TCCTGACGGG GCTTCAGGCC GTGGAGCACG TGCGCCTAAA

5051 CGGCTCCAAC AATGTCCTGA CGGACAATGG CCGCATAACA GCGGTCATTG
     GCCGAGGTTG TTACAGGACT GCCTGTTACC GGCGTATTGT CGCCAGTAAC

5101 ACTGGAGCGA GGCGATGTTC GGGGATTCCC AATACGAGGT CGCCAACATC
     TGACCTCGCT CCGCTACAAG CCCCTAAGGG TTATGCTCCA GCGGTTGTAG

5151 TTCTTCTGGA GGCCGTGGTT GGCTTGTATG GAGCAGCAGA CGCGCTACTT
     AAGAAGACCT CCGGCACCAA CCGAACATAC CTCGTCGTCT GCGCGATGAA

5201 CGAGCGGAGG CATCCGGAGC TTGCAGGATC GCCGCGGCTC CGGGCGTATA
     GCTCGCCTCC GTAGGCCTCG AACGTCCTAG CGGCGCCGAG GCCCGCATAT

5251 TGCTCCGCAT TGGTCTTGAC CAACTCTATC AGAGCTTGGT TGACGGCAAT
     ACGAGGCGTA ACCAGAACTG GTTGAGATAG TCTCGAACCA ACTGCCGTTA

5301 TTCGATGATG CAGCTTGGGC GCAGGGTCGA TGCGACGCAA TCGTCCGATC
     AAGCTACTAC GTCGAACCCG CGTCCCAGCT ACGCTGCGTT AGCAGGCTAG

5351 CGGAGCCGGG ACTGTCGGGC GTACACAAAT CGCCCGCAGA AGCGCGGCCG
     GCCTCGGCCC TGACAGCCCG CATGTGTTTA GCGGGCGTCT TCGCGCCGGC

5401 TCTGGACCGA TGGCTGTGTA GAAGTACTCG CCGATAGTGG AAACCGACGC
     AGACCTGGCT ACCGACACAT CTTCATGAGC GGCTATCACC TTTGGCTGCG

5451 CCCAGCACTC GTCCGAGGGC AAAGGAATAG AGTAGATGCC GACCGGGATC
     GGGTCGTGAG CAGGCTCCCG TTTCCTTATC TCATCTACGG CTGGCCCTAG

5501 TATCGATAAA ATAAAAGATT TTATTTAGTC TCCAGAAAAA GGGGGGAATG
     ATAGCTATTT TATTTTCTAA AATAAATCAG AGGTCTTTTT CCCCCCTTAC

5551 AAAGACCCCA CCTGTAGGTT TGGCAAGCTA GCTTAAGTAA CGCCATTTTG
     TTTCTGGGGT GGACATCCAA ACCGTTCGAT CGAATTCATT GCGGTAAAAC

5601 CAAGGCATGG AAAATACAT AACTGAGAAT AGAGAAGTTC AGATCAAGGT
     GTTCCGTACC TTTTTATGTA TTGACTCTTA TCTCTTCAAG TCTAGTTCCA

5651 CAGGAACAGA TGGAACAGCT GAATATGGGC CAAACAGGAT ATCTGTGGTA
     GTCCTTGTCT ACCTTGTCGA CTTATACCCG GTTTGTCCTA TAGACACCAT
```

FIGURE 13G

```
5701 AGCAGTTCCT GCCCCGGCTC AGGGCCAAGA ACAGATGGAA CAGCTGAATA
     TCGTCAAGGA CGGGGCCGAG TCCCGGTTCT TGTCTACCTT GTCGACTTAT

5751 TGGGCCAAAC AGGATATCTG TGGTAAGCAG TTCCTGCCCC GGCTCAGGGC
     ACCCGGTTTG TCCTATAGAC ACCATTCGTC AAGGACGGGG CCGAGTCCCG

5801 CAAGAACAGA TGGTCCCCAG ATGCGGTCCA GCCCTCAGCA GTTTCTAGAG
     GTTCTTGTCT ACCAGGGGTC TACGCCAGGT CGGGAGTCGT CAAAGATCTC

5851 AACCATCAGA TGTTTCCAGG GTGCCCCAAG GACCTGAAAT GACCCTGTGC
     TTGGTAGTCT ACAAAGGTCC CACGGGGTTC CTGGACTTTA CTGGGACACG

5901 CTTATTTGAA CTAACCAATC AGTTCGCTTC TCGCTTCTGT TCGCGCGCTT
     GAATAAACTT GATTGGTTAG TCAAGCGAAG AGCGAAGACA AGCGCGCGAA

5951 CTGCTCCCCG AGCTCAATAA AAGAGCCCAC AACCCCTCAC TCGGGGCGCC
     GACGAGGGGC TCGAGTTATT TTCTCGGGTG TTGGGGAGTG AGCCCCGCGG

6001 AGTCCTCCGA TTGACTGAGT CGCCCGGGTA CCCGTGTATC CAATAAACCC
     TCAGGAGGCT AACTGACTCA GCGGGCCCAT GGGCACATAG GTTATTTGGG

6051 TCTTGCAGTT GCATCCGACT TGTGGTCTCG CTGTTCCTTG GGAGGGTCTC
     AGAACGTCAA CGTAGGCTGA ACACCAGAGC GACAAGGAAC CCTCCCAGAG

6101 CTCTGAGTGA TTGACTACCC GTCAGCGGGG GTCTTTCATT CATGCAGCAT
     GAGACTCACT AACTGATGGG CAGTCGCCCC CAGAAAGTAA GTACGTCGTA

6151 GTATCAAAAT TAATTTGGTT TTTTTTCTTA AGTATTTACA TTAAATGGCC
     CATAGTTTTA ATTAAACCAA AAAAAAGAAT TCATAAATGT AATTTACCGG

6201 ATAGTTGCAT TAATGAATCG GCCAACGCGC GGGGAGAGGC GGTTTGCGTA
     TATCAACGTA ATTACTTAGC CGGTTGCGCG CCCCTCTCCG CCAAACGCAT

6251 TTGGCGCTCT TCCGCTTCCT CGCTCACTGA CTCGCTGCGC TCGGTCGTTC
     AACCGCGAGA AGGCGAAGGA GCGAGTGACT GAGCGACGCG AGCCAGCAAG

6301 GGCTGCGGCG AGCGGTATCA GCTCACTCAA AGGCGGTAAT ACGGTTATCC
     CCGACGCCGC TCGCCATAGT CGAGTGAGTT TCCGCCATTA TGCCAATAGG

6351 ACAGAATCAG GGGATAACGC AGGAAAGAAC ATGTGAGCAA AAGGCCAGCA
     TGTCTTAGTC CCCTATTGCG TCCTTTCTTG TACACTCGTT TTCCGGTCGT

6401 AAAGGCCAGG AACCGTAAAA AGGCCGCGTT GCTGGCGTTT TTCCATAGGC
     TTTCCGGTCC TTGGCATTTT TCCGGCGCAA CGACCGCAAA AAGGTATCCG

6451 TCCGCCCCCC TGACGAGCAT CACAAAAATC GACGCTCAAG TCAGAGGTGG
     AGGCGGGGGG ACTGCTCGTA GTGTTTTTAG CTGCGAGTTC AGTCTCCACC

6501 CGAAACCCGA CAGGACTATA AAGATACCAG GCGTTTCCCC CTGGAAGCTC
     GCTTTGGGCT GTCCTGATAT TTCTATGGTC CGCAAAGGGG GACCTTCGAG

6551 CCTCGTGCGC TCTCCTGTTC CGACCCTGCC GCTTACCGGA TACCTGTCCG
     GGAGCACGCG AGAGGACAAG GCTGGGACGG CGAATGGCCT ATGGACAGGC

6601 CCTTTCTCCC TTCGGGAAGC GTGGCGCTTT CTCATAGCTC ACGCTGTAGG
     GGAAAGAGGG AAGCCCTTCG CACCGCGAAA GAGTATCGAG TGCGACATCC
```

FIGURE 13H

```
6651 TATCTCAGTT CGGTGTAGGT CGTTCGCTCC AAGCTGGGCT GTGTGCACGA
     ATAGAGTCAA GCCACATCCA GCAAGCGAGG TTCGACCCGA CACACGTGCT

6701 ACCCCCCGTT CAGCCCGACC GCTGCGCCTT ATCCGGTAAC TATCGTCTTG
     TGGGGGGCAA GTCGGGCTGG CGACGCGGAA TAGGCCATTG ATAGCAGAAC

6751 AGTCCAACCC GGTAAGACAC GACTTATCGC CACTGGCAGC AGCCACTGGT
     TCAGGTTGGG CCATTCTGTG CTGAATAGCG GTGACCGTCG TCGGTGACCA

6801 AACAGGATTA GCAGAGCGAG GTATGTAGGC GGTGCTACAG AGTTCTTGAA
     TTGTCCTAAT CGTCTCGCTC CATACATCCG CCACGATGTC TCAAGAACTT

6851 GTGGTGGCCT AACTACGGCT ACACTAGAAG AACAGTATTT GGTATCTGCG
     CACCACCGGA TTGATGCCGA TGTGATCTTC TTGTCATAAA CCATAGACGC

6901 CTCTGCTGAA GCCAGTTACC TTCGGAAAAA GAGTTGGTAG CTCTTGATCC
     GAGACGACTT CGGTCAATGG AAGCCTTTTT CTCAACCATC GAGAACTAGG

6951 GGCAAACAAA CCACCGCTGG TAGCGGTGGT TTTTTTGTTT GCAAGCAGCA
     CCGTTTGTTT GGTGGCGACC ATCGCCACCA AAAAAACAAA CGTTCGTCGT

7001 GATTACGCGC AGAAAAAAAG GATCTCAAGA AGATCCTTTG ATCTTTTCTA
     CTAATGCGCG TCTTTTTTTC CTAGAGTTCT TCTAGGAAAC TAGAAAAGAT

7051 CGGGGTCTGA CGCTCAGTGG AACGAAAACT CACGTTAAGG GATTTTGGTC
     GCCCCAGACT GCGAGTCACC TTGCTTTTGA GTGCAATTCC CTAAAACCAG

7101 ATGAGATTAT CAAAAAGGAT CTTCACCTAG ATCCTTTTGC GGCCGCAAAT
     TACTCTAATA GTTTTTCCTA GAAGTGGATC TAGGAAAACG CCGGCGTTTA

7151 CAATCTAAAG TATATATGAG TAAACTTGGT CTGACAGTTA CCAATGCTTA
     GTTAGATTTC ATATATACTC ATTTGAACCA GACTGTCAAT GGTTACGAAT

7201 ATCAGTGAGG CACCTATCTC AGCGATCTGT CTATTTCGTT CATCCATAGT
     TAGTCACTCC GTGGATAGAG TCGCTAGACA GATAAAGCAA GTAGGTATCA

7251 TGCCTGACTC CCCGTCGTGT AGATAACTAC GATACGGGAG GGCTTACCAT
     ACGGACTGAG GGGCAGCACA TCTATTGATG CTATGCCCTC CCGAATGGTA

7301 CTGGCCCCAG TGCTGCAATG ATACCGCGAG ACCCACGCTC ACCGGCTCCA
     GACCGGGGTC ACGACGTTAC TATGGCGCTC TGGGTGCGAG TGGCCGAGGT

7351 GATTTATCAG CAATAAACCA GCCAGCCGGA AGGGCCGAGC GCAGAAGTGG
     CTAAATAGTC GTTATTTGGT CGGTCGGCCT TCCCGGCTCG CGTCTTCACC

7401 TCCTGCAACT TTATCCGCCT CCATCCAGTC TATTAATTGT TGCCGGGAAG
     AGGACGTTGA AATAGGCGGA GGTAGGTCAG ATAATTAACA ACGGCCCTTC

7451 CTAGAGTAAG TAGTTCGCCA GTTAATAGTT TGCGCAACGT TGTTGCCATT
     GATCTCATTC ATCAAGCGGT CAATTATCAA ACGCGTTGCA ACAACGGTAA

7501 GCTACAGGCA TCGTGGTGTC ACGCTCGTCG TTTGGTATGG CTTCATTCAG
     CGATGTCCGT AGCACCACAG TGCGAGCAGC AAACCATACC GAAGTAAGTC

7551 CTCCGGTTCC CAACGATCAA GGCGAGTTAC ATGATCCCCC ATGTTGTGCA
     GAGGCCAAGG GTTGCTAGTT CCGCTCAATG TACTAGGGGG TACAACACGT
```

FIGURE 13I

```
7601 AAAAAGCGGT TAGCTCCTTC GGTCCTCCGA TCGTTGTCAG AAGTAAGTTG
     TTTTTCGCCA ATCGAGGAAG CCAGGAGGCT AGCAACAGTC TTCATTCAAC

7651 GCCGCAGTGT TATCACTCAT GGTTATGGCA GCACTGCATA ATTCTCTTAC
     CGGCGTCACA ATAGTGAGTA CCAATACCGT CGTGACGTAT TAAGAGAATG

7701 TGTCATGCCA TCCGTAAGAT GCTTTTCTGT GACTGGTGAG TACTCAACCA
     ACAGTACGGT AGGCATTCTA CGAAAAGACA CTGACCACTC ATGAGTTGGT

7751 AGTCATTCTG AGAATAGTGT ATGCGGCGAC CGAGTTGCTC TTGCCCGGCG
     TCAGTAAGAC TCTTATCACA TACGCCGCTG GCTCAACGAG AACGGGCCGC

7801 TCAATACGGG ATAATACCGC GCCACATAGC AGAACTTTAA AAGTGCTCAT
     AGTTATGCCC TATTATGGCG CGGTGTATCG TCTTGAAATT TTCACGAGTA

7851 CATTGGAAAA CGTTCTTCGG GGCGAAAACT CTCAAGGATC TTACCGCTGT
     GTAACCTTTT GCAAGAAGCC CCGCTTTTGA GAGTTCCTAG AATGGCGACA

7901 TGAGATCCAG TTCGATGTAA CCCACTCGTG CACCCAACTG ATCTTCAGCA
     ACTCTAGGTC AAGCTACATT GGGTGAGCAC GTGGGTTGAC TAGAAGTCGT

7951 TCTTTTACTT TCACCAGCGT TTCTGGGTGA GCAAAAACAG GAAGGCAAAA
     AGAAAATGAA AGTGGTCGCA AAGACCCACT CGTTTTTGTC CTTCCGTTTT

8001 TGCCGCAAAA AAGGGAATAA GGGCGACACG GAAATGTTGA ATACTCATAC
     ACGGCGTTTT TTCCCTTATT CCCGCTGTGC CTTTACAACT TATGAGTATG

8051 TCTTCCTTTT TCAATATTAT TGAAGCATTT ATCAGGGTTA TTGTCTCATG
     AGAAGGAAAA AGTTATAATA ACTTCGTAAA TAGTCCCAAT AACAGAGTAC

8101 AGCGGATACA TATTTGAATG TATTTAGAAA AATAAACAAA TAGGGGTTCC
     TCGCCTATGT ATAAACTTAC ATAAATCTTT TTATTTGTTT ATCCCCAAGG

8151 GCGCACATTT C
     CGCGTGTAAA G
```

FIGURE 13J

Vector for Expression of a GPCR with inserted
Seronine/Threonine amino acid sequences as a fusion with β-gal Δα.

Vector for Expression of mutant (R170E) β-arrestin2 as a fusion with β-gal Δω.

Ligand Fishing for Orphan Receptors by β-galactosidase mutant complementation in ICAST™ System

SYSTEMS FOR SENSITIVE DETECTION OF G-PROTEIN COUPLED RECEPTOR AND ORPHAN RECEPTOR FUNCTION USING REPORTER ENZYME MUTANT COMPLEMENTATION

CROSS REFERENCE TO RELATED APPLICATIONS

This application is a continuation of application Ser. No. 09/759,152, filed Jan. 16, 2001 now U.S. Pat. No. 6,800,445, which is a continuation-in-part of application Ser. No. 09/654,499, filed Sep. 1, 2000 now U.S. Pat. No. 6,893,827, which claims the benefit from Provisional Application No. 60/180,669, filed Feb. 7, 2000, which are all incorporated herein by reference.

FIELD OF THE INVENTION

The present invention relates to methods of detecting G-protein-coupled receptor (GPCR) activity, and provides methods of assaying GPCR activity, methods for screening for GPCR ligands, agonists and/or antagonists, methods for screening natural and surrogate ligands for orphan GPCRs, and methods for screening compounds that interact with components of the GPCR regulatory process.

BACKGROUND OF THE TECHNOLOGY

The actions of many extracellular signals are mediated by the interaction of G-protein-coupled receptors (GPCRs) and guanine nucleotide-binding regulatory proteins (G-proteins). G-protein-mediated signaling systems have been identified in many divergent organisms, such as mammals and yeast. The GPCRs represent a large super family of proteins which have divergent amino acid sequences, but share common structural features, in particular, the presence of seven transmembrane helical domains. GPCRs respond to, among other extracellular signals, neurotransmitters, hormones, odorants and light. Individual GPCR types activate a particular signal transduction pathway; at least ten different signal transduction pathways are known to be activated via GPCRs. For example, the beta 2-adrenergic receptor ($\beta$2AR) is a prototype mammalian GPCR. In response to agonist binding, $\beta$2AR receptors activate a G-protein (Gs) which in turn stimulates adenylate cyclase activity and results in increased cyclic adenosine monophosphate (cAMP) production in the cell.

The signaling pathway and final cellular response that result from GPCR stimulation depends on the specific class of G-protein with which the particular receptor is coupled (Hamm, "The Many Faces of G-Protein Signaling." J. Biol. Chem., 273:669–672 (1998)). For instance, coupling to the Gs class of G-proteins stimulates cAMP production and activation of the Protein Kinase A and C pathways, whereas coupling to the Gi class of G-proteins down regulates cAMP. Other second messenger systems such as calcium, phospholipase C, and phosphatidylinositol 3 may also be utilized. As a consequence, GPCR signaling events have predominantly been measured via quantification of these second messenger products.

The decrease of a response to a persistent stimulus is a widespread biological phenomenon. Signaling by diverse GPCRs is believed to be terminated by a uniform two-step mechanism. Activated receptor is first phosphorylated by a GPCR kinase (GRK). An arrestin protein binds to the activated and phosphorylated receptor, thus blocking G-protein interaction. This process is commonly referred to as desensitization, a general mechanism that has been demonstrated in a variety of functionally diverse GPCRs. Arrestin also plays a part in regulating GPCR internalization and resensitization, processes that are heterogenous among different GPCRs (Oakley, et al., J. Biol. Chem., 274:32248–32257 (1999)). The interaction between an arrestin and GPCR in processes of internalization and resensitization is dictated by the specific sequence motif in the carboxyl terminus of a given GPCR. Only a subset of GPCRs, which possess clusters of three serine or threonine residues at the carboxyl termini, were found to co-traffick with the arrestins into the endocytic vesicles after ligand stimulation. The number of receptor kinases and arrestins involved in desensitization of GPCRs is rather limited.

A common feature of GPCR physiology is desensitization and recycling of the receptor through the processes of receptor phosphorylation, endocytosis and dephosphorylation (Ferguson, et al., "G-protein-coupled receptor regulation: role of G-protein-coupled receptor kinases and arresting." Can. J. Physiol. Pharmacol., 74:1095–1110 (1996)). Ligand-occupied GPCRs can be phosphorylated by two families of serine/threonine kinases, the G-protein-coupled receptor kinases (GRKs) and the second messenger-dependent protein kinases such as protein kinase A and protein kinase C. Phosphorylation by either class of kinases serves to down-regulate the receptor by uncoupling it from its corresponding G-protein. GRK-phosphorylation also serves to down-regulate the receptor by recruitment of a class of proteins known as the arrestins that bind the cytoplasmic domain of the receptor and promote clustering of the receptor into endocytic vescicles. Once the receptor is endocytosed, it will either be degraded in lysosomes or dephosphorylated and recycled back to the plasma membrane as a fully-functional receptor.

Binding of an arrestin protein to an activated receptor has been documented as a common phenomenon of a variety of GPCRs ranging from rhodopsin to $\beta$2AR to the neurotensin receptor (Barak, et al., "A $\beta$-arrestin/Green Fluorescent Fusion Protein Biosensor for Detecting G-Protein-Coupled Receptor Activation," J. Biol. Chem., 272:27497–500 (1997)). Consequently, monitoring arrestin interaction with a specific GPCR can be utilized as a generic tool for measuring GPCR activation. Similarly, a single G-protein and GRK also partner with a variety of receptors (Hamm, et al. (1998) and Pitcher et al., "G-Protein-Coupled Receptor Kinases," Annu. Rev. Biochem., 67:653–92 (1998)), such that these protein/protein interactions may also be monitored to determine receptor activity.

Many therapeutic drugs in use today target GPCRs, as they regulate vital physiological responses, including vasodilation, heart rate, bronchodilation, endocrine secretion and gut peristalsis. See, e.g., Lefkowitz et al., Annu. Rev. Biochem., 52:159 (1983). Some of these drugs mimic the ligand for this receptor. Other drugs act to antagonize the receptor in cases when disease arises from spontaneous activity of the receptor.

Efforts such as the Human Genome Project are identifying new GPCRs ("orphan" receptors) whose physiological roles and ligands are unknown. It is estimated that several thousand GPCRs exist in the human genome.

Various approaches have been used to monitor intracellular activity in response to a stimulant, e.g., enzyme-linked immunosorbent assay (ELISA); Fluorescense Imaging Plate Reader assay (FLIPR™, Molecular Devices Corp., Sunnyvale, Calif.); EVOscreen™, EVOTEC™, Evotec Biosystems Gmbh, Hamburg, Germany; and techniques developed by CELLOMICS™, Cellomics, Inc., Pittsburgh, Pa.

Germino et al., "Screening for in vivo protein-protein interactions." Proc. Natl. Acad. Sci., 90(3):933–937 (1993), discloses an in vivo approach for the isolation of proteins interacting with a protein of interest.

Phizicky et al., "Protein-protein interactions: methods for detection and analysis." Microbiol. Rev., 59(1): 94–123 (1995), discloses a review of biochemical, molecular biological and genetic methods used to study protein-protein interactions.

Offermanns et al., "$G\alpha_{15}$ and $G\alpha_{16}$ Couple a Wide Variety of Receptors to Phospholipase C." J. Biol. Chem., 270(25): 15175–15180 (1995), discloses that $G\alpha_{15}$ and $G\alpha_{16}$ can be activated by a wide variety of G-protein-coupled receptors. The selective coupling of an activated receptor to a distinct pattern of G-proteins is regarded as an important requirement to achieve accurate signal transduction. Id.

Barak et al., "A β-arrestin/Green Fluorescent Protein Biosensor for Detecting G Protein-coupled Receptor Activation." J. Biol. Chem., 272(44):27497–27500 (1997) and U.S. Pat. Nos. 5,891,646 and 6,110,693 disclose the use of a β-arrestin/green fluorescent fusion protein (GFP) for imaging protein translocation upon stimulation of GPCR with optical devices.

Each of the references described above has drawbacks. For example,

The prior art methodologies require over-expression of the proteins, which could cause artifact and tip the balance of cellular regulatory machineries.

The prior art visualization or imaging assays are low throughput and lack thorough quantification. Therefore, they are not suitable for high throughput pharmacological and kinetic assays.

In addition, many of the prior art assays require isolation of the GPCR rather than observation of the GPCR in a cell. There thus exists a need for improved methods for monitoring GPCR function.

SUMMARY OF THE INVENTION

The present invention provides modifications to the disclosure in U.S. application Ser. No. 09/654,499. In particular, the present invention is directed to modifications of the below aspects of the invention to further enhance assay sensitivity. The modifications include the use of genetically modified arrestins that exhibit enhanced binding to activated GPCR regardless of whether the GPCR is phosphorylated or non-phosphorylated; the use of a serine/threonine cluster strategy to facilitate screening assays for orphan receptors that do not possess this structural motif on their own; and the use of a combination of the above modifications to achieve even more enhanced detection.

A first aspect of the present invention is a method that monitors GPCR function proximally at the site of receptor activation, thus providing more information for drug discovery purposes due to fewer competing mechanisms. Activation of the GPCR is measured by a read-out for interaction of the receptor with a regulatory component such as arrestin, G-protein, GRK or other kinases, the binding of which to the receptor is dependent upon agonist occupation of the receptor. The present invention involves the detection of protein/protein interaction by complementation of mutant reporter enzymes.

Binding of arrestin to activated GPCR is a common process in the first step of desensitization that has been demonstrated for most, if not all, GPCRs studied so far. Measurement of GPCR interaction with arrestin via mutant enzyme complementation (ie., ICAST) provides a more generic assay technology applicable for a wide variety of GPCRs and orphan receptors.

A further aspect of the present invention is a method of assessing GPCR pathway activity under test conditions by providing a test cell that expresses a GPCR, e.g. muscarinic, adrenergic, dopamine, angiotensin or endothelin, as a fusion protein to a mutant reporter enzyme and interacting a protein in the GPCR pathway, e.g., G-protein, arrestin or GRK, as a fusion protein with a complementing mutant reporter enzyme. When test cells are exposed to a known agonist to the target GPCR under test conditions, activation of the GPCR will be monitored by complementation of the reporter enzyme. Increased reporter enzyme activity reflects interaction of the GPCR with its interacting protein partner.

A further aspect of the present invention is a method of assessing GPCR pathway activity in the presence of a test arrestin, e.g. β-arrestin.

A further aspect of the present invention is a method of assessing GPCR pathway activity in the presence of a test G-protein.

A further aspect of the present invention is a method of assessing GPCR pathway activity upon exposure of the test cell to a test ligand.

A further aspect of the present invention is a method of assessing GPCR activity upon co-expression in the test cell of a second receptor. The second receptor could be the same GPCR or orphan receptor (i.e., homo-dimerization), a different GPCR or orphan receptor (i.e. hetero-dimerization) or could be a receptor of another type.

A further aspect of the present invention is a method for screening for a ligand or agonist to an orphan GPCR. The ligand or agonist could be contained in natural or synthetic libraries or mixtures or could be a physical stimulus. A test cell is provided that expresses the orphan GPCR as a fusion protein with a mutant reporter enzyme, e.g., a β-galactosidase mutant, and, for example, an arrestin or mutant form of arrestin as a fusion protein with a complementing mutant reporter enzyme, e.g., another β-galactosidase mutant. The interaction of the arrestin with the orphan GPCR upon receptor activation is measured by enzymatic activity of the complemented reporter enzyme. The test cell is exposed to a test compound, and an increase in reporter enzyme activity indicates the presence of a ligand or agonist.

A further aspect of the present invention is a method for screening a protein of interest, for example, an arrestin protein (or mutant form of the arrestin protein) for the ability to bind to a phosphorylated, or activated, GPCR. A test cell is provided that expresses a GPCR as a fusion protein with a mutant reporter enzyme, e.g., a β-galactosidase mutant, and contains arrestin (or a mutant form of arrestin) as a fusion protein with a complementing mutant reporter enzyme, e.g., another β-galactosidase mutant. The interaction of arrestin with the GPCR upon receptor activation is measured by enzymatic activity of the complemented reporter enzyme. The test cell is exposed to a known GPCR agonist and then reporter enzyme activity is detected. Increased reporter enzyme activity indicates that the β-arrestin molecule can bind to phosphorylated, or activated, GPCR in the test cell.

A further aspect of the present invention is a method to screen for an agonist to a specific GPCR. The agonist could be contained in natural or synthetic libraries or could be a physical stimulus. A test cell is provided that expresses a GPCR as a fusion protein with a mutant reporter enzyme, e.g., a β-galactosidase mutant, and, for example, an arrestin as a fusion protein with a complementing mutant reporter enzyme, e.g. another β-galactosidase mutant. The interaction of arrestin with the GPCR upon receptor activation is measured by enzymatic activity of the complemented reporter enzyme. The test cell is exposed to a test compound, and an increase in reporter enzyme activity indicates the presence of an agonist. The test cell may express a known GPCR or a variety of known GPCRs, or may express an unknown GPCR or a variety of unknown GPCRs. The GPCR may be, for example, an odorant GPCR or a βAR GPCR.

A further aspect of the present invention is a method for screening a test compound for GPCR antagonist activity. A test cell is provided that expresses a GPCR as a fusion protein with a mutant reporter enzyme, e.g., a β-galactosidase mutant, and, for example, an arrestin as a fusion protein with a complementing mutant reporter enzyme, e.g., another β-galactosidase mutant. The interaction of arrestin with the GPCR upon receptor activation is measured by enzymatic activity of the complemented reporter enzyme. The test cell is exposed to a test compound, and an increase in reporter enzyme activity indicates the presence of an agonist. The cell is exposed to a test compound and to a GPCR agonist, and reporter enzyme activity is detected. When exposure to the agonist occurs at the same time as or subsequent to exposure to the test compound, a decrease in reporter enzyme activity after exposure to the test compound indicates that the test compound has antagonist activity to the GPCR.

A further aspect of the present invention is a method of screening a sample solution for the presence of an agonist, antagonist or ligand to a GPCR. A test cell is provided that expresses GPCR as a fusion protein with a mutant reporter enzyme, e.g., a β-galactosidase mutant, and contains, for example, a β-arrestin as a fusion protein with a complementing reporter, e.g., another β-galactosidase mutant. The test cell is exposed to a sample solution, and reporter enzyme activity is assessed. Changed reporter enzyme activity after exposure to the sample solution indicates the sample solution contains an agonist, antagonist or ligand for a GPCR expressed in the cell.

A further aspect of the present invention is a method of screening a cell for the presence of a GPCR. According to this aspect, an arrestin fusion protein with a mutant reporter enzyme and a GPCR downstream signaling fusion protein with a mutant reporter enzyme are employed to detect GPCR action. A modification of this aspect of the invention can be employed to provide a method of screening a plurality of cells for those cells which contain a GPCR. According to this aspect, a plurality of cells containing a conjugate comprising a β-arrestin protein as a fusion protein with a reporter enzyme are provided; the plurality of cells are exposed to a GPCR agonist; and activity of reporter enzyme activity is detected. An increase in reporter enzymatic activity after exposure to the GPCR agonist indicates β-arrestin protein binding to a GPCR, thereby indicating that the cell contains a GPCR responsive to the GPCR agonist.

A further aspect of the invention is a method for mapping GPCR-mediated signaling pathways. For instance, the system could be utilized to monitor interaction of c-src with β-arrestin-1 upon GPCR activation. Additionally, the system could be used to monitor protein/protein interactions involved in cross-talk between GPCR signaling pathways and other pathways such as that of the receptor tyrosine kinases or Ras/Raf. According to this aspect, a test cell is provided that expresses a GPCR or other related protein with a mutant reporter enzyme, e.g., a β-galactosidase mutant, and contains a protein from another pathway as a fusion protein with a complementing mutant reporter enzyme, e.g., another β-galactosidase mutant. Increased reporter enzymatic activity indicates protein/protein interaction.

A further aspect of the invention is a method for monitoring homo- or hetero-dimerization of GPCRs upon agonist or antagonist stimulation. Increasing evidence indicates that GPCR dimerization is important for biological activity (AbdAlla, et al., "AT1-receptor heterodimers show enhanced G-protein activation and altered receptor sequestration." Nature, 407:94–98 (2000); Bockaert, et al., "Molecular tinkering of G protein-coupled receptors: an evolutionary success." EMBO J. 18:1723–29 (1999)). Jordan, et al. "G-protein-coupled receptor heterodimerization modulates receptor function." Nature, 399:697–700 (1999), demonstrated that two non-functional opioid receptors, κ and δ, heterodimerize to form a functional receptor. Gordon et al., "Dopamine D2 receptor dimers and receptor blocking peptides." Bioch. Biophys. Res. Commun. 227:200–204 (1996), showed different pharmacological properties associated with the monomeric and dimeric forms of Dopamine receptor D2. The D2 receptors exist either as monomers that are selective targets for spiperone or as dimer forms that are targets for nemonapride. Herbert, et al., "A peptide derived from a β2-adrenergic receptor transmembrane domain inhibits both receptor dimerization and activation." J.B.C. 271:16384–92 (1996), demonstrated that the agonist stimulation was found to stabilize the dimeric state of the receptor, whereas inverse agonists favored the monomeric form. Indeed, the same study showed that a peptide corresponding to the sixth transmembrane domain of the β2-adrenergic receptor inhibited both receptor dimerization and activation. Further, Angers et al. Detection of beta-2-adrenergic receptor dimerization in living cells using bioluminescence resonance energy transfer, Proc. Natl. Acad. Sci. USA, 97(7):3684–3689, discloses the use of β2-adrenergic receptor fusion proteins (i.e., β2-adrenergic receptor fused to luciferase and β2-adrenergic receptor fused to an enhanced red-shifted green fluorescent protein) to study β2-adrenergic receptor dimerization.

GPCR dimerization in the context of cellular physiology and pharmacology can be monitored in accordance with the invention. For example, β-galactosidase complementation can be measured in test cells that co-express GPCR fusion proteins of β-galactosidase mutant enzymes, e.g., $GPCR_1\Delta\alpha$ and $GPCR_2\Delta\omega$ (FIG. 27). According to this aspect, the interconversion between monomeric to dimeric forms of the GPCRs or orphan receptors can be measured by mutant reporter enzyme complementation. FIG. 27 illustrates a test cell co-expressing GPCR or an orphan receptor as a fusion protein with $\Delta\alpha$ form of β-galactosidase mutant (e.g., $GPCR_1\Delta\alpha$), and the same GPCR or orphan receptor as a fusion protein with $\Delta\omega$ form of β-galactosidase mutant e.g., $GPCR_1\Delta\omega$). Formation of the GPCR homodimer is reflected by formation of an active enzyme, which can be measured by enzyme activity assays, such as the Gal-Screen™ assay. Similarly, hetero-dimerization between two distinct GPCRs, or two distinct orphan receptors, or between one known GPCR and one orphan receptor can be analyzed in test cells co-expressing two fusion proteins, e.g., $GPCR_1\Delta\alpha$ and $GPCR_2\Delta\omega$. The increased β-galactosidase activity indicates that the two receptors can form a heterodimer.

A further aspect of the invention is a method of monitoring the interconversion between the monomeric and dimeric form of GPCRs under the influence of agonist or antagonist treatment. The test receptor(s) can be between the same GPCR or orphan receptor (homodimer), or between two distinct GPCRs or orphan receptors (heterodimer). The increased β-galactosidase activity after treatment with a compound means that the compound binds to and/or stabilizes the dimeric form of the receptor. The decreased β-galactosidase activity after treatment with a compound means that the compound binds to and/or stabilizes the monomeric form of the receptor.

A further aspect of the invention is a method of screening a cell for the presence of a GPCR responsive to a GPCR agonist. A cell is provided that contains protein partners that interact downstream in the GPCR's pathway. The protein partners are expressed as fusion proteins to the mutant, complementing enzyme and are used to monitor activation of the GPCR. The cell is exposed to a GPCR agonist and then enzymatic activity of the reporter enzyme is detected. Increased reporter enzyme activity indicates that the cell contains a GPCR responsive to the agonist.

The present invention involves the use of a combination of proprietary technologies (including ICAST™, Intercistronic Complementation Analysis Screening Technology, Gal-Screen™, etc.) to monitor protein/protein interactions in GPCR signaling. As disclosed in U.S. application Ser. No. 09/654,499, the method of the invention in part involves using ICAST™, which in turn involves the use of two inactive β-galactosidase mutants, each of which is fused with one of two interacting target protein pairs, such as a GPCR and an arrestin. The formation of an active β-galactosidase complex is driven by interaction of the target proteins. In this system, β-galactosidase activity can be detected using, e.g., the Gal-Screen™ assay system, wherein direct cell lysis is combined with rapid ultrasensitive chemiluminescent detection of β-galactosidase reporter enzyme. This system uses, e.g., a Galacton-Star® chemiluminescent substrate for measurement in a luminometer as a read out of GPCR activity.

FIG. 23 is a schematic depicting the use of the complementation technology in the method of the present invention. FIG. 23 shows two inactive β-galactosidase mutants that become active when they are forced together by specific interactions between the fusion partners of an arrestin molecule and an activated GPCR or orphan receptor. This assay technology will be especially useful in high throughput screening assays for ligand fishing for orphan receptors, a process called de-orphaning. As illustrated in FIG. 28, a β-galactosidase fusion protein of an orphan receptor (e.g., GPCR$_{orphan}$Δα) is co-expressed in the test cell with a fusion protein of β-arrestin (e.g., β-ArrΔω). When the test cell is subjected to compounds, which could be natural or synthetic, the increased β-galactosidase activity means the compound is either a natural or surrogate ligand for this GPCR. The same assay system can be used to find drug leads for the new GPCRs. The increased β-galactosidase activity in the test cell after treatment indicates the agonist activity of the compound. The decreased β-galactosidase activity in the test cell indicates antagonist activity or inverse agonist activity of the compound. In addition, the method of the invention could be used to monitor GPCR-mediated signaling pathways via other downstream signaling components such as G-proteins, GRKs or the proto-oncogene c-Src.

The invention is achieved in part by using ICAST™ protein/protein interaction screening to map signaling pathways. This technology is applicable to a variety of known and unknown GPCRs with diverse functions. They include, but are not limited to, the following sub-families of GPCRs:
(a) receptors that bind to amine-like ligands-Acetylcholine muscarinic receptor (M1 to M5), alpha and beta Adrenoceptors, Dopamine receptors (D1, D2, D3 and D4), Histamine receptors (H1 and H2), Octopamine receptor and Serotonin receptors (5HT1, 5HT2, 5HT4, 5HT5, 5HT6, 5HT7);
(b) receptors that bind to a peptide ligand-Angiotensin receptor, Bombesin receptor, Bradykinin receptor, C-C chemokine receptors (CCR1 to CCR8, and CCR10), C-X-C type Chemokine receptors (CXC-R5), Cholecystokinin type A receptor, CCK type receptors, Endothelin receptor, Neurotesin receptor, FMLP-related receptors, Somatostatin receptors (type 1 to type 5) and Opioid receptors (type D, K, M, X);
(c) receptors that bind to hormone proteins-Follic stimulating hormone receptor, Thyrotrophin receptor and Lutropin-choriogonadotropic hormone receptor;
(d) receptors that bind to neurotransmitters-substance P receptor, Substance K receptor and neuropeptide Y receptor;
(e) Olfactory receptors-Olfactory type 1 to type 11, Gustatory and odorant receptors;
(f) Prostanoid receptors-Prostaglandin E2 (EP1 to EP4 subtypes), Prostacyclin and Thromboxane;
(g) receptors that bind to metabotropic substances-Metabotropic glutamate group I to group III receptors;
(h) receptors that respond to physical stimuli, such as light, or to chemical stimuli, such as taste and smell; and
(i) orphan GPCRs-the natural ligand to the receptor is undefined.

Use of the ICAST™ technology in combination with the invention provides many benefits to the GPCR screening process, including the ability to monitor protein interactions in any sub-cellular compartment-membrane, cytosol and nucleus; the ability to achieve a more physiologically relevant model without requiring protein overexpression; and the ability to achieve a functional assay for receptor binding allowing high information content.

BRIEF DESCRIPTION OF THE DRAWINGS

FIG. 1. Cellular expression levels of β2 adrenergic receptor (β2AR) and β-arrestin-2 (βArr2) in C2 clones. Quantification of β-galactosidase (β-gal) fusion protein was performed using antibodies against β-gal and purified β-gal protein in a titration curve by a standardized ELISA assay.

FIG. 3. Interaction of activated receptor β2AR and arrestin can be measured by β-galactosidase complementation.

FIG. 4. Agonist dose response for interaction of β2AR and arrestin can be measured by β-galactosidase complementation.

FIG. 5. Antagonist mediated inhibition of receptor activity can be measured by β-galactosidase complementation in cells co-expressing β2AR-βgalΔα and βArr-βgalΔω.

FIG. 8. Variety of mammalian cell lines can be used to generate stable cells for monitoring GPCR and arrestin interactions.

FIG. 9. Beta-gal complementation can be used to monitor β2 adrenergic receptor homo-dimerization.

FIG. 10B–10J. Nucleotide sequence for pICAST ALC (SEQ ID NO:1).

FIG. 11B–11J. Nucleotide sequence for pICAST ALN (SEQ ID NO:2).

FIG. 12B–12J. Nucleotide sequence for pICAST OMC (SEQ ID NO:3).

FIG. 13B–13J. Nucleotide sequence for pICAST OMN (SEQ ID NO:4).

FIG. 23 shows two inactive mutant reporter enzymes that become active when the corresponding fusion partners, GPCR and β-arrestin interact.

DETAILED DESCRIPTION OF PREFERRED EMBODIMENTS

Figure 1A:
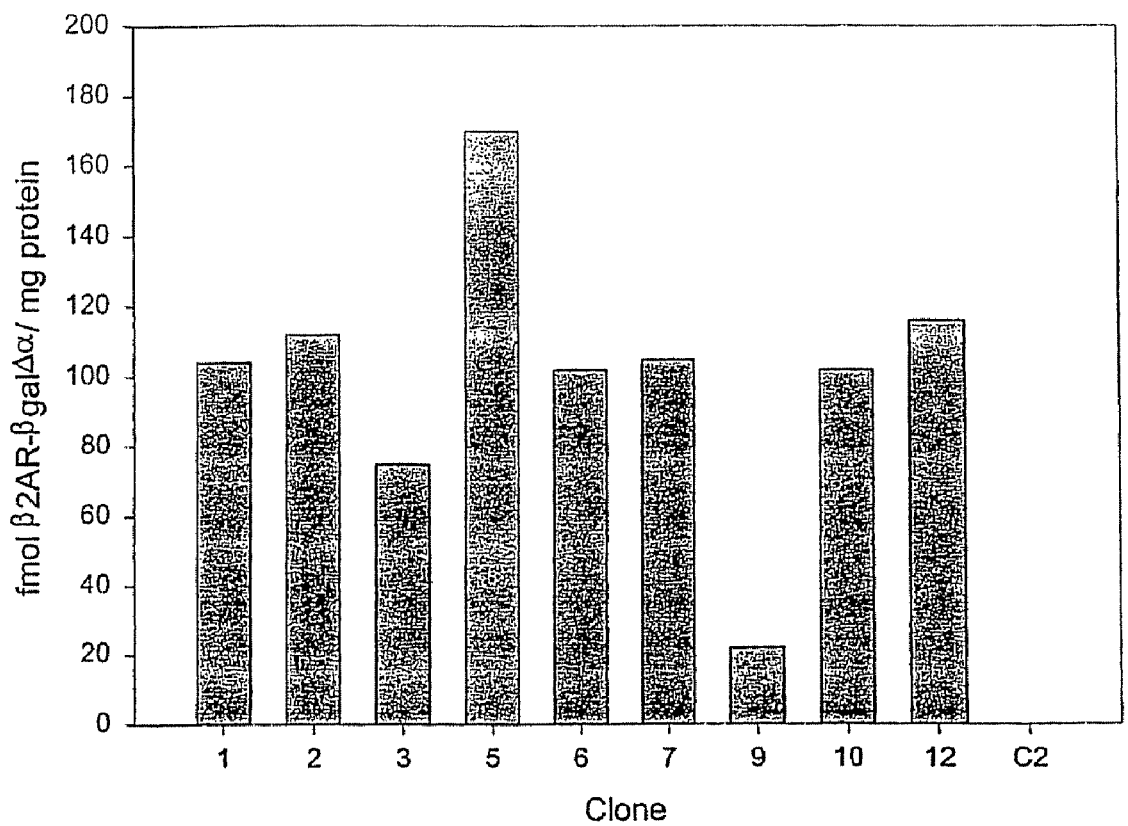
FIG. 1A shows expression levels of β2AR-βgalΔα clones (in expression vector pICAST ALC).
Figure 1B:
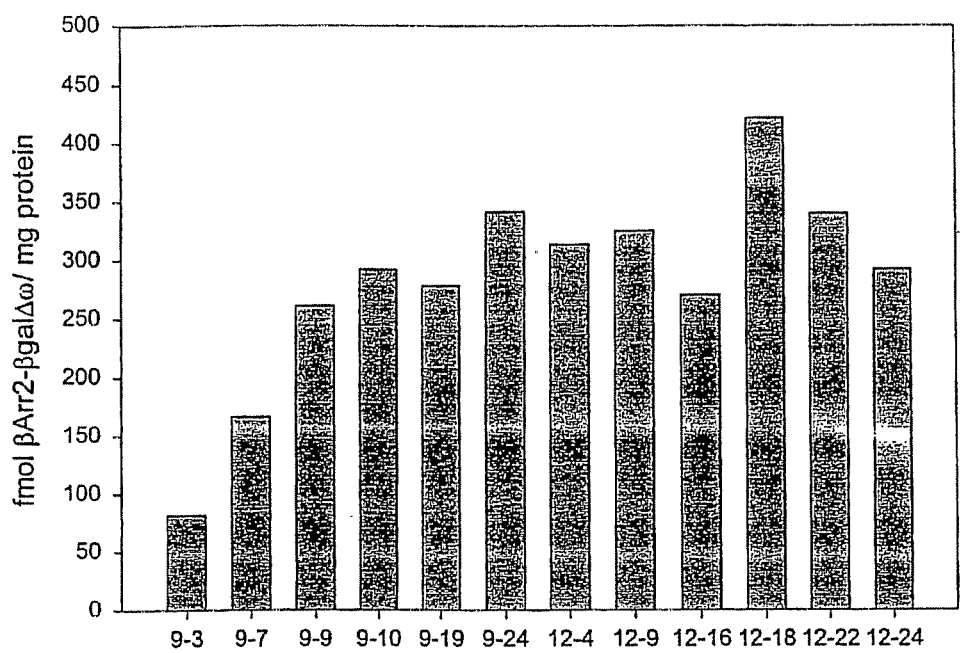
FIG. 1B shows expression levels of βArr2-βgalΔω in expression vector pICAST OMC4 for clones 9-3, -7, -9, -10, -19 and -24, or in expression vector pICAST OMN4 for clones 12-4, -9, -16, -18, -22 and -24.
Figure 2:
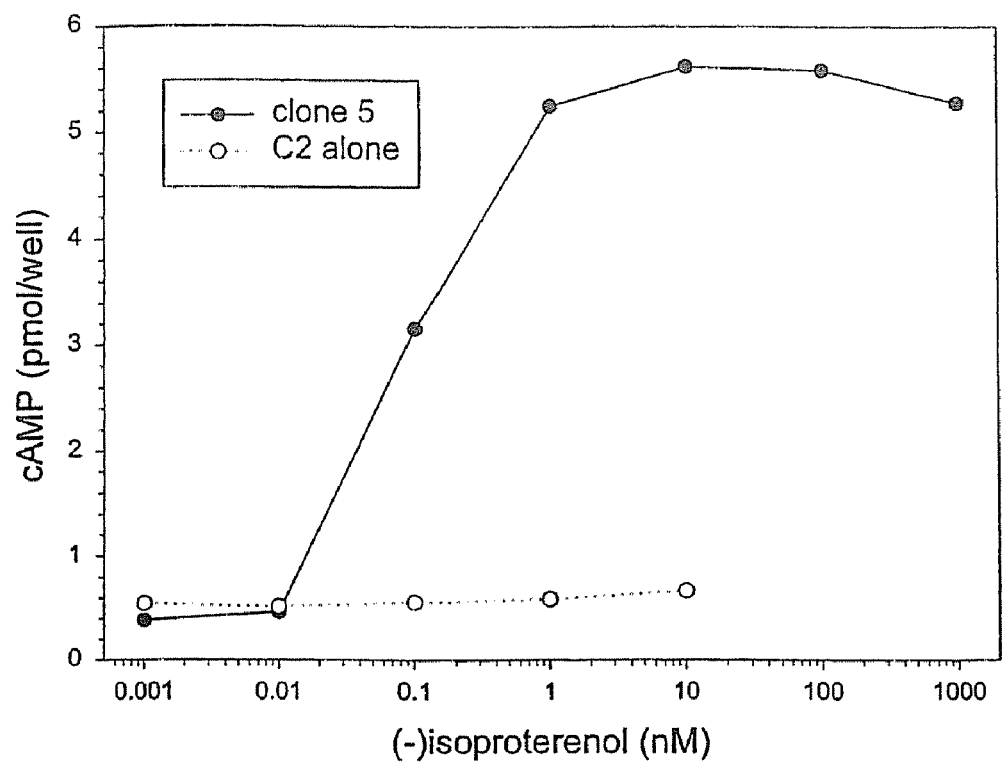
FIG. 2. Receptor β2AR activation was measured by agonist-stimulated cAMP production. C2 cells expressing pICAST ALC β2AR (clone 5) or parental cells were treated with increasing concentrations of (−)isoproterenol and 0.1 mM IBMX. The quantification of cAMP level was expressed as pmol/well.

The present invention provides a method to interrogate GPCR function and pathways. The G-protein-coupled superfamily continues to expand rapidly as new receptors are discovered through automated sequencing of cDNA libraries or genomic DNA. It is estimated that several thousand GPCRs may exist in the human genome. Only a portion have been cloned and even fewer have been associated with ligands. The means by which these, or newly discovered orphan receptors, will be associated with their cognate ligands and physiological functions represents a major challenge to biological and biomedical research. The identification of an orphan receptor generally requires an individualized assay and a guess as to its function. The present invention involves the interrogation of GPCR function by monitoring the activation of the receptor using activation dependent protein-protein interactions between the test GPCR or orphan receptor and a β-arrestin. The specific protein-protein interactions are measured using the mutant enzyme complementation technology disclosed herein. This assay system eliminates the prerequisite guessing because it can be performed with and without prior knowledge of other signaling events. It is sensitive, rapid and easily performed and is applicable to nearly all GPCRs because the majority of these receptors desensitize by a common mechanism.

The present invention provides a complete assay system for monitoring protein-protein interactions in GPCR pathways. The invention employs the complementation technology, ICAST™ (Intercistronic Complementation Analysis Screening Technology as disclosed in pending U.S. patent application Ser. No. 053,614, filed Apr. 1, 1998, the entire contents of which are incorporated herein by reference). The ICAST™ technology involves the use of two mutant forms of a reporter enzyme fused to proteins of interest. When the proteins of interest do not interact, the reporter enzyme remains inactive. When the proteins of interest do interact, the reporter enzyme mutants come together and form an active enzyme. According to an embodiment of the invention, the activity of β-galactosidase may be detected with the Gal-Screen™ assay system developed by Advanced Discovery Sciences™, which involves the use of Galacton-Star®, an ultrasensitive chemiluminescent substrate. The Gal-Screen™ assay system and the Galacton-Star® chemiluminescent substrate are disclosed in U.S. Pat. Nos. 5,851,771; 5,538,847; 5,326,882; 5,145,772; 4,978,614; and 4,931,569, the contents of which are incorporated herein by reference in their entirety. The invention provides an array of assays, including GPCR binding assays, that can be achieved directly within the cellular environment in a rapid, non-radioactive assay format. The methods of the invention are an advancement over the invention disclosed in U.S. Pat. Nos. 5,891,646 and 6,110,693 and the method disclosed in Angers et al., supra. which rely on microscopic imaging or spectrometry of GPCR components as fusion with Green-fluorescent-protein. The imaging technique disclosed in U.S. Pat. Nos. 5,891,646 and 6,110,693 and spectrometry-based technique in Angers et al. are limited by low-throughput and lack of thorough quantification.

The assay system of the invention combined with Advanced Discovery Sciences™ technologies provide highly sensitive cell-based methods for interrogating GPCR pathways which are amenable to high-throughput screening (HTS). Among some of the technologies developed by Advanced Discovery Sciences™ that may be used with the present invention are the Gal-Screen™ assay system (discussed above) and the cAMP-Screen™ immunoassay system. The cAMP-Screen™ immunoassay system provides ultrasensitive determination of cAMP levels in cell lysates. The cAMP-Screen™ assay utilizes the high-sensitivity chemiluminescent alkaline phosphatase (AP) substrate CSPD® (disodium 3-(4-methoxyspiro {1,2-dioxetane-3,2'-(5'-chloro) tricyclo $3.3.1.1.^{3,7}$} decan-4-yl phenyl phosphate) with Sapphire-II™ luminescence enhancer.

Unlike yeast-based-two-hybrid assays used to monitor protein/protein interactions in high-throughput assays, the present invention (1) is applicable to a variety of cells including mammalian cells, plant cells, protozoa cells such as E. coli and cells of invertebrate origin such as yeast, slime mold (Dictyostelium) and insects; (2) detects interactions at the membrane at the site of the receptor target or in the cytosol at the site of downstream target proteins rather than a limited cellular localization, i.e., nucleus; and (3) does not rely on indirect read-outs such as transcriptional activation. The present invention thus provides assays with greater physiological relevance and fewer false positives.

The present inventors have developed modifications to the embodiment disclosed in U.S. patent application Ser. No. 053,614 described above in order to enhance the sensitivity of the inventive GPCR assay. According to an embodiment, the invention incorporates the use of serine/threonine clusters to enhance and prolong the interaction of GPCR with arrestin in order to make the detection more robust. The clusters can be utilized for orphan receptors or known GPCRs, which do not have this sequence motif. By adding this sequence to the C-terminal tail of the receptor, the activation of the receptor can be detected more readily by readouts of arrestin binding to GPCR, i.e., β-galactosidase complementation from fusion proteins of target proteins with β-galactosidase mutants.

According to another embodiment, the invention incorporates the use of arrestin point mutations to bypass the requirement of phosphorylation, by the action of specific GRK, on the C-terminal tail or intracellular loops of GPCR upon activation. The applications include i) wherein the cognate GRK for a particular GPCR or orphan receptor is unknown; and ii) wherein the specific GRK for the receptor of interest (or under test) may not be present or may have low activity in the host cell that is used for receptor activation assay.

According to another embodiment, the invention incorporates the use of a super arrestin to increase the binding efficiency of arrestin to an activated GPCR and to stabilize the GPCR/arrestin complex during GPCR desensitization. This application can be used to increase the robustness of ICAST/GPCR applications in cases where the GPCR is normally resensitized rapidly post desensitization.

Each of these methodologies is discussed below.

The invention will now be described in the following non-limiting examples.

EXAMPLE

Figure 23:
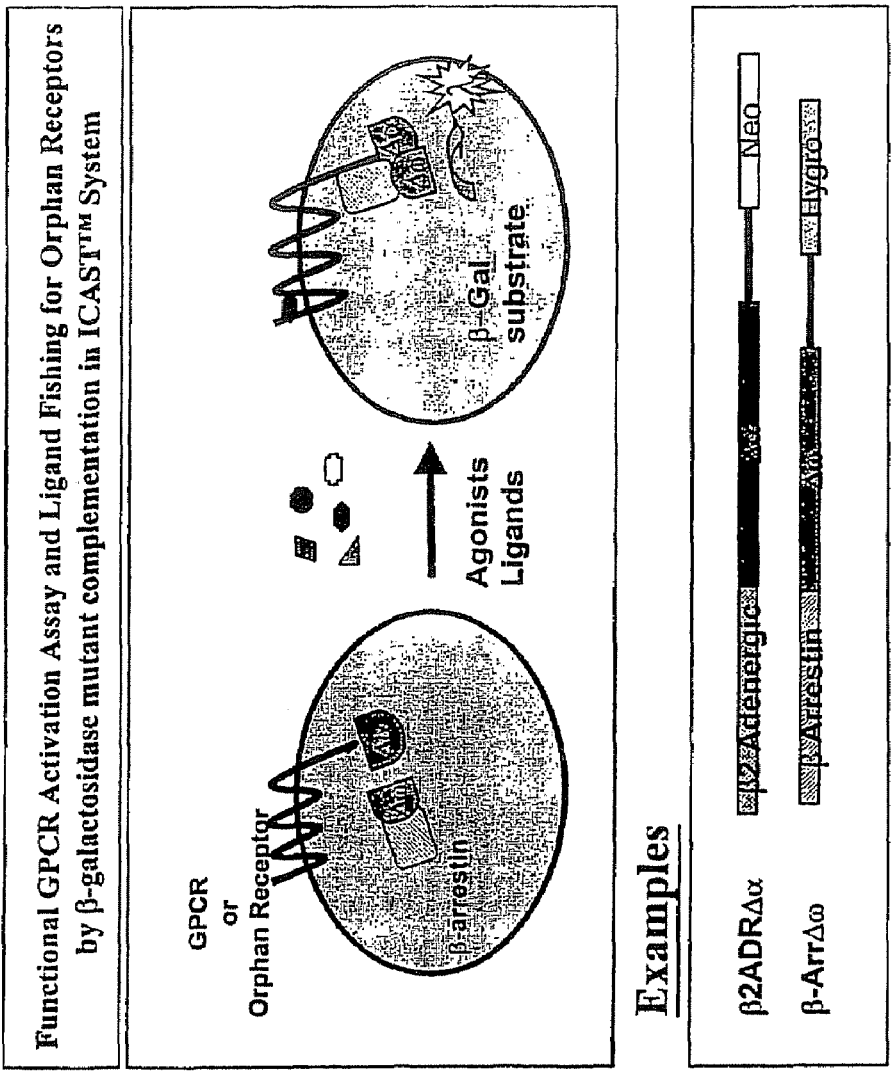
FIG. 23. A schematic depicting use of the complementation technology in the method of the invention.

According to an embodiment of the invention, GPCR activation is measured through monitoring the binding of arrestin to ligand-activated GPCR. In this assay system, a GPCR, e.g., β-adrenergic receptor (β2AR), and an arrestin, e.g., β-arrestin, are co-expressed in the same cell as fusion proteins with mutant forms of a reporter enzyme, e.g., β-galactosidase (β-gal). As illustrated in FIG. 23, the β2AR is expressed as a fusion protein with Δα form of β-gal mutant (β2ARΔα) and the β-arrestin as a fusion protein with the Δω form of β-gal mutant (β-ArrΔω). The two fusion proteins, which at first exist in a resting (or un-stimulated) cell in separate compartments, i.e. the membrane for GPCR and the cytosol for arrestin, cannot form an active β-galactosidase enzyme. When such a cell is treated with an agonist or a ligand, the ligand-occupied and activated receptor becomes a high affinity binding site for arrestin. The interaction between an activated GPCR, β2ARΔα, and arrestin, β-ArrΔω, drives the β-gal mutant complementation. The enzyme activity can be measured by using an enzyme substrate, which upon cleavage releases a product measurable by colorimetry, fluorescence, or chemiluminescence (e.g. the Gal-Screen™ assay system).

Experiment Protocol

Figure 15:
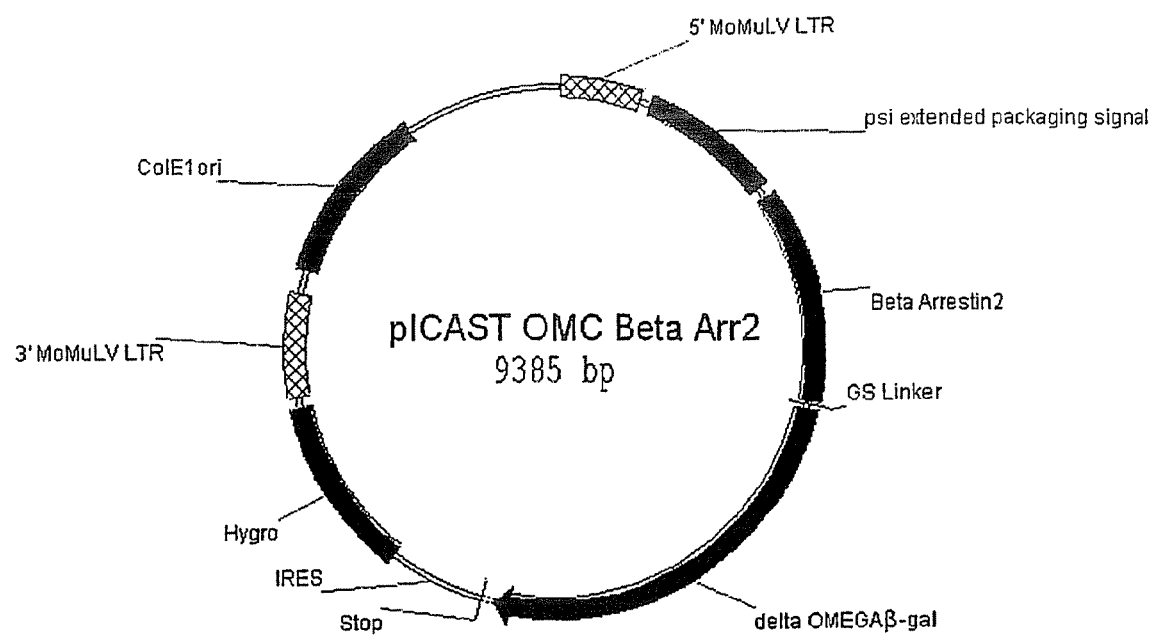
FIG. 15. pICAST OMC βArr2: Vector for expression of β-galΔω as a C-terminal fusion to β-arrestin-2. The coding sequence of human β-arrestin-2 (Genebank Accession Number: NM_004313) was cloned in frame to β-galΔω in a pICAST OMC vector.
Figure 16:
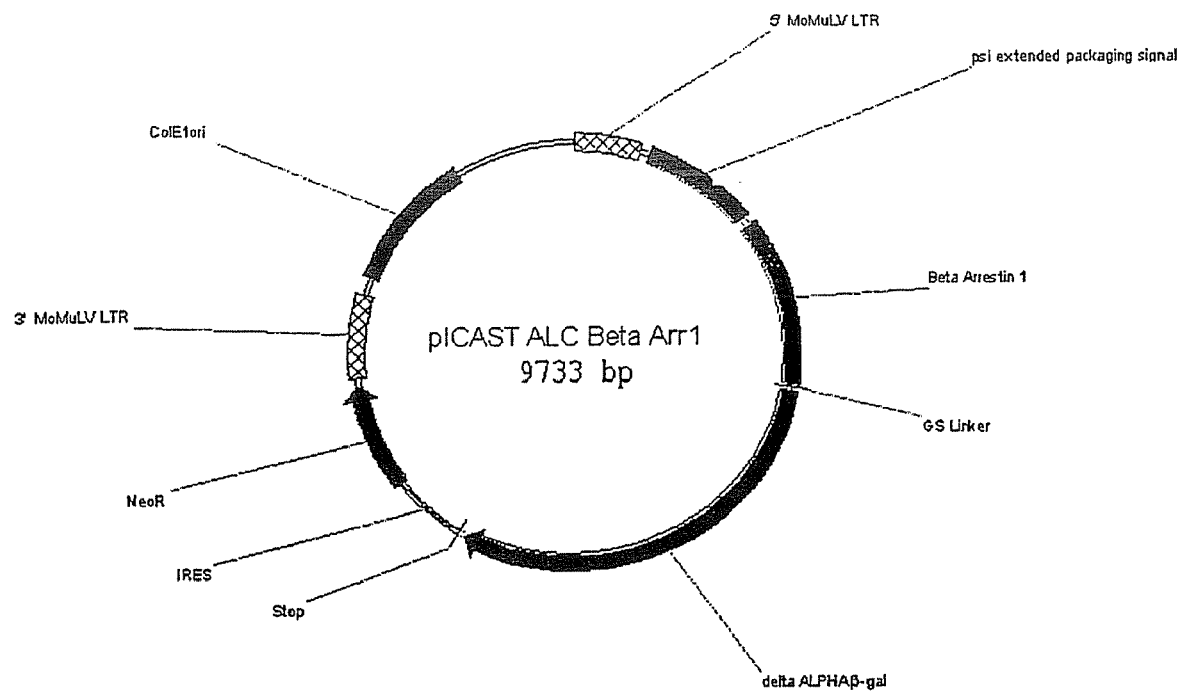
FIG. 16. pICAST ALC βArr1: Vector for expression of β-galΔα as a C-terminal fusion to β-arrestin-1. The coding sequence of human β-arrestin-1 (Genebank Accession Number: NM_004041) was cloned in frame to β-galΔα in a pICAST ALC vector.
Figure 17:
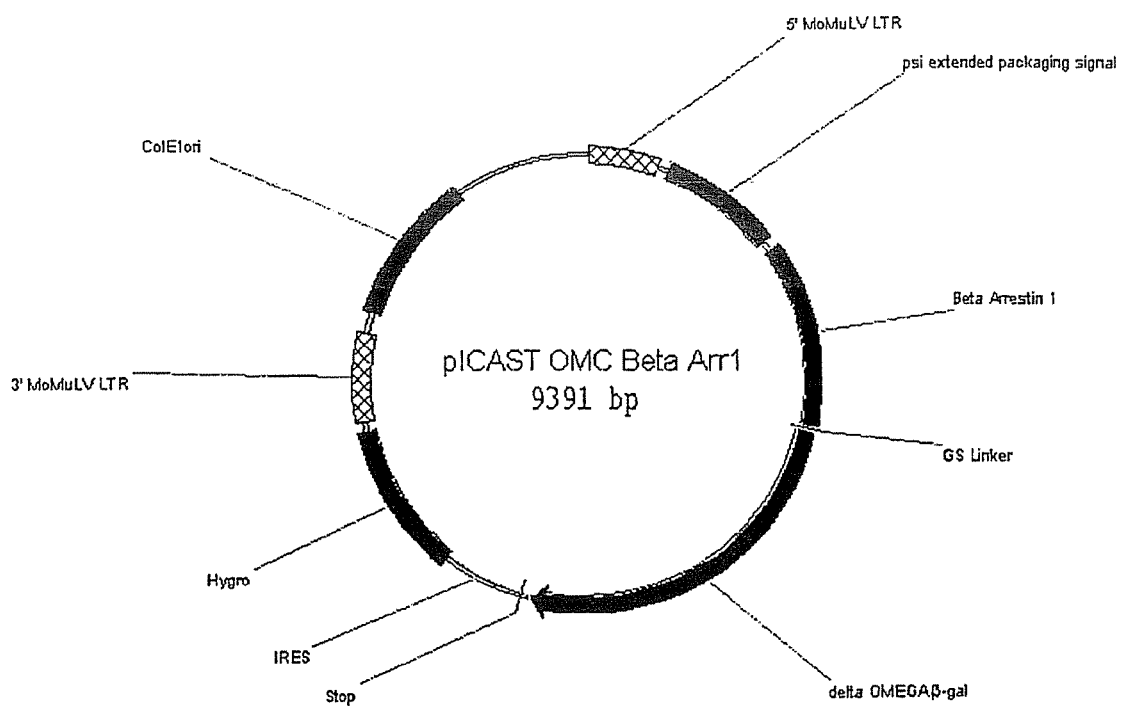
FIG. 17. pICAST OMC βArr1: Vector for expression of β-galΔω as a C-terminal fusion to β-arrestin-1. The coding sequence of human β-arrestin-1 (Genebank Accession Number: NM_004041) was cloned in frame to β-galΔω in a pICAST OMC vector.
Figure 18:
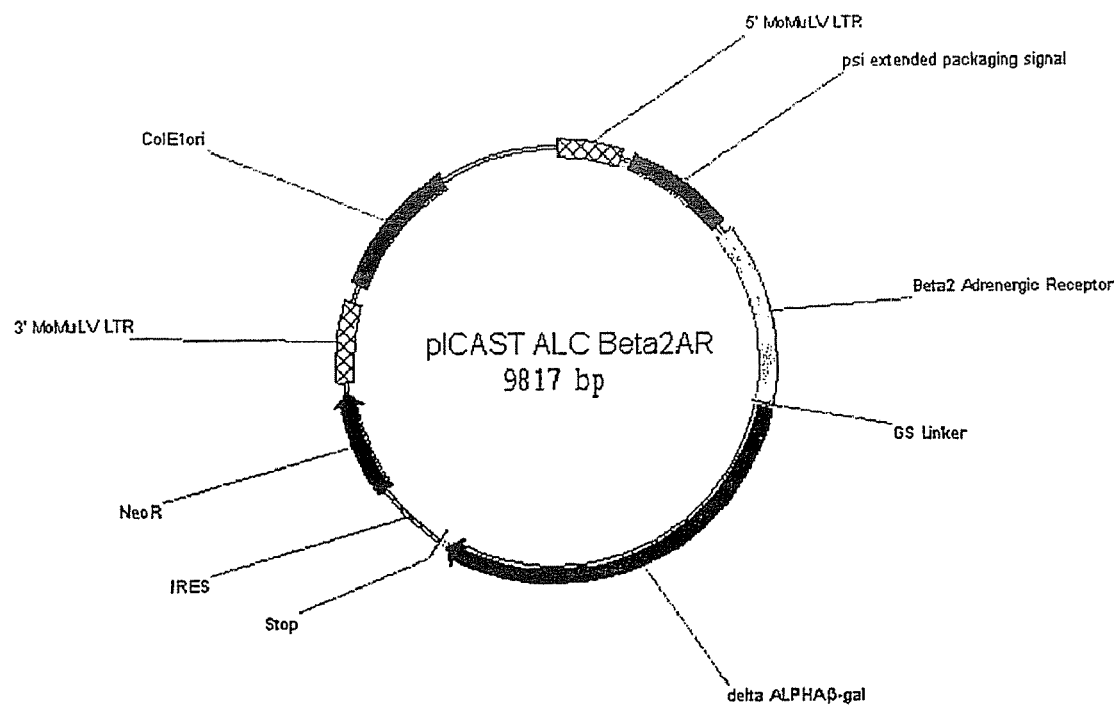
FIG. 18. pICAST ALC β2AR: Vector for expression of β-galΔα as a C-terminal fusion to β2 Adrenergic Receptor. The coding sequence of human β2 Adrenergic Receptor (Genebank Accession Number: NM_000024) was cloned in frame to β-galΔα in a pICAST ALC vector.
Figure 19:
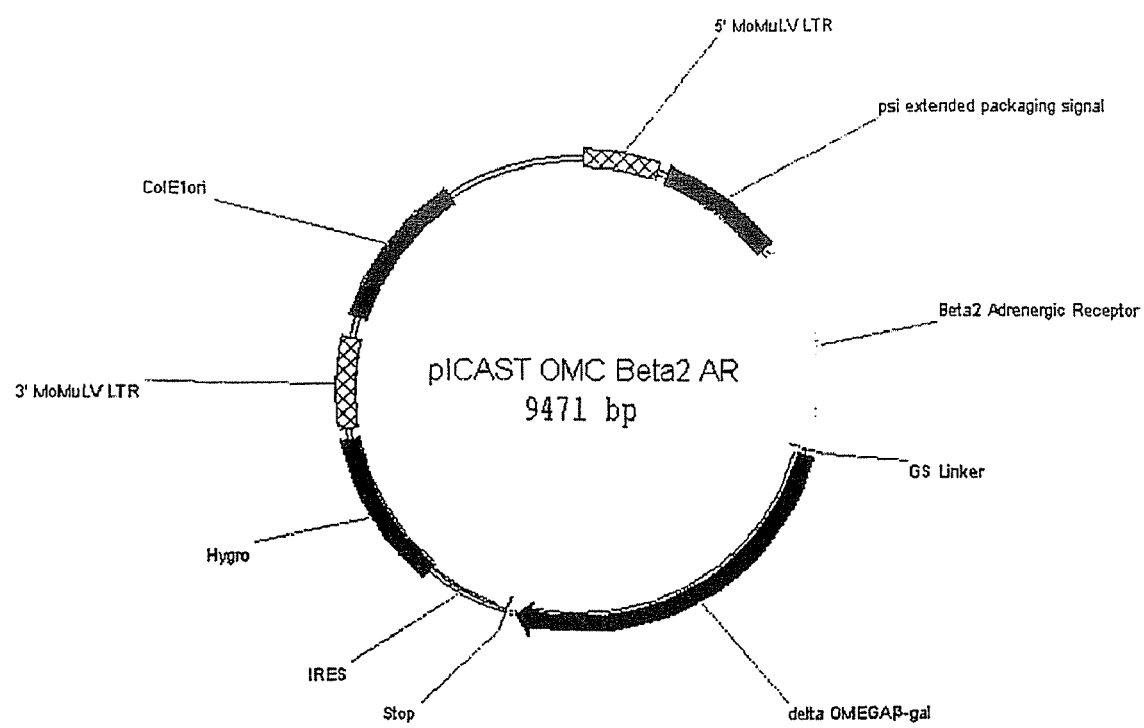
FIG. 19. pICAST OMC β2AR: Vector for expression of β-galΔω as a C-terminal fusion β2 Adrenergic Receptor. The coding sequence of human β2 Adrenergic Receptor (Genebank Accession Number: NM_000024) was cloned in frame to β-galΔω in a pICAST OMC vector.
Figure 20:
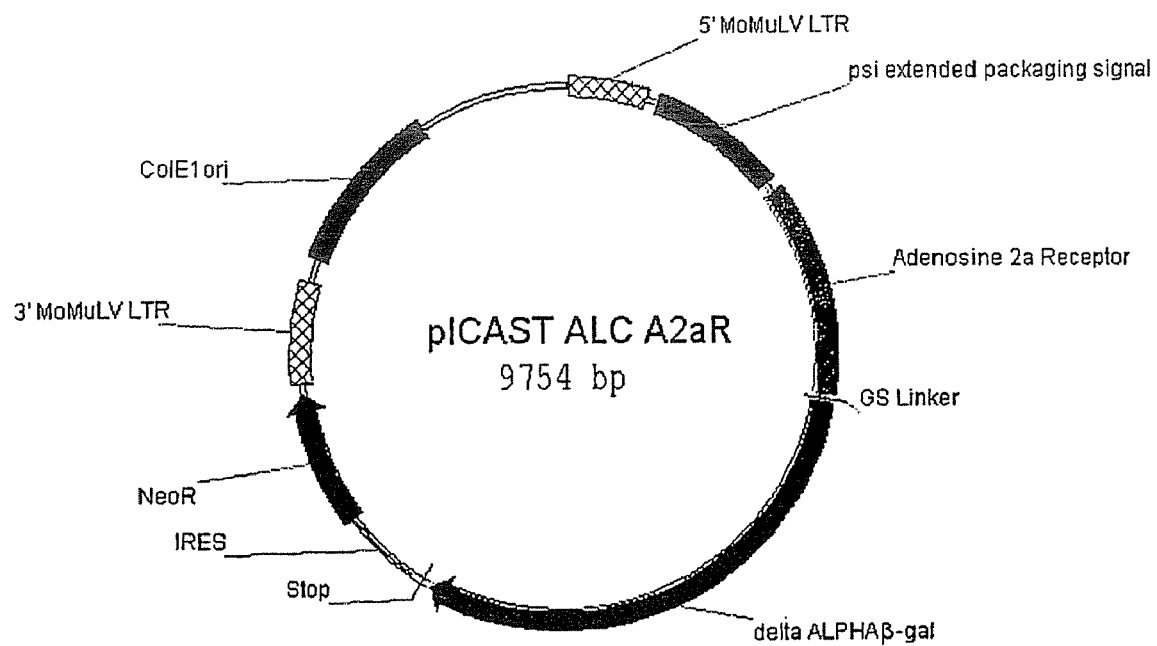
FIG. 20. pICAST ALC A2aR: Vector for expression of β-galΔα as a C-terminal fusion to Adenosine 2a Receptor. The coding sequence of human Adenosine 2a Receptor (Genebank Accession Number: NM_000675) was cloned in frame to β-galΔα in a pICAST ALC vector.
Figure 21:
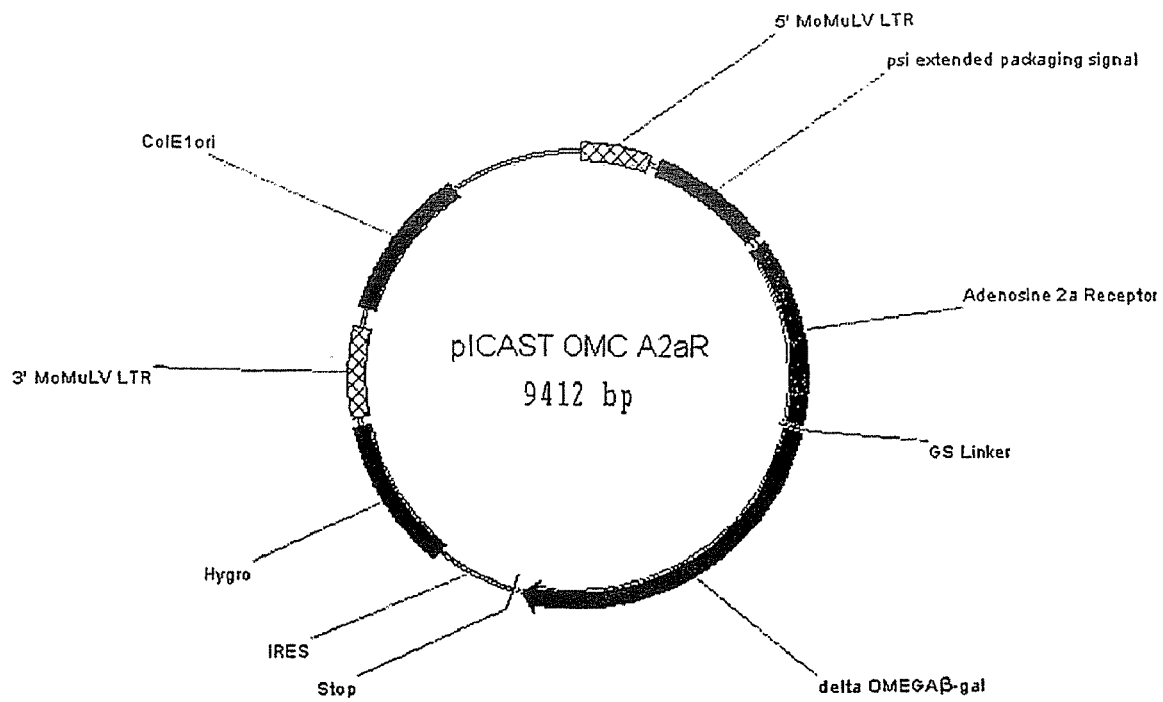
FIG. 21. pICAST OMC A2aR: Vector for expression of β-galΔω as a C-terminal fusion to Adenosine 2a Receptor. The coding sequence of human Adenosine 2a Receptor (Genebank Accession Number. NM_000675) was cloned in frame to β-galΔω in a pICAST OMC vector.
Figure 22:
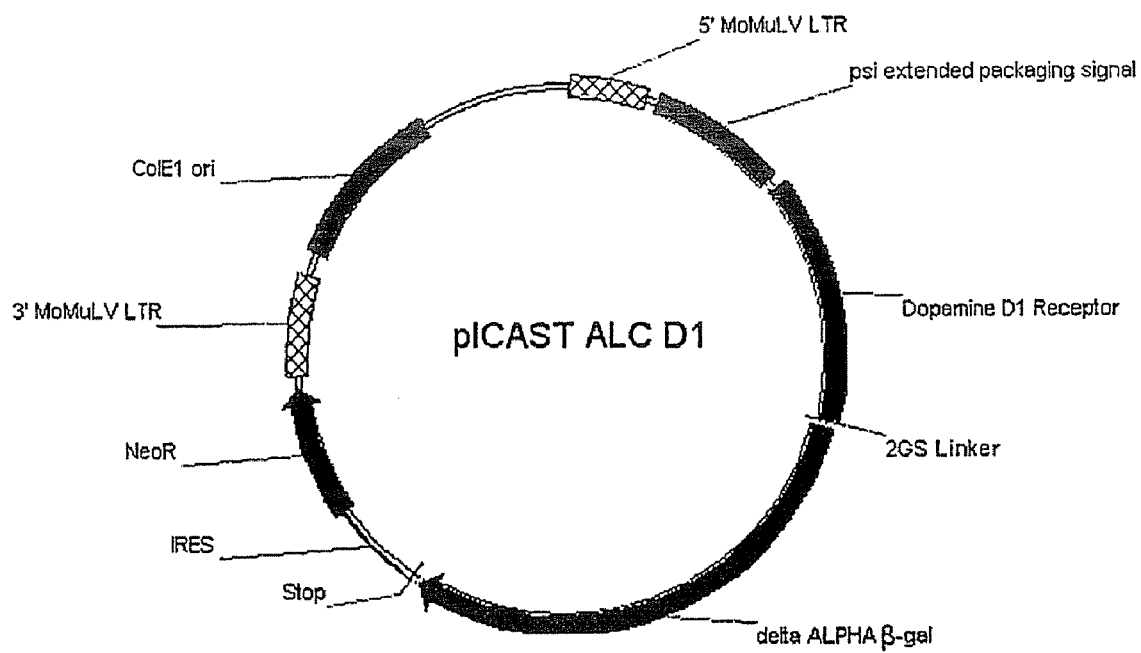
FIG. 22. pICAST ALC D1: Vector for expression of β-galΔα as a C-terminal fusion to Dopamine D1 Receptor. The coding sequence of human Dopamine D1 Receptor (Genebank Accession Number: X58987) was cloned in frame to β-galΔα in a pICAST ALC vector.

1. In the first step, the expression vectors for β2ARΔα and βArr2Δω were engineered in selectable retroviral vectors pICAST ALC, as described in FIG. 18 and pICAST OMC, as described in FIG. 15.

2. In the second step, the two expression constructs were transduced into either C2C12 myoblast cells, or other mammalian cell lines, such as COS-7, CHO, A431, HEK 293, and CHW. Following selection with antibiotic drugs, stable clones expressing both fusion proteins at appropriate levels were selected.

Figure 3A:
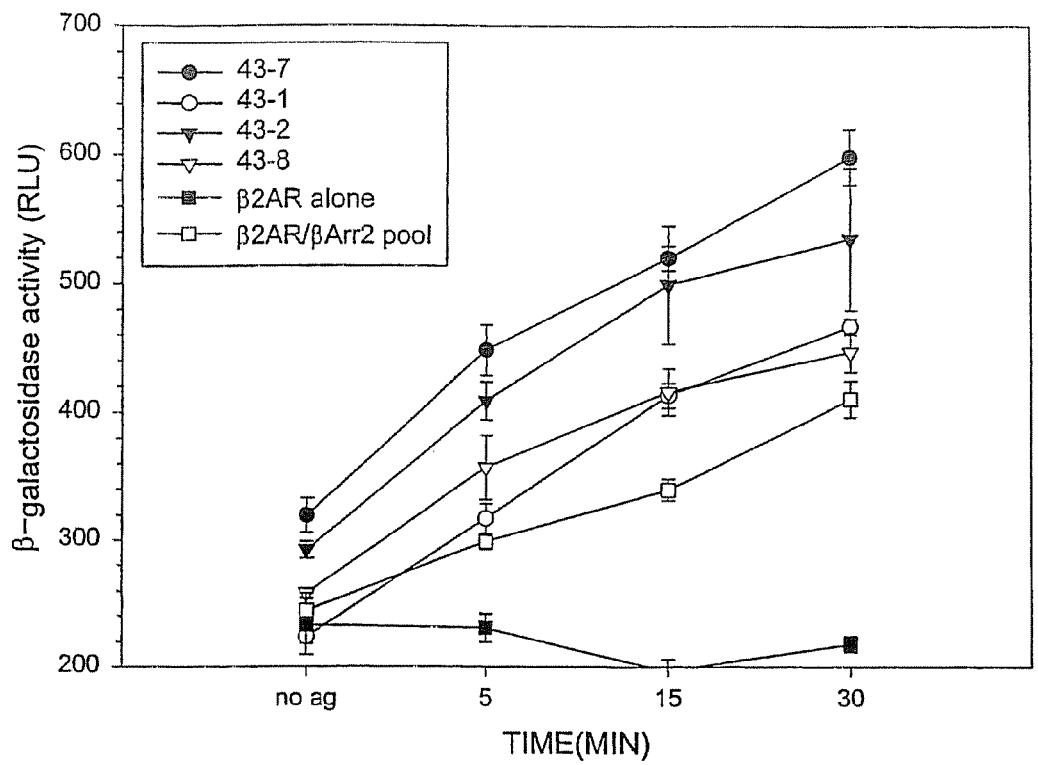
FIG. 3A shows a time course of β-galactosidase activity in response to agonist (−)isoproterenol stimulation in C2 expressing β2AR-βgalΔα (β2AR alone, in expression vector pICAST ALC), or a pool of doubly transduced C2 co-expressing β2AR-βgalΔα and βArr2-βgalΔω (in expression vectors pICAST ALC and pICAST OMC and clones isolated from the same pod (43-1, 43-2, 43-7 and 43-8)).
Figure 3B:
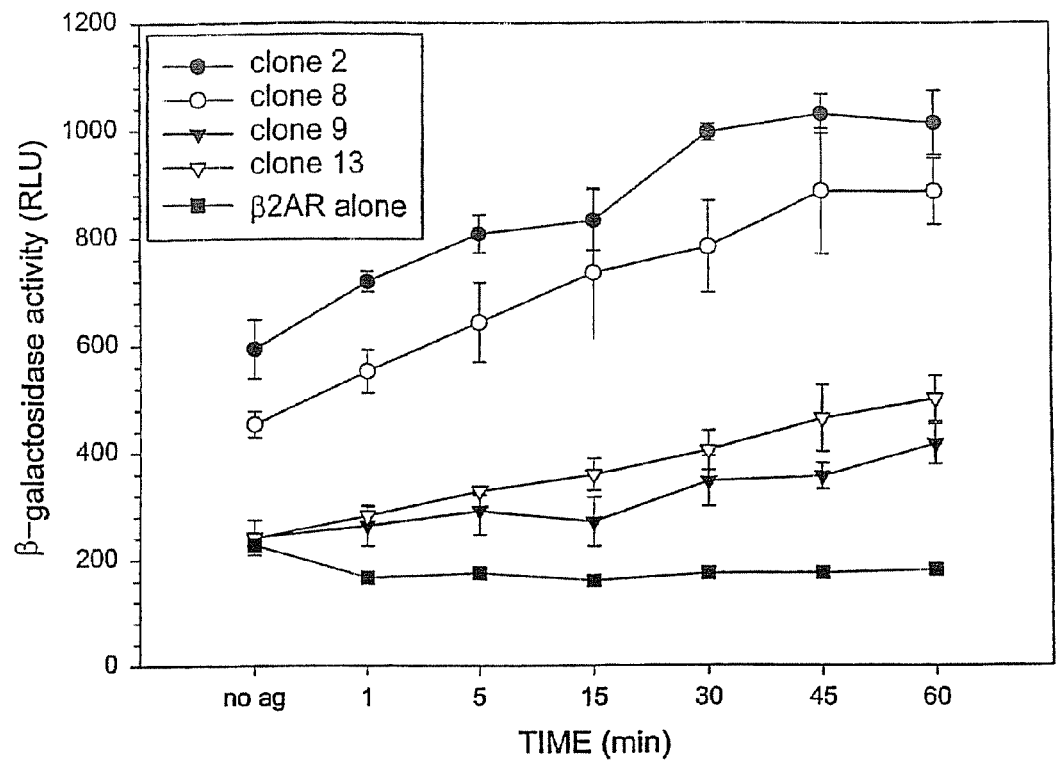
FIG. 3B shows a time course of β-galactosidase activity in response to agonist (−)isoproterenol stimulation in C2 cells expressing β2AR-βgalΔα alone (in expression vector pICAST ALC) and C2 clones co-expressing β2AR-βgalΔα and βArr1-βgalΔω (in expression vectors ICAST ALC and pICAST OMC).
Figure 4A:
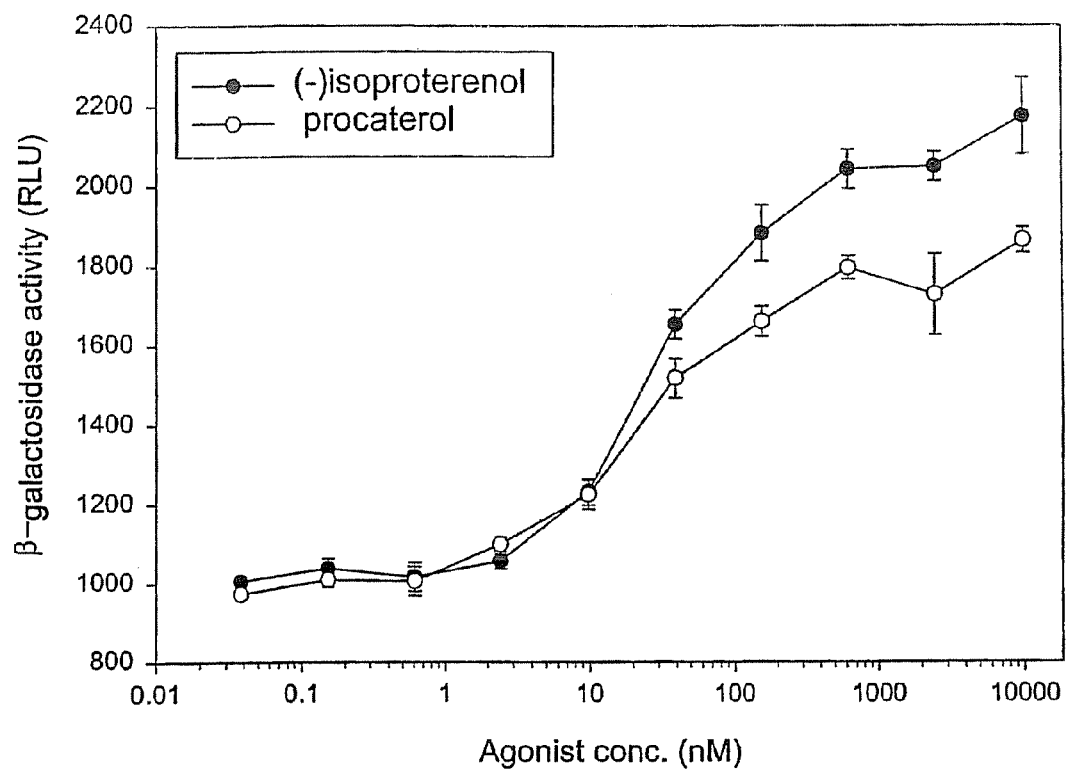
FIG. 4A shows a dose response to agonists (−)isoproterenol and procaterol in C2 cells co-expressing β2AR-βgalΔα and βArr2-βgal-Δω fusion constructs.
Figure 4B:
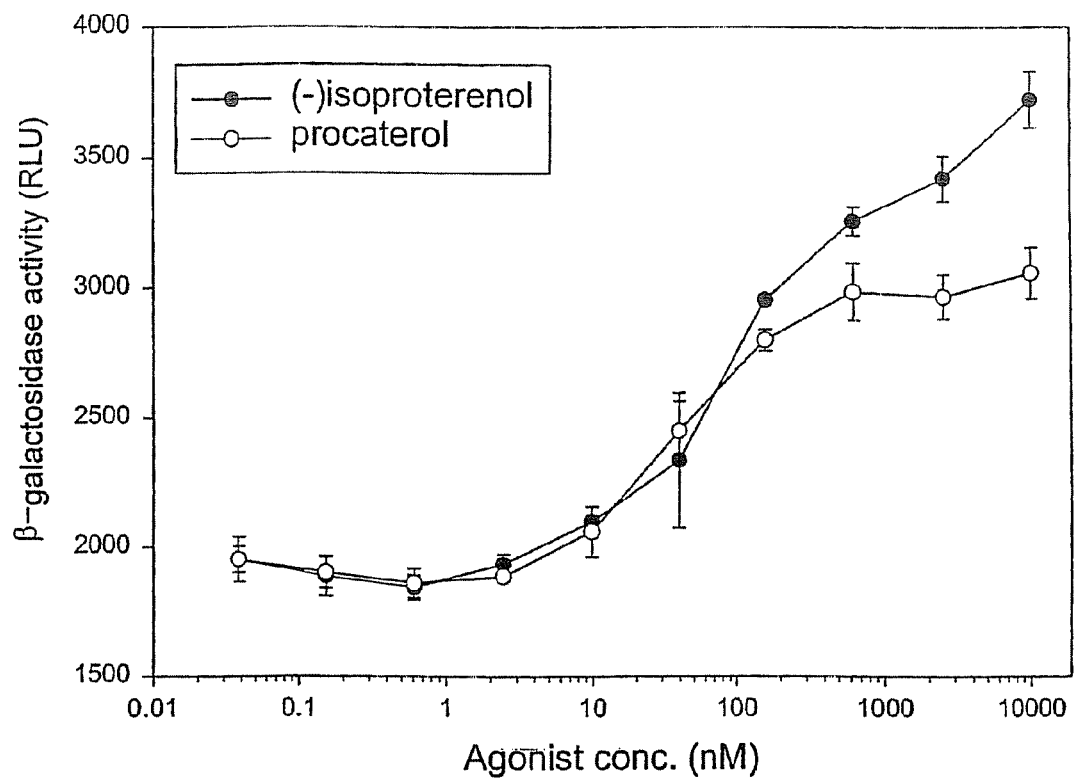
FIG. 4B shows a dose response to agonists (−)isoproterenol and procaterol in C2 cells co-expressing β2AR-βgalΔα and βArr1-βgalΔω fusion constructs.
Figure 5A:
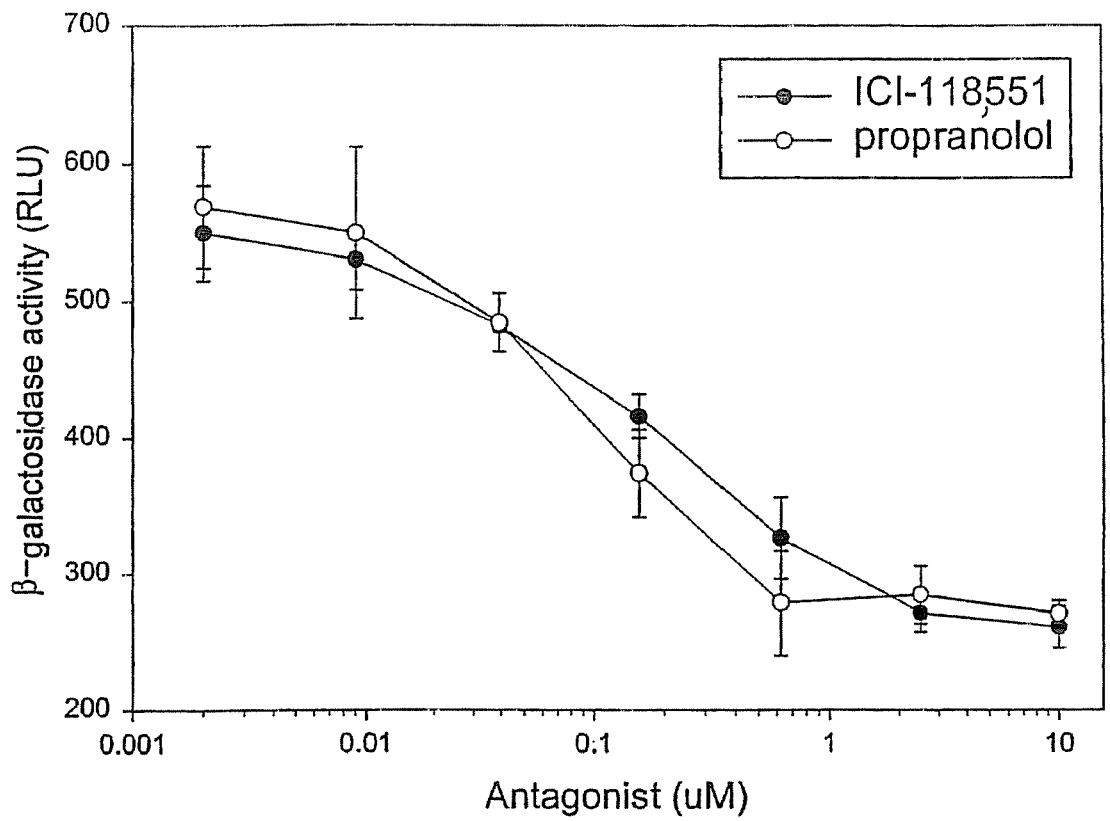
FIG. 5A shows specific inhibition with adrenergic antagonists ICI-118,551 and propranolol of β-galactosidase activity in C2 clones co-expressing β2AR-βgalΔα and βArr2-βgalΔω fusion constructs after incubation with agonist (−)isoproterenol.
Figure 5B:
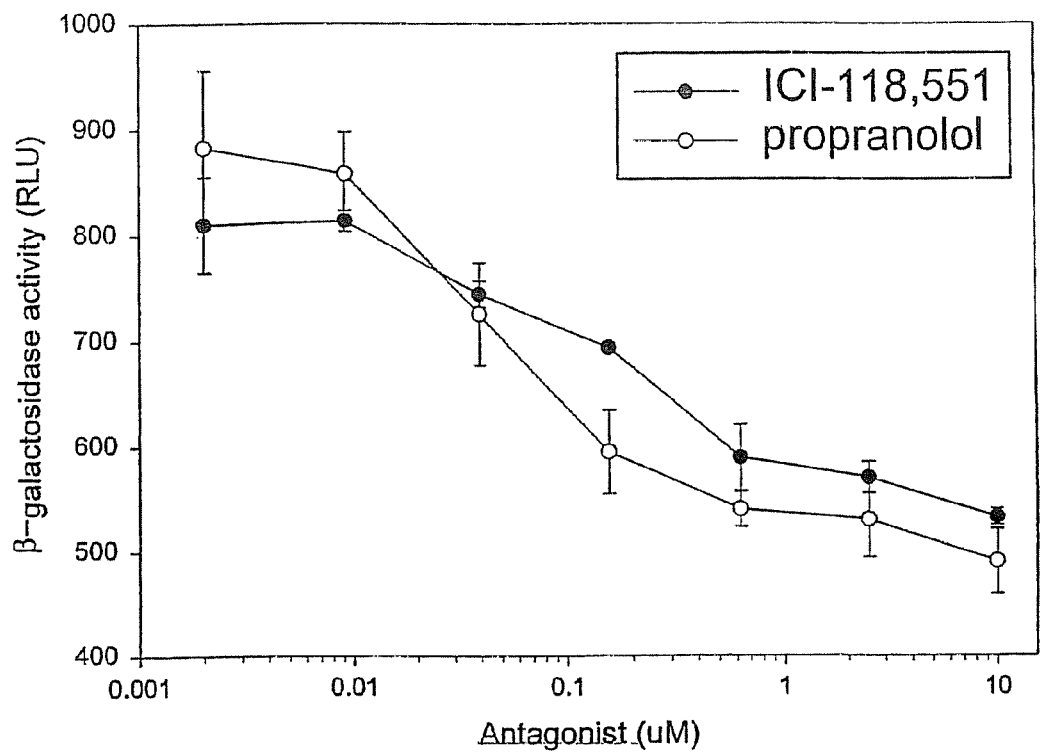
FIG. 5B shows specific inhibition of β-galactosidase activity with adrenergic antagonists ICI-118,551 and propranolol in C2 clones co-expressing β2AR-βgalΔα and βArr1-βgalΔω fusion constructs in the presence of agonist (−)isoproterenol.
Figure 6:
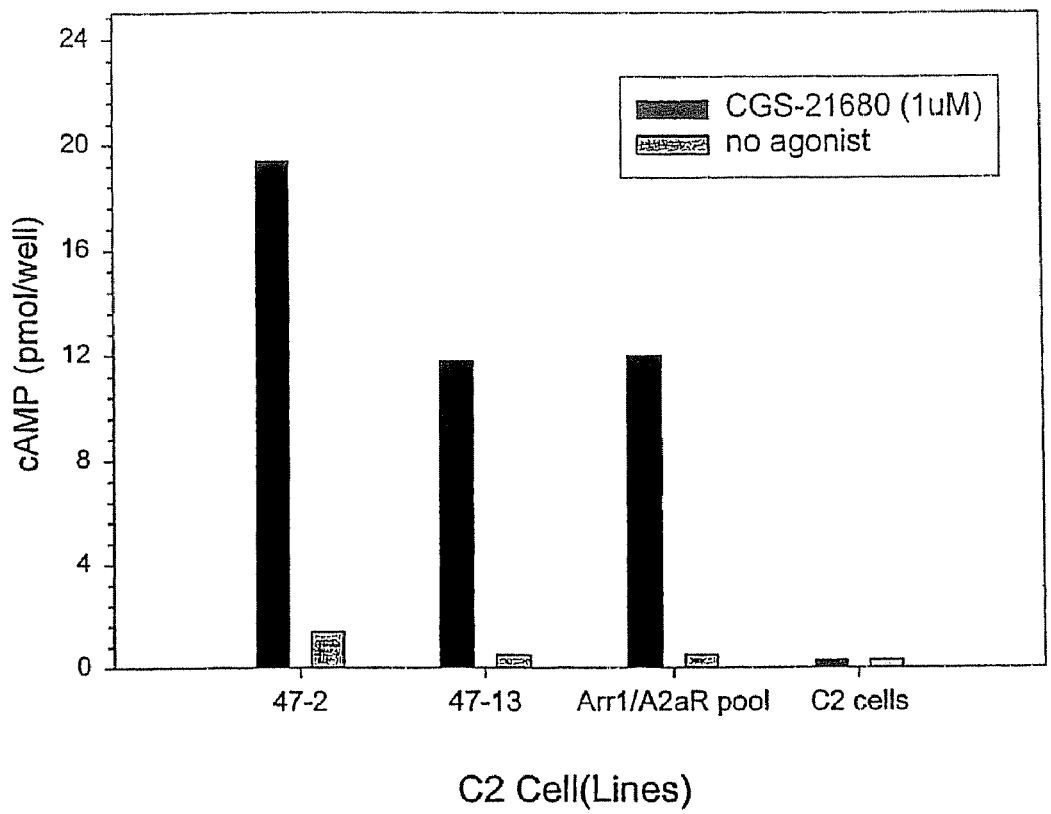
FIG. 6. C2 cells expressing adenosine receptor A2a show cAMP induction in response to agonist (CGS-21680) treatment. C2 parental cells and C2 cells co-expressing A2aR-βgalΔα and βArr1-βgalΔω as a pool or as selected clones (47-2 and 47-13) were measured for agonist-induced cAMP response (pmol/well).
Figure 7:
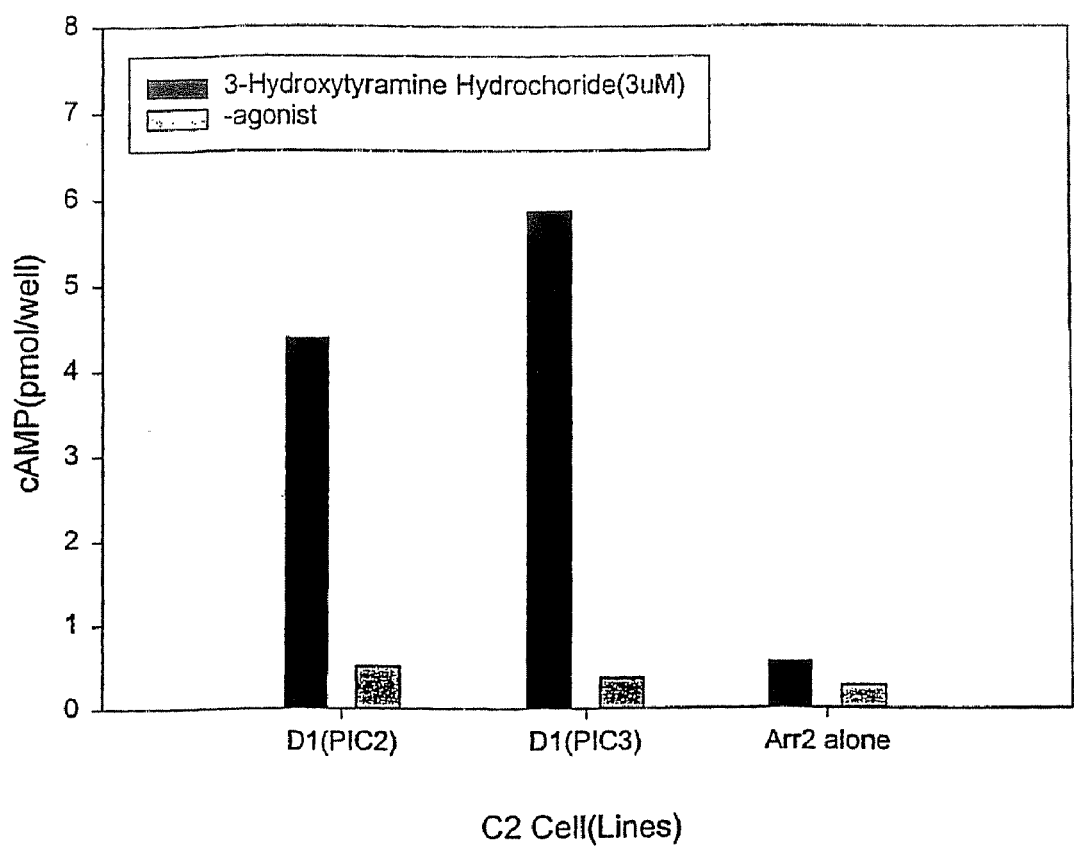
FIG. 7. Agonist stimulated cAMP response in C2 cells co-expressing Dopamine receptor D1 (D1-βgalΔα) and β-arrestin-2 (βArr2-βgalΔω). The clone expressing βArr2-βgalΔω (Arr2 alone) was used as a negative control in the assay. Cells expressing D1-βgalΔα in addition to βArr2-βgalΔω responded agonist treatment (3-hydroxytyramine hydrochloride at 3 μM). D1(PIC2) or D1(PIC3) designate D1 in expression vector pICAST ALC2 or pICAST ALC4, respectively.
Figure 8A:
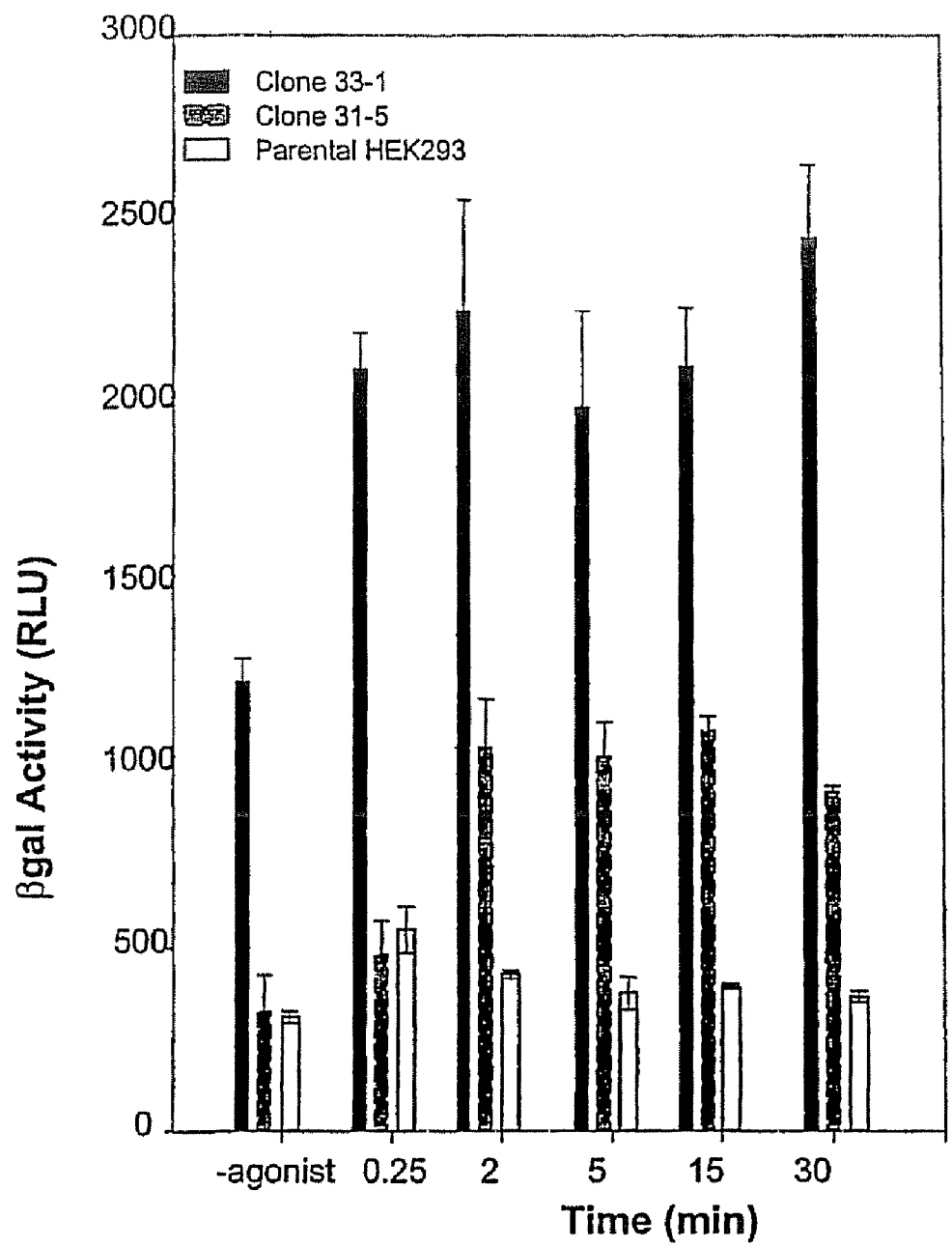
FIG. 8A, FIG. 8B and FIG. 8C show the examples of HEK 293, CHO and CHW cell lines co-expressing adrenergic receptor β2AR and arrestin fusion proteins of β-galactosidase mutants. The β-galactosidase activity was used to monitor agonist-induced interaction of β2AR and arrestin proteins.
Figure 8B:
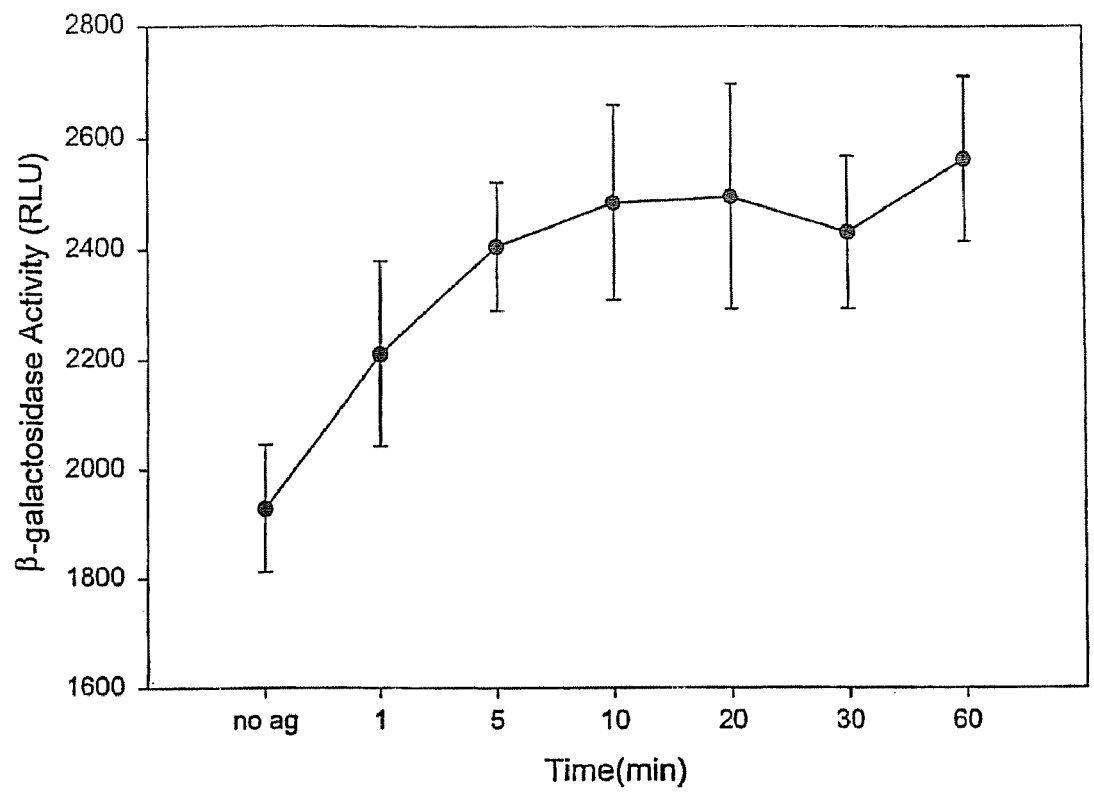
Figure 8C:
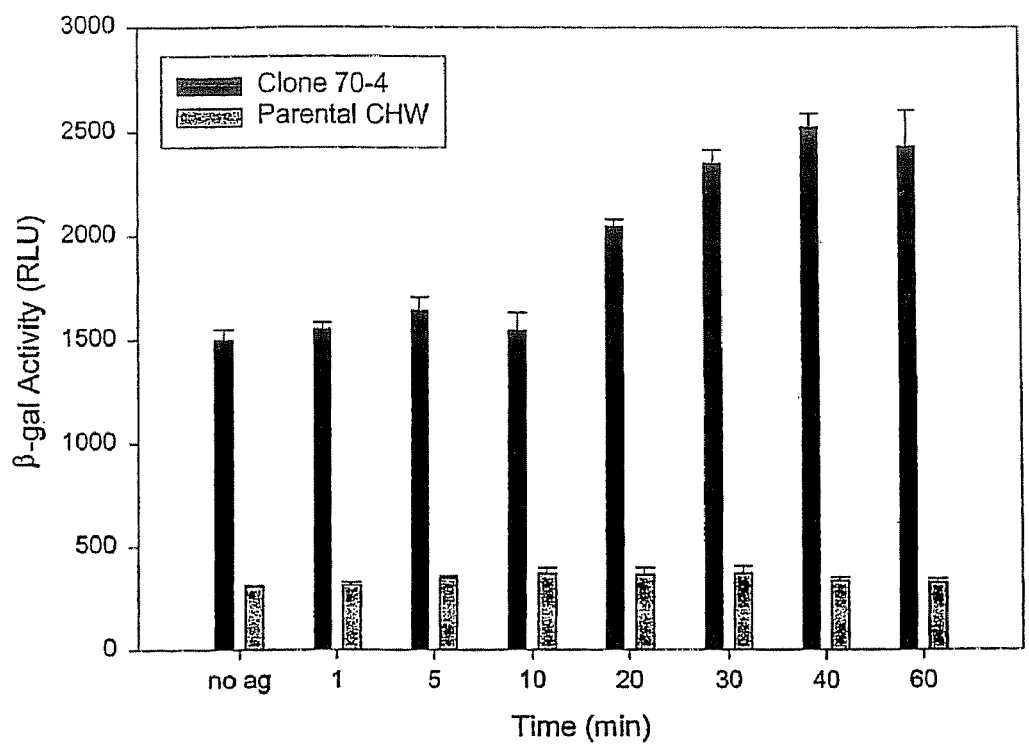
Figure 9A:
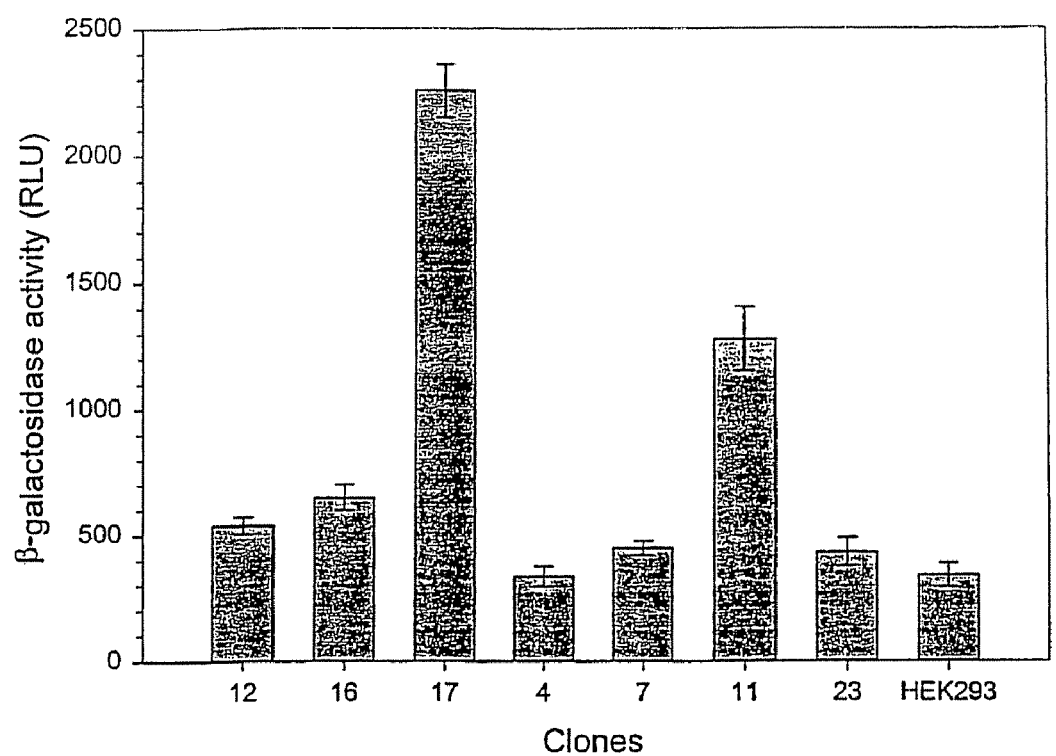
FIG. 9A shows β-galactosidase activity in HEK 293 clones co-expressing β2AR-βgalΔα and β2AR-βgalΔω.
Figure 9B:
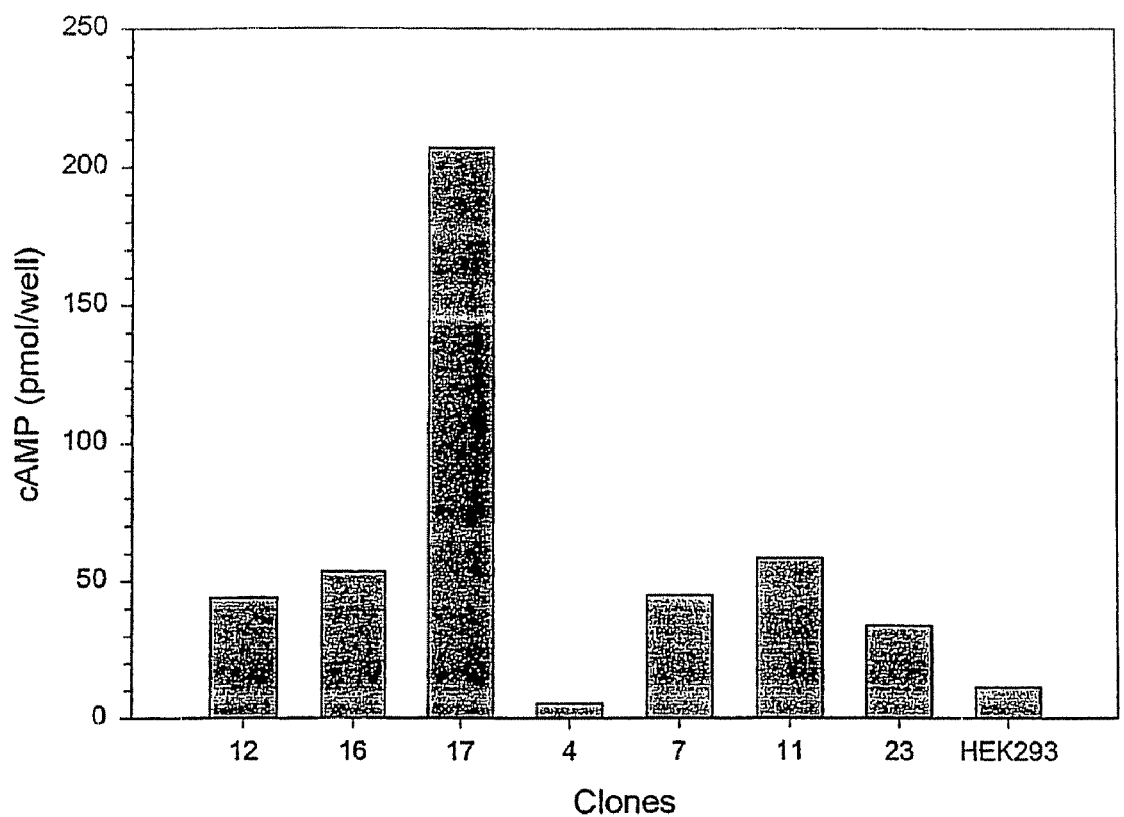
FIG. 9B shows a cAMP response to agonist (−)isoproterenol in HEK 293 clones co-expressing β2AR-βgalΔα and β2AR-βgalΔω. HEK293 parental cells were included in the assays as negative controls.

3. In the last step, the cells expressing both β2ARΔα and βArr2Δω were tested for response by agonist/ligand stimulated β-galactosidase activity. Triplicate samples of cells were plated at 10,000 cells in 100 microliter volume into a well of 96-well culture plate. Cells were cultured for 24 hours before assay. For agonist assay (FIGS. 3 and 4), cells were treated with variable concentrations of agonist, for example, (–) isoproterenol, procaterol, dobutamine, terbutaline or L-L-phenylephrine for 60 min at 37° C. The induced β-galactosidase activity was measured by addition of Tropix Gal-Screen™ assay system substrate (Applied Biosystems) and luminescence measured in a Tropix TR717™ luminometer (Applied Biosystems). For antagonist assay (FIG. 5), cells were pre-incubated for 10 min in fresh medium without serum in the presence of ICI-118,551 or propranolol followed by addition of 10 micro molar (–) isoproterenol.

Serine/Threonine Cluster Strategy

Background

Based on structure-function relationship studies on β-arrestins, a large region within the amino-terminal half of β-arrestins (termed the activation-recognition domain) recognizes the agonist-activated state of GPCRs. This region of β-arrestin also contains a small positively charged domain (approximately 20 amino acids with net charge +7) called the phosphorylation-recognition domain, which appears to interact with the GRK-phosphorylated carboxyl termini of GPCRs.

GPCRs can be divided into two classes based on their affinities for β-arrestins. Oakley et al., "Association of β-Arrestin with G Protein-Coupled Receptors During Clathrin-Mediated Endocytosis Dictates the Profile of Receptor Resensitization." J. Biol. Chem., 274(45):32248–32257 (1999). The molecular determinants underlying this classification appear to reside in specific serine or threonine residues located in the carboxyl-terminal tail of the receptor. The receptor class that contains serine/threonine clusters (defined as serine or threonine residues occupying three consecutive or three out of four positions) in the carboxyl-termini binds β-arrestin with high affinity upon activation and phosphorylation and remains bound with β-arrestin even after receptor internalization, whereas the receptor class that contains only scattered serine and threonine residues in the carboxy-terminal tail binds β-arrestins with less affinity and disassociates from the β-arrestin upon internalization. Several known GPCRs, such as vasopressin V2 receptor (Oakley, et al.), neurotensin receptor 1 and angiotensin II receptor type 1A (Zhang, et al., "Cellular Trafficking of G Protein-Coupled Receptor/β-Arrestin Endocytic Complexes." J. Biol. Chem., 274(16):10999–11006 (1999)), which possess one or more of such serine/threonine clusters in their carboxyl-termini, were shown to bind β-arrestins with high affinity.

EXAMPLE

Figure 24:
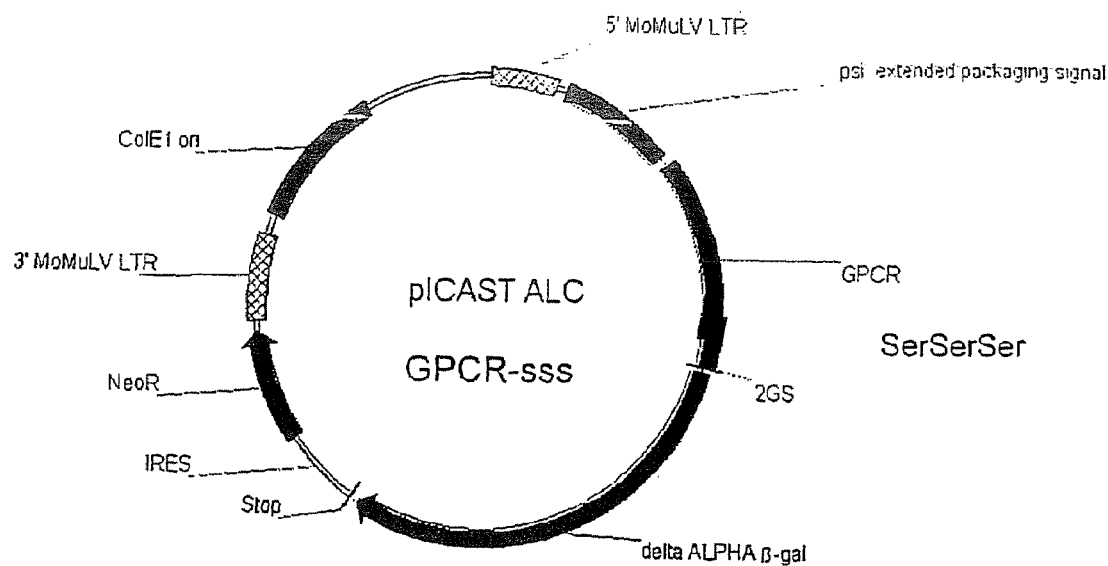
FIG. 24. Vector for expression of a GPCR with inserted seronine/threonine amino acid sequences as a fusion with β-galΔα. The open reading frame of a known or orphan GPCR is engineered to contain additional seronine/threonine sequences, such as SSS (seronine, seronine, seronine), within the C-terminal tail. The engineered GPCR is cloned in frame with β-galΔα in a pICAST ALC vector. The pICAST ALC vector contains the following features: MCS, multiple cloning site for cloning the target protein in frame with the β-galΔα; GS Linker, (GGGGS)n; NeoR, neomycin resistance gene; IRES, internal ribosome entry site; ColE1ori, origin of replication for growth in $E.\ coli$; 5'MoMuLV LTR and 3'MoMuLV LTR, viral promotor and polyadenylation signals from the Moloney Murine leukemia virus.

According to an embodiment of the invention, a serine/threonine cluster strategy is used to facilitate screening assays for orphan receptors that do not possess this structural motif of their own. The orphan receptors are easily classified by sequence alignment. Orphan receptors lacking the serine/threonine clusters are each cloned into an expression vector that is modified to introduce one or more serine/threonine cluster(s) to the carboxyl-terminal tail of the receptor (FIG. 24). The serine/threonine clusters enhance the receptor activation dependent interaction between the activated and phosphorylated receptor (negative charges) and β-arrestin (positive charges in the phosphorylation-recognition domain) through strong ionic interactions, thus prolonging interaction between the receptor and arrestin. The modification of the orphan receptor tail thus makes detection of receptor activation more robust.

Experiment Protocol

Figure 10A:
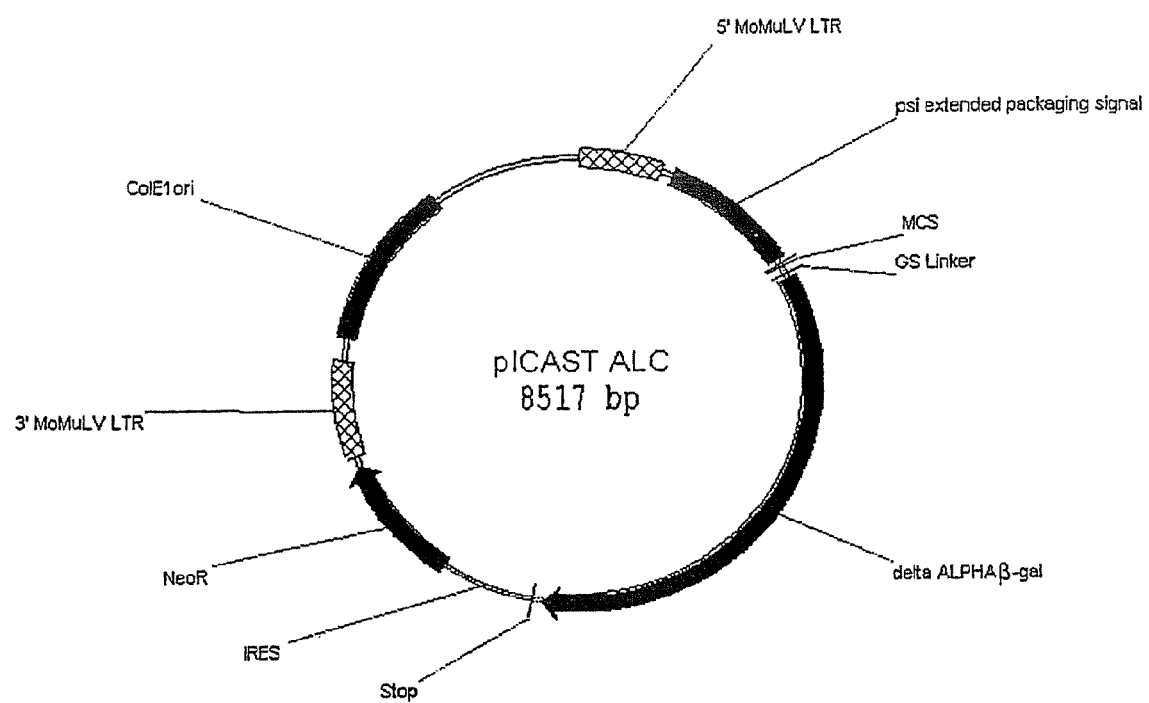
FIG. 10A. pICAST ALC: Vector for expression of β-galΔα as a C-terminal fusion to the target protein. This construct contains the following features: MCS, multiple cloning site for cloning the target protein in frame with the β-galΔα; GS Linker, (GGGGS)n; NeoR, neomycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 11A:
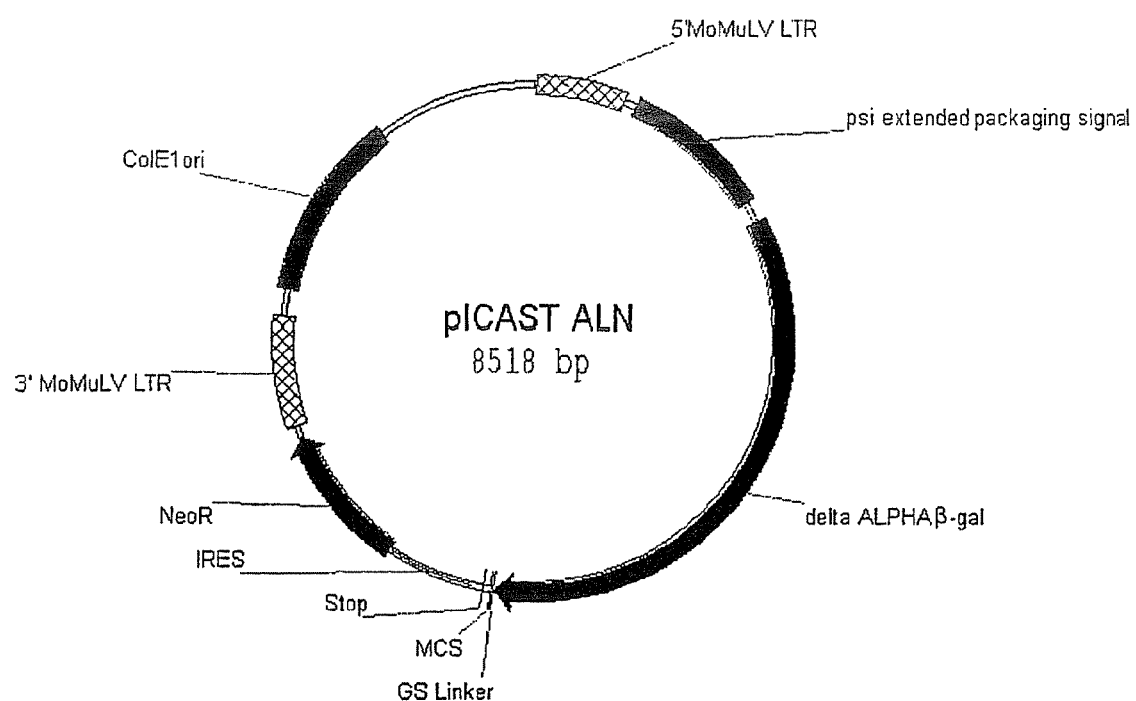
FIG. 11A. pICAST ALN: Vector for expression of β-galΔα as an N-terminal fusion to the target protein. This construct contains the following features: MCS, multiple cloning site for cloning the target protein in frame with the β-galΔα; GS Linker, (GGGGS)n; NeoR, neomycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 12A:
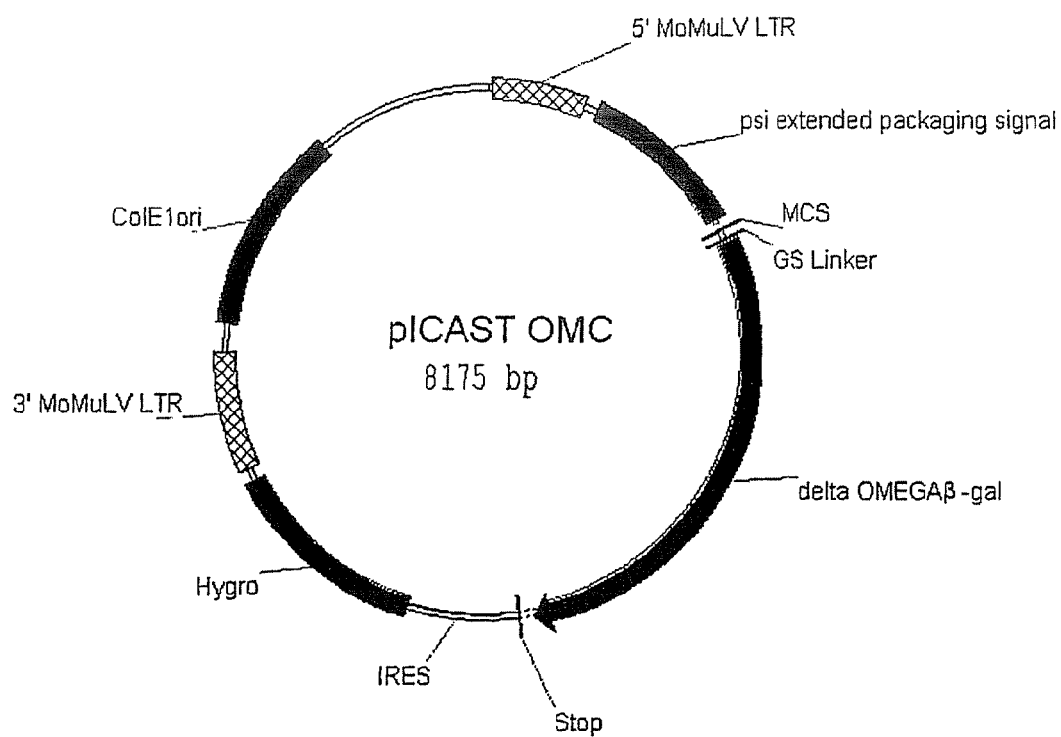
FIG. 12A. pICAST OMC: Vector for expression of β-galΔω as a C-terminal fusion to the target protein. This construct contains the following features: MCS, multiple cloning site for cloning the target protein in frame with the β-galΔω; GS Linker, (GGGGS)$_n$; Hygro, hygromycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 13A:
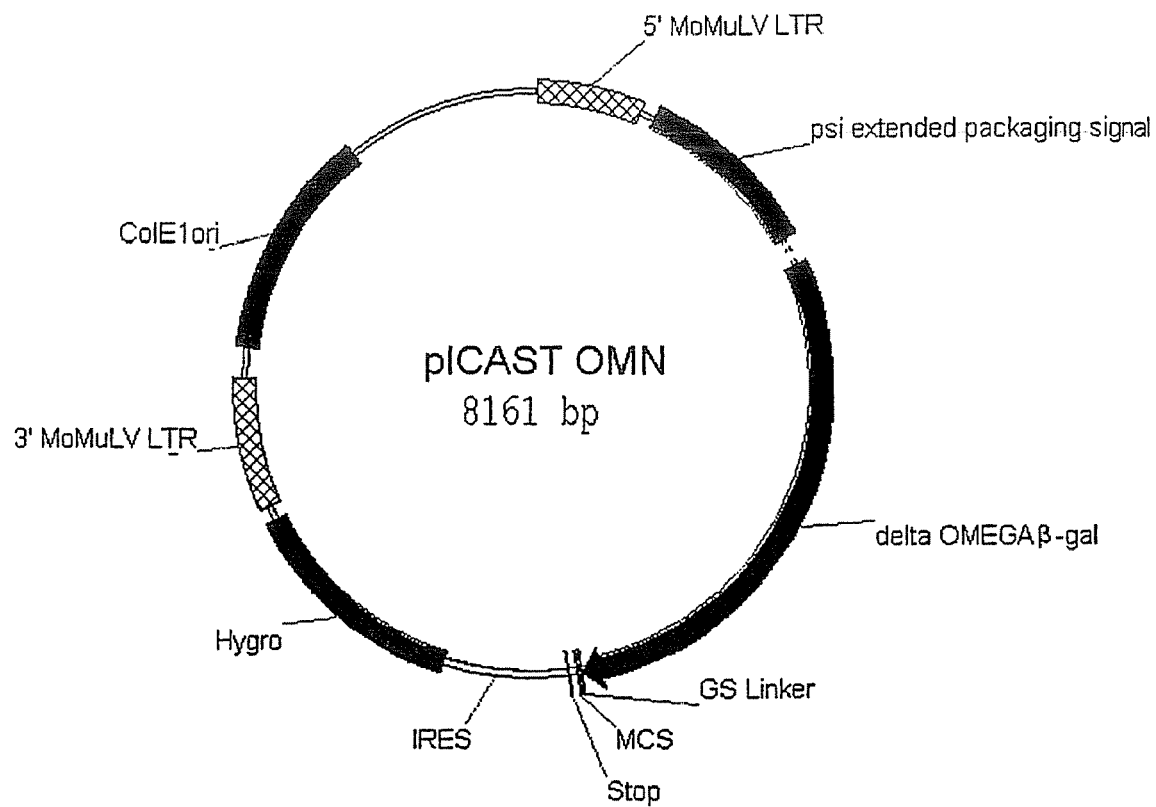
FIG. 13A. pICAST OMN: Vector for expression of β-galΔω as an N-terminal fusion to the target protein. This construct contains the following features: MCS, multiple cloning site for cloning the target protein in frame with the β-galΔω; GS Linker, (GGGGS)n; Hygro, hygromycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 14:
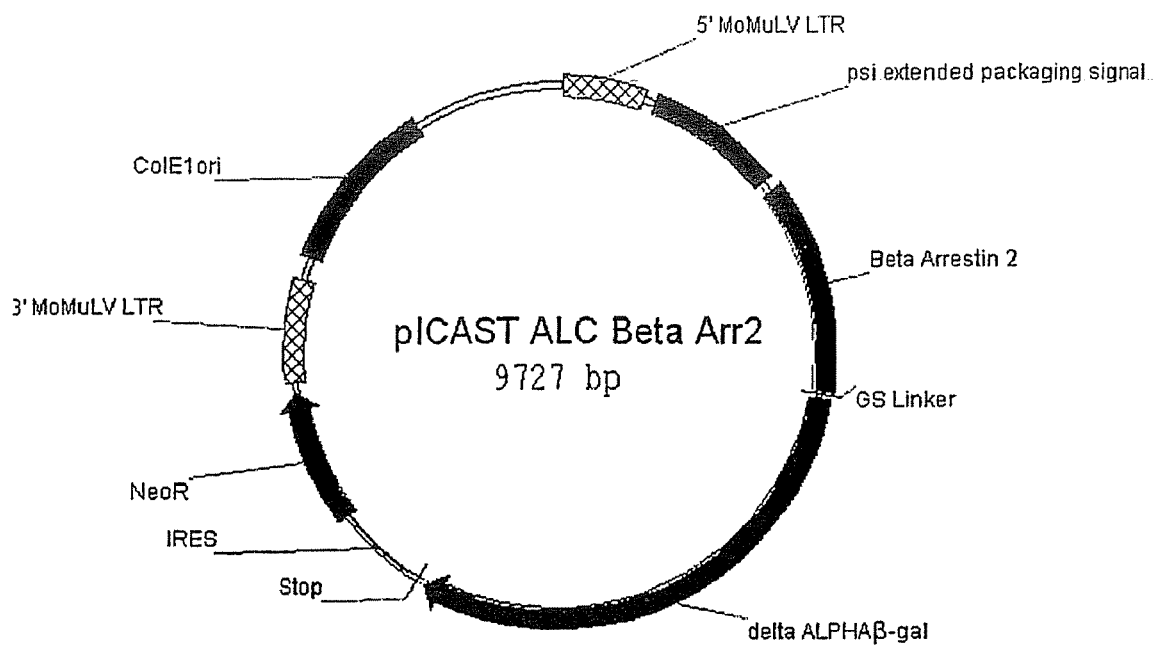
FIG. 14. pICAST ALC βArr2: Vector for expression of β-galΔα as a C-terminal fusion to β-arrestin-2. The coding sequence of human β-arrestin-2 (Genebank Accession Number: NM_004313) was cloned in frame to β-galΔα in a pICAST ALC vector.

1. In a first step, the open-reading-frame (ORF) of an orphan receptor, which lacks the serine/threonine clusters, is cloned into a modified expression vector such as pICAST ALC described in FIG. 10A. The modified pICAST ALC includes coding sequences for one or more sets of serine/threonine clusters (for example, SSS or SST) located downstream from the insert of the ORF of an orphan receptor (FIG. 24).

2. In a second step, chimeric orphan receptor, $ORF_{orphan}$ $R-(SSS)_n-\Delta\alpha$, is co-expressed in a mammalian cell with a β-arrestin chimera, such as βArr2Δω described in FIG. 15.

3. In a third step, the cell is treated with an agonist or a ligand and the activated receptor with phosphorylated serine cluster(s) binds the β-arrestin with high affinity producing strong signals in readouts of β-gal complementation.

Figure 28:
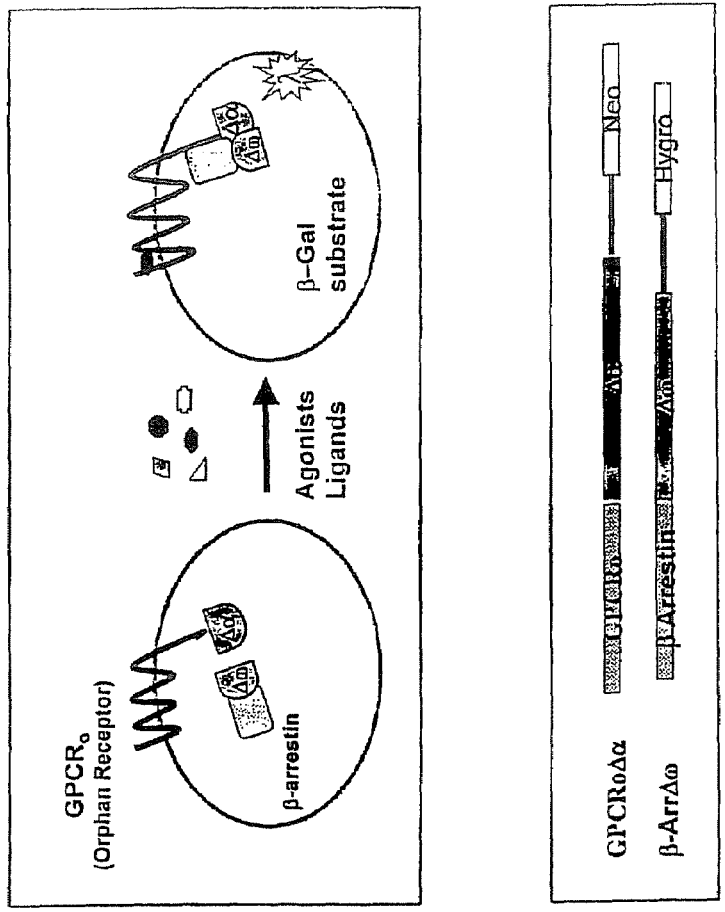
FIG. 28. Ligand fishing for orphan receptors by β-galactosidase mutant complementation in ICAST™ system. A schematic depicting the utilization of the invention for ligand fishing and agonist/antagonist screening for orphan GPCRs. As an example, a test cell expressing two β-gal fusion proteins, GPCR$_{orphan}$-Δα and Arrestin-Δω, is subjected to treatments with samples from natural or synthetic compound libraries, or from tissue extracts, or from conditioned media of cultured cells. An increased β-gal activity after treatment indicates the activation of the orphan receptor by a ligand in the testing sample. The readout of increased β-gal activity reflects the interaction of an activated GPCR orphan receptor with a β-arrestin. Therefore, a cognate or a surrogate ligand for the testing receptor is identified.

This assay, which provides a means for sensitive measurement of functional activation of the orphan receptors, can be used to screen for natural or surrogate ligands for orphan receptors, a process called de-orphaning or target discovery for new GPCRs (FIG. 28). Furthermore, this assay is also useful in screening for potential agonists and antagonists for lead discovery of GPCRs.

Enhanced Binding of Arrestin in the Presence and in the Absence of GPCR

Phosphorylation

Background

Six different classes of G-protein coupled receptor kinases (GRKs) have been identified and each of these has been reported to be expressed as multiple splice variants. Krupnick et al., "The role of receptor kinases and arrestins in G protein-coupled receptor regulation." Ann. Rev. Pharmacol. Toxicol., 38:289–319 (1998). Although many cell lines express a variety of GRKs, the specific GRK required for phosphorylation of a given GPCR may not always be present in the cell line used for recombinant GPCR and arrestin expression. This is particularly an issue for applications using orphan receptors, in which case the cognate GRK will likely be unknown. In other cases, the cell line used for recombinant expression work may have the required GRK, but may express the GRK at low levels. In order to bypass such caveats, genetically modified arrestins that bind specifically to activated GPCRs, but without the requirement of GRK phosphorylation are employed.

Mutagenesis studies on arrestins demonstrate that point mutations in the phosphorylation-recognition domain, particularly mutations converting Arg175 (of visual arrestin) to an oppositely charged residue such as glutamate (R175E mutation), result in an arrestin which specifically binds to activated GPCRs, but does so without the requirement for phosphorylation.

Numerous observations have led to the hypothesis that arrestin exists in an inactive state that has a low affinity for GPCRs. Once a GPCR is both activated and phosphorylated, the phosphorylated region of the GPCR C-terminus interacts with the phosphorylation-recognition domain of arrestin causing the arrestin to change conformations allowing the activation-recognition region to be exposed for binding to the activated/phosphorylated receptor. Vishnivetskiy et al., "How does arrestin respond to the phosphorylated state of rhodopsin?" J. Biol. Chem., 274(17):11451–11454 (1999); Gurevich et al., "Arrestin interactions with G protein-coupled receptors. Direct binding studies of wild-type and mutant arrestins with rhodopsin, beta 2-adrenergic and m2 muscarinic cholinergic receptors." J. Biol. Chem., 270(2):720–731, (1995); Gurevich et al., "Mechanism of phosphorylation-recognition by visual arrestin and the transition of arrestin into a high affinity binding site." Mol. Pharmacol., 51(1):161–169 (1997); Kovoor et al., "Targeted construction of phosphorylation-independent beta-arrestin mutants with constitutive activity in cells." J. Biol. Chem., 274(11):6831–6834 (1999). In summary, binding studies of single mutation, double mutation, deletion, and chimerical arrestins with inactive, inactive and phosphorylated, activated but not phosphorylated, or activated and phosphorylated visual or non-visual GPCRs all support this model.

EXAMPLE

A phosphorylation insensitive mutant of arrestin fused to mutant reporter protein can be produced that will bind to activated GPCRs in a phosphorylation independent manner. As proof of concept, a point mutation for β-arrestin2, R170E β-arrestin2, has been produced and its interaction with β2AR has been analyzed in accordance with the invention.

Figure 25:
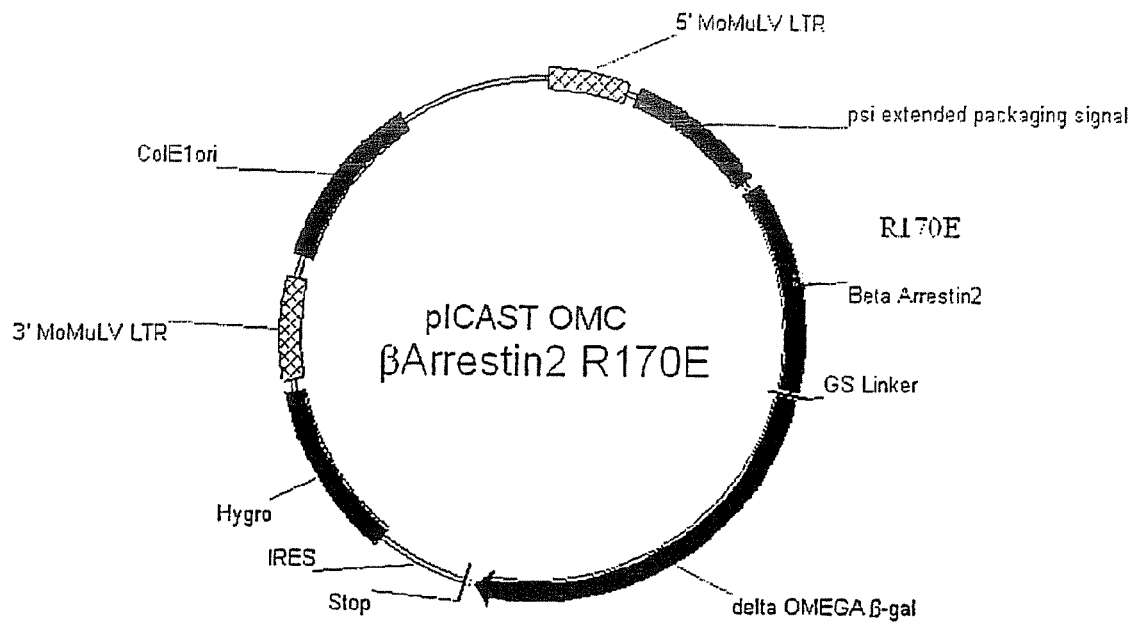
FIG. 25. Vector for expression of mutant (R170E) β-arrestin2 as a fusion with β-galΔω. The open reading frame of β-arrestin2 is engineered to contain a point mutation that converts arginine 170 to a glutamate. The mutant β-arrestin 2 is cloned in frame with β-galΔω in a pICAST OMC vector. The pICAST OMC vector contains the following features: MCS, multiple cloning site for cloning the target protein in frame with the β-galΔα; GS Linker, (GGGGS)n; Hygro, hygromycin resistance gene; IRES, internal ribosome entry site; ColE1ori, origin of replication for growth in $E.\ coli$; 5'MoMuLV LTR and 3'MoMuLV LTR, viral promotor and polyadenylation signals from the Moloney Murine leukemia virus.
Figure 26:
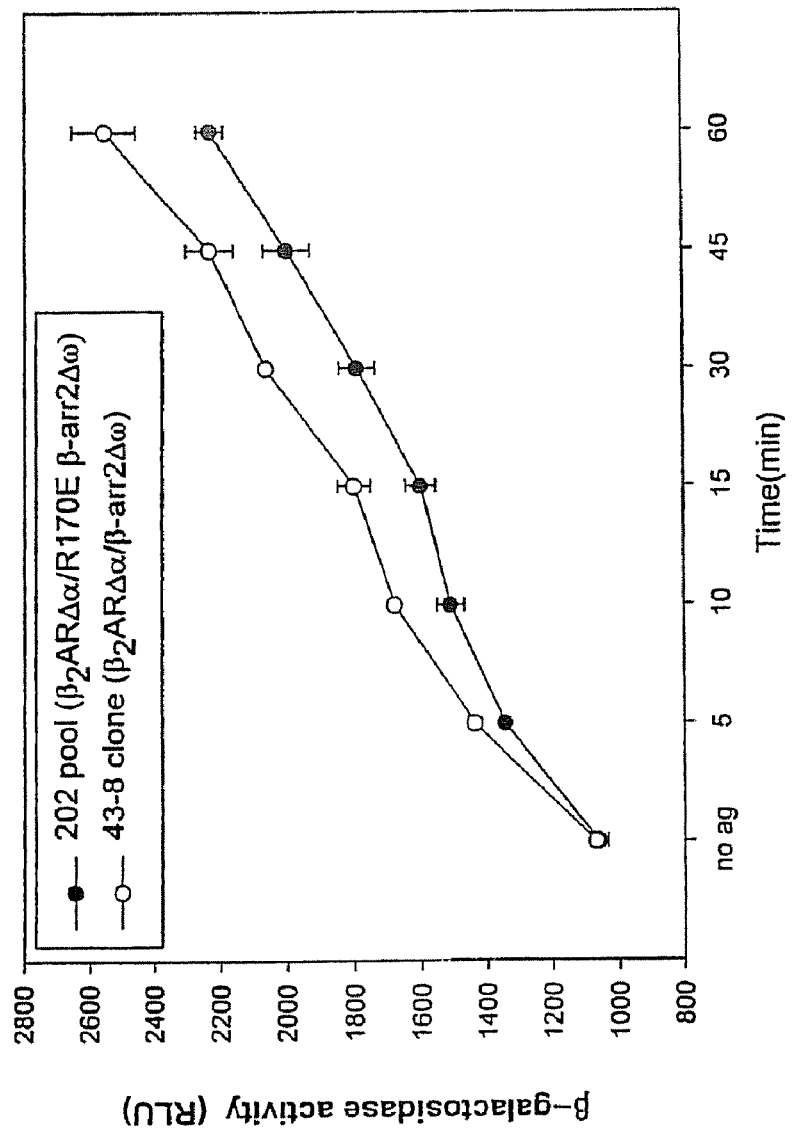
FIG. 26. Phosphorylation insensitive Mutant R170E β-Arrestin2Δω binds to β2ARΔα in Response to Agonist Activation. A parental β2ARΔα C2 cell line was tranduced with the Mutant R170E β-Arrestin2Δω construct. Clonal populations co-expressing the two constructions were plated at 10,000 cells/well in 96 well plates and treated with 10 μM (−)isoproterenol, 0.3 mM ascorbic acid for the indicated time period. β-galactosidase activity was measured by addition of Tropix Gal-Screen™ assay system substrate (Applied Biosystems) and luminescence was measured using a Tropix TR717™ luminometer (Applied Biosystems). Treatments were performed in triplicate. For comparison, a clonal cell line (43-8) co-expressing β2ARΔα and wild-type β-Arrestin2Δω was also plated at 10,000 cells/well and given the same agonist treatment regimen. Minutes of (−)isoproterenol treatment is shown on the X-axis and β-galactosidase activity indicated by relative light units (RLU) is shown on the Y-axis.
Figure 27:
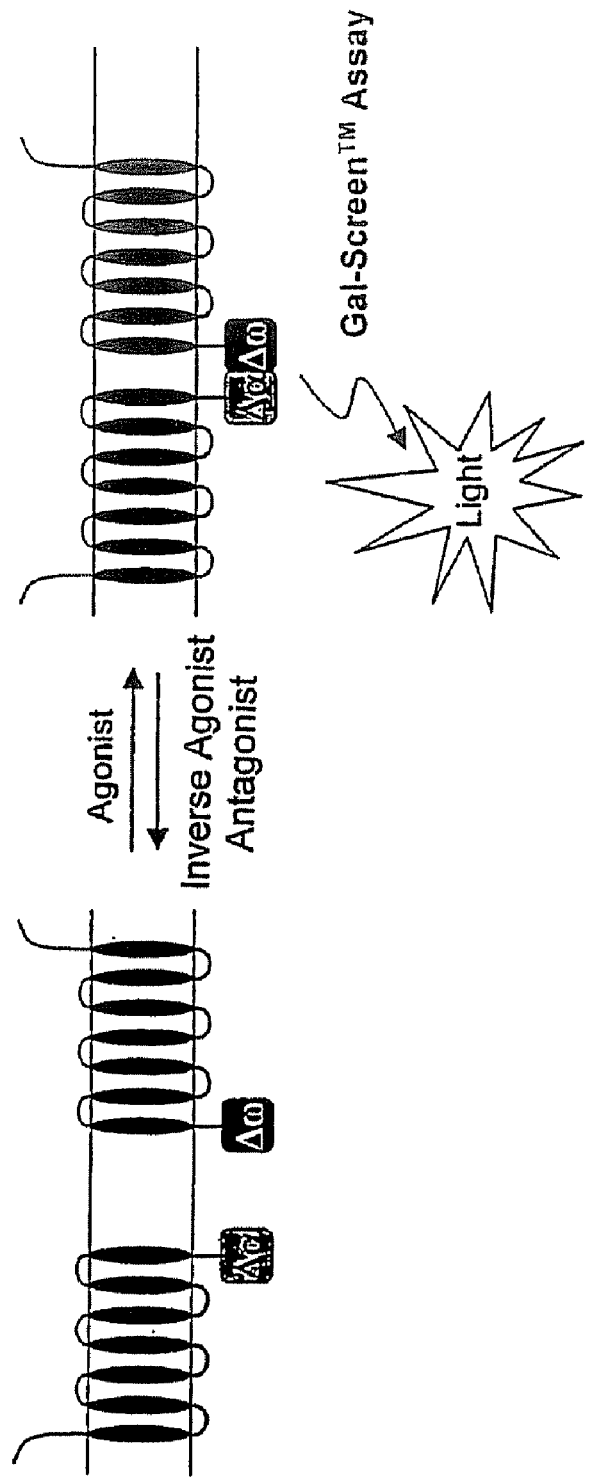
FIG. 27. GPCR dimerization measured by β-galactosidase complementation. A schematic depicting the utilization of the invention for monitoring GPCR homo- or heterodimerization. One GPCR is fused to one complement enzyme fragment, while the second GPCR is fused to the second complement enzyme fragment. Interaction of the two GPCRs is monitored by complementation of the enzyme fragments to produce an active enzyme complex (i.e., β-galactosidase activity). GPCR homo- or hetero-dimerization can be monitored in the absence or presence of ligand, agonists, inverse agonists or antagonists.

Experimental Protocol:
1) In the first step, β-arrestin2 was mutated such that Arg170 was converted to Glu. This mutation is equivalent to the R175E mutation of visual arrestin. The mutant β-arrestin2 open reading frame was cloned in frame with Δω-β-galactosidase in the pICAST OMC expression vector to produce a modified expression vector R170E β-arrestin2 (FIG. 25).
2) In the second step, the R170E β-arrestin2 expression construct was transduced into a C2C12 myoblast cell line that had been engineered to express β2AR as a fusion to Δα-β-galactosidase as described in FIG. 18 of U.S. application Ser. No. 09/654,499. Following selection with antibiotic drugs, a population of clones expressing both fusion proteins was obtained.
3) In the last step, this population of cells expressing both R170E β-arrestin 2Δω and β2ARΔα were tested for response by agonist/ligand stimulated β-galactosidase activity as demonstrated in FIG. 26. The C2C12 clone 43-8 co-expressing β2ARΔα and wild-type β-arrestin2Δω (FIG. 26) was used as reference control. Triplicate samples of cells were plated at 10,000 cells in 100 microliter volume into wells of a 96-well culture plate. Cells were cultured for 24 hours before assay. For agonist assay as in FIG. 26, cells were treated with 10 μm (−)isoproterenol stabilized with 0.3 mM ascorbic acid 37° C. for 0, 5, 10, 15, 30, 45 or 60 minutes. The induced β-galactosidase activity was measured by addition of Tropix Gal-Screen™ assay system substrate (Applied Biosystems) and luminescence measured in a Tropix TR717™ luminometer (Applied Biosystems). As shown in FIG. 26, the mutant arrestin interacts with β2AR in an agonist-dependent manner and was comparable with that of wild-type arrestin.
4) To expand the application of phosphorylation-insensitive arrestin, cell lines such as C2C12, CHO or HEK 293, are developed that express the R170E β-arrestin 2Δω construction. These cell lines can be used to transduce orphan or known GPCRs as fusions with Δα-β-galactosidase in order to develop cell lines for agonist and antagonist screening and Development of Super Arrestins:

Background

Attenuation of GPCR signaling by the arrestin pathway serves to ensure that a cell or organism does not over-react to a stimulus. At the same time, the arrestin pathway often serves to recycle the GPCR such that it can be temporarily inactivated but then quickly resensitized to allow for sensitivity to new stimuli. The down-regulation process involves phosphorylation of the receptor, binding to arrestin and endocytosis. Following endocytosis of the desensitized receptor, the receptor is either degraded in lysosomes or resensitized and sent back to the membrane. Resensitization involves release of arrestin from the receptor, dephosphorylation and cycling back to the membrane. The actual route a GPCR follows upon activation depends on its biological function and the needs of the organism. Because of these diverse pathways that may be required of the down-regulation pathway, arrestin affinities for activated GPCRs vary from receptor to receptor. It would thus be very advantageous to engineer super arrestins that have a higher affinity and avidity for activated GPCRs than what nature has provided.

Although mutational, deletion and chimerical studies of arrestins have focused on understanding regulatory switches in the molecule that respond to GPCR phosphorylation states, several of these altered recombinant forms of arrestin have resulted in molecules with enhanced binding to activated, phosphorylated GPCRs. Conversion of Arg175 to histidine, tyrosine, phenylalanine or threonine results in significantly higher amounts of binding to phosphorylated, activated rhodopsin than wild-type arrestin or R175E arrestin, although these mutations result in less binding to activated, non-phosphorylated receptor. Gurevich et al. (1997). In addition, conversion of Valine 170 to alanine increased the constitutive affect of the R175E mutation, but also nearly doubled the amount of interaction of wild-type arrestin with activated, phosphorylated rhodopsin. Gurevich et al. (1997).

Truncation of β-arrestin1 at amino acid 382 has been reported to enhance binding of both R169E (equivalent to arrestin R175E) and wild-type β-arrestin1 to activated or activated and phosphorylated receptor, respectively. Kovoor et al. Chimerical arrestins in which functional regions of visual arrestin were swapped with those of β-arrestin1 have been reported to be altered in binding affinity to activated, phosphorylated GPCRs. Gurevich et al. (1995). Several of these chimeras, such as β-arrestin1 containing the visual arrestin extreme N-terminus, show increased specific binding to phosphorylated activated GPCRs compared to wild-type β-arrestin1 (Gurevich et al. (1995)). Modifications that enhance arrestin affinity for the activated GPCR such as described above, whether phosphorylated or non-phosphorylated, could also enhance signal to noise of β-galactosidase activity since the arrestin/GPCR complex is stabilized and/or more long-lived. The use of mutant arrestins with higher activated-GPCR affinity would improve the inventive technology for GPCR targets, without compromising receptor/ligand biology.

In addition, this "super arrestin" approach can be combined with the use of arrestin point mutations to provide a stronger signal to noise with or without GRK requirements.

EXAMPLE

An arrestin mutant fused to mutant reporter protein can be produced to enhance binding of the arrestin to an activated GPCR to enhance sensitivity of detection.

Experiment Protocol
1) In the first step, mutant β-arrestin2 constructions will be generated which include R170E/T/Y/or H, V165A, substitution of a.a 1-43 with a.a. 1-47 of visual arrestin, or deletion of the C-terminal and combinations of these alterations. The mutant β-arrestin2 open reading frames will be cloned in frame with Δω-β-galactosidase in the pICAST OMC expression vector similar to cloning of the R170E β-arrestin2 mutation shown in FIG. 25.
2) In the second step, mutant expression constructs will be transduced into a C2C12 myoblast blast cell line that has been engineered to express β2AR as a fusion to Δα-β-galactosidase. Following selection with antibiotic drugs, a population of clones expressing both fusion proteins will be obtained. Wild type and R170E β-arrestin2 constructions will be transduced to generate control, reference clonal populations.
3) In the third step, populations of cells expressing both β-arrestin2Δω (mutant or wild type) and β2ARΔα will be tested for response by agonist/ligand stimulated β-galactosidase activity.
4) In the next step, mutant (super) β-arrestin2Δω constructions that show a significantly higher signal to noise ratio in the agonist assay compared with wild-type β-arrestin2Δω will be chosen. These constructions will be used to develop stable cell lines expressing the "super" β-arrestin2Δω that can be used for transducing in known or orphan GPCRs. Use of a super β-arrestin2Δ107 could increase the signal to noise of ICAST/GPCR applications allowing improved screening capabilities for lead and ligand discovery.

Super Arrestin is used to increase the binding efficiency of arrestin to an activated GPCR and to stabilize the GPCR/arrestin complex during GPCR desensitization. This application can be used to increase the robustness of ICAST/GPCR applications in cases where the GPCR is normally resensitized rapidly post desensitization.

The assays of this invention, and their application and preparation have been described both generically, and by specific example. The examples are not intended as limiting. Other substituent identities, characteristics and assays will occur to those of ordinary skill in the art, without the exercise of inventive faculty. Such modifications remain within the scope of the invention, unless excluded by the express recitation of the claims advanced below.

What is claimed is:

1. A method of assessing the effect of a test condition on G-protein-coupled receptor (GPCR) pathway activity, comprising:
   a) providing a cell that expresses a GPCR as a fusion protein to one mutant form of reporter enzyme and an interacting protein partner as a fusion to another mutant form of enzyme;
   wherein said GPCR fusion protein is modified to include one or more sets of serine/threonine clusters, wherein said one or more sets of serine/threonine clusters enhance binding of said GPCR to arrestin, wherein said enhanced binding between said GPCR and said arrestin increases sensitivity of detection of said effect of said test condition;
   b) exposing the cell to a ligand for said GPCR under said test condition; and
   c) monitoring activation of said GPCR by complementation of said reporter enzyme;
   wherein increased reporter enzyme activity in the cell compared to that which occurs in the absence of said test condition indicates increased GPCR interaction with interacting protein partner compared to that which occurs in the absence of said test condition, and decreased reporter enzyme activity in the cell compared to that which occurs in the absence of said test condition indicates decreased GPCR interaction with interacting protein partner compared to that which occurs in the absence of said test condition.

2. A method of assessing the effect of a test condition on G-protein-coupled receptor (GPCR) pathway activity, comprising:
   a) providing a cell that expresses a GPCR as a fusion protein to one mutant form of reporter enzyme and an interacting protein partner as a fusion to another mutant form of enzyme;
   wherein said GPCR fusion protein is modified to include one or more sets of serine/threonine clusters, said one or more serine/threonine clusters defined as serine or threonine residues occupying three consecutive or three out of four positions in a carboxyl-termini of said GPCR, wherein said one or more sets of serine/threonine clusters enhance binding of said GPCR to arrestin, wherein said enhanced binding between said GPCR and said arrestin increases sensitivity of detection of said effect of said test condition;
   b) exposing the cell to a ligand for said GPCR under said test condition; and
   c) monitoring activation of said GPCR by complementation of said reporter enzyme;
   wherein increased reporter enzyme activity in the cell compared to that which occurs in the absence of said test condition indicates increased GPCR interaction with said interacting protein partner compared to that which occurs in the absence of said test condition, and decreased reporter enzyme activity in the cell compared to that which occurs in the absence of said test condition indicates decreased GPCR interaction with interacting protein partner compared to that which occurs in the absence of said test condition.

3. A DNA molecule comprising a sequence encoding a biologically active hybrid GPCR, wherein said hybrid GPCR comprises a GPCR as a fusion protein to one mutant form of reporter enzyme and wherein said hybrid GPCR is modified to include one or more sets of serine/threonine clusters, wherein said one or more sets of serine/threonine clusters enhance binding of said hybrid GPCR to arrestin.

4. A DNA construct capable of directing the expression of a biologically active hybrid GPCR in a cell, comprising the following operatively linked elements:
   a promoter; and
   a DNA molecule comprising a sequence encoding a biologically active hybrid GPCR, wherein said hybrid GPCR comprises a GPCR as a fusion protein to one mutant form of reporter enzyme and wherein said hybrid GPCR is modified to include one or more sets of serine/threonine clusters, wherein said one or more sets of serine/threonine clusters enhance binding of said hybrid GPCR to arrestin.

5. A cell transformed with a DNA construct capable of expressing a biologically active hybrid GPCR in a cell, comprising the following operatively linked elements:
   a promoter; and
   a DNA molecule comprising a sequence encoding a biologically active hybrid GPCR, wherein said hybrid GPCR comprises a GPCR as a fusion protein to one mutant form of reporter enzyme and wherein said hybrid GPCR is modified to include one or more sets of serine/threonine clusters, wherein said one or more sets of serine/threonine clusters enhance binding of said hybrid GPCR to arrestin.

* * * * *

UNITED STATES PATENT AND TRADEMARK OFFICE
CERTIFICATE OF CORRECTION

| | |
|---|---|
| PATENT NO. | : 7,235,374 B2 |
| APPLICATION NO. | : 10/959611 |
| DATED | : June 26, 2007 |
| INVENTOR(S) | : Palmer et al. |

It is certified that error appears in the above-identified patent and that said Letters Patent is hereby corrected as shown below:

In column 85, line 1, before "interacting" please insert --said--;

In column 85, line 16, before "said" please insert --wherein--;

In column 85, line 17, before "serine/threonine" please insert --sets of--;

In column 85, line 17, please delete second instance of "or" and insert --/--;

In column 85, line 18, before "threonine" please insert --clusters--;

In column 86, line 11, please delete "biologically" and insert --biological--.

Signed and Sealed this

Sixteenth Day of February, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 6700
<212> TYPE: DNA
<213> ORGANISM: Unknown
<220> FEATURE:
<223> OTHER INFORMATION: pICAST ALC.
<220> FEATURE:
<221> NAME/KEY: CDS
<222> LOCATION: (1457)..(4486)

<400> SEQUENCE: 1
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctcccccga    300 gctcaataaa agagcccaca acccctcact cggggcgcca gtcctccgat tgactgagtc     360
gcccgggtac ccgtgtatcc aataaaccct cttgcagttg catccgactt gtggtctcgc     420
tgttccttgg gagggtctcc tctgagtgat tgactacccg tcagcggggg tctttcattt     480
gggggctcgt ccgggatcgg gagaccctg cccagggacc accgacccac caccgggagg     540
caagctggcc agcaacttat ctgtgtctgt ccgattgtct agtgtctatg actgatttta     600
tgcgcctgcg tcggtactag ttagctaact agctctgtat ctggcggacc cgtggtggaa     660
ctgacgagtt ctgaacaccc ggccgcaacc ctgggagacg tcccagggac tttgggggcc     720 gttttttgtgg cccgacctga ggaagggagt cgatgtggaa tccgaccccg tcaggatatg    780
tggttctggt aggagacgag aacctaaaac agttcccgcc tccgtctgaa tttttgcttt     840
cggtttggaa ccgaagccgc gcgtcttgtc tgctgcagca tcgttctgtg ttgtctctgt     900
ccgactgtgt ttctgtattt gtctgaaaat tagggccaga ctgttaccac tcccttaagt     960
ttgaccttag gtaactggaa agatgtcgag cggctcgctc acaaccagtc ggtagatgtc    1020
aagaagagac gttgggttac cttctgctct gcagaatggc caacctttaa cgtcggatgg    1080
ccgcgagacg gcacctttaa ccgagacctc atcacccagg ttaagatcaa ggtcttttca    1140
```

-continued

```
cctggcccgc atggacaccc agaccaggtc ccctacatcg tgacctggga agccttggct    1200 tttgacccccc ctccctgggt caagcccttt gtacacccta gcctccgcc tcctcttcct    1260 ccatccgccc cgtctctccc ccttgaacct cctcgttcga ccccgcctcg atcctccctt    1320
tatccagccc tcactccttc tctaggcgcc ggccgctcta gcccattaat acgactcact    1380 ataggcgat tcgaatcagg ccttggcgcg ccggatcctt aattaagcgc aattgggagg     1440
tggcggtagc ctcgag atg ggc gtg att acg gat tca ctg gcc gtc gtg gcc    1492
              Met Gly Val Ile Thr Asp Ser Leu Ala Val Val Ala
                1               5                  10 cgc acc gat cgc cct tcc caa cag tta cgc agc ctg aat ggc gaa tgg      1540
Arg Thr Asp Arg Pro Ser Gln Gln Leu Arg Ser Leu Asn Gly Glu Trp
       15                  20                  25 cgc ttt gcc tgg ttt ccg gca cca gaa gcg gtg ccg gaa agc tgg ctg      1588
Arg Phe Ala Trp Phe Pro Ala Pro Glu Ala Val Pro Glu Ser Trp Leu
   30                  35                  40 gag tgc gat ctt cct gag gcc gat act gtc gtc gtc ccc tca aac tgg      1636
Glu Cys Asp Leu Pro Glu Ala Asp Thr Val Val Val Pro Ser Asn Trp
45                  50                  55                  60 cag atg cac ggt tac gat gcg ccc atc tac acc aac gtg acc tat ccc      1684
Gln Met His Gly Tyr Asp Ala Pro Ile Tyr Thr Asn Val Thr Tyr Pro
                65                  70                  75 att acg gtc aat ccg ccg ttt gtt ccc acg gag aat ccg acg ggt tgt      1732
Ile Thr Val Asn Pro Pro Phe Val Pro Thr Glu Asn Pro Thr Gly Cys
       80                  85                  90 tac tcg ctc aca ttt aat gtt gat gaa agc tgg cta cag gaa ggc cag      1780
Tyr Ser Leu Thr Phe Asn Val Asp Glu Ser Trp Leu Gln Glu Gly Gln
   95                  100                 105 acg cga att att ttt gat ggc gtt aac tcg gcg ttt cat ctg tgg tgc      1828
Thr Arg Ile Ile Phe Asp Gly Val Asn Ser Ala Phe His Leu Trp Cys
110                 115                 120 aac ggg cgc tgg gtc ggt tac ggc cag gac agt cgt ttg ccg tct gaa      1876
Asn Gly Arg Trp Val Gly Tyr Gly Gln Asp Ser Arg Leu Pro Ser Glu
125                 130                 135                 140 ttt gac ctg agc gca ttt tta cgc gcc gga gaa aac cgc ctc gcg gtg      1924
Phe Asp Leu Ser Ala Phe Leu Arg Ala Gly Glu Asn Arg Leu Ala Val
                145                 150                 155 atg gtg ctg cgc tgg agt gac ggc agt tat ctg gaa gat cag gat atg      1972
Met Val Leu Arg Trp Ser Asp Gly Ser Tyr Leu Glu Asp Gln Asp Met
       160                 165                 170 tgg cgg atg agc ggc att ttc cgt gac gtc tcg ttg ctg cat aaa ccg      2020
Trp Arg Met Ser Gly Ile Phe Arg Asp Val Ser Leu Leu His Lys Pro
   175                 180                 185 act aca caa atc agc gat ttc cat gtt gcc act cgc ttt aat gat gat      2068
Thr Thr Gln Ile Ser Asp Phe His Val Ala Thr Arg Phe Asn Asp Asp
190                 195                 200 ttc agc cgc gct gta ctg gag gct gaa gtt cag atg tgc ggc gag ttg      2116
Phe Ser Arg Ala Val Leu Glu Ala Glu Val Gln Met Cys Gly Glu Leu
205                 210                 215                 220 cgt gac tac cta cgg gta aca gtt tct tta tgg cag ggt gaa acg cag      2164
Arg Asp Tyr Leu Arg Val Thr Val Ser Leu Trp Gln Gly Glu Thr Gln
                225                 230                 235 gtc gcc agc ggc acc gcg cct ttc ggc ggt gaa att atc gat gag cgt      2212
Val Ala Ser Gly Thr Ala Pro Phe Gly Gly Glu Ile Ile Asp Glu Arg
       240                 245                 250 ggt ggt tat gcc gat cgc gtc aca cta cgt ctg aac gtc gaa aac ccg      2260
Gly Gly Tyr Ala Asp Arg Val Thr Leu Arg Leu Asn Val Glu Asn Pro
   255                 260                 265 aaa ctg tgg agc gcc gaa atc ccg aat ctc tat cgt gcg gtg gtt gaa      2308
Lys Leu Trp Ser Ala Glu Ile Pro Asn Leu Tyr Arg Ala Val Val Glu
```

```
                    Lys Leu Trp Ser Ala Glu Ile Pro Asn Leu Tyr Arg Ala Val Val Glu
                        270                 275                 280 ctg cac acc gcc gac ggc acg ctg att gaa gca gaa gcc tgc gat gtc             2356
Leu His Thr Ala Asp Gly Thr Leu Ile Glu Ala Glu Ala Cys Asp Val
285                 290                 295                 300 ggt ttc cgc gag gtg cgg att gaa aat ggt ctg ctg ctg ctg aac ggc             2404
Gly Phe Arg Glu Val Arg Ile Glu Asn Gly Leu Leu Leu Leu Asn Gly
                305                 310                 315 aag ccg ttg ctg att cga ggc gtt aac cgt cac gag cat cat cct ctg             2452
Lys Pro Leu Leu Ile Arg Gly Val Asn Arg His Glu His His Pro Leu
            320                 325                 330 cat ggt cag gtc atg gat gag cag acg atg gtg cag gat atc ctg ctg             2500
His Gly Gln Val Met Asp Glu Gln Thr Met Val Gln Asp Ile Leu Leu
        335                 340                 345 atg aag cag aac aac ttt aac gcc gtg cgc tgt tcg cat tat ccg aac             2548
Met Lys Gln Asn Asn Phe Asn Ala Val Arg Cys Ser His Tyr Pro Asn
350                 355                 360 cat ccg ctg tgg tac acg ctg tgc gac cgc tac ggc ctg tat gtg gtg             2596
His Pro Leu Trp Tyr Thr Leu Cys Asp Arg Tyr Gly Leu Tyr Val Val
365                 370                 375                 380 gat gaa gcc aat att gaa acc cac ggc atg gtg cca atg aat cgt ctg             2644
Asp Glu Ala Asn Ile Glu Thr His Gly Met Val Pro Met Asn Arg Leu
                385                 390                 395 acc gat gat ccg cgc tgg cta ccg gcg atg agc gaa cgc gta acg cga             2692
Thr Asp Asp Pro Arg Trp Leu Pro Ala Met Ser Glu Arg Val Thr Arg
            400                 405                 410 atg gtg cag cgc gat cgt aat cac ccg agt gtg atc atc tgg tcg ctg             2740
Met Val Gln Arg Asp Arg Asn His Pro Ser Val Ile Ile Trp Ser Leu
        415                 420                 425 ggg aat gaa tca ggc cac ggc gct aat cac gac gcg ctg tat cgc tgg             2788
Gly Asn Glu Ser Gly His Gly Ala Asn His Asp Ala Leu Tyr Arg Trp
430                 435                 440 atc aaa tct gtc gat cct tcc cgc ccg gtg cag tat gaa ggc ggc gga             2836
Ile Lys Ser Val Asp Pro Ser Arg Pro Val Gln Tyr Glu Gly Gly Gly
445                 450                 455                 460 gcc gac acc acg gcc acc gat att att tgc ccg atg tac gcg cgc gtg             2884
Ala Asp Thr Thr Ala Thr Asp Ile Ile Cys Pro Met Tyr Ala Arg Val
                465                 470                 475 gat gaa gac cag ccc ttc ccg gct gtg ccg aaa tgg tcc atc aaa aaa             2932
Asp Glu Asp Gln Pro Phe Pro Ala Val Pro Lys Trp Ser Ile Lys Lys
            480                 485                 490 tgg ctt tcg cta cct gga gag acg cgc ccg ctg atc ctt tgc gaa tac             2980
Trp Leu Ser Leu Pro Gly Glu Thr Arg Pro Leu Ile Leu Cys Glu Tyr
        495                 500                 505 gcc cac gcg atg ggt aac agt ctt ggt ggt ttc gct aaa tac tgg cag             3028
Ala His Ala Met Gly Asn Ser Leu Gly Gly Phe Ala Lys Tyr Trp Gln
510                 515                 520 gcg ttt cgt cag tat ccc cgt tta cag ggc ggc ttc gtc tgg gac tgg             3076
Ala Phe Arg Gln Tyr Pro Arg Leu Gln Gly Gly Phe Val Trp Asp Trp
525                 530                 535                 540 gtg gat cag tcg ctg att aaa tat gat gaa aac ggc aac ccg tgg tcg             3124
Val Asp Gln Ser Leu Ile Lys Tyr Asp Glu Asn Gly Asn Pro Trp Ser
                545                 550                 555 gct tac ggc ggt gat ttt ggc gat acg ccg aac gat cgc cag ttc tgt             3172
Ala Tyr Gly Gly Asp Phe Gly Asp Thr Pro Asn Asp Arg Gln Phe Cys
            560                 565                 570 atg aac ggt ctg gtc ttt gcc gac cgc acg ccg cat cca gcg ctg acg             3220
Met Asn Gly Leu Val Phe Ala Asp Arg Thr Pro His Pro Ala Leu Thr
        575                 580                 585
```

```
                                                           -continued gaa gca aaa cac cag cag cag ttt ttc cag ttc cgt tta tcc ggg caa    3268
Glu Ala Lys His Gln Gln Gln Phe Phe Gln Phe Arg Leu Ser Gly Gln
590                 595                 600 acc atc gaa gtg acc agc gaa tac ctg ttc cgt cat agc gat aac gag    3316
Thr Ile Glu Val Thr Ser Glu Tyr Leu Phe Arg His Ser Asp Asn Glu
605                 610                 615                 620 ctc ctg cac tgg atg gtg gcg ctg gat ggt aag ccg ctg gca agc ggt    3364
Leu Leu His Trp Met Val Ala Leu Asp Gly Lys Pro Leu Ala Ser Gly
                625                 630                 635 gaa gtg cct ctg gat gtc gct cca caa ggt aaa cag ttg att gaa ctg    3412
Glu Val Pro Leu Asp Val Ala Pro Gln Gly Lys Gln Leu Ile Glu Leu
            640                 645                 650 cct gaa cta ccg cag ccg gag agc gcc ggg caa ctc tgg ctc aca gta    3460
Pro Glu Leu Pro Gln Pro Glu Ser Ala Gly Gln Leu Trp Leu Thr Val
                655                 660                 665 cgc gta gtg caa ccg aac gcg acc gca tgg tca gaa gcc ggg cac atc    3508
Arg Val Val Gln Pro Asn Ala Thr Ala Trp Ser Glu Ala Gly His Ile
670                 675                 680 agc gcc tgg cag cag tgg cgt ctg gcg gaa aac ctc agt gtg acg ctc    3556
Ser Ala Trp Gln Gln Trp Arg Leu Ala Glu Asn Leu Ser Val Thr Leu
685                 690                 695                 700 ccc gcc gcg tcc cac gcc atc ccg cat ctg acc acc agc gaa atg gat    3604
Pro Ala Ala Ser His Ala Ile Pro His Leu Thr Thr Ser Glu Met Asp
                705                 710                 715 ttt tgc atc gag ctg ggt aat aag cgt tgg caa ttt aac cgc cag tca    3652
Phe Cys Ile Glu Leu Gly Asn Lys Arg Trp Gln Phe Asn Arg Gln Ser
            720                 725                 730 ggc ttt ctt tca cag atg tgg att ggc gat aaa aaa caa ctg ctg acg    3700
Gly Phe Leu Ser Gln Met Trp Ile Gly Asp Lys Lys Gln Leu Leu Thr
                735                 740                 745 ccg ctg cgc gat cag ttc acc cgt gca ccg ctg gat aac gac att ggc    3748
Pro Leu Arg Asp Gln Phe Thr Arg Ala Pro Leu Asp Asn Asp Ile Gly
750                 755                 760 gta agt gaa gcg acc cgc att gac cct aac gcc tgg gtc gaa cgc tgg    3796
Val Ser Glu Ala Thr Arg Ile Asp Pro Asn Ala Trp Val Glu Arg Trp
765                 770                 775                 780 aag gcg gcg ggc cat tac cag gcc gaa gca gcg ttg ttg cag tgc acg    3844
Lys Ala Ala Gly His Tyr Gln Ala Glu Ala Ala Leu Leu Gln Cys Thr
                785                 790                 795 gca gat aca ctt gct gat gcg gtg ctg att acg acc gct cac gcg tgg    3892
Ala Asp Thr Leu Ala Asp Ala Val Leu Ile Thr Thr Ala His Ala Trp
            800                 805                 810 cag cat cag ggg aaa acc tta ttt atc agc cgg aaa acc tac cgg att    3940
Gln His Gln Gly Lys Thr Leu Phe Ile Ser Arg Lys Thr Tyr Arg Ile
                815                 820                 825 gat ggt agt ggt caa atg gcg att acc gtt gat gtt gaa gtg gcg agc    3988
Asp Gly Ser Gly Gln Met Ala Ile Thr Val Asp Val Glu Val Ala Ser
830                 835                 840 gat aca ccg cat ccg gcg cgg att ggc ctg aac tgc cag ctg gcg cag    4036
Asp Thr Pro His Pro Ala Arg Ile Gly Leu Asn Cys Gln Leu Ala Gln
845                 850                 855                 860 gta gca gag cgg gta aac tgg ctc gga tta ggg ccg caa gaa aac tat    4084
Val Ala Glu Arg Val Asn Trp Leu Gly Leu Gly Pro Gln Glu Asn Tyr
                865                 870                 875 ccc gac cgc ctt act gcc gcc tgt ttt gac cgc tgg gat ctg cca ttg    4132
Pro Asp Arg Leu Thr Ala Ala Cys Phe Asp Arg Trp Asp Leu Pro Leu
            880                 885                 890 tca gac atg tat acc ccg tac gtc ttc ccg agc gaa aac ggt ctg cgc    4180
Ser Asp Met Tyr Thr Pro Tyr Val Phe Pro Ser Glu Asn Gly Leu Arg
                895                 900                 905
```

```
tgc ggg acg cgc gaa ttg aat tat ggc cca cac cag tgg cgc ggc gac      4228
Cys Gly Thr Arg Glu Leu Asn Tyr Gly Pro His Gln Trp Arg Gly Asp
910                 915                 920 ttc cag ttc aac atc agc cgc tac agt caa cag caa ctg atg gaa acc      4276
Phe Gln Phe Asn Ile Ser Arg Tyr Ser Gln Gln Gln Leu Met Glu Thr
925                 930                 935                 940 agc cat cgc cat ctg ctg cac gcg gaa gaa ggc aca tgg ctg aat atc      4324
Ser His Arg His Leu Leu His Ala Glu Glu Gly Thr Trp Leu Asn Ile
                945                 950                 955 gac ggt ttc cat atg ggg att ggt ggc gac gac tcc tgg agc ccg tca      4372
Asp Gly Phe His Met Gly Ile Gly Gly Asp Asp Ser Trp Ser Pro Ser
            960                 965                 970 gta tcg gcg gaa ttc cag ctg agc gcc ggt cgc tac cat tac cag ttg      4420
Val Ser Ala Glu Phe Gln Leu Ser Ala Gly Arg Tyr His Tyr Gln Leu
        975                 980                 985 gtc tgg tgt caa aaa aga tct gac tat aaa gat gag  gac ctc gac cat     4468
Val Trp Cys Gln Lys Arg Ser Asp Tyr Lys Asp Glu  Asp Leu Asp His
    990                 995                 1000 cat  cat cat cat cac cgg  taataatagg tagataagtg actgattaga           4516
His  His His His His Arg
1005                 1010 tgcattgatc cctcgaccaa ttccggttat tttccaccat attgccgtct tttggcaatg    4576
tgagggcccg gaaacctggc cctgtcttct tgacgagcat tcctaggggt cttccccctc    4636
tcgccaaagg aatgcaaggt ctgttgaatg tcgtgaagga agcagttcct ctggaagctt    4696
cttgaagaca acaacgtct gtagcgaccc tttgcaggca gcggaacccc ccacctggcg     4756
acaggtgcct ctgcggccaa agccacgtg tataagatac acctgcaaag gcggcacaac     4816
cccagtgcca cgttgtgagt tggatagttg tggaaagagt caaatggctc tcctcaagcg    4876
tattcaacaa ggggctgaag gatgcccaga aggtacccca ttgtatggga tctgatctgg    4936
ggcctcggtg cacatgcttt acatgtgttt agtcgaggtt aaaaaacgtc taggccccccc   4996 gaaccacggg gacgtggttt tccttttgaaa acacgatga taataccatg attgaacaag    5056
atggattgca cgcaggttct ccggccgctt ggtggagag gctattcggc tatgactggg     5116
cacaacagac aatcggctgc tctgatgccg ccgtgttccg gctgtcagcg caggggcgcc    5176
cggttctttt tgtcaagacc gacctgtccg gtgccctgaa tgaactgcag gacgaggcag    5236
cgcggctatc gtggctggcc acgacgggcg ttccttgcgc agctgtgctc gacgttgtca    5296
ctgaagcggg aagggactgg ctgctattgg gcgaagtgcc ggggcaggat ctcctgtcat    5356
ctcaccttgc tcctgccgag aaagtatcca tcatggctga tgcaatgcgg cggctgcata    5416
cgcttgatcc ggctacctgc ccattcgacc accaagcgaa acatcgcatc gagcgagcac    5476
gtactcggat ggaagccggt cttgtcgatc aggatgatct ggacgaagag catcaggggc    5536
tcgcgccagc cgaactgttc gccaggctca aggcgcgcat gcccgacggc gaggatctcg    5596
tcgtgaccca tggcgatgcc tgcttgccga atatcatggt ggaaaatggc cgcttttctg    5656
gattcatcga ctgtggccgg ctgggtgtgg cggaccgcta tcaggacata gcgttggcta    5716
cccgtgatat tgctgaagag cttggcggcg aatgggctga ccgcttcctc gtgctttacg    5776
gtatcgccgc tcccgattcg cagcgcatcg ccttctatcg ccttcttgac gagttcttct    5836
gagcgggact ctggggttcg catcgataaa ataaagatt ttatttagtc tccagaaaaa     5896
ggggggaatg aaagacccca cctgtaggtt tggcaagcta gcttaagtaa cgccattttg    5956
caaggcatgg aaaaatacat aactgagaat agagaagttc agatcaaggt caggaacaga    6016
```

-continued

```
tggaacagct gaatatgggc caaacaggat atctgtggta agcagttcct gccccggctc    6076
agggccaaga acagatggaa cagctgaata tgggccaaac aggatatctg tggtaagcag    6136
ttcctgcccc ggctcagggc caagaacaga tggtccccag atgcggtcca gccctcagca    6196
gtttctagag aaccatcaga tgtttccagg gtgcccaag gacctgaaat gaccctgtgc     6256
cttatttgaa ctaaccaatc agttcgcttc tcgcttctgt tcgcgcgctt ctgctccccg    6316
agctcaataa aagagcccac aacccctcac tcggggcgcc agtcctccga ttgactgagt    6376
cgcccgggta cccgtgtatc caataaaccc tcttgcagtt gcatccgact tgtggtctcg    6436
ctgttccttg ggagggtctc ctctgagtga ttgactaccc gtcagcgggg gtctttcatt    6496
catgcagcat gtatcaaaat taatttggtt tttttcttta agtatttaca ttaaatggcc    6556
atagttgcat taatgaatcg gccaacgcgc ggggagaggc ggtttgcgta ttggcgctct    6616
tccgcttcct cgctcactga ctcgctgcgc tcggtcgttc ggctgcggcg agcggtatca    6676
gctcactcaa aggcggtaat acgg                                           6700
```

<210> SEQ ID NO 2
<211> LENGTH: 1010
<212> TYPE: PRT
<213> ORGANISM: Unknown
<220> FEATURE:
<223> OTHER INFORMATION: pICAST ALC.

<400> SEQUENCE: 2

```
Met Gly Val Ile Thr Asp Ser Leu Ala Val Ala Arg Thr Asp Arg
1               5                   10                  15

Pro Ser Gln Gln Leu Arg Ser Leu Asn Gly Glu Trp Arg Phe Ala Trp
                20                  25                  30

Phe Pro Ala Pro Glu Ala Val Pro Glu Ser Trp Leu Glu Cys Asp Leu
            35                  40                  45

Pro Glu Ala Asp Thr Val Val Pro Ser Asn Trp Gln Met His Gly
        50                  55                  60

Tyr Asp Ala Pro Ile Tyr Thr Asn Val Thr Tyr Pro Ile Thr Val Asn
65                  70                  75                  80

Pro Pro Phe Val Pro Thr Glu Asn Pro Thr Gly Cys Tyr Ser Leu Thr
                85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
        115                 120                 125

Val Gly Tyr Gly Gln Asp Ser Arg Leu Pro Ser Glu Phe Asp Leu Ser
130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
        195                 200                 205

Val Leu Glu Ala Glu Val Gln Met Cys Gly Glu Leu Arg Asp Tyr Leu
210                 215                 220

Arg Val Thr Val Ser Leu Trp Gln Gly Glu Thr Gln Val Ala Ser Gly
225                 230                 235                 240
```

```
Thr Ala Pro Phe Gly Gly Glu Ile Ile Asp Glu Arg Gly Gly Tyr Ala
            245                 250                 255
Asp Arg Val Thr Leu Arg Leu Asn Val Glu Asn Pro Lys Leu Trp Ser
            260                 265                 270
Ala Glu Ile Pro Asn Leu Tyr Arg Ala Val Glu Leu His Thr Ala
            275                 280                 285
Asp Gly Thr Leu Ile Glu Ala Glu Ala Cys Asp Val Gly Phe Arg Glu
            290                 295                 300
Val Arg Ile Glu Asn Gly Leu Leu Leu Asn Gly Lys Pro Leu Leu
305             310                 315                 320
Ile Arg Gly Val Asn Arg His Glu His His Pro Leu His Gly Gln Val
                325                 330                 335
Met Asp Glu Gln Thr Met Val Gln Asp Ile Leu Leu Met Lys Gln Asn
            340                 345                 350
Asn Phe Asn Ala Val Arg Cys Ser His Tyr Pro Asn His Pro Leu Trp
            355                 360                 365
Tyr Thr Leu Cys Asp Arg Tyr Gly Leu Tyr Val Val Asp Glu Ala Asn
    370                 375                 380
Ile Glu Thr His Gly Met Val Pro Met Asn Arg Leu Thr Asp Asp Pro
385                 390                 395                 400
Arg Trp Leu Pro Ala Met Ser Glu Arg Val Thr Arg Met Val Gln Arg
                405                 410                 415
Asp Arg Asn His Pro Ser Val Ile Ile Trp Ser Leu Gly Asn Glu Ser
                420                 425                 430
Gly His Gly Ala Asn His Asp Ala Leu Tyr Arg Trp Ile Lys Ser Val
        435                 440                 445
Asp Pro Ser Arg Pro Val Gln Tyr Glu Gly Gly Gly Ala Asp Thr Thr
    450                 455                 460
Ala Thr Asp Ile Ile Cys Pro Met Tyr Ala Arg Val Asp Glu Asp Gln
465                 470                 475                 480
Pro Phe Pro Ala Val Pro Lys Trp Ser Ile Lys Lys Trp Leu Ser Leu
                485                 490                 495
Pro Gly Glu Thr Arg Pro Leu Ile Leu Cys Glu Tyr Ala His Ala Met
            500                 505                 510
Gly Asn Ser Leu Gly Gly Phe Ala Lys Tyr Trp Gln Ala Phe Arg Gln
            515                 520                 525
Tyr Pro Arg Leu Gln Gly Gly Phe Val Trp Asp Trp Val Asp Gln Ser
    530                 535                 540
Leu Ile Lys Tyr Asp Glu Asn Gly Asn Pro Trp Ser Ala Tyr Gly Gly
545                 550                 555                 560
Asp Phe Gly Asp Thr Pro Asn Asp Arg Gln Phe Cys Met Asn Gly Leu
                565                 570                 575
Val Phe Ala Asp Arg Thr Pro His Pro Ala Leu Thr Glu Ala Lys His
            580                 585                 590
Gln Gln Gln Phe Phe Gln Phe Arg Leu Ser Gly Gln Thr Ile Glu Val
            595                 600                 605
Thr Ser Glu Tyr Leu Phe Arg His Ser Asp Asn Glu Leu Leu His Trp
    610                 615                 620
Met Val Ala Leu Asp Gly Lys Pro Leu Ala Ser Gly Glu Val Pro Leu
625                 630                 635                 640
Asp Val Ala Pro Gln Gly Lys Gln Leu Ile Glu Leu Pro Glu Leu Pro
                645                 650                 655
Gln Pro Glu Ser Ala Gly Gln Leu Trp Leu Thr Val Arg Val Val Gln
```

```
                    660             665             670
Pro Asn Ala Thr Ala Trp Ser Glu Ala Gly His Ile Ser Ala Trp Gln
            675             680             685
Gln Trp Arg Leu Ala Glu Asn Leu Ser Val Thr Leu Pro Ala Ala Ser
        690             695             700
His Ala Ile Pro His Leu Thr Thr Ser Glu Met Asp Phe Cys Ile Glu
705             710             715             720
Leu Gly Asn Lys Arg Trp Gln Phe Asn Arg Gln Ser Gly Phe Leu Ser
                725             730             735
Gln Met Trp Ile Gly Asp Lys Lys Gln Leu Leu Thr Pro Leu Arg Asp
            740             745             750
Gln Phe Thr Arg Ala Pro Leu Asp Asn Asp Ile Gly Val Ser Glu Ala
        755             760             765
Thr Arg Ile Asp Pro Asn Ala Trp Val Glu Arg Trp Lys Ala Ala Gly
770             775             780
His Tyr Gln Ala Glu Ala Leu Leu Gln Cys Thr Ala Asp Thr Leu
785             790             795             800
Ala Asp Ala Val Leu Ile Thr Thr Ala His Ala Trp Gln His Gln Gly
            805             810             815
Lys Thr Leu Phe Ile Ser Arg Lys Thr Tyr Arg Ile Asp Gly Ser Gly
        820             825             830
Gln Met Ala Ile Thr Val Asp Val Glu Val Ala Ser Asp Thr Pro His
        835             840             845
Pro Ala Arg Ile Gly Leu Asn Cys Gln Leu Ala Gln Val Ala Glu Arg
    850             855             860
Val Asn Trp Leu Gly Leu Gly Pro Gln Glu Asn Tyr Pro Asp Arg Leu
865             870             875             880
Thr Ala Ala Cys Phe Asp Arg Trp Asp Leu Pro Leu Ser Asp Met Tyr
                885             890             895
Thr Pro Tyr Val Phe Pro Ser Glu Asn Gly Leu Arg Cys Gly Thr Arg
            900             905             910
Glu Leu Asn Tyr Gly Pro His Gln Trp Arg Gly Asp Phe Gln Phe Asn
        915             920             925
Ile Ser Arg Tyr Ser Gln Gln Gln Leu Met Glu Thr Ser His Arg His
    930             935             940
Leu Leu His Ala Glu Glu Gly Thr Trp Leu Asn Ile Asp Gly Phe His
945             950             955             960
Met Gly Ile Gly Gly Asp Asp Ser Trp Ser Pro Ser Val Ser Ala Glu
                965             970             975
Phe Gln Leu Ser Ala Gly Arg Tyr His Tyr Gln Leu Val Trp Cys Gln
            980             985             990
Lys Arg Ser Asp Tyr Lys Asp Glu  Asp Leu Asp His His  His His His
        995             1000             1005
His Arg
    1010

<210> SEQ ID NO 3
<211> LENGTH: 6700
<212> TYPE: DNA
<213> ORGANISM: Unknown
<220> FEATURE:
<223> OTHER INFORMATION: pICAST ALC.

<400> SEQUENCE: 3
gacgtcggac ttatacccgg tttgtcctat agacaccatt cgtcaaggac ggggccgagt      60
```

-continued

```
cccggttctt gtctaccttg tcgacttata cccggtttgt cctatagaca ccattcgtca        120 aggacgggc cgagtcccgg ttcttgtcta ccaggggtct acgccaggtc gggagtcgtc         180
aaagatctct tggtagtcta caaaggtccc acggggttcc tggactttac tgggacacgg        240
aataaacttg attggttagt caagcgaaga gcgaagacaa gcgcgcgaag acgaggggct        300
cgagttattt tctcgggtgt tggggagtga gccccgcggt caggaggcta actgactcag        360
cgggcccatg ggcacatagg ttatttggga gaacgtcaac gtaggctgaa caccagagcg        420
acaaggaacc ctcccagagg agactcacta actgatgggc agtcgccccc agaaagtaaa        480
cccccgagca ggccctagcc ctctggggac gggtccctgg tggctgggtg gtggccctcc        540
gttcgaccgg tcgttgaata gacacagaca ggctaacaga tcacagatac tgactaaaat        600
acgcggacgc agccatgatc aatcgattga tcgagacata gaccgcctgg gcaccacctt        660
gactgctcaa gacttgtggg ccggcgttgg gaccctctgc agggtccctg aaaccccgg         720 caaaaacacc gggctggact ccttccctca gctacacctt aggctggggc agtcctatac        780
accaagacca tcctctgctc ttggattttg tcaagggcgg aggcagactt aaaaacgaaa        840
gccaaacctt ggcttcggcg cgcagaacag acgacgtcgt agcaagacac aacagagaca        900
gactgacaca aagacataaa cagacttta atcccggtct gacaatggtg agggaattca        960
aactggaatc cattgacctt tctacagctc gccgagcgag tgttggtcag ccatctacag       1020
ttcttctctg caacccaatg gaagacgaga cgtcttaccg gttggaaatt gcagcctacc       1080
ggcgctctgc cgtggaaatt ggctctggag tagtgggtcc aattctagtt ccagaaaagt       1140
ggaccgggcg tacctgtggg tctggtccag gggatgtagc actggaccct tcggaaccga       1200
aaactggggg gagggaccca gttcgggaaa catgtgggat tcggaggcgg aggagaagga       1260
ggtaggcggg gcagagaggg ggaacttgga ggagcaagct ggggcggagc taggagggaa       1320
ataggtcggg agtgaggaag agatccgcgg ccggcgagat cgggtaatta tgctgagtga       1380
tatcccgcta agcttagtcc ggaaccgcgc ggcctaggaa ttaattcgcg ttaaccctcc       1440
accgccatcg gagctctacc cgcactaatg cctaagtgac cggcagcacc gggcgtggct       1500
agcgggaagg gttgtcaatg cgtcggactt accgcttacc gcgaaacgga ccaaaggccg       1560
tggtcttcgc cacggccttt cgaccgacct cacgctagaa ggactccggc tatgacagca       1620 gcagggagt ttgaccgtct acgtgccaat gctacgcggg tagatgtggt tgcactggat        1680
agggtaatgc cagttaggcg gcaaacaagg gtgcctctta ggctgcccaa caatgagcga       1740
gtgtaaatta caactacttt cgaccgatgt ccttccggtc tgcgcttaat aaaaactacc       1800
gcaattgagc cgcaaagtag acaccacgtt gcccgcgacc cagccaatgc cggtcctgtc       1860
agcaaacggc agacttaaac tggactcgcg taaaaatgcg cggcctcttt tggcggagcg       1920
ccactaccac gacgcgacct cactgccgtc aatagacctt ctagtcctat acaccgccta       1980
ctcgccgtaa aaggcactgc agagcaacga cgtatttggc tgatgtgttt agtcgctaaa       2040
ggtacaacgg tgagcgaaat tactactaaa gtcggcgcga catgacctcc gacttcaagt       2100
ctacacgccg ctcaacgcac tgatggatgc ccattgtcaa agaaataccg tcccactttg       2160
cgtccagcgg tcgccgtggc gcggaaagcc gccactttaa tagctactcg caccaccaat       2220
acggctagcg cagtgtgatg cagacttgca gcttttgggc tttgacacct cgcggcttta       2280
gggcttagag atagcacgcc accaacttga cgtgtggcgg ctgccgtgcg actaacttcg       2340
tcttcggacg ctacagccaa aggcgctcca cgcctaactt ttaccagacg acgacgactt       2400
```

```
gccgttcggc aacgactaag ctccgcaatt ggcagtgctc gtagtaggag acgtaccagt    2460
ccagtaccta ctcgtctgct accacgtcct ataggacgac tacttcgtct tgttgaaatt    2520
gcggcacgcg acaagcgtaa taggcttggt aggcgacacc atgtgcgaca cgctggcgat    2580
gccggacata caccacctac ttcggttata actttgggtg ccgtaccacg gttacttagc    2640
agactggcta ctaggcgcga ccgatggccg ctactcgctt gcgcattgcg cttaccacgt    2700
cgcgctagca ttagtgggct cacactagta gaccagcgac cccttactta gtccggtgcc    2760
gcgattagtg ctgcgcgaca tagcgaccta gtttagacag ctaggaaggg cgggccacgt    2820
catacttccg ccgcctcggc tgtggtgccg gtggctataa taaacgggct acatgcgcgc    2880
gcacctactt ctggtcggga agggccgaca cggctttacc aggtagtttt ttaccgaaag    2940
cgatggacct ctctgcgcgg gcgactagga aacgcttatg cgggtgcgct acccattgtc    3000
agaaccgcca aagcgattta tgaccgtccg caaagcagtc ataggggcaa atgtcccgcc    3060
gaagcagacc ctgacccacc tagtcagcga ctaatttata ctacttttgc cgttgggcac    3120
cagccgaatg ccgccactaa aaccgctatg cggcttgcta gcggtcaaga catacttgcc    3180
agaccagaaa cggctggcgt gcggcgtagg tcgcgactgc cttcgttttg tggtcgtcgt    3240
caaaaaggtc aaggcaaata ggcccgtttg gtagcttcac tggtcgctta tggacaaggc    3300
agtatcgcta ttgctcgagg acgtgaccta ccaccgcgac ctaccattcg gcgaccgttc    3360
gccacttcac ggagacctac agcgaggtgt tccatttgtc aactaacttg acggacttga    3420
tggcgtcggc ctctcgcggc ccgttgagac cgagtgtcat gcgcatcacg ttggcttgcg    3480
ctggcgtacc agtcttcggc ccgtgtagtc gcggaccgtc gtcaccgcag accgcctttt    3540
ggagtcacac tgcgaggggc ggcgcagggt gcggtagggc gtagactggt ggtcgcttta    3600
cctaaaaacg tagctcgacc cattattcgc aaccgttaaa ttggcggtca gtccgaaaga    3660
aagtgtctac acctaaccgc tattttttgt tgacgactgc ggcgacgcgc tagtcaagtg    3720
ggcacgtggc gacctattgc tgtaaccgca ttcacttcgc tgggcgtaac tgggattgcg    3780
gacccagctt gcgaccttcc gccgcccggt aatggtccgg cttcgtcgca acaacgtcac    3840
gtgccgtcta tgtgaacgac tacgccacga ctaatgctgg cgagtgcgca ccgtcgtagt    3900
ccccttttgg aataaatagt cggccttttg gatggcctaa ctaccatcac cagtttaccg    3960
ctaatggcaa ctacaacttc accgctcgct atgtggcgta ggccgcgcct aaccggactt    4020
gacggtcgac cgcgtccatc gtctcgccca tttgaccgag cctaatcccg gcgttctttt    4080
gatagggctg gcgaatgac ggcggacaaa actggcgacc ctagacggta acagtctgta    4140 catatgggc atgcagaagg gctcgctttt gccagacgcg acgccctgcg cgcttaactt    4200
aataccgggt gtggtcaccg cgccgctgaa ggtcaagttg tagtcggcga tgtcagttgt    4260
cgttgactac ctttggtcgg tagcggtaga cgacgtgcgc cttcttccgt gtaccgactt    4320
atagctggca aaggtatacc cctaaccacc gctgctgagg acctcgggca gtcatagccg    4380
ccttaaggtc gactcgcggc cagcgatggt aatggtcaac cagaccacag ttttttctag    4440
actgatattt ctactcctgg agctggtagt agtagtagta gtggccatta ttatccatct    4500
attcactgac taatctacgt aactagggag ctggttaagg ccaataaaag gtggtataac    4560
ggcagaaaac cgttacactc ccgggccttt ggacgggac agaagaactg ctcgtaagga    4620
tccccagaaa ggggagagcg gtttccttac gttccagaca acttacagca cttccttcgt    4680
caaggagacc ttcgaagaac ttctgttttgt tgcagacatc gctgggaaac gtccgtcgcc    4740 ttgggggggtg gaccgctgtc cacggagacg ccggttttcg gtgcacatat tctatgtgga    4800
```

-continued

```
cgtttccgcc gtgttggggt cacggtgcaa cactcaacct atcaacacct ttctcagttt      4860
accgagagga gttcgcataa gttgttcccc gacttcctac gggtcttcca tggggtaaca      4920 tacccctagac tagaccccgg agccacgtgt acgaaatgta cacaaatcag ctccaatttt     4980
ttgcagatcc ggggggcttg gtgcccctgc accaaaagga aactttttgt gctactatta     5040
tggtactaac ttgttctacc taacgtgcgt ccaagaggcc ggcgaaccca cctctccgat      5100
aagccgatac tgacccgtgt tgtctgttag ccgacgagac tacggcggca caaggccgac     5160
agtcgcgtcc ccgcgggcca agaaaaacag ttctggctgg acaggccacg ggacttactt     5220
gacgtcctgc tccgtcgcgc cgatagcacc gaccggtgct gcccgcaagg aacgcgtcga     5280
cacgagctgc aacagtgact cgcccttcc ctgaccgacg ataacccgct tcacggcccc      5340
gtcctagagg acagtagagt ggaacgagga cggctctttc ataggtagta ccgactacgt     5400
tacgccgccg acgtatgcga actaggccga tggacgggta agctggtggt tcgctttgta     5460
gcgtagctcg ctcgtgcatg agcctacctt cggccagaac agctagtcct actagacctg     5520
cttctcgtag tccccgagcg cggtcggctt gacaagcggt ccgagttccg cgcgtacggg     5580
ctgccgctcc tagagcagca ctgggtaccg ctacggacga acggcttata gtaccacctt     5640
ttaccggcga aaagacctaa gtagctgaca ccggccgacc cacaccgcct ggcgatagtc     5700
ctgtatcgca accgatgggc actataacga cttctcgaac cgccgcttac ccgactggcg     5760
aaggagcacg aaatgccata gcggcgaggg ctaagcgtcg cgtagcggaa gatagcggaa     5820
gaactgctca agaagactcg ccctgagacc ccaagcgtag ctattttatt ttctaaaata     5880
aatcagaggt cttttccccc ccttactttc tggggtggac atccaaaccg ttcgatcgaa     5940
ttcattgcgg taaaacgttc cgtacctttt tatgtattga ctcttatctc ttcaagtcta     6000
gttccagtcc ttgtctacct tgtcgactta tacccggttt gtcctataga caccattcgt     6060
caaggacggg gccgagtccc ggttcttgtc taccttgtcg acttataccc ggtttgtcct     6120
atagacacca ttcgtcaagg acggggccga gtcccggttc ttgtctacca ggggtctacg     6180
ccaggtcgga agtcgtcaaa gatctcttgg tagtctacaa aggtcccacg gggttcctgg     6240
actttactgg gacacggaat aaacttgatt ggttagtcaa gcgaagagcg aagacaagcg     6300
cgcgaagacg aggggctcga gttatttttct cgggtgttgg ggagtgagcc ccgcggtcag     6360
gaggctaact gactcagcgg gcccatgggc acataggtta tttgggagaa cgtcaacgta     6420
ggctgaacac cagagcgaca aggaaccctc ccagaggaga ctcactaact gatgggcagt     6480
cgcccccaga aagtaagtac gtcgtacata gttttaatta aaccaaaaaa aagaattcat     6540
aaatgtaatt taccggtatc aacgtaatta cttagccggt tgcgcgcccc tctccgccaa     6600
acgcataacc gcgagaaggc gaaggagcga gtgactgagc gacgcgagcc agcaagccga     6660
cgccgctcgc catagtcgag tgagtttccg ccattatgcc                           6700
```

<210> SEQ ID NO 4
<211> LENGTH: 8518
<212> TYPE: DNA
<213> ORGANISM: Unknown
<220> FEATURE:
<223> OTHER INFORMATION: pICAST ALN.

<400> SEQUENCE: 4

```
ctgcagcctg aatatgggcc aaacaggata tctgtggtaa gcagttcctg ccccggctca       60
gggccaagaa cagatggaac agctgaatat gggccaaaca ggatatctgt ggtaagcagt      120
```

-continued

```
tcctgccccg gctcagggcc aagaacagat ggtccccaga tgcggtccag ccctcagcag    180
tttctagaga accatcagat gtttccaggg tgccccaagg acctgaaatg accctgtgcc    240
ttatttgaac taaccaatca gttcgcttct cgcttctgtt cgcgcgcttc tgctccccga    300
gctcaataaa agagcccaca acccgtcact cggggcgcca gtcctccgat tgactgagtc    360
gcccgggtac ccgtgtatcc aataaaccct cttgcagttg catccgactt gtggtctcgc    420
tgttccttgg gagggtctcc tctgagtgat tgactacccg tcagcggggg tctttcattt    480
gggggctcgt ccgggatcgg gagacccctg cccagggacc accgacccac caccgggagg    540
caagctggcc agcaacttat ctgtgtctgt ccgattgtct agtgtctatg actgattttα    600 tgcgcctgcg tcggtactag ttagctaact agctctgtat ctggcggacc cgtggtggaa    660
ctgacgagtt ctgaacaccc ggccgcaacc ctggagacg tcccagggac tttgggggcc    720 gttttttgtgg cccgacctga ggaagggagt cgatgtggaa tccgaccccg tcaggatatg    780
tggttctggt aggagacgag aacctaaaac agttcccgcc tccgtctgaa tttttgcttt    840
cggtttggaa ccgaagccgc gcgtcttgtc tgctgcagca tcgttctgtg ttgtctctgt    900
ctgactgtgt ttctgtatt gtctgaaat tagggccaga ctgttaccac tcccttaagt    960
ttgaccttag gtaactggaa agatgtcgag cggctcgctc acaaccagtc ggtagatgtc   1020
aagaagagac gttgggttac cttctgctct gcagaatggc caacctttaa cgtcggatgg   1080
ccgcgagacg gcacctttaa ccgagacctc atcacccagg ttaagatcaa ggtcttttca   1140
cctggcccgc atggacaccc agaccaggtc ccctacatcg tgacctggga agccttggct   1200
tttgaccccc ctccctgggt caagccctt gtacacccta gcctccgcc tcctcttcct   1260 ccatccgccc cgtctctccc ccttgaacct cctcgttcga cccgcctcg atcctccctt   1320 tatccagccc tcactccttc tctaggcgcc ggccgctcta gcccattaat acgactcact   1380 ataggggcgat tcgaacacca tgcaccatca tcatcatcac gtcgactata aagatgagga   1440
cctcgagatg ggcgtgatta cggattcact ggccgtcgtg gcccgcaccg atcgcccttc   1500
ccaacagtta cgcagcctga atggcgaatg cgcctttgcc tggtttccgg caccagaagc   1560
ggtgccggaa agctggctgg agtgcgatct tcctgaggcc gatactgtcg tcgtcccctc   1620
aaactggcag atgcacggtt acgatgcgcc catctacacc aacgtgacct atcccattac   1680
ggtcaatccg ccgtttgttc ccacggagaa tccgacgggt tgttactcgc tcacatttaa   1740
tgttgatgaa agctggctac aggaaggcca gacgcgaatt attttgatg gcgttaactc   1800 ggcgtttcat ctgtggtgca acgggcgctg gtcggttac ggccaggaca gtcgtttgcc   1860
gtctgaattt gacctgagcg cattttacg cgccggagaa aaccgcctcg cggtgatggt   1920
gctgggctag agtgacggca gttatctgga agatcaggat atgtggcgga tgagcggcat   1980 ttccgtgac gtctcgttgc tgcataaacc gactacacaa atcagcgatt ccatgttgc    2040 cactcgcttt aatgatgatt rcagccgcgc tgtactggag gctgaagttc agatgtgcgg   2100
cgagttgcgt gactacctac gggtaacagt ttctttatgg cagggtgaaa cgcaggtcgc   2160
cagcggcacc gcgcctttcg gcggtgaaat tatcgatgag cgtggtggtt atgccgatcg   2220
cgtcacacta cgtctgaacg tcgaaaaccc gaaactgtgg agcgccgaaa tcccgaatct   2280
ctatcgtgcg gtggttgaac tgcacaccgc cgacggcacg ctgattgaag cagaagcctg   2340
cgatgtcggt ttccgcgagg tgcggattga aaatggtctg ctgctgctga acggcaagcc   2400
gttgctgatt cgaggcgtta accgtcacga gcatcatcct ctgcatggtc aggtcatgga   2460
tgagcagacg atggtgcagg atatcctgct gatgaagcag aacaactttta acgccgtgcg   2520
```

```
ctgttcgcat tatccgaacc atccgctgtg gtacacgctg tgcgaccgct acggcctgta   2580
tgtggtggat gaagccaata ttgaaaccca cggcatggtg ccaatgaatc gtctgaccga   2640
tgatccgcgc tggctaccgg cgatgagcga acgcgtaacg cgaatggtgc agcgcgatcg   2700
taatcacccg agtgtgatca tctggtcgct ggggaatgaa tcaggccacg gcgctaatca   2760
cgacgcgctg tatcgctgga tcaaatctgt cgatccttcc cgcccggtgc agtatgaagg   2820
cggcggagcc gacaccacgg ccaccgatat tatttgcccg atgtacgcgc gcgtggatga   2880
agaccagccc ttcccggctg tgccgaaatg gtccatcaaa aaatggcttt cgctacctgg   2940
agagacgcgc ccgctgatcc tttgcgaata cgcccacgcg atgggtaaca gtcttggcgg   3000
tttcgctaaa tactggcagg cgtttcgtca gtatccccgt ttacagggcg gcttcgtctg   3060
ggactgggtg gatcagtcgc tgattaaata tgatgaaaac ggcaacccgt ggtcggctta   3120
cggcggtgat tttggcgata cgccgaacga tcgccagttc tgtatgaacg gtctggtctt   3180
tgccgaccgc acgccgcatc agcgctgac ggaagcaaaa caccagcagc agttttccca   3240
gttccgttta tccgggcaaa ccatcgaagt gaccagcgaa tacctgttcc gtcatagcga   3300
taacgagctc ctgcactgga tggtggcgct ggatggtaag ccgctggcaa gcggtgaagt   3360
gcctctggat gtcgctccac aaggtaaaca gttgattgaa ctgcctgaac taccgcagcc   3420
ggagagcgcc gggcaactct ggctcacagt acgcgtagtg caaccgaacg cgaccgcatg   3480
gtcagaagcc gggcacatca gcgcctggca gcagtggcgt ctgcggaaaa acctcagtgt   3540
gacgctcccc gccgcgtccc acgccatccc gcatctgacc accagcgaaa tggatttttg   3600
catcgagctg ggtaataagc gttggcaatt taaccgccag tcaggctttc tttcacagat   3660
gtggattggc gataaaaaac aactgctgac gccgctgcgc gatcagttca cccgtgcacc   3720
gctggataac gacattggcg taagtgaagc gacccgcatt gaccctaacg cctgggtcga   3780
acgctggaag gcggcgggcc attaccaggc cgaagcagcg ttgttgcagt gcacggcaga   3840
tacacttgct gatgcggtgc tgattacgac cgctcacgcg tggcagcatc aggggaaaac   3900
cttatttatc agccggaaaa cctaccggat tgatggtagt ggtcaaatgg cgattaccgt   3960
tgatgttgaa gtggcgagcg atacaccgca tccggcgcgg attggcctga actgccagct   4020
ggcgcaggta gcagagcggg taaactggct cggattaggg ccgcaagaaa actatcccga   4080
ccgccttact gccgcctgtt ttgaccgctg ggatctgcca ttgtcagaca tgtataccc   4140
gtacgtcttc ccgagcgaaa acggtctgcg ctgcgggacg cgcgaattga attatggccc   4200
acaccagtgg cgcggcgact tccagttcaa catcagccgc tacagtcaac agcaactgat   4260
ggaaaccagc catcgccatc tgctgcacgc ggaagaaggc acatggctga atatcgacgg   4320
tttccatatg gggattggtg gcgacgactc ctggagcccg tcagtatcgg cggaattcca   4380
gctgagcgcc ggtcgctacc attaccagtt ggtctggtgt caaaaaagat ctggaggtgg   4440
tggcagcagg ccttggcgcg ccggatcctt aattaacaat tgaccggtaa taataggtag   4500
ataagtgact gattagatgc attgatccct cgaccaattc cggttatttt ccaccatatt   4560
gccgtctttt ggcaatgtga gggcccggaa acctggccct gtcttcttga cgagcattcc   4620
tagggtctt tccctctcg ccaaaggaat gcaaggtctg ttgaatgtcg tgaaggaagc   4680
agttcctctg gaagcttctt gaagacaaac aacgtctgta gcgacccttt gcaggcagcg   4740
gaaccccca cctggcgaca ggtgcctctg cggccaaaag ccacgtgtat aagatacacc   4800
tgcaaaggcg gcacaacccc agtgccacgt tgtgagttgg atagttgtgg aaagagtcaa   4860
```

```
atggctctcc tcaagcgtat tcaacaaggg gctgaaggat gcccagaagg tacccccattg    4920 tatgggatct gatctggggc ctcggtgcac atgctttaca tgtgtttagt cgaggttaaa    4980
aaacgtctag gccccccgaa ccacggggac gtggttttcc tttgaaaaac acgatgataa    5040
taccatgatt gaacaagatg gattgcacgc aggttctccg gccgcttggg tggagaggct    5100
attcggctat gactgggcac aacagacaat cggctgctct gatgccgccg tgttccggct    5160
gtcagcgcag gggcgcccgg ttcttttttgt caagaccgac ctgtccggtg ccctgaatga    5220
actgcaggac gaggcagcgc ggctatcgtg gctggccacg acgggcgttc cttgcgcagc    5280
tgtgctcgac gttgtcactg aagcgggaag ggactggctg ctattgggcg aagtgccggg    5340
gcaggatctc ctgtcatctc accttgctcc tgccgagaaa gtatccatca tggctgatgc    5400
aatgcggcgg ctgcatacgc ttgatccggc tacctgccca ttcgaccacc aagcgaaaca    5460
tcgcatcgag cgagcacgta ctcggatgga agccggtctt gtcgatcagg atgatctgga    5520
cgaagagcat caggggctcg cgccagccga actgttcgcc aggctcaagg cgcgcatgcc    5580
cgacggcgag gatctcgtcg tgacccatgg cgatgcctgc ttgccgaata tcatggtgga    5640
aaatggccgc ttttctggat tcatcgactg tggccggctg ggtgtggcgg accgctatca    5700
ggacatagcg ttggctaccc gtgatattgc tgaagagctt ggcggcgaat gggctgaccg    5760
cttcctcgtg ctttacggta tcgccgctcc cgattcgcag cgcatcgcct tctatcgcct    5820
tcttgacgag ttcttctgag cgggactctg gggttcgcat cgataaaata aaagatttta    5880
tttagtctcc agaaaaaggg gggaatgaaa gaccccacct gtaggtttgg caagctagct    5940
taagtaacgc cattttgcaa ggcatggaaa atacataac tgagaataga aagttcaga    6000 tcaaggtcag gaacagatgg aacagctgaa tatgggccaa acaggatatc tgtggtaagc    6060
agttcctgcc ccggctcagg gccaagaaca gatggaacag ctgaatatgg gccaaacagg    6120
atatctgtgg taagcagttc ctgccccggc tcagggccaa gaacagatgg tccccagatg    6180
cggtccagcc ctcagcagtt tctagagaac catcagatgt ttccagggtg ccccaaggac    6240
ctgaaatgac cctgtgcctt atttgaacta accaatcagt tcgcttctcg cttctgttcg    6300
cgcgcttctg ctccccgagc tcaataaaag agcccacaac ccctcactcg gggcgccagt    6360
cctccgattg actgagtcgc ccgggtaccc gtgtatccaa taaaccctct tgcagttgca    6420
tccgacttgt ggtctcgctg ttccttggga gggtctcctc tgagtgattg actacccgtc    6480
agcgggggtc tttcattcat gcagcatgta tcaaaattaa tttggttttt tttcttaagt    6540
atttacatta aatggccata gttgcattaa tgaatcggcc aacgcgcggg gagaggcggt    6600
ttgcgtattg gcgctcttcc gcttcctcgc tcactgactc gctgcgctcg gtcgttcggc    6660
tgcggcgagc ggtatcagct cactcaaagg cggtaatacg gttatccaca gaatcagggg    6720
ataacgcagg aaagaacatg tgagcaaaag gccagcaaaa ggccaggaac cgtaaaaagg    6780
ccgcgttgct ggcgtttttc cataggctcc gcccccctga cgagcatcac aaaaatcgac    6840
gctcaagtca gaggtggcga aacccgacag gactataaag ataccaggcg tttccccctg    6900
gaagctccct cgtgcgctct cctgttccga ccctgccgct taccggatac ctgtccgcct    6960
ttctcccttc gggaagcgtg gcgctttctc atagctcacg ctgtaggtat ctcagttcgg    7020
tgtaggtcgt tcgctccaag ctgggctgtg tgcacgaacc cccgttcag cccgaccgct    7080 gcgccttatc cggtaactat cgtcttgagt ccaacccggt aagacacgac ttatcgccac    7140
tggcagcagc cactggtaac aggattagca gagcgaggta tgtaggcggt gctacagagt    7200
tcttgaagtg gtggcctaac tacggctaca ctagaagaac agtatttggt atctgcgctc    7260
```

-continued

| | |
|---|---|
| tgctgaagcc agttaccttc ggaaaaagag ttggtagctc ttgatccggc aaacaaacca | 7320 |
| ccgctggtag cggtggtttt tttgtttgca agcagcagat tacgcgcaga aaaaaggat | 7380 |
| ctcaagaaga tcctttgatc ttttctacgg ggtctgacgc tcagtggaac gaaaactcac | 7440 |
| gttaagggat tttggtcatg agattatcaa aaaggatctt cacctagatc cttttgcggc | 7500 |
| cgcaaatcaa tctaaagtat atatgagtaa acttggtctg acagttacca atgcttaatc | 7560 |
| agtgaggcac ctatctcagc gatctgtcta tttcgttcat ccatagttgc ctgactcccc | 7620 |
| gtcgtgtaga taactacgat acgggagggc ttaccatctg gccccagtgc tgcaatgata | 7680 |
| ccgcgagacc cacgctcacc ggctccagat ttatcagcaa taaaccagcc agccggaagg | 7740 |
| gccgagcgca gaagtggtcc tgcaacttta tccgcctcca tccagtctat taattgttgc | 7800 |
| cgggaagcta gagtaagtag ttcgccagtt aatagtttgc gcaacgttgt tgccattgct | 7860 |
| acaggcatcg tggtgtcacg ctcgtcgttt ggtatggctt cattcagctc cggttcccaa | 7920 |
| cgatcaaggc gagttacatg atcccccatg ttgtgcaaaa aagcggttag ctccttcggt | 7980 |
| cctccgatcg ttgtcagaag taagttggcc gcagtgttat cactcatggt tatggcagca | 8040 |
| ctgcataatt ctcttactgt catgccatcc gtaagatgct tttctgtgac tggtgagtac | 8100 |
| tcaaccaagt cattctgaga atagtgtatg cggcgaccga gttgctcttg cccggcgtca | 8160 |
| atacgggata ataccgcgcc acatagcaga actttaaaag tgctcatcat tggaaaacgt | 8220 |
| tcttcgggc gaaaactctc aaggatctta ccgctgttga tccagttc gatgtaaccc | 8280 |
| actcgtgcac ccaactgatc ttcagcatct tttactttca ccagcgtttc tgggtgagca | 8340 |
| aaaacaggaa ggcaaaatgc cgcaaaaaag gaataaggg cgacacggaa atgttgaata | 8400 |
| ctcatactct tcctttttca atattattga agcatttatc agggttattg tctcatgagc | 8460 |
| ggatacatat ttgaatgtat ttagaaaaat aaacaaatag gggttccgcg cacatttc | 8518 |

<210> SEQ ID NO 5
<211> LENGTH: 8518
<212> TYPE: DNA
<213> ORGANISM: Unknown
<220> FEATURE:
<223> OTHER INFORMATION: pICAST ALN.

<400> SEQUENCE: 5

| | |
|---|---|
| gacgtcggac ttatacccgg tttgtcctat agacaccatt cgtcaaggac ggggccgagt | 60 |
| cccggttctt gtctaccttg tcgacttata cccggtttgt cctatagaca ccattcgtca | 120 |
| aggacggggc cgagtcccgg ttcttgtcta ccaggggtct acgccaggtc gggagtcgtc | 180 |
| aaagatctct tggtagtcta caaaggtccc acggggttcc tggactttac tgggacacgg | 240 |
| aataaacttg attggttagt caagcgaaga gcgaagacaa gcgcgcgaag acgaggggct | 300 |
| cgagttattt tctcgggtgt tggggagtga gcccgcggt caggaggcta actgactcag | 360 |
| cgggcccatg ggcacatagg ttatttggga gaacgtcaac gtaggctgaa caccagagcg | 420 |
| acaaggaacc ctcccagagg agactcacta actgatgggc agtcgccccc agaaagtaaa | 480 |
| cccccgagca ggccctagcc ctctggggac gggtccctgg tggctgggtg gtggccctcc | 540 |
| gttcgaccgg tcgttgaata gacacagaca ggctaacaga tcacagatac tgactaaaat | 600 |
| acgcggacgc agccatgatc aatcgattga tcgagacata gaccgcctgg gcaccacctt | 660 |
| gactgctcaa gacttgtggg ccggcgttgg gaccctctgc aggtccctg aaaccccgg | 720 |
| caaaaacacc gggctggact ccttcccctca gctacacctt aggctggggc agtcctatac | 780 |

```
accaagacca tcctctgctc ttggattttg tcaagggcgg aggcagactt aaaaacgaaa    840
gccaaacctt ggcttcggcg cgcagaacag acgacgtcgt agcaagacac aacagagaca    900
gactgacaca aagacataaa cagacttttta atcccggtct gacaatggtg agggaattca   960
aactggaatc cattgacctt tctacagctc gccgagcgag tgttggtcag ccatctacag   1020
ttcttctctg caacccaatg gaagacgaga cgtcttaccg gttggaaatt gcagcctacc   1080
ggcgctctgc cgtggaaatt ggctctggag tagtgggtcc aattctagtt ccagaaaagt   1140
ggaccgggcg tacctgtggg tctggtccag gggatgtagc actggaccct tcggaaccga   1200
aaactggggg gagggaccca gttcgggaaa catgtgggat tcggaggcgg aggagaagga   1260
ggtaggcggg gcagagaggg ggaacttgga ggagcaagct ggggcggagc taggagggaa   1320
ataggtcggg agtgaggaag agatccgcgg ccggcgagat cggtaattta tgctgagtga   1380
tatcccgcta agcttgtggt acgtggtagt agtagtagtg cagctgatat ttctactcct   1440
ggagctctac ccgcactaat gcctaagtga ccggcagcac cggcgtggc tagcgggaag   1500
ggttgtcaat gcgtcggact taccgcttac cgcgaaacgg accaaaggcc gtggtcttcg   1560
ccacggcctt tcgaccgacc tcacgctaga aggactccgg ctatgacagc agcaggggag   1620
tttgaccgtc tacgtgccaa tgctacgcgg gtagatgtgg ttgcactgga tagggtaatg   1680
ccagttaggc ggcaaacaag ggtgcctctt aggctgccca acaatgagcg agtgtaaatt   1740
acaactactt tcgaccgatg tccttccggt ctgcgcttaa taaaaactac cgcaattgag   1800
ccgcaaagta gacaccacgt tgcccgcgac ccagccaatg ccggtcctgt cagcaaacgg   1860
cagacttaaa ctggactcgc gtaaaaatgc gcggcctctt ttggcggagc gccactacca   1920
cgacgcgacc tcactgccgt caatagacct tctagtccta tacaccgcct actcgccgta   1980
aaaggcactg cagagcaacg acgtatttgg ctgatgtgtt tagtcgctaa aggtacaacg   2040
gtgagcgaaa ttactactaa agtcggcgcg acatgacctc cgacttcaag tctacacgcc   2100
gctcaacgca ctgatggatg cccattgtca agaaataccc gtcccacttt gcgtccagcg   2160
gtcgccgtgg cgcggaaagc cgccactttta atagctactc gcaccaccaa tacggctagc   2220
gcagtgtgat gcagacttgc agcttttggg ctttgacacc tcgcggcttt agggcttaga   2280
gatagcacgc caccaacttg acgtgtggcg gctgccgtgc gactaacttc gtcttcggac   2340
gctacagcca aaggcgctcc acgcctaact tttaccagac gacgacgact tgccgttcgg   2400
caacgactaa gctccgcaat tggcagtgct cgtagtagga gacgtaccag tccagtacct   2460
actcgtctgc taccacgtcc tataggacga ctacttcgtc ttgttgaaat tgcggcacgc   2520
gacaagcgta ataggcttgg taggcgacac catgtgcgac acgctggcga tgccggacat   2580
acaccaccta cttcggttat aactttgggt gccgtaccac ggttacttag cagactggct   2640
actaggcgcg accgatggcc gctactcgct tgcgcattgc gcttaccacg tcgcgctagc   2700
attagtgggc tcacactagt agaccagcga ccccttactt agtccggtgc cgcgattagt   2760
gctgcgcgac atagcgacct agtttagaca gctaggaagg gcgggccacg tcatacttcc   2820
gccgcctcgc ctgtggtgcc ggtggctata ataaacgggc tacatgcgcg cgcacctact   2880
tctggtcggg aagggccgac acggctttac caggtagttt tttaccgaaa gcgatggacc   2940
tctctgcgcg ggcgactagg aaacgcttat gcgggtgcgc tacccattgt cagaaccgcc   3000
aaagcgattt atgaccgtcc gcaaagcagt cataggggca aatgtcccgc cgaagcagac   3060
cctgacccac ctagtcagcg actaatttat actacttttg ccgttgggca ccagccgaat   3120
gccgccacta aaaccgctat gcggcttgct agcggtcaag acatacttgc cagaccagaa   3180
```

-continued

```
acggctggcg tgcggcgtag gtcgcgactg ccttcgtttt gtggtcgtcg tcaaaaaggt      3240
caaggcaaat aggcccgttt ggtagcttca ctggtcgctt atggacaagg cagtatcgct      3300
attgctcgag gacgtgacct accaccgcga cctaccattc ggcgaccgtt cgccacttca      3360
cggagaccta cagcgaggtg ttccatttgt caactaactt gacggacttg atggcgtcgg      3420
cctctcgcgg cccgttgaga ccgagtgtca tgcgcatcac gttggcttgc gctggcgtac      3480
cagtcttcgg cccgtgtagt cgcggaccgt cgtcaccgca gaccgccttt tggagtcaca      3540
ctgcgagggg cggcgcaggg tgcggtaggg cgtagactgg tggtcgcttt acctaaaaac      3600
gtagctcgac ccattattcg caaccgttaa attggcggtc agtccgaaag aaagtgtcta      3660
cacctaaccg ctattttttg ttgacgactg cggcgacgcg ctagtcaagt gggcacgtgg      3720
cgacctattg ctgtaaccgc attcacttcg ctgggcgtaa ctgggattgc ggacccagct      3780
tgcgaccttc cgccgcccgg taatggtccg gcttcgtcgc aacaacgtca cgtgccgtct      3840
atgtgaacga ctacgccacg actaatgctg gcgagtgcgc accgtcgtag tccccttttg      3900
gaataaatag tcggccttt ggatggccta actaccatca ccagtttacc gctaatggca      3960
actacaactt caccgctcgc tatgtggcgt aggccgcgcc taaccggact tgacggtcga      4020
ccgcgtccat cgtctcgccc atttgaccga gcctaatccc ggcgttcttt tgatagggct      4080
ggcggaatga cggcggacaa aactggcgac cctagacggt aacagtctgt acatatgggg      4140
catgcagaag ggctcgcttt tgccagacgc gacgccctgc gcgcttaact taataccggg      4200
tgtggtcacc gcgccgctga aggtcaagtt gtagtcggcg atgtcagttg tcgttgacta      4260
cctttggtcg gtagcggtag acgacgtgcg ccttcttccg tgtaccgact tatagctgcc      4320
aaaggtatac ccctaaccac cgctgctgag gacctcgggc agtcatagcc gccttaaggt      4380
cgactcgcgg ccagcgatgg taatggtcaa ccagaccaca gttttttcta gacctccacc      4440
accgtcgtcc ggaaccgcgc ggcctaggaa ttaattgtta actggccatt attatccatc      4500
tattcactga ctaatctacg taactaggga gctggttaag gccaataaaa ggtggtataa      4560
cggcagaaaa ccgttacact cccgggcctt tggaccggga cagaagaact gctcgtaagg      4620
atccccagaa aggggagagc ggtttcctta cgttccagac aacttacagc acttccttcg      4680
tcaaggagac cttcgaagaa cttctgtttg ttgcagacat cgctgggaaa cgtccgtcgc      4740
cttgggggt ggaccgctgt ccacggagac gccggttttc ggtgcacata ttctatgtgg       4800
acgtttccgc cgtgttgggg tcacggtgca acactcaacc tatcaacacc tttctcagtt      4860
taccgagagg agttcgcata agttgttccc cgacttccta cgggtcttcc atgggtaac       4920
atacccctaga ctagacccccg gagccacgtg tacgaaatgt acacaaatca gctccaattt   4980
tttgcagatc cggggggctt ggtgcccctg caccaaaagg aaactttttg tgctactatt      5040
atggtactaa cttgttctac ctaacgtgcg tccaagaggc cggcgaaccc acctctccga      5100
taagccgata ctgacccgtg ttgtctgtta gccgacgaga ctacggcggc acaaggccga      5160
cagtcgcgtc cccgcgggcc aagaaaaaca gttctggctg gacaggccac gggacttact      5220
tgacgtcctg ctccgtcgcg ccgatagcac cgaccggtgc tgcccgcaag gaacgcgtcg      5280
acacgagctg caacagtgac ttcgcccttc cctgaccgac gataacccgc ttcacggccc      5340
cgtcctagag gacagtagag tggaacgagg acggctcttt cataggtagt accgactacg      5400
ttacgccgcc gacgtatgcg aactaggccg atggacgggt aagctggtgg ttcgctttgt      5460
agcgtagctc gctcgtgcat gagcctacct tcggccagaa cagctagtcc tactagacct      5520
```

```
gcttctcgta gtccccgagc gcggtcggct tgacaagcgg tccgagttcc gcgcgtacgg   5580
gctgccgctc ctagagcagc actgggtacc gctacgacaa acggcttat agtaccacct    5640
tttaccggcg aaaagaccta agtagctgac accggccgac ccacaccgcc tggcgatagt   5700
cctgtatcgc aaccgatggg cactataacg acttctcgaa ccgccgctta cccgactggc   5760
gaaggagcac gaaatgccat agcggcgagg ctaagcgtc gcgtagcgga agatagcgga    5820
agaactgctc aagaagactc gccctgagac cccaagcgta gctattttat tttctaaaat   5880
aaatcagagg tcttttttccc cccttacttt ctggggtgga catccaaacc gttcgatcga  5940
attcattgcg gtaaaacgtt ccgtaccttt ttatgtattg actcttatct cttcaagtct   6000
agttccagtc cttgtctacc ttgtcgactt atacccggtt tgtcctatag acaccattcg   6060
tcaaggacgg ggccgagtcc cggttcttgt ctaccttgtc gacttatacc cggtttgtcc   6120
tatagacacc attcgtcaag gacggggccg agtcccggtt cttgtctacc aggggtctac   6180
gccaggtcgg gagtcgtcaa agatctcttg gtagtctaca aaggtcccac ggggttcctg   6240
gactttactg ggacacggaa taaacttgat tggttagtca agcgaagagc gaagacaagc   6300
gcgcgaagac gaggggctcg agttattttc tcgggtgttg gggagtgagc cccgcggtca   6360
ggaggctaac tgactcagcg ggcccatggg cacataggtt atttgggaga acgtcaacgt   6420
aggctgaaca ccagagcgac aaggaaccct cccagaggag actcactaac tgatgggcag   6480
tcgcccccag aaagtaagta cgtcgtacat agttttaatt aaaccaaaaa aaagaattca   6540
taaatgtaat ttaccggtat caacgtaatt acttagccgg ttgcgcgccc ctctccgcca   6600
aacgcataac cgcgagaagg cgaaggagcg agtgactgag cgacgcgagc cagcaagccg   6660
acgccgctcg ccatagtcga gtgagtttcc gccattatgc caataggtgt cttagtcccc   6720
tattgcgtcc tttcttgtac actcgttttc cggtcgtttt ccggtccttg gcatttttcc   6780
ggcgcaacga ccgcaaaaag gtatccgagg cggggggact gctcgtagtg tttttagctg   6840
cgagttcagt ctccaccgct ttgggctgtc ctgatatttc tatggtccgc aaaggggggac  6900
cttcgaggga gcacgcgaga ggacaaggct gggacggcga atggcctatg gacaggcgga   6960
aagagggaag cccttcgcac cgcgaaagag tatcgagtgc gacatccata gagtcaagcc   7020
acatccagca agcgaggttc gacccgacac acgtgcttgg ggggcaagtc gggctggcga   7080
cgcggaatag gccattgata gcagaactca ggttgggcca ttctgtgctg aatagcggtg   7140
accgtcgtcg gtgaccattg tcctaatcgt ctcgctccat acatccgcca cgatgtctca   7200
agaacttcac caccggattg atgccgatgt gatcttcttg tcataaacca tagacgcgag   7260
acgacttcgg tcaatggaag ccttttctc aaccatcgag aactaggccg tttgtttggt    7320
ggcgaccatc gccaccaaaa aaacaaacgt tcgtcgtcta atgcgcgtct tttttttccta  7380
gagttcttct aggaaactag aaaagatgcc ccagactgcg agtcaccttg cttttgagtg   7440
caattcccta aaaccagtac tctaatagtt tttcctagaa gtggatctag gaaaacgccg   7500
gcgtttagtt agatttcata tatactcatt tgaaccagac tgtcaatggt tacgaattag   7560
tcactccgtg gatagagtcg ctagacagat aaagcaagta ggtatcaacg gactgagggg   7620
cagcacatct attgatgcta tgccctcccg aatggtagac cggggtcacg acgttactat   7680
ggcgctctgg gtgcgagtgg ccgaggtcta aatagtcgtt attggtcgg tcggccttcc    7740
cggctcgcgt cttcaccagg acgttgaaat aggcggaggt aggtcagata attaacaacg   7800
gcccttcgat ctcattcatc aagcggtcaa ttatcaaacg cgttgcaaca acggtaacga   7860
tgtccgtagc accacagtgc gagcagcaaa ccataccgaa gtaagtcgag gccaagggtt   7920
```

```
gctagttccg ctcaatgtac tagggggtac aacacgtttt ttcgccaatc gaggaagcca    7980
ggaggctagc aacagtcttc attcaaccgg cgtcacaata gtgagtacca ataccgtcgt    8040
gacgtattaa gagaatgaca gtacggtagg cattctacga aaagacactg accactcatg    8100
agttggttca gtaagactct tatcacatac gccgctggct caacgagaac gggccgcagt    8160
tatgccctat tatggcgcgg tgtatcgtct tgaaattttc acgagtagta accttttgca    8220
agaagccccg cttttgagag ttcctagaat ggcgacaact ctaggtcaag ctacattggg    8280
tgagcacgtg ggttgactag aagtcgtaga aaatgaaagt ggtcgcaaag acccactcgt    8340
ttttgtcctt ccgtttacg gcgtttttc ccttattccc gctgtgcctt tacaacttat    8400
gagtatgaga aggaaaaagt tataataact tcgtaaatag tcccaataac agagtactcg    8460
cctatgtata aacttacata aatcttttta tttgtttatc cccaaggcgc gtgtaaag     8518

<210> SEQ ID NO 6
<211> LENGTH: 8175
<212> TYPE: DNA
<213> ORGANISM: Unknown
<220> FEATURE:
<223> OTHER INFORMATION: pICAST OMC.

<400> SEQUENCE: 6
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca acccctcact cggggcgcca gtcctccgat tgactgagtc     360
gcccgggtac ccgtgtatcc aataaaccct cttgcagttg catccgactt gtggtctcgc     420
tgttccttgg gaggytctcc tctgagtgat tgactacccg tcagcggggg tctttcattt     480
gggggctcgt ccgggatcgg gagaccctg cccaggacc accgacccac caccgggagg     540
caagctggcc agcaacttat ctgtgtctgt ccgattgtct agtgtctatg actgatttta     600
tgcgcctgcg tcgtactag ttagctaact agctctgtat ctggcggacc cgtggtggaa     660
ctgacgagtt ctgaacaccc ggccgcaacc ctgggagacg tcccagggac tttggggggcc     720 gtttttgtgg cccgacctga ggaagggagt cgatgtggaa tccgacccg tcaggatatg     780 tggttctggt aggagacgag aacctaaaac agttcccgcc tccgtctgaa tttttgcttt     840
cggtttggaa ccgaagccgc gcgtcttgtc tgctgcagca tcgttctgtg ttgtctctgt     900
ctgactgtgt ttctgtattt gtctgaaaat tagggccaga ctgttaccac tcccttaagt     960
ttgaccttag gtaactggaa agatgtcgag cggctcgctc acaaccagtc ggtagatgtc    1020
aagaagagac gttgggttac cttctgctct gcagaatggc caacctttaa cgtcggatgg    1080
ccgcgagacg gcacctttaa ccgagacctc atcacccagg ttaagatcaa gtcttttca    1140 cctggcccgc atggacaccc agaccaggtc cctacatcg tgacctggga agccttggct    1200
tttgaccccc ctccctgggt caagcccttt gtacacccta gcctccgcc tcctcttcct    1260 ccatccgccc cgtctctccc ccttgaacct cctcgttcga cccgcctcg atcctccctt    1320 tatccagccc tcactccttc tctaggcgcc ggccgctcta gcccattaat acgactcact    1380 ataggggcgat tcgaatcagg ccttggcgcg ccggatcctt aattaagcgc aattgggagg    1440
```

-continued

```
tggcggtagc ctcgagatgg gcgtgattac ggattcactg gccgtcgttt tacaacgtcg   1500
tgactgggaa aaccctggcg ttacccaact taatcgcctt gcagcacatc cccctttcgc   1560
cagctggcgt aatagcgaag aggcccgcac cgatcgccct tcccaacagt tacgcagcct   1620
gaatggcgaa tggcgctttg cctggtttcc ggcaccagaa gcggtgccgg aaagctggct   1680
ggagtgcgat cttcctgagg ccgatactgt cgtcgtcccc tcaaactggc agatgcacgg   1740
ttacgatgcg cccatctaca ccaacgtgac ctatcccatt acggtcaatc cgccgtttgt   1800
tcccacggag aatccgacgg gttgttactc gctcacattt aatgttgatg aaagctggct   1860
acaggaaggc cagacgcgaa ttatttttga tggcgttaac tcggcgtttc atctgtggtg   1920
caacgggcgc tgggtcggtt acggccagga cagtcgtttg ccgtctgaat ttgacctgag   1980 cgcatttttta cgcgccggag aaaaccgcct cgcggtgatg gtgctgcgct ggagtgacgg   2040
cagttatctg gaagatcagg atatgtggcg gatgagcggc attttccgtg acgtctcgtt   2100
gctgcataaa ccgactacac aaatcagcga tttccatgtt gccactcgct ttaatgatga   2160
tttcagccgc gctgtactgg aggctgaagt tcagatgtgc ggcgagttgc gtgactacct   2220
acgggtaaca gtttctttat ggcagggtga aacgcaggtc gccagcggca ccgcgccttt   2280
cggcggtgaa attatcgatg agcgtggtgg ttatgccgat cgcgtcacac tacgtctgaa   2340
cgtcgaaaac ccgaaactgt ggagcgccga atcccgaat ctctatcgtg cggtggttga   2400
actgcacacc gccgacggca cgctgattga agcagaagcc tgcgatgtcg gtttccgcga   2460
ggtgcggatt gaaaatggtc tgctgctgct gaacggcaag ccgttgctga ttcgaggcgt   2520
taaccgtcac gagcatcatc ctctgcatgg tcaggtcatg gatgagcaga cgatggtgca   2580
ggatatcctg ctgatgaagc agaacaactt taacgccgtg cgctgttcgc attatccgaa   2640
ccatccgctg tggtacacgc tgtgcgaccg ctacggcctg tatgtggtgg atgaagccaa   2700
tattgaaacc cacggcatgg tgccaatgaa tcgtctgacc gatgatccgc gctggctacc   2760
ggcgatgagc gaacgcgtaa cgcgaatggt gcagcgcgat cgtaatcacc cgagtgtgat   2820
catctggtcg ctgggaatg aatcaggcca cggcgctaat cacgacgcgc tgtatcgctg   2880
gatcaaatct gtcgatcctt cccgcccggt gcagtatgaa ggcggcggag ccgacaccac   2940
ggccaccgat attatttgcc cgatgtacgc gcgcgtggat gaagaccagc ccttcccggc   3000
tgtgccgaaa tggtccatca aaaaatggct ttcgctacct ggagagacgc gcccgctgat   3060
cctttgcgaa tacgcccacg cgatgggtaa cagtcttggc ggtttcgcta aatactggca   3120
ggcgtttcgt cagtatcccc gtttacaggg cggcttcgtc tgggactggg tggatcagtc   3180
gctgattaaa tatgatgaaa acggcaaccc gtggtcggct tacggcggtg attttggcga   3240
tacgccgaac gatcgccagt tctgtatgaa cggtctggtc tttgccgacc gcacgccgca   3300
tccagcgctg acggaagcaa aacaccagcg gcagtttttc cagttccgtt tatccgggca   3360
aaccatcgaa gtgaccagcg aatacctgtt ccgtcatagc gataacgagc tcctgcactg   3420
gatggtggcg ctggatggta agccgctggc aagcggtgaa gtgcctctgg atgtcgctcc   3480
acaaggtaaa cagttgattg aactgcctga actaccgcag ccgagagcg ccgggcaact   3540 ctggctcaca gtacgcgtag tgcaaccgaa cgcgaccgca tggtcagaag ccgggcacat   3600
cagcgcctgg cagcagtggc gtctggcgga aaacctcagt gtgacgctcc ccgccgcgtc   3660
ccacgccatc ccgcatctga ccaccagcga aatggatttt tgcatcgagc tgggtaataa   3720
gcgttggcaa tttaaccgcc agtcaggctt tctttcacag atgtggattg gcgataaaaa   3780
acaactgctg acgccgctgc gcgatcagtt cacccgtgtc gatagatctg aacagaaact   3840
```

```
catttccgaa gaagacctag tcgaccatca tcatcatcat caccggtaat aataggtaga   3900
taagtgactg attagatgca tttcgactag atccctcgac caattccggt tatttccac    3960
catattgccg tcttttggca atgtgagggc ccggaaacct ggccctgtct tcttgacgag   4020
cattcctagg ggtctttccc ctctcgccaa aggaatgcaa ggtctgttga atgtcgtgaa   4080
ggaagcagtt cctctggaag cttcttgaag acaaacaacg tctgtagcga ccctttgcag   4140
gcagcggaac cccccacctg gcgacaggtg cctctgcggc aaaagccac gtgtataaga    4200
tacacctgca aggcggcac aaccccagtg ccacgttgtg agttggatag ttgtggaaag    4260
agtcaaatgg ctctcctcaa gcgtattcaa caaggggctg aaggatgccc agaaggtacc   4320
ccattgtatg ggatctgatc tggggcctcg gtgcacatgc tttacatgtg tttagtcgag   4380
gttaaaaaac gtctaggccc cccgaaccac ggggacgtgg ttttcctttg aaaaacacga   4440
tgataatacc atgaaaaagc ctgaactcac cgcgacgtct gtcgagaagt ttctgatcga   4500
aaagttcgac agcgtctccg acctgatgca gctctcggag ggcgaagaat ctcgtgcttt   4560
cagcttcgat gtaggagggc gtggatatgt cctgcgggta atagctgcg ccgatggttt    4620
ctacaaagat cgttatgttt atcggcactt tgcatcggcc gcgctcccga ttccggaagt   4680
gcttgacatt ggggaattta gcgagagcct gacctattgc atctcccgcc gtgcacaggg   4740
tgtcacgttg caagacctgc ctgaaaccga actgcccgct gttctgcagc cggtcgcgga   4800
ggccatggat gcgatcgctg cggccgatct tagccgacg agcgggttcg gcccattcgg    4860
accgcaagga atcggtcaat acactacatg gcgtgatttc atatgcgcga ttgctgatcc   4920
ccatgtgtat cactggcaaa ctgtgatgga cgacaccgtc agtgcgtccg tcgcgcaggc   4980
tctcgatgag ctgatgcttt gggccgagga ctgccccgaa gtccggcacc tcgtgcacgc   5040
ggatttcggc tccaacaatg tcctgacgga caatggccgc ataacagcgg tcattgactg   5100
gagcgaggcg atgttcgggg attcccaata cgaggtcgcc aacatcttct tctggaggcc   5160
gtggttggct tgtatggagc agcagacgcg ctacttcgag cggaggcatc cggagcttgc   5220
aggatcgccg cggctccggg cgtatatgct ccgcattggt cttgaccaac tctatcagag   5280
cttggttgac ggcaatttcg atgatgcagc ttgggcgcag ggtcgatgcg acgcaatcgt   5340
ccgatccgga gccgggactg tcgggcgtac acaaatcgcc cgcagaagcg cggccgtctg   5400
gaccgatggc tgtgtagaag tactcgccga tagtggaaac cgacgcccca gcactcgtcc   5460
gagggcaaag gaatagagta gatgccgacc gggatctatc gataaaataa agatttttat   5520
ttagtctcca gaaaagggg ggaatgaaag accccacctg taggtttggc aagctagctt    5580
aagtaacgcc attttgcaag gcatggaaaa atacataact gagaatagag aagttcagat   5640
caaggtcagg aacagatgga acagctgaat atgggccaaa caggatatct gtggtaagca   5700
gttcctgccc cggctcaggg ccaagaacag atggaacagc tgaatatggg ccaaacagga   5760
tatctgtggt aagcagttcc tgccccggct cagggccaag aacagatggt ccccagatgc   5820
ggtccagccc tcagcagttt ctagagaacc atcagatgtt tccagggtgc cccaaggacc   5880
tgaaatgacc ctgtgcctta tttgaactaa ccaatcagtt cgcttctcgc ttctgttcgc   5940
gcgcttctgc tccccgagct caataaaaga gcccacaacc cctcactcgg ggcgccagtc   6000
ctccgattga ctgagtcgcc cgggtacccg tgtatccaat aaaccctctt gcagttgcat   6060
ccgacttgtg gtctcgctgt tccttgggag ggtctcctct gagtgattga ctacccgtca   6120
gcgggggtct ttcattcatg cagcatgtat caaaattaat ttggtttttt tcttaagta    6180
```

```
tttacattaa atggccatag ttgcattaat gaatcggcca acgcgcgggg agaggcggtt      6240
tgcgtattgg cgctcttccg cttcctcgct cactgactcg ctgcgctcgg tcgttcggct      6300
gcggcgagcg gtatcagctc actcaaaggc ggtaatacgg ttatccacag aatcagggga      6360
taacgcagga agaacatgt gagcaaaagg ccagcaaaag gccaggaacc gtaaaaaggc      6420
cgcgttgctg gcgttttccc ataggctccg ccccctgac gagcatcaca aaaatcgacg      6480
ctcaagtcag aggtggcgaa acccgacagg actataaaga taccaggcgt ttccccctgg      6540
aagctccctc gtgcgctctc ctgttccgac cctgccgctt accggatacc tgtccgcctt      6600
tctcccttcg ggaagcgtgg cgctttctca tagctcacgc tgtaggtatc tcagttcggt      6660
gtaggtcgtt cgctccaagc tgggctgtgt gcacgaaccc cccgttcagc ccgaccgctg      6720
cgccttatcc ggtaactatc gtcttgagtc aacccggta agacacgact tatcgccact      6780
ggcagcagcc actggtaaca ggattagcag agcgaggtat gtaggcggtg ctacagagtt      6840
cttgaagtgg tggcctaact acggctacac tagaagaaca gtatttggta tctgcgctct      6900
gctgaagcca gttaccttcg gaaaaagagt tggtagctct tgatccggca acaaaccac      6960 cgctggtagc ggtggttttt ttgtttgcaa gcagcagatt acgcgcagaa aaaaaggatc      7020
tcaagaagat cctttgatct tttctacggg gtctgacgct cagtggaacg aaaactcacg      7080
ttaagggatt ttggtcatga gattatcaaa aaggatcttc acctagatcc ttttaaatta      7140
aaaatgaagt ttgcggccgc aaatcaatct aaagtatata tgagtaaact tggtctgaca      7200
gttaccaatg cttaatcagt gaggcaccta tctcagcgat ctgtctattt cgttcatcca      7260
tagttgcctg actccccgtc gtgtagataa ctacgatacg ggagggctta ccatctggcc      7320
ccagtgctgc aatgataccg cgagacccac gctcaccggc tccagattta tcagcaataa      7380
accagccagc cggaagggcc gagcgcagaa gtggtcctgc aactttatcc gcctccatcc      7440
agtctattaa ttgttgccgg gaagctagag taagtagttc gccagttaat agtttgcgca      7500
acgttgttgc cattgctaca ggcatcgtgg tgtcacgctc gtcgtttggt atggcttcat      7560
tcagctccgg ttcccaacga tcaaggcgag ttacatgatc ccccatgttg tgcaaaaaag      7620
cggttagctc cttcggtcct ccgatcgttg tcagaagtaa gttggccgca gtgttatcac      7680
tcatggttat ggcagcactg cataattctc ttactgtcat gccatccgta agatgctttt      7740
ctgtgactgg tgagtactca accaagtcat tctgagaata gtgtatgcgg cgaccgagtt      7800
gctcttgccc ggcgtcaata cgggataata ccgcgccaca tagcagaact ttaaaagtgc      7860
tcatcattgg aaaacgttct tcggggcgaa aactctcaag gatcttaccg ctgttgagat      7920
ccagttcgat gtaacccact cgtgcaccca actgatcttc agcatctttt actttcacca      7980
gcgtttctgg gtgagcaaaa acaggaaggc aaaatgccgc aaaaaaggga ataagggcga      8040
cacggaaatg ttgaatactc atactcttcc ttttcaata ttattgaagc atttatcagg      8100
gttattgtct catgagcgga tacatatttg aatgtattta gaaaaataaa caatagggg      8160 ttccgcgcac atttc                                                        8175
```

<210> SEQ ID NO 7
<211> LENGTH: 8175
<212> TYPE: DNA
<213> ORGANISM: Unknown
<220> FEATURE:
<223> OTHER INFORMATION: pICAST OMC.

<400> SEQUENCE: 7

```
gacgtcggac ttatacccgg tttgtcctat agacaccatt cgtcaaggac ggggccgagt        60
```

```
cccggttctt gtctaccttg tcgacttata cccggtttgt cctatagaca ccattcgtca    120 aggacgggc cgagtcccgg ttcttgtcta ccaggggtct acgccaggtc gggagtcgtc    180
aaagatctct tggtagtcta caaaggtccc acggggttcc tggactttac tgggacacgg    240
aataaacttg attggttagt caagcgaaga gcgaagacaa gcgcgcgaag acgaggggct    300
cgagttattt tctcgggtgt tggggagtga gccccgcggt caggaggcta actgactcag    360
cgggcccatg ggcacatagg ttatttggga gaacgtcaac gtaggctgaa caccagagcg    420
acaaggaacc ctcccagagg agactcacta actgatgggc agtcgccccc agaaagtaaa    480
cccccgagca ggccctagcc ctctggggac gggtccctgg tggctgggtg gtggccctcc    540
gttcgaccgg tcgttgaata gacacagaca ggctaacaga tcacagatac tgactaaaat    600
acgcggacgc agccatgatc aatcgattga tcgagacata gaccgcctgg gcaccacctt    660
gactgctcaa gacttgtggg ccggcgttgg gaccctctgc agggtccctg aaaccccccgg    720 caaaaacacc gggctggact ccttccctca gctacacctt aggctggggc agtcctatac    780
accaagacca tcctctgctc ttggattttg tcaagggcgg aggcagactt aaaaacgaaa    840
gccaaacctt ggcttcggcg cgcagaacag acgacgtcgt agcaagacac aacagagaca    900
gactgacaca aagacataaa cagactttta atcccggtct gacaatggtg agggaattca    960
aactggaatc cattgacctt tctacagctc gccgagcgag tgttggtcag ccatctacag   1020
ttcttctctg caacccaatg gaagacgaga cgtcttaccg gttggaaatt gcagcctacc   1080
ggcgctctgc cgtggaaatt ggctctggag tagtgggtcc aattctagtt ccagaaaagt   1140
ggaccgggcg tacctgtggg tctggtccag gggatgtagc actggaccct tcggaaccga   1200
aaactggggg gagggaccca gttcgggaaa catgtgggat tcggaggcgg aggagaagga   1260
ggtaggcggg gcagagaggg ggaacttgga ggagcaagct ggggcggagc taggagggaa   1320
ataggtcggg agtgaggaag agatccgcgg ccggcgagat cgggtaatta tgctgagtga   1380
tatcccgcta agcttagtcc ggaaccgcgc ggcctaggaa ttaattcgcg ttaaccctcc   1440
accgccatcg gagctctacc cgcactaatg cctaagtgac cggcagcaaa atgttgcagc   1500 actgacccttt ttgggaccgc aatgggttga attagcggaa cgtcgtgtag ggggaaagcg   1560
gtcgaccgca ttatcgcttc tccggcgtg gctagcggga agggttgtca atgcgtcgga   1620
cttaccgctt accgcgaaac ggaccaaagg ccgtggtctt cgccacggcc tttcgaccga   1680
cctcacgcta gaaggactcc ggctatgaca gcagcagggg agtttgaccg tctacgtgcc   1740
aatgctacgc gggtagatgt ggttgcactg gatagggtaa tgccagttag gcggcaaaca   1800
agggtgcctc ttaggctgcc caacaatgag cgagtgtaaa ttacaactac tttcgaccga   1860
tgtccttccg gtctgcgctt aataaaaact accgcaattg agccgcaaag tagacaccac   1920
gttgcccgcg acccagccaa tgccggtcct gtcagcaaac ggcagactta aactggactc   1980
gcgtaaaaat gcgcggcctc ttttggcgga gcgccactac cacgacgcga cctcactgcc   2040
gtcaatagac cttctagtcc tatacaccgc ctactcgccg taaaaggcac tgcagagcaa   2100
cgacgtattt ggctgatgtg tttagtcgct aaaggtacaa cggtgagcga aattactact   2160
aaagtcggcg cgacatgacc tccgacttca agtctacacg ccgctcaacg cactgatgga   2220
tgcccattgt caaagaaata ccgtcccact ttgcgtccag cggtcgccgt ggcgcggaaa   2280
gccgccactt taatagctac tcgcaccacc aatacggcta gcgcagtgtg atgcagactt   2340
gcagcttttg ggctttgaca cctcgcggct ttagggctta gagatagcac gccaccaact   2400
```

-continued

```
tgacgtgtgg cggctgccgt gcgactaact tcgtcttcgg acgctacagc caaaggcgct    2460
ccacgcctaa cttttaccag acgacgacga cttgccgttc ggcaacgact aagctccgca    2520
attggcagtg ctcgtagtag gagacgtacc agtccagtac ctactcgtct gctaccacgt    2580
cctataggac gactacttcg tcttgttgaa attgcggcac gcgacaagcg taataggctt    2640
ggtaggcgac accatgtgcg cacgctggc gatgccggac atacaccacc tacttcggtt    2700
ataactttgg gtgccgtacc acggttactt agcagactgg ctactaggcg cgaccgatgg    2760
ccgctactcg cttgcgcatt gcgcttacca cgtcgcgcta gcattagtgg gctcacacta    2820
gtagaccagc gaccccttac ttagtccggt gccgcgatta gtgctgcgcg acatagcgac    2880
ctagtttaga cagctaggaa gggcgggcca cgtcatactt ccgccgcctc ggctgtggtg    2940
ccggtggcta taataaacgg gctacatgcg cgcgcaccta cttctggtcg ggaagggccg    3000
acacggcttt accaggtagt tttttaccga aagcgatgga cctctctgcg cgggcgacta    3060
ggaaacgctt atgcgggtgc gctacccatt gtcagaaccg ccaaagcgat ttatgaccgt    3120
ccgcaaagca gtcataggg caaatgtccc gccgaagcag accctgaccc acctagtcag    3180
cgactaattt atactacttt tgccgttggg caccagccga atgccgccac taaaaccgct    3240
atgcggcttg ctagcggtca agacatactt gccagaccag aaacggctgg cgtgcggcgt    3300
aggtcgcgac tgccttcgtt ttgtggtcgt cgtcaaaaag gtcaaggcaa ataggcccgt    3360
ttggtagctt cactggtcgc ttatggacaa ggcagtatcg ctattgctcg aggacgtgac    3420
ctaccaccgc gacctaccat tcggcgaccg ttcgccactt cacggagacc tacagcgagg    3480
tgttccattt gtcaactaac ttgacggact tgatggcgtc ggcctctcgc ggcccgttga    3540
gaccgagtgt catgcgcatc acgttggctt gcgctggcgt accagtcttc ggcccgtgta    3600
gtcgcggacc gtcgtcaccg cagaccgcct tttggagtca cactgcgagg ggcggcgcag    3660
ggtgcggtag ggcgtagact ggtggtcgct ttacctaaaa acgtagctcg acccattatt    3720
cgcaaccgtt aaattggcgg tcagtccgaa agaaagtgtc tacacctaac cgctatttt    3780 tgttgacgac tgcggcgacg cgctagtcaa gtgggcacag ctatctagac ttgtctttga    3840
gtaaaggctt cttctggatc agctggtagt agtagtagta gtggccatta ttatccatct    3900
attcactgac taatctacgt aaagctgatc tagggagctg gttaaggcca ataaaaggtg    3960
gtataacggc agaaaaccgt tacactcccg ggcctttgga ccgggacaga agaactgctc    4020
gtaaggatcc ccagaaaggg gagagcggtt tccttacgtt ccagacaact tacagcactt    4080
ccttcgtcaa ggagaccttc gaagaacttc tgtttgttgc agacatcgct gggaaacgtc    4140
cgtcgccttg gggggtggac cgctgtccac ggagacgccg gttttcggtg cacatattct    4200
atgtggacgt ttccgccgtg ttggggtcac ggtgcaaaac tcaacctatc aacacctttc    4260
tcagtttacc gagaggagtt cgcataagtt gttccccgac ttcctacggg tcttccatgg    4320
ggtaacatac cctagactag accccggagc cacgtgtacg aaatgtacac aaatcagctc    4380 caatttttg cagatccggg gggcttggtg cccctgcacc aaaaggaaac ttttgtgct    4440 actattatgg tacttttcg gacttgagtg gcgctgcaga cagctcttca aagactagct    4500
tttcaagctg tcgcagaggc tggactacgt cgagagcctc ccgcttctta gagcacgaaa    4560
gtcgaagcta catcctcccg cacctataca ggacgcccat ttatcgacgc ggctaccaaa    4620
gatgtttcta gcaatacaaa tagccgtgaa acgtagccgg cgcgagggct aaggccttca    4680
cgaactgtaa ccccttaaat cgcrctcgga ctggataacg tagagggcgg cacgtgtccc    4740
acagtgcaac gttctggacg gactttggct tgacgggcga caagacgtcg gccagcgcct    4800
```

-continued

```
ccggtaccta cgctagcgac gccggctaga atcggtctgc tcgcccaagc cgggtaagcc    4860
tggcgttcct tagccagtta tgtgatgtac cgcactaaag tatacgcgct aacgactagg    4920
ggtacacata gtgaccgttt gacactacct gctgtggcag tcacgcaggc agcgcgtccg    4980
agagctactc gactacgaaa cccggctcct gacggggctt caggccgtgg agcacgtgcg    5040
cctaaagccg aggttgttac aggactgcct gttaccggcg tattgtcgcc agtaactgac    5100
ctcgctccgc tacaagcccc taagggttat gctccagcgg ttgtagaaga agacctccgg    5160
caccaaccga acatacctcg tcgtctgcgc gatgaagctc gcctccgtag gcctcgaacg    5220
tcctagcggc gccgaggccc gcatatacga ggcgtaacca gaactgcttg agatagtctc    5280
gaaccaactg ccgttaaagc tactacgtcg aacccgcgtc ccagctacgc tgcgttagca    5340
ggctaggcct cggccctgac agcccgcatg tgtttagcgg gcgtcttcgc gccggcagac    5400
ctggctaccg acacatcttc atgagcggct atcacctttg gctgcgggt cgtgagcagg    5460 ctcccgtttc cttatctcat ctacggctgg ccctagatag ctattttatt ttctaaaata    5520
aatcagaggt cttttccccc ccttactttc tggggtggac atccaaaccg ttcgatcgaa    5580
ttcattgcgg taaaacgttc cgtacctttt tatgtattga ctcttatctc ttcaagtcta    5640
gttccagtcc ttgtctacct tgtcgactta tacccggttt gtcctataga caccattcgt    5700
caaggacggg gccgagtccc ggttcttgtc taccttgtcg acttatcccc ggtttgtcct    5760
atagacacca ttcgtcaagg acggggccga gtcccggttc ttgtctacca ggggtctacg    5820
ccaggtcggg agtcgtcaaa gatctcttgg tagtctacaa aggtcccacg gggttcctgg    5880
actttactgg gacacggaat aaacttgatt ggttagtcaa gcgaagagcg aagacaagcg    5940
cgcgaagacg aggggctcga gttatttct cgggtgttgg ggagtgagcc ccgcggtcag    6000
gaggctaact gactcagcgg gcccatgggc acataggtta tttgggagaa cgtcaacgta    6060
ggctgaacac cagagcgaca aggaaccctc ccagaggaga ctcactaact gatgggcagt    6120
cgcccccaga aagtaagtac gtcgtacata gttttaatta aaccaaaaaa aagaattcat    6180
aaatgtaatt taccggtatc aacgtaatta cttagccggt tgcgcgcccc tctccgccaa    6240
acgcataacc gcgagaaggc gaaggagcga gtgactgagc gacgcgagcc agcaagccga    6300
cgccgctcgc catagtcgag tgagtttccg ccattatgcc aataggtgtc ttagtcccct    6360
attgcgtcct ttcttgtaca ctcgttttcc ggtcgttttc cggtccttgg catttttccg    6420
gcgcaacgac cgcaaaaagg tatccgaggc gggggggactg ctcgtagtgt ttttagctgc    6480
gagttcagtc tccaccgctt tgggctgtcc tgatatttct atggtccgca aaggggggacc    6540 ttcgagggag cacgcgagag gacaaggctg ggacggcgaa tggcctatgg acaggcggaa    6600
agagggaagc ccttcgcacc gcgaaagagt atcgagtgcg acatccatag agtcaagcca    6660
catccagcaa gcgaggttcg acccgacaca cgtgcttggg gggcaagtcg ggctggcgac    6720
gcggaatagg ccattgatag cagaactcag gttgggccat tctgtgctga atagcggtga    6780
ccgtcgtcgg tgaccattgt cctaatcgtc tcgctccata catccgccac gatgtctcaa    6840
gaacttcacc accggattga tgccgatgtg atcttcttgt cataaaccat agacgcgaga    6900
cgacttcggt caatggaagc cttttttctca accatcgaga actaggccgt tgtttggtg    6960 gcgaccatcg ccaccaaaaa aacaaacgtt cgtcgtctaa tgcgcgtctt ttttcctag    7020 agttcttcta ggaaactaga aaagatgccc cagactgcga gtcaccttgc ttttgagtgc    7080
aattccctaa aaccagtact ctaatagttt ttcctagaag tggatctagg aaaatttaat    7140
```

```
ttttacttca aacgccggcg tttagttaga tttcatatat actcatttga accagactgt      7200
caatggttac gaattagtca ctccgtggat agagtcgcta gacagataaa gcaagtaggt      7260
atcaacggac tgaggggcag cacatctatt gatgctatgc cctcccgaat ggtagaccgg      7320
ggtcacgacg ttactatggc gctctgggtg cgagtggccg aggtctaaat agtcgttatt      7380
tggtcggtcg gccttccgg ctcgcgtctt caccaggacg ttgaaatagg cggaggtagg       7440
tcagataatt aacaacggcc cttcgatctc attcatcaag cggtcaatta tcaaacgcgt      7500
tgcaacaacg gtaacgatgt ccgtagcacc acagtgcgag cagcaaacca taccgaagta      7560
agtcgaggcc aagggttgct agttccgctc aatgtactag ggggtacaac acgttttttc      7620
gccaatcgag aagccagga ggctagcaac agtcttcatt caaccggcgt cacaatagtg       7680
agtaccaata ccgtcgtgac gtattaagag aatgacagta cggtaggcat tctacgaaaa      7740
gacactgacc actcatgagt tggttcagta agactcttat cacatacgcc gctggctcaa      7800
cgagaacggg ccgcagttat gccctattat ggcgcgtgt atcgtcttga aattttcacg       7860
agtagtaacc ttttgcaaga agccccgctt ttgagagttc ctagaatggc gacaactcta     7920
ggtcaagcta cattgggtga gcacgtgggt tgactagaag tcgtagaaaa tgaaagtggt     7980
cgcaaagacc cactcgtttt tgtccttccg ttttacggcg tttttcccct tattcccgct     8040
gtgcctttac aacttatgag tatgagaagg aaaaagttat aataacttcg taaatagtcc     8100
caataacaga gtactcgcct atgtataaac ttacataaat cttttatttt gtttatcccc     8160
aaggcgcgtg taaag                                                      8175
```

<210> SEQ ID NO 8
<211> LENGTH: 8161
<212> TYPE: DNA
<213> ORGANISM: Unknown
<220> FEATURE:
<223> OTHER INFORMATION: pICAST OMN.

<400> SEQUENCE: 8

```
ctgcagcctg aatatgggcc aaacaggata tctgtggtaa gcagttcctg ccccggctca       60
gggccaagaa cagatggaac agctgaatat gggccaaaca ggatatctgt ggtaagcagt      120
tcctgccccg gctcagggcc aagaacagat ggtccccaga tgcggtccag ccctcagcag      180
tttctagaga accatcagat gtttccaggg tgccccaagg acctgaaatg accctgtgcc      240
ttatttgaac taaccaatca gttcgcttct cgcttctgtt cgcgcgcttc tgctccccga      300
gctcaataaa agagcccaca acccctcact cggggcgcca gtcctccgat tgactgagtc      360
gcccgggtac ccgtgtatcc aataaaccct cttgcagttg catccgactt gtggtctcgc      420
tgttccttgg gagggtctcc tctgagtgat tgactacccg tcagcggggg tctttcattt      480
gggggctcgt ccgggatcgg gagacccctg cccagggacc accgacccac caccgggagg      540
caagctggcc agcaacttat ctgtgtctgt ccgattgtct agtgtctatg actgattta       600 tgcgcctgcg tcggtactag ttagctaact agctctgtat ctggcggacc cgtggtggaa      660
ctgacgagtt ctgaacaccc ggccgcaacc ctggagacg tcccagggac tttgggggcc       720
gtttttgtgg cccgacctga ggaagggagt cgatgtggaa tccgaccccg tcaggatatg      780
tggttctggt aggagacgag aacctaaaac agttcccgcc tccgtctgaa ttttttgcttt     840 cggtttggaa ccgaagccgc gcgtcttgtc tgctgcagca tcgttctgtg ttgtctctgt      900
ctgactgtgt ttctgtattt gtctgaaaat taggccaga ctgttaccac tcccttaagt       960 ttgacctag gtaactggaa agatgtcgag cggctcgctc acaaccagtc ggtagatgtc      1020
```

-continued

```
aagaagagac gttgggttac cttctgctct gcagaatggc caacctttaa cgtcggatgg      1080
ccgcgagacg gcacctttaa ccgagacctc atcacccagg ttaagatcaa ggtcttttca      1140
cctggcccgc atggacaccc agaccaggtc ccctacatcg tgacctggga agccttggct      1200 tttgacccce ctccctgggt caagccettt gtacacccta agcctccgcc tcctcttcct      1260
ccatccgccc cgtctctccc ccttgaacct cctcgttcga cccgcctcg atcctccctt       1320 tatccagccc tcactccttc tctaggcgcc ggccgctcta gcccattaat acgactcact      1380
ataggggcat tcgaacacca tgcaccatca tcatcatcac gtcgacgaac agaaactcat     1440
ttccgaagaa gacctactcg agatgggcgt gattacggat tcactggccg tcgttttaca     1500
acgtcgtgac tgggaaaacc ctggcgttac ccaacttaat cgccttgcag cacatccccc     1560
tttcgccagc tggcgtaata gcgaagaggc ccgcaccgat cgcccttccc aacagttacg     1620
cagcctgaat ggcgaatggc gctttgcctg gtttccggca ccagaagcgg tgccggaaag     1680
ctggctggag tgcgatcttc ctgaggccga tactgtcgtc gtccctcaa actggcagat       1740 gcacggttac gatgcgccca tctacaccaa cgtgacctat cccattacgg tcaatccgcc     1800
gtttgttccc acggagaatc cgacggggttg ttactcgctc acatttaatg ttgatgaaag    1860
ctggctacag gaaggccaga cgcgaattat ttttgatggc gttaactcgg cgtttcatct    1920
gtggtgcaac gggcgctggg tcggttacgg ccaggacagt cgtttgccgt ctgaatttga    1980
cctgagcgca tttttacgcg ccggagaaaa ccgcctcgcg gtgatggtgc tgcgctggag    2040
tgacggcagt tatctggaag atcaggatat gtggcggatg agcggcattt ccgtgacgt     2100 ctcgttgctg cataaaccga ctacacaaat cagcgatttc catgttgcca ctcgctttaa    2160
tgatgatttc agccgcgctg tactggaggc tgaagttcag atgtgcggcg agttgcgtga    2220
ctacctacgg gtaacagttt ctttatggca gggtgaaacg caggtcgcca gcggcaccgc    2280
gcctttcggc ggtgaaatta tcgatgagcg tggtggttat gccgatcgcg tcacactacg    2340
tctgaacgtc gaaaacccga actgtggag cgccgaaatc ccgaatctct atcgtgcggt      2400
ggttgaactg cacaccgccg acggcacgct gattgaagca gaagcctgcg atgtcggttt     2460
ccgcgaggtg cggattgaaa atggtctgct gctgctgaac ggcaagccgt tgctgattcg    2520
aggcgttaac cgtcacgagc atcatcctct gcatggtcag gtcatggatg agcagacgat   2580
ggtgcaggat atcctgctga tgaagcagaa caactttaac gccgtgcgct gttcgcatta   2640
tccgaaccat ccgctgtggt acacgctgtg cgaccgctac ggcctgtatg tggtggatga   2700
agccaatatt gaaacccacg gcatggtgcc aatgaatcgt ctgaccgatg atccgcgctg   2760
gctaccggcg atgagcgaac gcgtaacgcg aatggtgcag cgcgatcgta atcacccgag   2820
tgtgatcatc tggtcgctgg ggaatgaatc aggccacggc gctaatcacg acgcgctgta   2880
tcgctggatc aaatcgtcg atccttcccg cccggtgcag tatgaaggcg gcggagccga    2940
caccacggcc accgatatta tttgcccgat gtacgcgcgc gtggatgaag accagccctt   3000
cccggctgtg ccgaaatggt ccatcaaaaa atggctttcg ctacctggag agacgcgccc   3060
gctgatcctt tgcgaatacg cccacgcgat gggtaacagt cttggcggtt cgctaaata    3120 ctggcaggcg tttcgtcagt atccccgttt acagggcggc ttcgtctggg actgggtgga   3180
tcagtcgctg attaaatatg atgaaaacgg caacccgtgg tcggcttacg gcggtgattt   3240
tggcgatacg ccgaacgatc gccagttctg tatgaacggt ctggtctttg ccgaccgcac   3300
gccgcatcca gcgctgacgg aagcaaaaca ccagcagcag ttttccagt tccgtttatc    3360
```

-continued

```
cgggcaaacc atcgaagtga ccagcgaata cctgttccgt catagcgata acgagctcct   3420
gcactggatg gtggcgctgg atggtaagcc gctggcaagc ggtgaagtgc ctctggatgt   3480
cgctccacaa ggtaaacagt tgattgaact gcctgaacta ccgcagccgg agagcgccgg   3540
gcaactctgg ctcacagtac gcgtagtgca accgaacgcg accgcatggt cagaagccgg   3600
gcacatcagc gcctggcagc agtggcgtct ggcggaaaac ctcagtgtga cgctccccgc   3660
cgcgtcccac gccatcccgc atctgaccac cagcgaaatg gattttgca tcgagctggg   3720
taataagcgt tggcaattta accgccagtc aggctttctt tcacagatgt ggattggcga   3780
taaaaaacaa ctgctgacgc cgctgcgcga tcagttcacc cgtgtcgata gatctggagg   3840
tggtggcagc aggccttggc gcgccggatc cttaattaac aattgaccgg taataatagg   3900
tagataagtg actgattaga tgcatttcga ctagatccct cgaccaattc cggttatttt   3960
ccaccatatt gccgtctttt ggcaatgtga gggcccggaa acctggccct gtcttcttga   4020
cgagcattcc taggggtctt tcccctctcg ccaaaggaat gcaaggtctg ttgaatgtcg   4080
tgaaggaagc agttcctctg gaagcttctt gaagacaaac aacgtctgta gcgacccttt   4140
gcaggcagcg gaaccccca cctggcgaca ggtgcctctg cggccaaaag ccacgtgtat   4200
aagatacacc tgcaaaggcg gcacaacccc agtgccacgt tgtgagttgg atagttgtgg   4260
aaagagtcaa atggctctcc tcaagcgtat tcaacaaggg gctgaaggat gcccagaagg   4320
taccccattg tatgggatct gatctggggc ctcggtgcac atgctttaca tgtgtttagt   4380
cgaggttaaa aaacgtctag gcccccgaa ccacggggac gtggttttcc tttgaaaaac   4440
acgatgataa taccatgaaa aagcctgaac tcaccgcgac gtctgtcgag aagtttctga   4500
tcgaaaagtt cgacagcgtc tccgacctga tgcagctctc ggagggcgaa gaatctcgtg   4560
ctttcagctt cgatgtagga gggcgtggat atgtcctgcg ggtaaatagc tgcgccgatg   4620
gtttctacaa agatcgttat gtttatcggc actttgcatc ggccgcgctc ccgattccgg   4680
aagtgcttga cattggggaa tttagcgaga gcctgaccta ttgcatctcc cgccgtgcac   4740
agggtgtcac gttgcaagac ctgcctgaaa ccgaactgcc cgctgttctg cagccggtcg   4800
cggaggccat ggatgcgatc gctgcggccg atcttagcca cgagcgggg ttcggcccat   4860
tcggaccgca aggaatcggt caatacacta catggcgtga tttcatatgc gcgattgctg   4920
atccccatgt gtatcactgg caaactgtga tggacgacac cgtcagtgcg tccgtcgcgc   4980
aggctctcga tgagctgatg ctttgggccg aggactgccc cgaagtccgg cacctcgtgc   5040
acgcggattt cggctccaac aatgtcctga cggacaatgg ccgcataaca gcggtcattg   5100
actggagcga ggcgatgttc gggattccc aatacgaggt cgccaacatc ttcttctgga   5160
ggccgtggtt ggcttgtatg gagcagcaga cgcgctactt cgagcggagg catccggagc   5220
ttgcaggatc gccgcggctc cgggcgtata tgctccgcat tggtcttgac caactctatc   5280
agagcttggt tgacggcaat ttcgatgatg cagcttgggc gcagggtcga tgcgacgcaa   5340
tcgtccgatc cggagccggg actgtcgggc gtacacaaat cgcccgcaga agcgcggccg   5400
tctggaccga tggctgtgta gaagtactcg ccgatagtgg aaaccgacgc cccagcactc   5460
gtccgagggc aaaggaatag agtagatgcc gaccgggatc tatcgataaa ataaaagatt   5520
ttatttagtc tccagaaaaa ggggggaatg aagaccccaa cctgtaggtt tggcaagcta   5580
gcttaagtaa cgccattttg caaggcatgg aaaatacat aactgagaat agagaagttc   5640
agatcaaggt caggaacaga tggaacagct gaatatgggc caaacaggat atctgtggta   5700
agcagttcct gccccggctc agggccaaga acagatggaa cagctgaata tgggccaaac   5760
```

```
aggatatctg tggtaagcag ttcctgcccc ggctcagggc caagaacaga tggtccccag    5820
atgcggtcca gccctcagca gtttctagag aaccatcaga tgtttccagg gtgccccaag    5880
gacctgaaat gaccctgtgc cttatttgaa ctaaccaatc agttcgcttc tcgcttctgt    5940
tcgcgcgctt ctgctccccg agctcaataa agagcccac aaccccctcac tcggggcgcc    6000 agtcctccga ttgactgagt cgcccgggta cccgtgtatc caataaaccc tcttgcagtt    6060
gcatccgact tgtggtctcg ctgttccttg ggagggtctc ctctgagtga ttgactaccc    6120
gtcagcgggg gtctttcatt catgcagcat gtatcaaaat taatttggtt ttttttctta    6180
agtatttaca ttaaatggcc atagttgcat taatgaatcg gccaacgcgc ggggagaggc    6240
ggtttgcgta ttggcgctct tccgcttcct cgctcactga ctcgctgcgc tcggtcgttc    6300
ggctgcggcg agcggtatca gctcactcaa aggcggtaat acggttatcc acagaatcag    6360
gggataacgc aggaaagaac atgtgagcaa aaggccagca aaaggccagg aaccgtaaaa    6420
aggccgcgtt gctggcgttt ttccataggc tccgcccccc tgacgagcat cacaaaaatc    6480
gacgctcaag tcagaggtgg cgaaacccga caggactata agataccag gcgtttcccc    6540 ctggaagctc cctcgtgcgc tctcctgttc cgaccctgcc gcttaccgga tacctgtccg    6600
cctttctccc ttcgggaagc gtggcgcttt ctcatagctc acgctgtagg tatctcagtt    6660
cggtgtaggt cgttcgctcc aagctgggct gtgtgcacga accccccgtt cagcccgacc    6720
gctgcgcctt atccggtaac tatcgtcttg agtccaaccc ggtaagacac gacttatcgc    6780
cactggcagc agccactggt aacaggatta gcagagcgag gtatgtaggc ggtgctacag    6840
agttcttgaa gtggtggcct aactacggct acactagaag aacagtattt ggtatctgcg    6900
ctctgctgaa gccagttacc ttcggaaaaa gagttggtag ctcttgatcc ggcaaacaaa    6960
ccaccgctgg tagcggtggt ttttttgttt gcaagcagca gattacgcgc agaaaaaaag    7020
gatctcaaga agatcctttg atcttttcta cggggtctga cgctcagtgg aacgaaaact    7080
cacgttaagg gattttggtc atgagattat caaaaaggat cttcacctag atccttttgc    7140
ggccgcaaat caatctaaag tatatatgag taaacttggt ctgacagtta ccaatgctta    7200
atcagtgagg cacctatctc agcgatctgt ctatttcgtt catccatagt tgcctgactc    7260
cccgtcgtgt agataactac gatacgggag ggcttaccat ctggccccag tgctgcaatg    7320
ataccgcgag acccacgctc accggctcca gatttatcag caataaacca gccagccgga    7380
agggccgagc gcagaagtgg tcctgcaact ttatccgcct ccatccagtc tattaattgt    7440
tgccgggaag ctagagtaag tagttcgcca gttaatagtt tgcgcaacgt tgttgccatt    7500
gctacaggca tcgtggtgtc acgctcgtcg tttggtatgg cttcattcag ctccggttcc    7560
caacgatcaa ggcgagttac atgatccccc atgttgtgca aaaaagcggt tagctccttc    7620
ggtcctccga tcgttgtcag aagtaagttg gccgcagtgt tatcactcat ggttatggca    7680
gcactgcata attctcttac tgtcatgcca tccgtaagat gcttttctgt gactggtgag    7740
tactcaacca agtcattctg agaatagtgt atgcggcgac cgagttgctc ttgcccggcg    7800
tcaatacggg ataataccgc gccacatagc agaactttaa aagtgctcat cattggaaaa    7860
cgttcttcgg ggcgaaaact ctcaaggatc ttaccgctgt tgagatccag ttcgatgtaa    7920
cccactcgtg cacccaactg atcttcagca tcttttactt tcaccagcgt ttctgggtga    7980
gcaaaaacag gaaggcaaaa tgccgcaaaa aagggaataa gggcgacacg gaaatgttga    8040
atactcatac tcttcctttt tcaatattat tgaagcattt atcagggtta ttgtctcatg    8100
```

| | |
|---|---|
| agcggataca tatttgaatg tatttagaaa aataaacaaa tagggggttcc gcgcacattt | 8160 |
| c | 8161 |

<210> SEQ ID NO 9
<211> LENGTH: 8161
<212> TYPE: DNA
<213> ORGANISM: Unknown
<220> FEATURE:
<223> OTHER INFORMATION: pICAST OMN.

<400> SEQUENCE: 9

| | |
|---|---|
| gacgtcggac ttatacccgg tttgtcctat agacaccatt cgtcaaggac ggggccgagt | 60 |
| cccggttctt gtctaccttg tcgacttata cccggtttgt cctatagaca ccattcgtca | 120 |
| aggacggggc cgagtcccgg ttcttgtcta ccagggtct acgccaggtc gggagtcgtc | 180 |
| aaagatctct tggtagtcta caaaggtccc acggggttcc tggactttac tgggacacgg | 240 |
| aataaacttg attggttagt caagcgaaga gcgaagacaa gcgcgcgaag acgaggggct | 300 |
| cgagttattt tctcgggtgt tggggagtga gccccgcggt caggaggcta actgactcag | 360 |
| cgggcccatg ggcacatagg ttatttggga gaacgtcaac gtaggctgaa caccagagcg | 420 |
| acaaggaacc ctcccagagg agactcacta actgatgggc agtcgccccc agaaagtaaa | 480 |
| ccccccgagca ggccctagcc ctctggggac gggtccctgg tggctgggtg gtggccctcc | 540 |
| gttcgaccgg tcgttgaata gacacagaca ggctaacaga tcacagatac tgactaaaat | 600 |
| acgcggacgc agccatgatc aatcgattga tcgagacata gaccgcctgg gcaccacctt | 660 |
| gactgctcaa gacttgtggg ccggcgttgg gaccctctgc agggtccctg aaaccccccgg | 720 |
| caaaaacacc gggctggact ccttcccctca gctacacctt aggctggggc agtcctatac | 780 |
| accaagacca tcctctgctc ttggatttttg tcaagggcgg aggcagactt aaaaacgaaa | 840 |
| gccaaacctt ggcttcggcg cgcagaacag acgacgtcgt agcaagacac aacagagaca | 900 |
| gactgacaca aagacataaa cagactttta atcccggtct gacaatggtg agggaattca | 960 |
| aactggaatc cattgacctt tctacagctc gccgagcgag tgttggtcag ccatctacag | 1020 |
| ttcttctctg caacccaatg aagacgaga cgtcttaccg gttggaaatt gcagcctacc | 1080 |
| ggcgctctgc cgtggaaatt ggctctggag tagtgggtcc aattctagtt ccagaaaagt | 1140 |
| ggaccgggcg tacctgtggg tctggtccag gggatgtagc actggaccct tcggaaccga | 1200 |
| aaactgggg gagggaccca gttcgggaaa catgtgggat tcggaggcgg aggagaagga | 1260 |
| ggtaggcggg gcagagaggg ggaacttgga ggagcaagct ggggcggagc taggagggaa | 1320 |
| ataggtcggg agtgaggaag agatccgcgg ccggcgagat cgggtaatta tgctgagtga | 1380 |
| tatcccgcta agcttgtggt acgtggtagt agtagtagtg cagctgcttg tctttgagta | 1440 |
| aaggcttctt ctggatgagc tctacccgca ctaatgccta agtgaccggc agcaaaatgt | 1500 |
| tgcagcactg acccttttgg gaccgcaatg ggttgaatta gcggaacgtc gtgtagggggg | 1560 |
| aaagcggtcg accgcattat cgcttctccg ggcgtggcta gcgggaaggg ttgtcaatgc | 1620 |
| gtcggactta ccgcttaccg cgaaacggac caaaggccgt ggtcttcgcc acggcctttc | 1680 |
| gaccgacctc acgctagaag gactccggct atgacagcag caggggagtt tgaccgtcta | 1740 |
| cgtgccaatg ctacgcgggt agatgtggtt gcactggata gggtaatgcc agttaggcgg | 1800 |
| caaacaaggg tgcctcttag gctgcccaac aatgagcgag tgtaaattac aactactttc | 1860 |
| gaccgatgtc cttccggtct gcgcttaata aaaactaccg caattgagcc gcaaagtaga | 1920 |
| caccacgttt cccgcgaccc agccaatgcc ggtcctgtca gcaaacggca gacttaaact | 1980 |

```
ggactcgcgt aaaaatgcgc ggcctctttt ggcggagcgc cactaccacg acgcgacctc    2040
actgccgtca atagaccttc tagtcctata caccgcctac tcgccgtaaa aggcactgca    2100
gagcaacgac gtatttggct gatgtgttta gtcgctaaag gtacaacggt gagcgaaatt    2160
actactaaag tcggcgcgac atgacctccg acttcaagtc tacacgccgc tcaacgcact    2220
gatggatgcc cattgtcaaa gaataccgt cccactttgc gtccagcggt cgccgtggcg     2280
cggaaagccg ccactttaat agctactcgc accaccaata cggctagcgc agtgtgatgc    2340
agacttgcag cttttgggct tgacaccctc gcggctttag ggcttagaga tagcacgcca    2400
ccaacttgac gtgtggcggc tgccgtgcga ctaacttcgt cttcggacgc tacagccaaa    2460
ggcgctccac gcctaacttt taccagacga cgacgacttg ccgttcggca acgactaagc    2520
tccgcaattg gcagtgctcg tagtaggaga cgtaccagtc cagtacctac tcgtctgcta    2580
ccacgtccta taggacgact acttcgtctt gttgaaattg cggcacgcga caagcgtaat    2640
aggcttggta ggcgacacca tgtgcgacac gctggcgatg ccggacatac accacctact    2700
tcggttataa ctttgggtgc cgtaccacgg ttacttagca gactggctac taggcgcgac    2760
cgatggccgc tactcgcttg cgcattgcgc ttaccacgtc gcgctagcat tagtgggctc    2820
acactagtag accagcgacc ccttacttag tccggtgccg cgattagtgc tgcgcgacat    2880
agcgacctag tttagacagc taggaagggc gggccacgtc atacttccgc cgcctcggct    2940
gtggtgccgg tggctataat aaacgggcta catgcgcgcg cacctacttc tggtcgggaa    3000
gggccgacac ggctttacca ggtagttttt taccgaaagc gatggacctc tctgcgcggg    3060
cgactaggaa acgcttatgc gggtgcgcta cccattgtca gaaccgccaa agcgatttat    3120
gaccgtccgc aaagcagtca taggggcaaa tgtcccgccg aagcagaccc tgacccacct    3180
agtcagcgac taatttatac tacttttgcc gttgggcacc agccgaatgc cgccactaaa    3240
accgctatgc ggcttgctag cggtcaagac atacttgcca gaccagaaac ggctggcgtg    3300
cggcgtaggt cgcgactgcc ttcgttttgt ggtcgtcgtc aaaaaggtca aggcaaatag    3360
gcccgtttgg tagcttcact ggtcgcttat ggacaaggca gtatcgctat tgctcgagga    3420
cgtgacctac caccgcgacc taccattcgg cgaccgttcg ccacttcacg gagacctaca    3480
gcgaggtgtt ccatttgtca actaacttga cggacttgat ggcgtcggcc tctcgcggcc    3540
cgttgagacc gagtgtcatg cgcatcacgt tggcttgcgc tggcgtacca gtcttcggcc    3600
cgtgtagtcg cggaccgtcg tcaccgcaga ccgccttttg gagtcacact gcgaggggcg    3660
gcgcagggtg cggtagggcg tagactggtg gtcgctttac ctaaaaacgt agctcgaccc    3720
attattcgca accgttaaat tggcggtcag tccgaaagaa agtgtctaca cctaaccgct    3780 atttttttgtt gacgactgcg gcgacgcgct agtcaagtgg gcacagctat ctagacctcc    3840
accaccgtcg tccggaaccg cgcggcctag gaattaattg ttaactggcc attattatcc    3900
atctattcac tgactaatct acgtaaagct gatctaggga gctggttaag gccaataaaa    3960
ggtggtataa cggcagaaaa ccgttacact cccgggcctt tggaccggga cagaagaact    4020
gctcgtaagg atccccagaa aggggagagc ggtttcctta cgttccagac aacttacagc    4080
acttccttcg tcaaggagac cttcgaagaa cttctgtttg ttgcagacat cgctgggaaa    4140
cgtccgtcgc cttgggggt ggaccgctgt ccacggagac gccggttttc ggtgcacata     4200
ttctatgtgg acgtttccgc cgtgttgggg tcacggtgca acactcaacc tatcaacacc    4260
tttctcagtt taccgagagg agttcgcata agttgttccc cgacttccta cgggtcttcc    4320
```

```
atgggtaac ataccctaga ctagaccccg gagccacgtg tacgaaatgt acacaaatca    4380
gctccaattt tttgcagatc cggggggctt ggtgcccctg caccaaaagg aaactttttg    4440
tgctactatt atggtacttt ttcggacttg agtggcgctg cagacagctc ttcaaagact    4500
agcttttcaa gctgtcgcag aggctggact acgtcgagag cctcccgctt cttagagcac    4560
gaaagtcgaa gctacatcct cccgcaccta tacaggacgc ccatttatcg acgcggctac    4620
caaagatgtt tctagcaata caaatagccg tgaaacgtag ccggcgcgag ggctaaggcc    4680
ttcacgaact gtaaccccttt aaatcgctct cggactggat aacgtagagg gcggcacgtg    4740
tcccacagtg caacgttctg gacggacttt ggcttgacgg gcgacaagac gtcggccagc    4800
gcctccggta cctacgctag cgacgccggc tagaatcggt ctgctcgccc aagccgggta    4860
agcctggcgt tccttagcca gttatgtgat gtaccgcact aaagtatacg cgctaacgac    4920 tagggtaca catagtgacc gtttgacact acctgctgtg gcagtcacgc aggcagcgcg    4980
tccgagagct actcgactac gaaacccggc tcctgacggg gcttcaggcc gtggagcacg    5040
tgcgcctaaa gccgaggttg ttacaggact gcctgttacc ggcgtattgt cgccagtaac    5100
tgacctcgct ccgctacaag cccctaaggg ttatgctcca gcggttgtag aagaagacct    5160
ccggcaccaa ccgaacatac ctcgtcgtct gcgcgatgaa gctcgcctcc gtaggcctcg    5220
aacgtcctag cggcgccgag gcccgcatat acgaggcgta accagaactg gttgagatag    5280
tctcgaacca actgccgtta aagctactac gtcgaacccg cgtcccagct acgctgcgtt    5340
agcaggctag gcctcggccc tgacagcccg catgtgttta gcgggcgtct tcgcgccggc    5400
agacctggct accgacacat cttcatgagc ggctatcacc tttggctgcg gggtcgtgag    5460
caggctcccg tttccttatc tcatctacgg ctggccctag atagctattt tattttctaa    5520
aataaatcag aggtcttttt ccccccttac tttctggggt ggacatccaa accgttcgat    5580
cgaattcatt gcgtaaaac gttccgtacc tttttatgta ttgactctta tctcttcaag    5640
tctagttcca gtccttgtct accttgtcga cttatacccg gtttgtccta tagacaccat    5700
tcgtcaagga cggggccgag tcccggttct tgtctacctt gtcgacttat acccggtttg    5760
tcctatagac accattcgtc aaggacgggg ccgagtcccg gttcttgtct accagggtc    5820 tacgccaggt cggagtcgt caaagatctc ttggtagtct acaaaggtcc cacgggttc    5880 ctggactta ctgggacacg aataaacttt gattggttag tcaagcgaag agcgaagaca    5940
agcgcgcgaa gacgagggc tcgagttatt ttctcgggtg ttgggagtg agcccgcgg    6000 tcaggaggct aactgactca gcgggcccat ggcacatag gttatttggg agaacgtcaa    6060
cgtaggctga acaccagagc gacaaggaac cctcccagag gagactcact aactgatggg    6120
cagtcgcccc cagaaagtaa gtacgtcgta catagtttta attaaaccaa aaaaaagaat    6180
tcataaatgt aatttaccgg tatcaacgta attacttagc cggttgcgcg cccctctccg    6240
ccaaacgcat aaccgcgaga aggcgaagga gcgagtgact gagcgacgcg agccagcaag    6300
ccgacgccgc tcgccatagt cgagtgagtt ccgccatta tgccaatagg tgtcttagtc    6360
ccctattgcg tcctttcttg tacactcgtt ttccggtcgt tttccggtcc ttggcatttt    6420
tccggcgcaa cgaccgcaaa aaggtatccg aggcgggggg actgctcgta gtgtttttag    6480
ctgcgagttc agtctccacc gctttgggct gtcctgatat ttctatgtc cgcaaagggg    6540 gaccttcgag ggagcacgcg agaggacaag gctgggacgg cgaatggcct atggacaggc    6600
ggaaagaggg aagcccttcg caccgcgaaa gagtatcgag tgcgacatcc atagagtcaa    6660
gccacatcca gcaagcgagg ttcgacccga cacacgtgct tgggggggcaa gtcgggctgg    6720
```

-continued

```
cgacgcggaa taggccattg atagcagaac tcaggttggg ccattctgtg ctgaatagcg    6780
gtgaccgtcg tcggtgacca ttgtcctaat cgtctcgctc catacatccg ccacgatgtc    6840
tcaagaactt caccaccgga ttgatgccga tgtgatcttc ttgtcataaa ccatagacgc    6900
gagacgactt cggtcaatgg aagcctttt ctcaaccatc gagaactagg ccgtttgttt    6960
ggtggcgacc atcgccacca aaaaaacaaa cgttcgtcgt ctaatgcgcg tcttttttc    7020 ctagagttct tctaggaaac tagaaaagat gccccagact gcgagtcacc ttgcttttga    7080
gtgcaattcc ctaaaaccag tactctaata gtttttccta gaagtggatc taggaaaacg    7140
ccggcgttta gttagatttc atatatactc atttgaacca gactgtcaat ggttacgaat    7200
tagtcactcc gtggatagag tcgctagaca gataaagcaa gtaggtatca acggactgag    7260
gggcagcaca tctattgatg ctatgccctc ccgaatggta gaccggggtc acgacgttac    7320
tatggcgctc tgggtgcgag tggccgaggt ctaaatagtc gttatttggt cggtcggcct    7380
tcccggctcg cgtcttcacc aggacgttga aataggcgga ggtaggtcag ataattaaca    7440
acggcccttc gatctcattc atcaagcggt caattatcaa acgcgttgca acaacggtaa    7500
cgatgtccgt agcaccacag tgcgagcagc aaaccatacc gaagtaagtc gaggccaagg    7560
gttgctagtt ccgctcaatg tactaggggg tacaacacgt tttttcgcca atcgaggaag    7620
ccaggaggct agcaacagtc ttcattcaac cggcgtcaca atagtgagta ccaataccgt    7680
cgtgacgtat taagagaatg acagtacggt aggcattcta cgaaaagaca ctgaccactc    7740
atgagttggt tcagtaagac tcttatcaca tacgccgctg gctcaacgag aacgggccgc    7800
agttatgccc tattatggcg cggtgtatcg tcttgaaatt ttcacgagta gtaacctttt    7860
gcaagaagcc ccgcttttga gagttcctag aatggcgaca actctaggtc aagctacatt    7920
gggtgagcac gtgggttgac tagaagtcgt agaaaatgaa agtggtcgca aagacccact    7980 cgttttttgtc cttccgtttt acggcgtttt ttcccttatt cccgctgtgc ctttacaact    8040
tatgagtatg agaaggaaaa agttataata acttcgtaaa tagtcccaat aacagagtac    8100
tcgcctatgt ataaacttac ataaatcttt ttatttgttt atccccaagg cgcgtgtaaa    8160
g                                                                    8161
```

<210> SEQ ID NO 10
<211> LENGTH: 5
<212> TYPE: PRT
<213> ORGANISM: Artificial Sequence
<220> FEATURE:
<223> OTHER INFORMATION: GS Linker

<400> SEQUENCE: 10

Gly Gly Gly Gly Ser
1               5